US012767689B2

(12) United States Patent
Lisowski et al.

(10) Patent No.: US 12,767,689 B2
(45) Date of Patent: Oct. 20, 2026

(54) ADENO-ASSOCIATED VIRUS CAPSID POLYPEPTIDES AND VECTORS

(71) Applicants: Children's Medical Research Institute, Westmead (AU); The Sydney Children's Hospitals Network (Randwick and Westmead) (Incorporating the Royal Alexandra Hospital for Children, Westmead (AU); LogicBio Therapeutics, Inc., Lexington, MA (US)

(72) Inventors: Leszek Lisowski, Redfern (AU); Marti Cabanes Creus, Bondi Beach (AU); Ian Alexander, Pennant Hills (AU); Matthias Charles Jerome Hebben, Le Coudray Monceaux (AU)

(73) Assignees: Children's Medical Research Institute, Westmead (AU); The Sydney Children's Hospitals Network (Randwick and Westmead) (Incorporating the Royal Alexandra Hospital for Children), Westmead (AU); LogicBio Therapeutics, Inc., Lexington, MA (US)

( * ) Notice: Subject to any disclaimer, the term of this patent is extended or adjusted under 35 U.S.C. 154(b) by 624 days.

(21) Appl. No.: 17/801,510

(22) PCT Filed: Feb. 25, 2021

(86) PCT No.: PCT/AU2021/050158

§ 371 (c)(1),
(2) Date: Aug. 22, 2022

(87) PCT Pub. No.: WO2021/168509

PCT Pub. Date: Sep. 2, 2021

(65) Prior Publication Data

US 2023/0093183 A1 Mar. 23, 2023

(30) Foreign Application Priority Data

Feb. 25, 2020 (AU) ................................ 2020900529

(51) Int. Cl.
*C07K 14/005* (2006.01)
*C12N 15/86* (2006.01)

(52) U.S. Cl.
CPC ............ *C07K 14/005* (2013.01); *C12N 15/86* (2013.01); *C12N 2750/14143* (2013.01)

(58) Field of Classification Search
CPC .................. C07K 14/005; C12N 15/86; C12N 2750/14143; C12N 2750/14122;
(Continued)

(56) References Cited

U.S. PATENT DOCUMENTS

| | | | | |
|---|---|---|---|---|
| 2013/0045186 A1* | 2/2013 | Gao | C12N 15/86 435/235.1 |
| 2017/0191079 A1 | 7/2017 | Vandenberghe et al. | |
| 2018/0230440 A1 | 8/2018 | Ho et al. | |

FOREIGN PATENT DOCUMENTS

| | | |
|---|---|---|
| WO | WO 2013/029030 A1 | 2/2013 |
| WO | WO 2016/181123 A1 | 11/2016 |

(Continued)

OTHER PUBLICATIONS

G. Gao, M.R. Alvira, L. Wang, R. Calcedo, J. Johnston, & J.M. Wilson, Novel adeno-associated viruses from rhesus monkeys as vectors for human gene therapy, Proc. Natl. Acad. Sci. U.S.A. 99 (18) 11854-11859, https://doi.org/10.1073/pnas.182412299 (2002). (Year: 2002).*

(Continued)

*Primary Examiner* — Robert B Mondesi
(74) *Attorney, Agent, or Firm* — Knobbe Martens Olson & Bear LLP

(57) ABSTRACT

The present disclosure relates generally to adeno-associated virus (AAV) capsid polypeptides and encoding nucleic acid
(Continued)

molecules. The disclosure also relates to AAV vectors comprising the capsid polypeptides, and nucleic acid vectors (e.g. plasmids) comprising the encoding nucleic acids molecules, as well as to host cells comprising the vectors. The disclosure also relates to methods and uses of the polypeptides, encoding nucleic acids molecules, vectors and host cells.

11 Claims, 24 Drawing Sheets

Specification includes a Sequence Listing.

(58) Field of Classification Search
CPC .................. C12N 2510/00; C12N 7/00; C12N 2750/14171; C12N 2800/107; C12N 5/067; C12N 2750/14121
USPC ........................................................ 435/23.72
See application file for complete search history.

(56) References Cited

FOREIGN PATENT DOCUMENTS

| | | | |
|---|---|---|---|
| WO | WO 2017/015102 | A1 | 1/2017 |
| WO | WO 2017/143100 | A1 | 8/2017 |
| WO | WO 2018/022608 | A2 | 2/2018 |
| WO | WO 2018/152333 | A9 | 8/2018 |
| WO | WO 2018/200419 | A1 | 11/2018 |
| WO | WO 2019/141765 | A1 | 7/2019 |
| WO | WO 2019/191701 | A1 | 10/2019 |
| WO | WO 2019/191701 | A9 | 10/2019 |
| WO | WO 2019/241324 | A1 | 12/2019 |

OTHER PUBLICATIONS

U.S. National Library of Medicine. Sep. 5, 2002). Adeno-associated virus 7 nonstructural protein and capsid protein gene-nucleotide—NCBI. National Center for Biotechnology Information. https://www.ncbi.nlm.nih.gov/nuccore/AF513851 (Year: 2002).*

Creus, Marti Cabanes "Novel AAV engineering technology: identification of improved AAV variants for gene addition and genome engineering in primary human cells" A thesis submitted for the degree of Doctor in Philosophy of University College London, Institute of Child Health, Nov. 2018.

Li, Wuping et al., "Engineering and Selection of Shuffled AAV Genomes: A New Strategy for Producing Targeted Biological Nanoparticles" Molecular Therapy, Jul. 2008, pp. 1252-1260, vol. 16, No. 7.

Paulk, Nicole K. et al., "Bioengineered AAV Capsids with Combined High Human Liver Transduction In Vivo and Unique Humoral Seroreactivity" Molecular Therapy, Jan. 2018, pp. 289-303, vol. 26, No. 1.

Pekrun, Katja et al., "Using a barcoded AAV capsid library to select for clinically relevant gene therapy vectors" JCI Insight, Nov. 2019, pp. 1-18, vol. 4, No. 22.

International Search Report for PCT/AU2021/050158 dated May 10, 2021.

* cited by examiner

Figure 1

```
          VP1 → (aa 1-735 of AAV2)
AAV2      MAADGYLPDWLEDTLSEGIRQWWKLKPGPPPPKPAERHKDDSRGLVLPGYKYLGPFNGLD   60
AAVC.01   MAADGYLPDWLEDNLSEGIREWWDLKPGAPKPKANQQKQDDGRGLVLPGYKYLGPFNGLD   60
AAVC.02   MAADGYLPDWLEDNLSEGIREWWALKPGAPKPKANQQKQDDGRGLVLPGYKYLGPFNGLD   60
AAVC.03   MAADGYLPDWLEDNLSEGIREWWDLKPGAPKPKANQQKQDDGRGLVLPGYKYLGPFNGLD   60
AAVC.04   MAADGYLPDWLEDNLSEGIREWWALKPGAPKPKANQQKQDDGRGLVLPGYKYLGPFNGLD   60
AAVC.05   MAADGYLPDWLEDNLSEGIREWWDLKPGAPKPKANQQKQDDGRGLVLPGYKYLGPFNGLD   60
AAVC.06   MAADGYLPDWLEDTLSEGIREWWALKPGAPQPKANQQHQDNGRGLVLPGYKYLGPFNGLD   60
AAVC.07   MAADGYLPDWLEDNLSEGIREWWDLKPGAPKPKANQQKQDDGRGLVLPGYKYLGPFNGLD   60
AAVC.08   MAADGYLPDWLEDNLSEGIREWWDLKPGAPKPKANQQKQDDGRGLVLPGYKYLGPFNGLD   60
AAVC.09   MAADGYLPDWLEDNLSEGIREWWDLKPGAPKPKANQQKQDDGRGLVLPGYKYLGPFNGLD   60
AAVC.10   MAADGYLPDWLEDNLSEGIREWWDLKPGAPKPKANQQKQDDGRGLVLPGYKYLGPFNGLD   60
AAVC.11   MAADGYLPDWLEDTLSEGIREWWALKPGAPQPKANQQHQDNGRGLVLPGYKYLGPFNGLD   60
AAVC.12   MAADGYLPDWLEDTLSEGIREWWALKPGAPQPKANQQHQDNGRGLVLPGYKYLGPFNGLD   60
AAVC.13   MAADGYLPDWLEDNLSEGIREWWDLKPGAPKPKANQQKQDDGRGLVLPGYKYLGPFNGLD   60
AAVC.14   MAADGYLPDWLEDNLSEGIREWWDLKPGAPKPKANQQKQDDGRGLVLPGYKYLGPFNGLD   60
AAVC.15   MAADGYLPDWLEDNLSEGIREWWDLKPGAPKPKANQQKQDDGRGLVLPGYKYLGPFNGLD   60
AAVC.16   MAADGYLPDWLEDTLSEGIREWWALKPGAPQPKANQQHQDNGRGLVLPGYKYLGPFNGLD   60
AAVC.17   MAADGYLPDWLEDNLSEGIREWWDLKPGAPKPKANQQKQDDGRGLVLPGYKYLGPFNGLD   60
AAVC.18   MAADGYLPDWLEDNLSEGIREWWDLKPGAPKPKANQQKQDDGRGLVLPGYKYLGPFNGLD   60
AAVC.19   MAADGYLPDWLEDNLSEGIREWWALKPGAPKPKANQQKQDDGRGLVLPGYKYLGPFNGLD   60
          *************.******:** **** * **  ::::*:.******************

AAV2      KGEPVNEADAAALEHDKAYDRQLDSGDNPYLKYNHADAEFQERLKEDTSFGGNLGRAVFQ   120
AAVC.01   KGEPVNAADAAALEHDKAYDQQLKAGDNPYLRYNHADAEFQERLQEDTSFGGNLGRAVFQ   120
AAVC.02   KGEPVNAADAAALEHDKAYDQQLKAGDNPYLRYNHADAEFQERLQEDTSFGGNLGRAVFQ   120
AAVC.03   KGEPVNAADAAALEHDKAYDQQLQAGDNPYLRYNHADAEFQERLQEDTSFGGNLGRAVFQ   120
AAVC.04   KGEPVNAADAAALEHDKAYDQQLQAGDNPYLRYNHADAEFQERLQEDTSFGGNLGRAVFQ   120
AAVC.05   KGEPVNAADAAALEHDKAYDQQLKAGDNPYLRYNHADAEFQERLQEDTSFGGNLGRAVFQ   120
AAVC.06   KGEPVNEADAAALEHDKAYDKQLEQGDNPYLKYNHADAEFQERLQEDTSFGGNLGRAVFQ   120
AAVC.07   KGEPVNAADAAALEHDKAYDQQLQAGDNPYLRYNHADAEFQERLQEDTSFGGNLGRAVFQ   120
AAVC.08   KGEPVNAADAAALEHDKAYDQQLKAGDNPYLRYNHADAEFQERLQEDTSFGGNLGRAVFQ   120
AAVC.09   KGEPVNAADAAALEHDKAYDQQLKAGDNPYLRYNHADAEFQERLQEDTSFGGNLGRAVFQ   120
AAVC.10   KGEPVNAADAAALEHDKAYDQQLQAGDNPYLRYNHADAEFQERLQEDTSFGGNLGRAVFQ   120
AAVC.11   KGEPVNEADAAALEHDKAYDKQLEQGDNPYLKYNHADAEFQERLQEDTSFGGNLGRAVFQ   120
AAVC.12   KGEPVNEADAAALEHDKAYDKQLEQGDNPYLKYNHADAEFQERLQEDTSFGGNLGRAVFQ   120
AAVC.13   KGEPVNAADAAALEHDKAYDQQLKAGDNPYLRYNHADAEFQERLQEDTSFGGNLGRAVFQ   120
AAVC.14   KGEPVNAADAAALEHDKAYDQQLQAGDNPYLRYNHADAEFQERLQEDTSFGGNLGRAVFQ   120
AAVC.15   KGEPVNAADAAALEHDKAYDQQLQAGDNPYLRYNHADAEFQERLQEDTSFGGNLGRAVFQ   120
AAVC.16   KGEPVNEADAAALEHDKAYDKQLEQGDNPYLKYNHADAEFQERLQEDTSFGGNLGRAVFQ   120
AAVC.17   KGEPVNAADAAALEHDKAYDQQLKAGDNPYLRYNHADAEFQERLQEDTSFGGNLGRAVFQ   120
AAVC.18   KGEPVNAADAAALEHDKAYDQQLKAGDNPYLRYNHADAEFQERLQEDTSFGGNLGRAVFQ   120
AAVC.19   KGEPVNEADAAALEHDKAYDQQLKAGDNPYLRYNHADAEFQERLQEDTSFGGNLGRAVFQ   120
          ****** *************:**. ******:************:***************

                         VP2 → (aa 138-735 of AAV2)
AAV2      AKKRVLEPLGLVEEPVKTAPGKKRPVEHSPV-EPDSSSGTGKAGQQPARKRLNFGQTGDA   179
AAVC.01   AKKRVLEPLGLVEEAAKTAPGKKRPVEPSPQRSPDSSSGIGKTGQQPAKKRLNFGQTGDS   180
AAVC.02   AKKRVLEPLGLVEEAAKTAPGKKRPVEPSPQRSPDSSSGIGKTGQQPAKKRLNFGQTGDS   180
AAVC.03   AKKRVLEPLGLVEEGAKTAPGKKRPVEPSPQRSPDSSTGIGKKGQQPARKRLNFGQTGDS   180
AAVC.04   AKKRVLEPLGLVEEGAKTAPGKKRPVEQSPQ-EPDSSSGIGKTGQQPAKKRLNFGQTGDS   179
AAVC.05   AKKRVLEPLGLVEEAAKTAPGKKRPVEPSPQRSPDSSSGIGKTGQQPAKKRLNFGQTGDS   180
AAVC.06   AKKRILEPLGLVEEAAKTAPGKKRPVEPSPQRSPDSSTGIGKKGQQPARKRLNFGQTGDS   180
AAVC.07   AKKRVLEPLGLVEEGAKTAPGKKRPVEQSPQ-EPDSSSGIGKTGQQPAKKRLNFGQTGDS   179
AAVC.08   AKKRVLEPLGLVEEAAKTAPGKKRPVEPSPQRSPDSSSGIGKTGQQPAKKRLNFGQTGDS   180
AAVC.09   AKKRVLEPLGLVEEAAKTAPGKKRPVEPSPQRSPDSSSGIGKTGQQPAKKRLNFGQTGDS   180
AAVC.10   AKKRVLEPLGLVEEGAKTAPGKKRPVEQSPQ-EPDSSSGIGKTGQQPAKKRLNFGQTGDS   179
AAVC.11   AKKRVLEPLGLVEEGAKTAPGKKRPVEPSPQRSPDSSTGIGKKGQQPARKRLNFGQTGDS   180
AAVC.12   AKKRILEPLGLVEEAAKTAPGKKRPVEPSPQRSPDSSTGIGKKGQQPARKRLNFGQTGDS   180
AAVC.13   AKKRILEPLGLVEEAAKTAPGKKRPVEPSPQRSPDSSTGIGKKGQQPARKRLNFGQTGDS   180
AAVC.14   AKKRVLEPLGLVEEGAKTAPGKKRPVEQSPQ-EPDSSSGIGKTGQQPAKKRLNFGQTGDS   179
AAVC.15   AKKRVLEPLGLVEEAAKTAPGKKRPVEPSPQRSPDSSTGIGKKGQQPARKRLNFGQTGDS   180
AAVC.16   AKKRILEPLGLVEEAAKTAPGKKRPVEPSPQRSPDSSTGIGKKGQQPARKRLNFGQTGDS   180
AAVC.17   AKKRVLEPLGLVEEAAKTAPGKKRPVEPSPQRSPDSSTGIGKKGQQPARKRLNFGQTGDS   180
AAVC.18   AKKRVLEPLGLVEEGAKTAPGKKRPVEPSPQRSPDSSSGIGKTGQQPAKKRLNFGQTGDS   180
AAVC.19   AKKRVLEPLGLVEEGAKTAPGKKRPVEPSPQRSPDSSTGIGKKGQQPARKRLNFGQTGDS   180
          ****:********* .*********** **  .****:* ** *****:**********:
```

Figure 1 (continued)

```
                           VP3 → (aa 203-735 of AAV2)
AAV2       DSVPDPQPLGQPPAAPSGLGTNTMATGSGAPMADNNEGADGVGNSSGNWHCDSTWMGDRV   239
AAVC.01    ESVPDPQPLGEPPAAPSGVGPNTMAAGGGAPMADNNEGADGVGSSSGNWHCDSTWLGDRV   240
AAVC.02    ESVPDPQPLGEPPAAPSGVGPNTMAAGGGAPMADNNEGADGVGSSSGNWHCDSTWLGDRV   240
AAVC.03    ESVPDPQPLGEPPATPAAVGPTTMASGGGAPMADNNEGADGVGNASGNWHCDSTWLGDRV   240
AAVC.04    ESVPDPQPLGEPPAGPSGLGSGTVAAGGGAPMADNNEGADGVGNSSGNWHCDSQWLGDRV   239
AAVC.05    ESVPDPQPLGEPPAAPSGVGPNTMAAGGGAPMADNNEGADGVGSSSGNWHCDSTWLGDRV   240
AAVC.06    ESVPDPQPLGEPPAAPSSVGSGTVAAGGGAPMADNNEGADGVGNASGNWHCDSTWLGDRV   240
AAVC.07    ESVPDPQPLGEPPAGPSGLGSGTVAAGGGAPMADNNEGADGVGNSSGNWHCDSQWLGDRV   239
AAVC.08    ESVPDPQPLGEPPAAPSGVGPNTMAAGGGAPMADNNEGADGVGSSSGNWHCDSTWLGDRV   240
AAVC.09    ESVPDPQPLGEPPAAPSGVGPNTMAAGGGAPMADNNEGADGVGSSSGNWHCDSTWLGDRV   240
AAVC.10    ESVPDPQPLGEPPAGPSGLGSGTVAAGGGAPMADNNEGADGVGNSSGNWHCDSQWLGDRV   239
AAVC.11    ESVPDPQPLGEPPAAPSSVGSGTVAAGGGAPMADNNEGADGVGNASGNWHCDSTWLGDRV   240
AAVC.12    ESVPDPQPLGEPPAAPSSVGSGTVAAGGGAPMADNNEGADGVGNASGNWHCDSTWLGDRV   240
AAVC.13    ESVPDPQPLGEPPAAPSSVGSGTVAAGGGAPMADNNEGADGVGNASGNWHCDSTWLGDRV   240
AAVC.14    ESVPDPQPLGEPPAGPSGLGSGTVASGGGAPMADNNEGADGVGNSSGNWHCDSQWLGDRV   239
AAVC.15    ESVPDPQPLGEPPAGPSGLGSGTVAAGGGAPMADNNEGADGVGNSSGNWHCDSQWLGDRV   240
AAVC.16    ESVPDPQPLGEPPAAPSSVGSGTVAAGGGAPMADNNEGADGVGNASGNWHCDSTWLGDRV   240
AAVC.17    ESVPDPQPLGEPPAAPSGVGSGTVAAGGGAPMADNNEGADGVGNASGNWHCDSTWLGDRV   240
AAVC.18    ESVPDPQPLGEPPAAPSSVGSGTVAAGGGAPMADNNEGADGVGNASGNWHCDSTWLGDRV   240
AAVC.19    ESVPDPQPLGEPPAAPSSVGSGTVAAGGGAPMADNNEGADGVGNASGNWHCDSTWLGDRV   240
           :*********:*** *:.:*  *:*:*.***************.:******** *:****

AAV2       ITTSTRTWALPTYNNHLYKQISSQ--SGASNDNHYFGYSTPWGYFDFNRFHCHFSPRDWQ   297
AAVC.01    ITTSTRTWALPTYNNHLYKQISSQ--SGASNDNHYFGYSTPWGYFDFNRFHCHFSPRDWQ   298
AAVC.02    ITTSTRTWALPTYNNHLYKQISSQ--SGASNDNHYFGYSTPWGYFDFNRFHCHFSPRDWQ   298
AAVC.03    ITTSTRTWALPTYNNHLYKQISSET-AGSTNDNTYFGYSTPWGYFDFNRFHCHFSPRDWQ   299
AAVC.04    ITTSTRTWALPTYNNHLYKQISSQ--SGASNDNHYFGYSTPWGYFDFNRFHCHFSPRDWQ   297
AAVC.05    ITTSTRTWALPTYNNHLYKQISSQ--SGASNDNHYFGYSTPWGYFDFNRFHCHFSPRDWQ   298
AAVC.06    ITTSTRTWALPTYNNHLYKQISSQ--SGASNDNHYFGYSTPWGYFDFNRFHCHFSPRDWQ   298
AAVC.07    ITTSTRTWALPTYNNHLYKQISSQ--SGASNDNHYFGYSTPWGYFDFNRFHCHFSPRDWQ   297
AAVC.08    ITTSTRTWALPTYNNHLYKQISSQ--SGASNDNHYFGYSTPWGYFDFNRFHCHFSPRDWQ   298
AAVC.09    ITTSTRTWALPTYNNHLYKQISSQ--SGASNDNHYFGYSTPWGYFDFNRFHCHFSPRDWQ   298
AAVC.10    ITTSTRTWALPTYNNHLYKQISSQ--SGASNDNHYFGYSTPWGYFDFNRFHCHFSPRDWQ   297
AAVC.11    ITTSTRTWALPTYNNHLYKQISSQ--SGASNDNHYFGYSTPWGYFDFNRFHCHFSPRDWQ   298
AAVC.12    ITTSTRTWALPTYNNHLYKQISSQ--SGASNDNHYFGYSTPWGYFDFNRFHCHFSPRDWQ   298
AAVC.13    ITTSTRTWALPTYNNHLYKQISSQ--SGASNDNHYFGYSTPWGYFDFNRFHCHFSPRDWQ   298
AAVC.14    ITTSTRTWALPTYNNHLYKQISNSTSGGSSNDNAYFGYSTPWGYFDFNRFHCHFSPRDWQ   299
AAVC.15    ITTSTRTWALPTYNNHLYKQISSQ--SGASNDNHYFGYSTPWGYFDFNRFHCHFSPRDWQ   298
AAVC.16    ITTSTRTWALPTYNNHLYKQISSQ--SGASNDNHYFGYSTPWGYFDFNRFHCHFSPRDWQ   298
AAVC.17    ITTSTRTWALPTYNNHLYKQISSQ--SGASNDNHYFGYSTPWGYFDFNRFHCHFSPRDWQ   298
AAVC.18    ITTSTRTWALPTYNNHLYKQISSQ--SGASNDNHYFGYSTPWGYFDFNRFHCHFSPRDWQ   298
AAVC.19    ITTSTRTWALPTYNNHLYKQISSQ--SGASNDNHYFGYSTPWGYFDFNRFHCHFSPRDWQ   298
           **********************..  .*::*** **************************

AAV2       RLINNNWGFRPKRLNFKLFNIQVKEVTQNDGTTTIANNLTSTVQVFTDSEYQLPYVLGSA   357
AAVC.01    RLINNNWGFRPKRLNFKLFNIQVKEVTDNNGVKTIANNLTSTVQVFTDSDYQLPYVLGSA   358
AAVC.02    RLINNNWGFRPKRLNFKLFNIQVKEVTTNDGVTTIANNLTSTVQVFSDSEYQLPYVLGSA   358
AAVC.03    RLINNNWGFRPKRLNFKLFNIQVKEVTTNDGVTTIANNLTSTVQVFSDSEYQLPYVLGSA   359
AAVC.04    RLINNNWGFRPKRLSFKLFNIQVKEVTTNDGVTTIANNLTSTVQVFSDSEYQLPYVLGSA   357
AAVC.05    RLINNNWGFRPKRLNFKLFNIQVKEVTDNNGVKTIANNLTSTVQVFTDSDYQLPYVLGSA   358
AAVC.06    RLINNNWGFRPKKLSFKLFNIQVKEVTQNDGTTTIANNLTSTVQVFTDSEYQLPYVLGSA   358
AAVC.07    RLINNNWGFRPKRLSFKLFNIQVKEVTTNDGVTTIANNLTSTVQVFSDSEYQLPYVLGSA   357
AAVC.08    RLINNNWGFRPKRLNFKLFNIQVKEVTDNNGVKTIANNLTSTVQVFTDSDYQLPYVLGSA   358
AAVC.09    RLINNNWGFRPKRLNFKLFNIQVKEVTDNNGVKTIANNLTSTVQVFTDSDYQLPYVLGSA   358
AAVC.10    RLINNNWGFRPKRLSFKLFNIQVKEVTTNDGVTTIANNLTSTVQVFSDSEYQLPYVLGSA   357
AAVC.11    RLINNNWGFRPKRLNFKLFNIQVKEVTTNDGVTTIANNLTSTVQVFSDSEYQLPYVLGSA   358
AAVC.12    RLINNNWGFRPKRLSFKLFNIQVKEVTTNDGVTTIANNLTSTVQVFSDSEYQLPYVLGSA   358
AAVC.13    RLINNNWGFRPKRLNFKLFNIQVKEVTTNDGVTTIANNLTSTVQVFSDSEYQLPYVLGSA   358
AAVC.14    RLINNNWGFRPKRLNFKLFNIQVKEVTTNDGVTTIANNLTSTVQVFSDSEYQLPYVLGSA   359
AAVC.15    RLINNNWGFRPKRLSFKLFNIQVKEVTTNDGVTTIANNLTSTVQVFSDSEYQLPYVLGSA   358
AAVC.16    RLINNNWGFRPKRLNFKLFNIQVKEVTTNDGVTTIANNLTSTVQVFSDSEYQLPYVLGSA   358
AAVC.17    RLINNNWGFRPKKLRFKLFNIQVKEVTTNDGVTTIANNLTSTIQVFSDSEYQLPYVLGSA   358
AAVC.18    RLINNNWGFRPKRLSFKLFNIQVKEVTTNDGVTTIANNLTSTVQVFSDSEYQLPYVLGSA   358
AAVC.19    RLINNNWGFRPKKLSFKLFNIQVKEVTQNDGTTTIANNLTSTVQVFTDSEYQLPYVLGSA   358
           ************:* ************ *:*..*********:***:**:**********
```

Figure 1 (continued)

```
AAV2       HQGCLPPFPADVFMVPQYGYLTLNNGSQAVGRSSFYCLEYFPSQMLRTGNNFTFSYTFED   417
AAVC.01    HQGCLPPFPADVFMIPQYGYLTLNNGSQAVGRSSFYCLEYFPSQMLRTGNNFTFSYTFED   418
AAVC.02    HQGCLPPFPADVFMIPQYGYLTLNNGSQAVGRSSFYCLEYFPSQMLRTGNNFEFSYSFED   418
AAVC.03    HQGCLPPFPADVFMIPQYGYLTLNNGSQAVGRSSFYCLEYFPSQMLRTGNNFTFSYTFEE   419
AAVC.04    HQGCLPPFPADVFMIPQYGYLTLNNGSQAVGRSSFYCLEYFPSQMLRTGNNFEFSYTFED   417
AAVC.05    HEGCLPPFPADVFMIPQYGYLTLNNGSQAVGRSSFYCLEYFPSQMLRTGNNFTFSYTFED   418
AAVC.06    HQGCLPPFPADVFMIPQYGYLTLNNGSQAVGRSSFYCLEYFPSQMLRTGNNFEFSYTFED   418
AAVC.07    HQGCLPPFPADVFMIPQYGYLTLNNGSQAVGRSSFYCLEYFPSQMLRTGNNFEFSYTFED   417
AAVC.08    HEGCLPPFPADVFMIPQYGYLTLNNGSQAVGRSSFYCLEYFPSQMLRTGNNFTFSYTFED   418
AAVC.09    HEGCLPPFPADVFMIPQYGYLTLNNGSQAVGRSSFYCLEYFPSQMLRTGNNFTFSYTFED   418
AAVC.10    HQGCLPPFPADVFMIPQYGYLTLNNGSQAVGRSSFYCLEYFPSQMLRTGNNFEFSYTFED   417
AAVC.11    HQGCLPPFPADVFMIPQYGYLTLNNGSQAVGRSSFYCLEYFPSQMLRTGNNFEFSYSFED   418
AAVC.12    HQGCLPPFPADVFMIPQYGYLTLNNGSQAVGRSSFYCLEYFPSQMLRTGNNFEFSYTFED   418
AAVC.13    HQGCLPPFPADVFMIPQYGYLTLNNGSQAVGRSSFYCLEYFPSQMLRTGNNFEFSYTFED   418
AAVC.14    HQGCLPPFPADVFMIPQYGYLTLNNGSQAVGRSSFYCLEYFPSQMLRTGNNFEFSYTFED   419
AAVC.15    HQGCLPPFPADVFMIPQYGYLTLNNGSQAVGRSSFYCLEYFPSQMLRTGNNFEFSYTFED   418
AAVC.16    HQGCLPPFPADVFMIPQYGYLTLNNGSQAVGRSSFYCLEYFPSQMLRTGNNFEFSYTFED   418
AAVC.17    HQGCLPPFPADVFMIPQYGYLTLNNGSQAVGRSSFYCLEYFPSQMLRTGNNFEFSYSFED   418
AAVC.18    HQGCLPPFPADVFMIPQYGYLTLNNGSQAVGRSSFYCLEYFPSQMLRTGNNFEFSYTFED   418
AAVC.19    HQGCLPPFPADVFMIPQYGYLTLNNGSQAVGRSSFYCLEYFPSQMLRTGNNFEFSYTFED   418
           *:************:************************************* ***:**:

AAV2       VPFHSSYAHSQSLDRLMNPLIDQYLYYLSRTNTPSG-TTTQSRLQFSQAGASDIRDQSRN   476
AAVC.01    VPFHSSYAHSQSLDRLMNPLIDQYLYYLSRTQS-TGGTQGTQQLLFSQAGPANMSAQAKN   477
AAVC.02    VPFHSSYAHSQSLDRLMNPLIDQYLYYLARTQSNPGGTAGNRELQFYQGGPSTMAEQAKN   478
AAVC.03    VPFHSSYAHSQSLDRLMNPLIDQYLYYLNRTQNQSG-SAQNKDLLFSRGSPAGMSVQPKN   478
AAVC.04    VPFHSSYAHSQSLDRLMNPLIDQYLYYLSRTQS-TGGTQGTQQLLFSQAGPANMSAQAKN   476
AAVC.05    VPFHSSYAHSQSLDRLMNPLIDQYLYYLSRTQS-TGGTQGTQQLLFSQAGPANMSAQAKN   477
AAVC.06    VPFHSSYAHSQSLDRLMNPLIDQYLYYLSRTQS-TGGTQGTQQLLFSQAGPANMSAQAKN   477
AAVC.07    VPFHSSYAHSQSLDRLMNPLIDQYLYYLSRTQS-TGGTQGTQQLLFSQAGPANMSAQAKN   476
AAVC.08    VPFHSSYAHSQSLDRLMNPLIDQYLYYLSRTQS-TGGTQGTQQLLFSQAGPANMSAQAKN   477
AAVC.09    VPFHSSYAHSQSLDRLMNPLIDQYLYYLSRTQS-TGGTQGTQQLLFSQAGPANMSAQAKN   477
AAVC.10    VPFHSSYAHSQSLDRLMNPLIDQYLYYLSRTQS-TGGTQGTQQLLFSQAGPANMSAQAKN   476
AAVC.11    VPFHSSYAHSQSLDRLMNPLIDQYLYYLSRTQS-TGGTQGTQQLLFSQAGPANMSAQAKN   477
AAVC.12    VPFHSSYAHSQSLDRLMNPLIDQYLYYLSRTQS-TGGTQGTQQLLFSQAGPANMSAQAKN   477
AAVC.13    VPFHSSYAHSQSLDRLMNPLIDQYLYYLSRTQS-TGGTQGTQQLLFSQAGPANMSAQAKN   477
AAVC.14    VPFHSSYAHSQSLDRLMNPLIDQYLYYLSRTQS-TGGTQGTQQLLFSQAGPANMSAQAKN   478
AAVC.15    VPFHSSYAHSQSLDRLMNPLIDQYLYYLSRTQS-TGGTQGTQQLLFSQAGPANMSAQAKN   477
AAVC.16    VPFHSSYAHSQSLDRLMNPLIDQYLYYLSRTQS-TGGTQGTQQLLFSQAGPANMSAQAKN   477
AAVC.17    VPFHSSYAHSQSLDRLMNPLIDQYLYYLSRTQS-TGGTQGTQQLLFSQAGPANMSAQAKN   477
AAVC.18    VPFHSSYAHSQSLDRLMNPLIDQYLYYLSRTQS-TGGTQGTQQLLFSQAGPANMSAQAKN   477
AAVC.19    VPFHSSYAHSQSLDRLMNPLIDQYLYYLSRTQS-TGGTQGTQQLLFSQAGPANMSAQAKN   477
           **************************** **:.  * :     * * :.. : :  * :*

AAV2       WLPGPCYRQQRVSKTSADNNNSEYSWTGATKYHLNGRDSLVNPGPAMASHKDDEEKFFPQ   536
AAVC.01    WLPGPCYRQQRVSTTLSQNNNSNFAWTGATKYHLNGRNSLVNPGVAMATHKDDEDRFFPS   537
AAVC.02    WLPGPCFRQQRVSKTLDQNNNSNFAWTGATKYHLNGRNSLVNPGVAMATHKDDEDRFFPS   538
AAVC.03    WLPGPCYRQQRVSKTKTDNNNSNFTWTGASKYNLNGRESIINPGTAMASHKDDEDKFFPM   538
AAVC.04    WLPGPCYRQQRVSTTLSQNNNSNFAWTGATKYHLNGRNSLVNPGVAMATHKDDEDRFFPS   536
AAVC.05    WLPGPCYRQQRVSTTLSQNNNSNFAWTGATKYHLNGRNSLVNPGVAMATHKDDEDRFFPS   537
AAVC.06    WLPGPCYRQQRVSTTLSQNNNSNFAWTGATKYHLNGRNSLVNPGVAMATHKDDEDRFFPS   537
AAVC.07    WLPGPCYRQQRVSTTLSQNNNSNFAWTGATKYHLNGRNSLVNPGVAMATHKDDEDRFFPS   536
AAVC.08    WLPGPCYRQQRVSTTLSQNNNSNFAWTGATKYHLNGRNSLVNPGVAMATHKDDEDRFFPS   537
AAVC.09    WLPGPCYRQQRVSTTLSQNNNSNFAWTGATKYHLNGRNSLVNPGVAMATHKDDEDRFFPS   537
AAVC.10    WLPGPCYRQQRVSTTLSQNNNSNFAWTGATKYHLNGRNSLVNPGVAMATHKDDEDRFFPS   536
AAVC.11    WLPGPCYRQQRVSTTLSQNNNSNFAWTGATKYHLNGRNSLVNPGVAMATHKDDEDRFFPS   537
AAVC.12    WLPGPCYRQQRVSTTLSQNNNSNFAWTGATKYHLNGRNSLVNPGVAMATHKDDEDRFFPS   537
AAVC.13    WLPGPCFRQQRVSKTLDQNNNSNFAWTGATKYHLNGRNSLVNPGVAMATHKDDEDRFFPS   537
AAVC.14    WLPGPCYRQQRVSTTLSQNNNSNFAWTGATKYHLNGRNSLVNPGVAMATHKDDEDRFFPS   538
AAVC.15    WLPGPCYRQQRVSTTLSQNNNSNFAWTGATKYHLNGRNSLVNPGVAMATHKDDEDRFFPS   537
AAVC.16    WLPGPCYRQQRVSTTLSQNNNSNFAWTGATKYHLNGRNSLVNPGVAMATHKDDEDRFFPS   537
AAVC.17    WLPGPCYRQQRVSTTLSQNNNSNFAWTGATKYHLNGRNSLVNPGVAMATHKDDEDRFFPS   537
AAVC.18    WLPGPCYRQQRVSTTLSQNNNSNFAWTGATKYHLNGRNSLVNPGVAMATHKDDEDRFFPS   537
AAVC.19    WLPGPCYRQQRVSTTLSQNNNSNFAWTGATKYHLNGRNSLVNPGVAMATHKDDEDRFFPS   537
           ******:******.*   :****:::****:**:****:*::*** ***:*****::***
```

Figure 1 (continued)

```
AAV2      SGVLIFGKQGSEKTNVDIEKVMITDEEEIRTTNPVATEQYGSVSTNLQRGNRQAATADVN  596
AAVC.01   SGVLIFGKTGAT-NKTTLENVLMTNEEEIRPTNPVATEEYGIVSSNLQAANTAAQTQVVN  596
AAVC.02   SGVLIFGKTGAT-NKTTLENVLMTNEEEIRPTNPVATEEYGIVSSNLQAANTAAQTQVVN  597
AAVC.03   SGVMIFGKESAGASNTALDNVMITDEEEIKATNPVATERFGTVAVNFQSSSTDPATGDVH  598
AAVC.04   SGVLIFGKTGAT-NKTTLENVLMTNEEEIRPTNPVATEEYGIVSSNLQAANTAAQTQVVN  595
AAVC.05   SGVLIFGKTGAT-NKTTLENVLMTNEEEIRPTNPVATEEYGIVSSNLQAANTAAQTQVVN  596
AAVC.06   SGVLIFGKTGAT-NKTTLENVLMTNEEEIRPTNPVATEEYGIVSSNLQAANTAAQTQVVN  596
AAVC.07   SGVLIFGKTGAT-NKTTLENVLMTNEEEIRPTNPVATEEYGIVSSNLQAANTAAQTQVVN  595
AAVC.08   SGVLIFGKTGAT-NKTTLENVLMTNEEEIRPTNPVATEEYGIVSSNLQAANTAAQTQVVN  596
AAVC.09   SGVLIFGKTGAT-NKTTLENVLMTNEEEIRPTNPVATEEYGIVSSNLQAANTAAQTQVVN  596
AAVC.10   SGVLIFGKTGAT-NKTTLENVLMTNEEEIRPTNPVATEEYGIVSSNLQAANTAAQTQVVN  595
AAVC.11   SGVLIFGKTGAT-NKTTLENVLMTNEEEIRPTNPVATEEYGIVSSNLQAANTAAQTQVVN  596
AAVC.12   SGVLIFGKTGAT-NKTTLENVLMTNEEEIRPTNPVATEEYGIVSSNLQAANTAAQTQVVN  596
AAVC.13   SGVLIFGKTGAT-NKTTLENVLMTNEEEIRPTNPVATEEYGIVSSNLQAANTAAQTQVVN  596
AAVC.14   SGVLIFGKTGAT-NKTTLENVLMTNEEEIRPTNPVATEEYGIVSSNLQAANTAAQTQVVN  597
AAVC.15   SGVLIFGKTGAT-NKTTLENVLMTNEEEIRPTNPVATEEYGIVSSNLQAANTAAQTQVVN  596
AAVC.16   SGVLIFGKTGAT-NKTTLENVLMTNEEEIRPTNPVATEEYGIVSSNLQAANTAAQTQVVN  596
AAVC.17   SGVLIFGKTGAT-NKTTLENVLMTNEEEIRPTNPVATEEYGIVSSNLQAANTAAQTQVVN  596
AAVC.18   SGVLIFGKTGAT-NKTTLENVLMTNEEEIRPTNPVATEEYGIVSSNLQAANTAAQTQVVN  596
AAVC.19   SGVLIFGKTGAT-NKTTLENVLMTNEEEIRPTNPVATEEYGIVSSNLQAANTAAQTQVVN  596
          ***:**** .:  .:. :::*::*:****: *******.:* *: *:* ..    *  *:
```

```
AAV2      TQGVLPGMVWQDRDVYLQGPIWAKIPHTDGHFHPSPLMGGFGLKHPPPQILIKNTPVPAN  656
AAVC.01   NQGALPGMVWQNRDVYLQGPIWAKIPHTDGNFHPSPLMGGFGLKHPPPQILIKNTPVPAD  656
AAVC.02   NQGALPGMVWQNRDVYLQGPIWAKIPHTDGNFHPSPLMGGFGLKHPPPQILIKNTPVPAN  657
AAVC.03   VMGALPGMVWQDRDVYLQGPIWAKIPHTDGHFHPSPLMGGFGLKHPPPQILIKNTPVPAD  658
AAVC.04   NQGALPGMVWQNRDVYLQGPIWAKIPHTDGNFHPSPLMGGFGLKHPPPQILIKNTPVPAN  655
AAVC.05   NQGALPGMVWQNRDVYLQGPIWAKIPHTDGNFHPSPLMGGFGLKHPPPQILIKNTPVPAN  656
AAVC.06   NQGALPGMVWQNRDVYLQGPIWAKIPHTDGNFHPSPLMGGFGLKHPPPQILIKNTPVPAN  656
AAVC.07   NQGALPGMVWQNRDVYLQGPIWAKIPHTDGNFHPSPLMGGFGLKHPPPQILIKNTPVPAN  655
AAVC.08   NQGALPGMVWQNRDVYLQGPIWAKIPHTDGNFHPSPLMGGFGLKHPPPQILIKNTPVPAN  656
AAVC.09   NQGALPGMVWQNRDVYLQGPIWAKIPHTDGNFHPSPLMGGFGLKHPPPQILIKNTPVPAD  656
AAVC.10   NQGALPGMVWQNRDVYLQGPIWAKIPHTDGNFHPSPLMGGFGLKHPPPQILIKNTPVPAD  655
AAVC.11   NQGALPGMVWQNRDVYLQGPIWAKIPHTDGHFHPSPLMGGFGLKNPPPQILIKNTPVPAN  656
AAVC.12   NQGALPGMVWQNRDVYLQGPIWAKIPHTDGNFHPSPLMGGFGLKHPPPQILIKNTPVPAN  656
AAVC.13   NQGALPGMVWQNRDVYLQGPIWAKIPHTDGNFHPSPLMGGFGLKHPPPQILIKNTPVPAN  656
AAVC.14   NQGALPGMVWQNRDVYLQGPIWAKIPHTDGNFHPSPLMGGFGLKHPPPQILIKNTPVPAN  657
AAVC.15   NQGALPGMVWQNRDVYLQGPIWAKIPHTDGHFHPSPLMGGFGLKNPPPQILIKNTPVPAN  656
AAVC.16   NQGALPGMVWQNRDVYLQGPIWAKIPHTDGNFHPSPLMGGFGLKHPPPQILIKNTPVPAD  656
AAVC.17   NQGALPGMVWQNRDVYLQGPIWAKIPHTDGNFHPSPLMGGFGLKHPPPQILIKNTPVPAN  656
AAVC.18   NQGALPGMVWQNRDVYLQGPIWAKIPHTDGNFHPSPLMGGFGLKHPPPQILIKNTPVPAN  656
AAVC.19   NQGALPGMVWQNRDVYLQGPIWAKIPHTDGNFHPSPLMGGFGLKHPPPQILIKNTPVPAN  656
            *.*******:******************:*************:**************:
```

```
AAV2      PSTTFSAAKFASFITQYSTGQVSVEIEWELQKENSKRWNPEIQYTSNYNKSVNVDFTVDT  716
AAVC.01   PPTTFSQAKLASFITQYSTGQVSVEIEWELQKENSKRWNPEVQYTSNYAKSANVDFTVDN  716
AAVC.02   PPAEFSATKFASFITQYSTGQVSVEIEWELQKENSKRWNPEVQYTSNYAKSANVDFTVDN  717
AAVC.03   PPTTFSQAKLASFITQYSTGQVSVEIEWELQKENSKRWNPEVQYTSNYAKSANVDFTVDN  718
AAVC.04   PPEVFTPAKFASFITQYSTGQVSVEIEWELQKENSKRWNPEIQYTSNYNKSVSVDFTVDT  715
AAVC.05   PPEVFTPAKFASFITQYSTGQVSVEIEWELQKENSKRWNPEIQYTSNYNKSVSVDFTVDT  716
AAVC.06   PPEVFTPAKFASFITQYSTGQVSVEIEWELQKENSKRWNPEIQYTSNYNKSVSVDFTVDT  716
AAVC.07   PPEVFTPAKFASFITQYSTGQVSVEIEWELQKENSKRWNPEIQYTSNYNKSVSVDFTVDT  715
AAVC.08   PPAEFSATKFASFITQYSTGQVSVEIEWELQKENSKRWNPEVQYTSNYAKSANVDFTVDN  716
AAVC.09   PPTTFSQAKLASFITQYSTGQVSVEIEWELQKENSKRWNPEVQYTSNYAKSANVDFTVDN  716
AAVC.10   PPTTFSQAKLASFITQYSTGQVSVEIEWELQKENSKRWNPEVQYTSNYAKSANVDFTVDN  715
AAVC.11   PPAEFSATKFASFITQYSTGQVSVEIEWELQKENSKRWNPEVQYTSNYAKSANVDFTVDN  716
AAVC.12   PPEVFTPAKFASFITQYSTGQVSVEIEWELQKENSKRWNPEIQYTSNYNKSVSVDFTVDT  716
AAVC.13   PPEVFTPAKFASFITQYSTGQVSVEIEWELQKENSKRWNPEIQYTSNYNKSVSVDFTVDT  716
AAVC.14   PPAEFSATKFASFITQYSTGQVSVEIEWELQKENSKRWNPEVQYTSNYAKSANVDFTVDN  717
AAVC.15   PPAEFSATKFASFITQYSTGQVSVEIEWELQKENSKRWNPEVQYTSNYAKSANVDFTVDN  716
AAVC.16   PPTTFSQAKLASFITQYSTGQVSVEIEWELQKENSKRWNPEVQYTSNYAKSANVDFTVDN  716
AAVC.17   PPEVFTPAKFASFITQYSTGQVSVEIEWELQKENSKRWNPEIQYTSNYNKSVSVDFTVDT  716
AAVC.18   PPEVFTPAKFASFITQYSTGQVSVEIEWELQKENSKRWNPEIQYTSNYNKSVSVDFTVDT  716
AAVC.19   PPEVFTPAKFASFITQYSTGQVSVEIEWELQKENSKRWNPEIQYTSNYNKSVSVDFTVDT  716
          *   *: :*:*******************************:****** **..******.
```

Figure 1 (continued)

```
AAV2        NGVYSEPRPIGTRYLTRNL  735
AAVC.01     NGLYTEPRPIGTRYLTRPL  735
AAVC.02     NGLYTEPRPIGTRYLTRPL  736
AAVC.03     NGLYTEPRPIGTRYLTRPL  737
AAVC.04     NGVYSEPRPIGTRYLTRNL  734
AAVC.05     NGVYSEPRPIGTRYLTRNL  735
AAVC.06     NGVYSEPRPIGTRYLTRNL  735
AAVC.07     NGVYSEPRPIGTRYLTRNL  734
AAVC.08     NGLYTEPRPIGTRYLTRPL  735
AAVC.09     NGLYTEPRPIGTRYLTRPL  735
AAVC.10     NGLYTEPRPIGTRYLTRNL  734
AAVC.11     NGLYTEPRPIGTRYLTRPL  735
AAVC.12     NGVYSEPRPIGTRYLTRNL  735
AAVC.13     NGVYSEPRPIGTRYLTRNL  735
AAVC.14     NGLYTEPRPIGTRYLTRPL  736
AAVC.15     NGLYTEPRPIGTRYLTRPL  735
AAVC.16     NGLYTEPRPIGTRYLTRPL  735
AAVC.17     NGVYSEPRPIGTRYLTRNL  735
AAVC.18     NGVYSEPRPIGTRYLTRNL  735
AAVC.19     NGVYSEPRPIGTRYLTRNL  735
            **:*:************ *
```

Figure 4
A
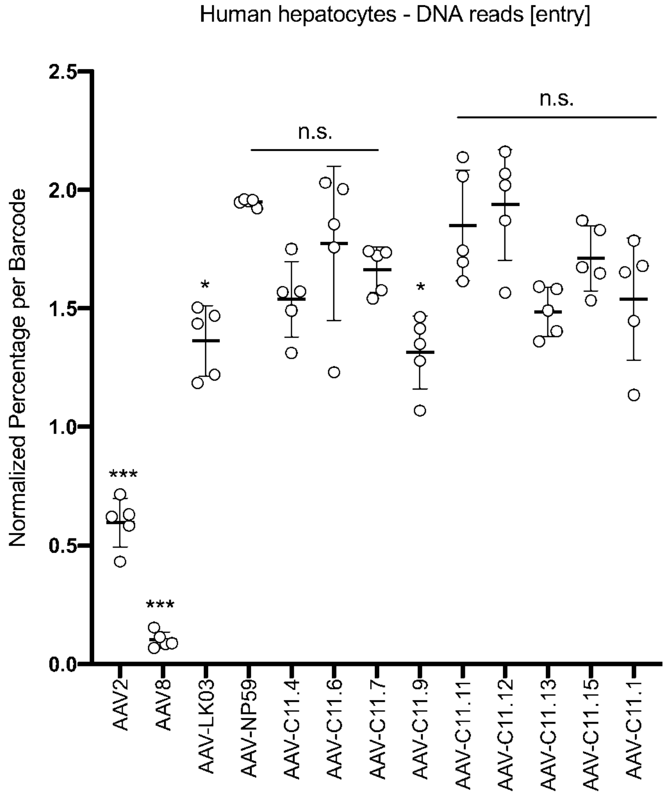
B
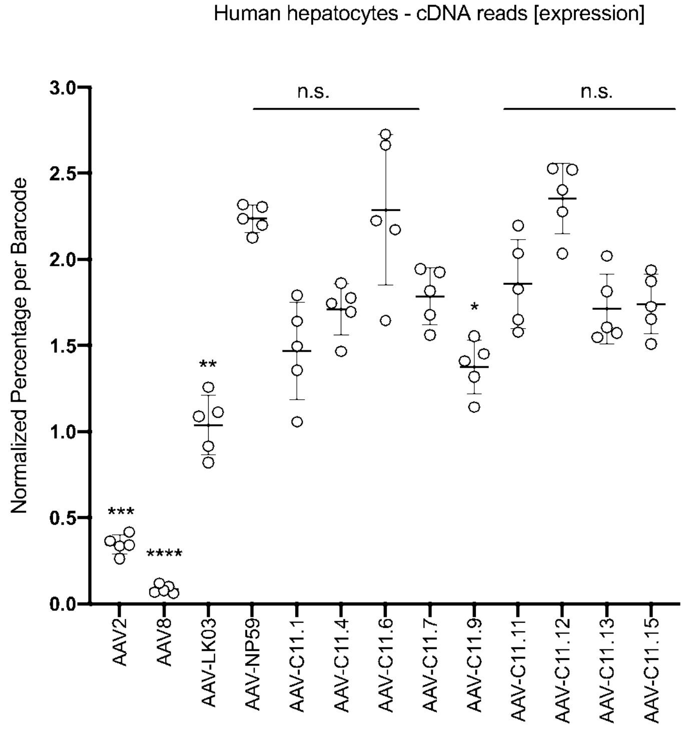

Figure 4 (continued)
C
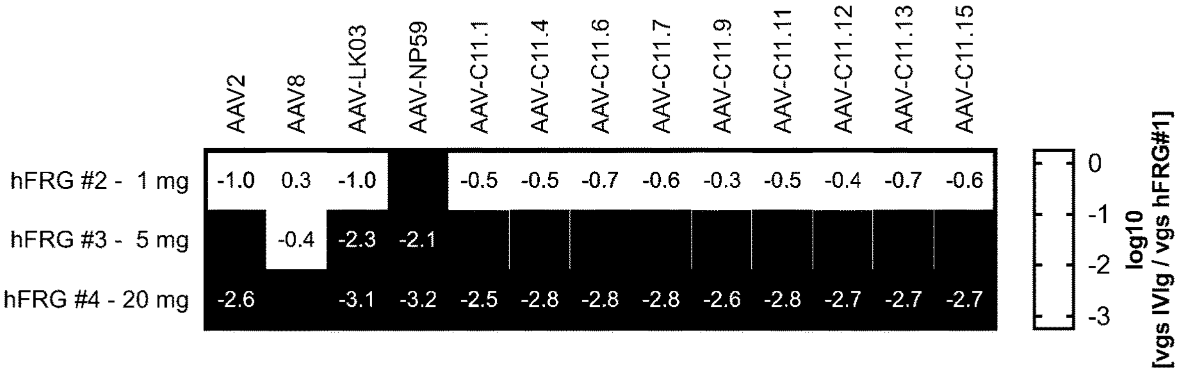
D
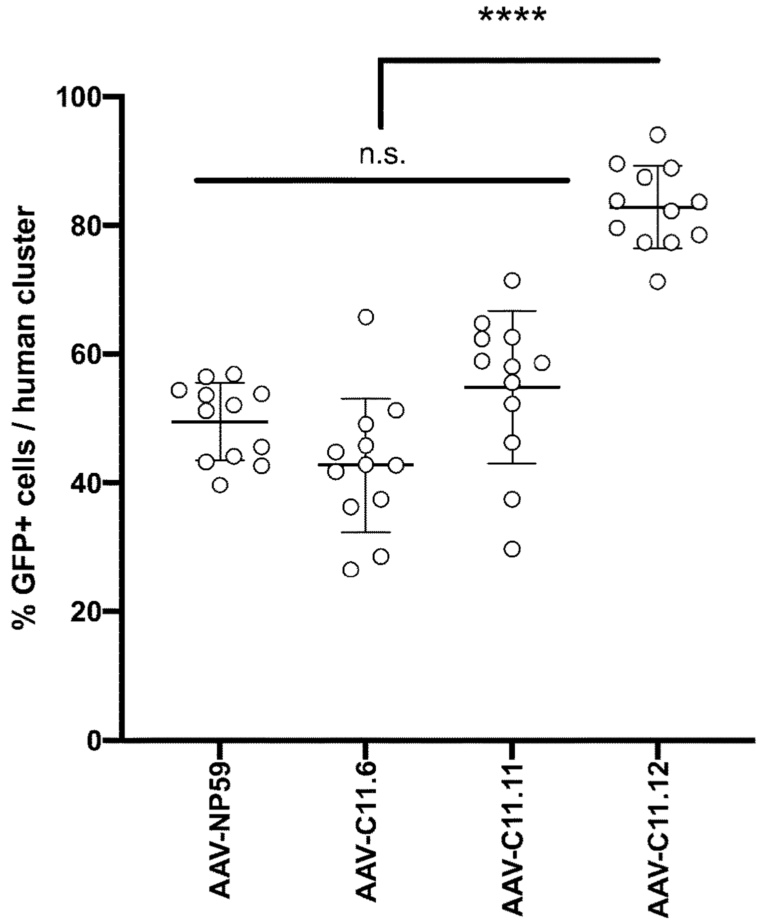

Figure 5 (continued)
E
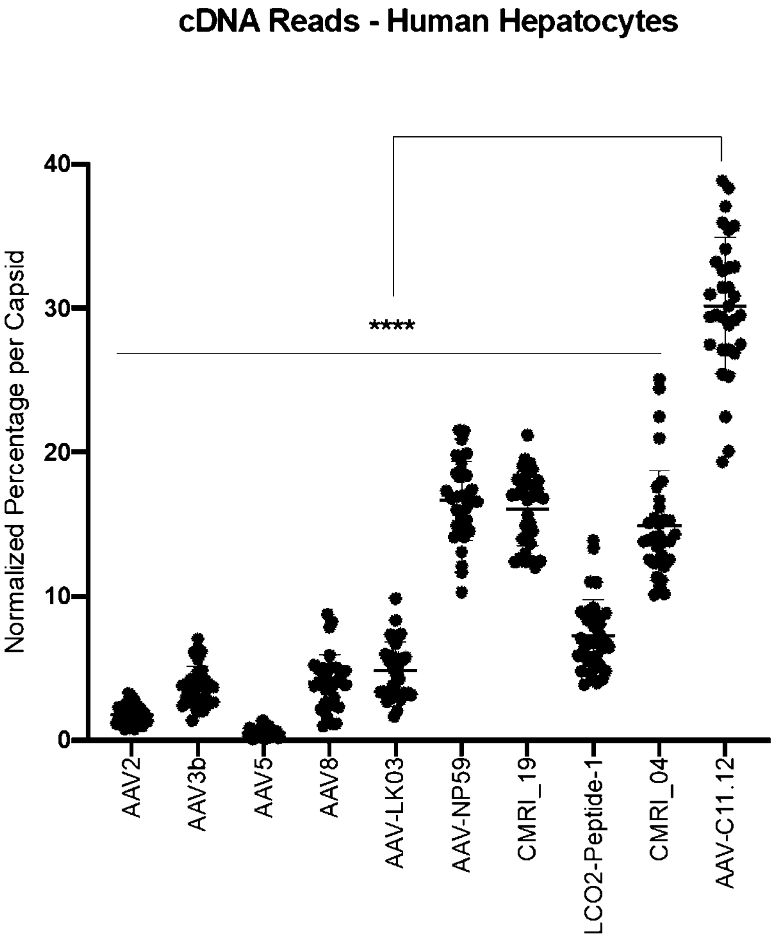
F
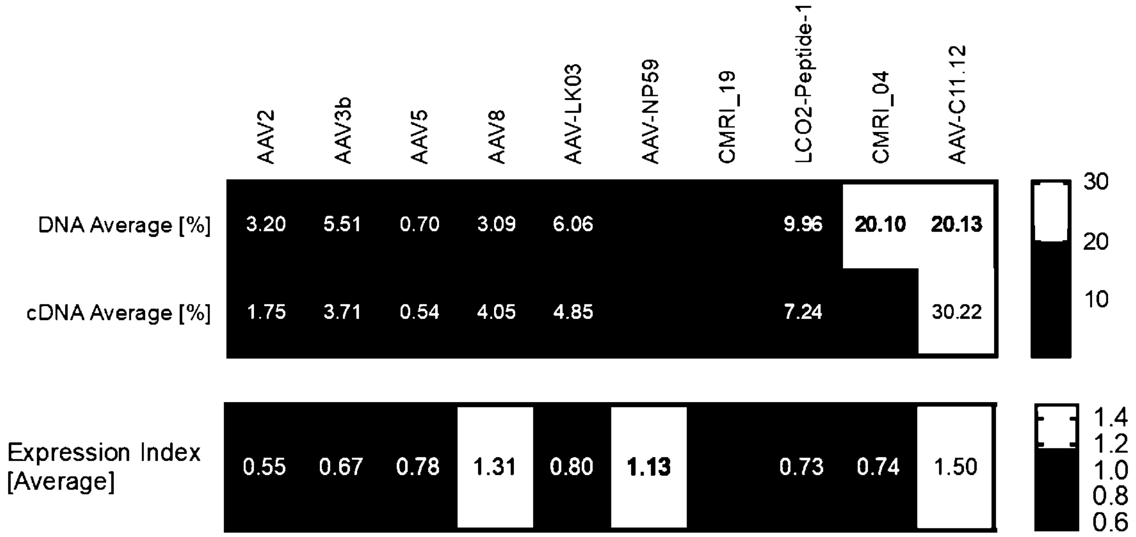

Figure 8
A
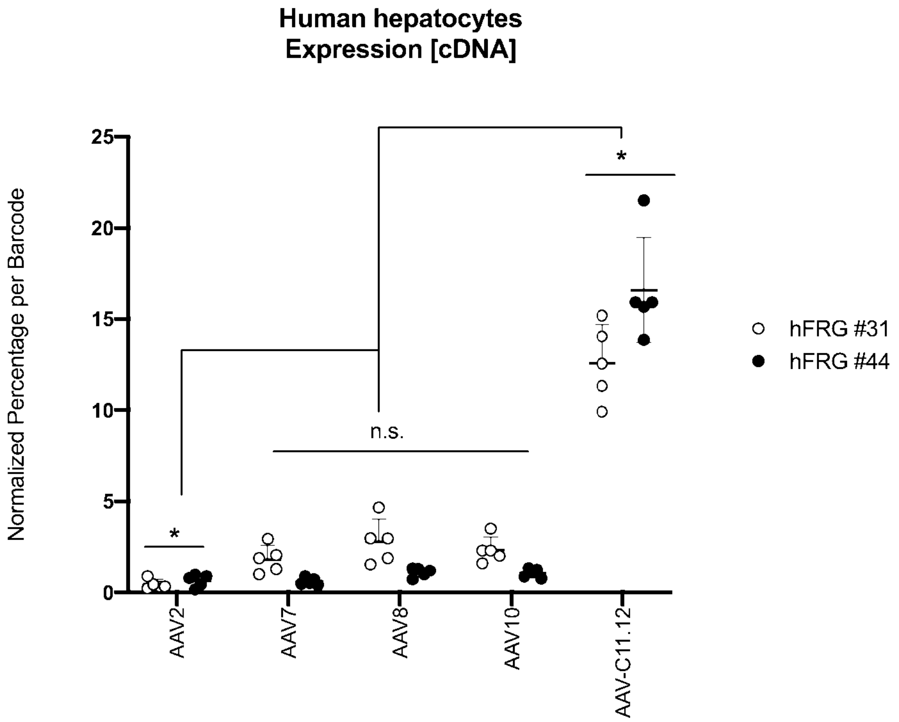
B
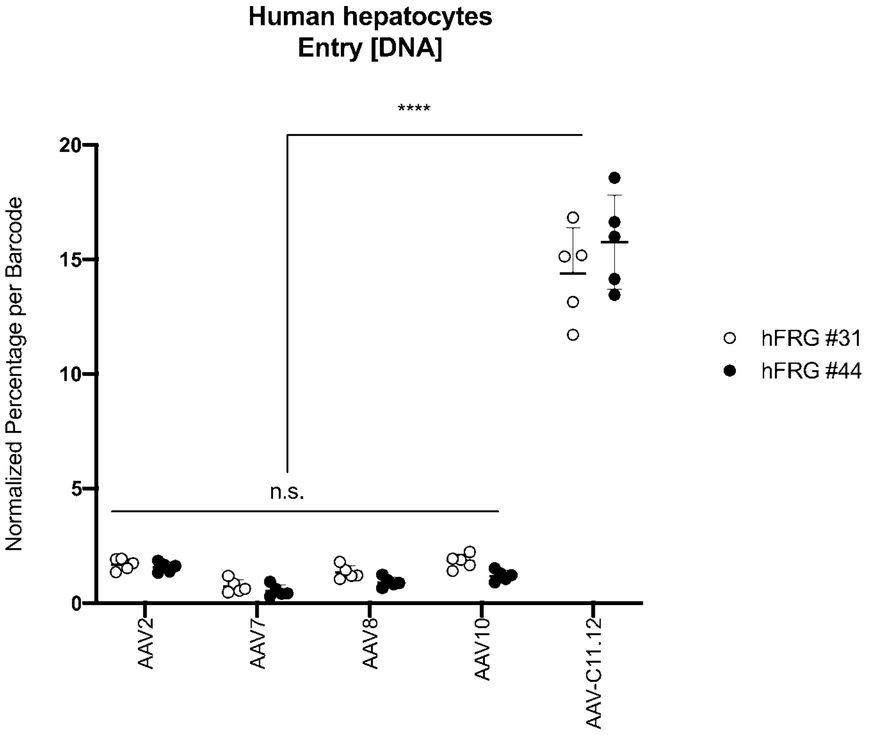

Figure 8 (continued)
C
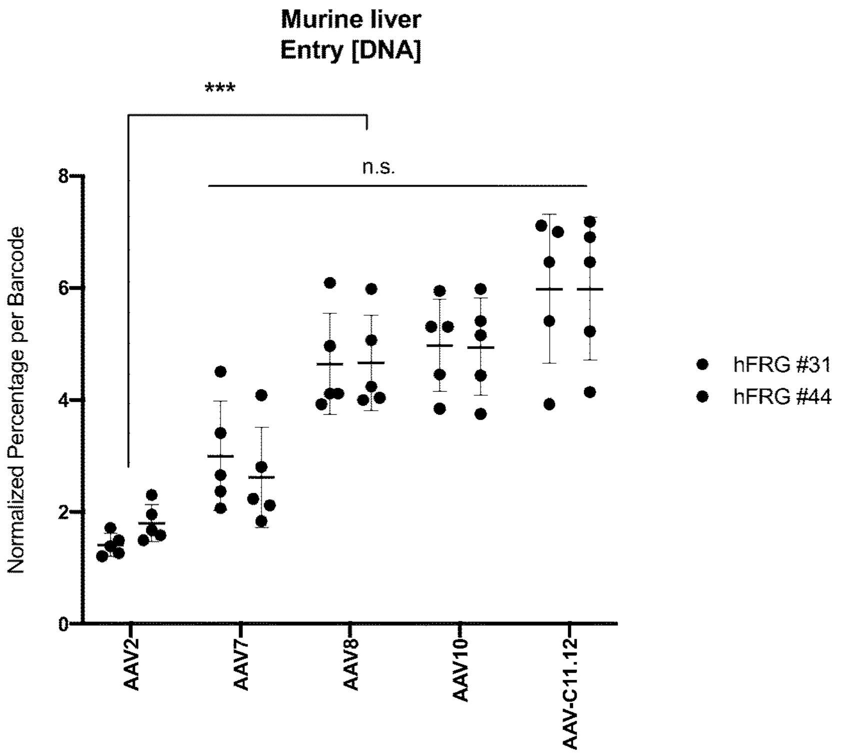
D
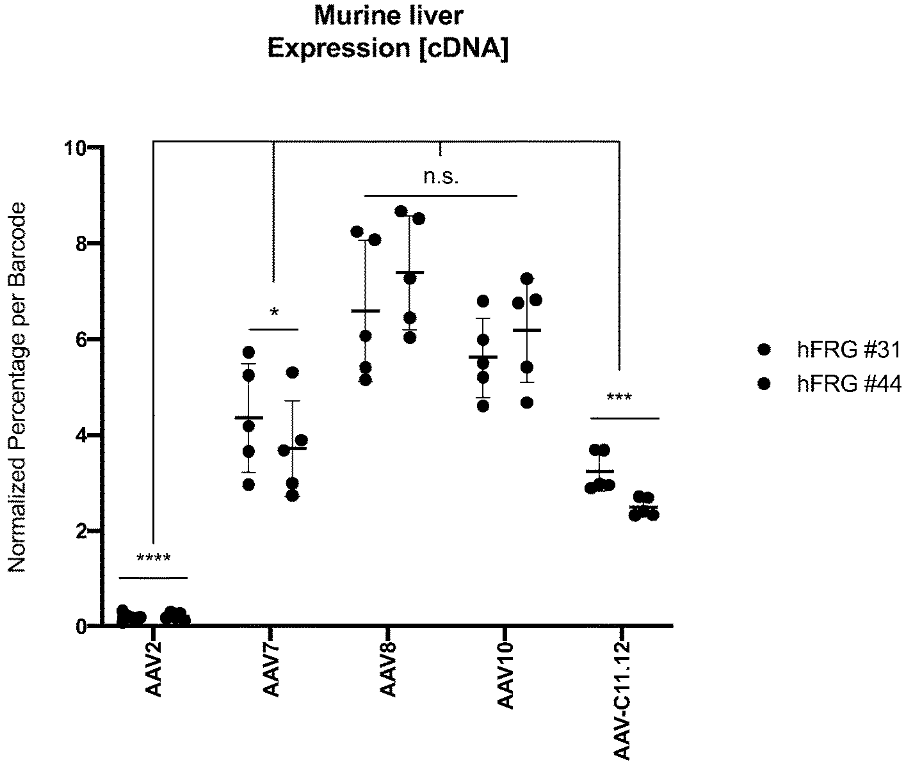

Figure 10

```
AAV8      1 MAADGYLPDWLEDNLSEGIREWWALKPGAPKPKANQQKQDDGRGLVLPGY   50
            |||||||||||||.||||||||||||||||:||||||.||:|||||||||
C11.12    1 MAADGYLPDWLEDTLSEGIREWWALKPGAPQPKANQQHQDNGRGLVLPGY   50

AAV8     51 KYLGPFNGLDKGEPVNAADAAALEHDKAYDQQLQAGDNPYLRYNHADAEF  100
            |||||||||||||||.|||||||||||||:||:.||||||:|||||||||
C11.12   51 KYLGPFNGLDKGEPVNEADAAALEHDKAYDKQLEQGDNPYLKYNHADAEF  100

AAV8    101 QERLQEDTSFGGNLGRAVFQAKKRVLEPLGLVEEGAKTAPGKKRPVEPSP  150
            |||||||||||||||||||||||||:|||||||||.||||||||||||||
C11.12  101 QERLQEDTSFGGNLGRAVFQAKKRILEPLGLVEEAAKTAPGKKRPVEPSP  150

AAV8    151 QRSPDSSTGIGKKGQQPARKRLNFGQTGDSESVPDPQPLGEPPAAPSGVG  200
            |||||||||||||||||||||||||||||||||||||||||||||||.||
C11.12  151 QRSPDSSTGIGKKGQQPARKRLNFGQTGDSESVPDPQPLGEPPAAPSSVG  200

AAV8    201 PNTMAAGGGAPMADNNEGADGVGSSSGNWHCDSTWLGDRVITTSTRTWAL  250
            ..|:|||||||||||||||||||::|||||||||||||||||||||||||
C11.12  201 SGTVAAGGGAPMADNNEGADGVGNASGNWHCDSTWLGDRVITTSTRTWAL  250

                       VR-I
AAV8    251 PTYNNHLYKQISNGTSGGATNDNTYFGYSTPWGYFDFNRFHCHFSPRDWQ  300
            ||||||||||||  :..||:|||.||||||||||||||||||||||||||
C11.12  251 PTYNNHLYKQIS--SQSGASNDNHYFGYSTPWGYFDFNRFHCHFSPRDWQ  298

AAV8    301 RLINNNWGFRPKRLSFKLFNIQVKEVTQNEGTKTIANNLTSTIQVFTDSE  350
            |||||||||||||||||||||||||||.|:|..|||||||||:|||:|||
C11.12  299 RLINNNWGFRPKRLSFKLFNIQVKEVTTNDGVTTIANNLTSTVQVFSDSE  348

AAV8    351 YQLPYVLGSAHQGCLPPFPADVFMIPQYGYLTLNNGSQAVGRSSFYCLEY  400
            ||||||||||||||||||||||||||||||||||||||||||||||||||
C11.12  349 YQLPYVLGSAHQGCLPPFPADVFMIPQYGYLTLNNGSQAVGRSSFYCLEY  398

AAV8    401 FPSQMLRTGNNFQFTYTFEDVPFHSSYAHSQSLDRLMNPLIDQYLYYLSR  450
            ||||||||||||:|:|||||||||||||||||||||||||||||||||||
C11.12  399 FPSQMLRTGNNFEFSYTFEDVPFHSSYAHSQSLDRLMNPLIDQYLYYLSR  448

                  VR-IV                                VR-V
AAV8    451 TQTTGGTANTQTLGFSQGGPNTMANQAKNWLPGPCYRQQRVSTTTGQNNN  500
            ||:||||..||.|.|||.||..|:.||||||||||||||||||||..|||
C11.12  449 TQSTGGTQGTQQLLFSQAGPANMSAQAKNWLPGPCYRQQRVSTTLSQNNN  498

                                           VR-VI         VR-VII
AAV8    501 SNFAWTAGTKYHLNGRNSLANPGIAMATHKDDEERFFPSNGILIFGKQNA  550
            ||||||..|||||||||||.|||:|||||||||:|||||:|:||||| .|
C11.12  499 SNFAWTGATKYHLNGRNSLVNPGVAMATHKDDEDRFFPSSGVLIFGKTGA  548

                                             VR-VIII
AAV8    551 ARDNADYSDVMLTSEEEIKTTNPVATEEYGIVADNLQQQNTAPQIGTVNS  600
             .:.....:|::|:||||:.||||||||||||:.|||..|||.|...||:
C11.12  549 T-NKTTLENVLMTNEEEIRPTNPVATEEYGIVSSNLQAANTAAQTQVVNN  597

AAV8    601 QGALPGMVWQNRDVYLQGPIWAKIPHTDGNFHPSPLMGGFGLKHPPPQIL  650
            ||||||||||||||||||||||||||||||||||||||||||||||||||
C11.12  598 QGALPGMVWQNRDVYLQGPIWAKIPHTDGNFHPSPLMGGFGLKHPPPQIL  647

AAV8    651 IKNTPVPADPPTTFNQSKLNSFITQYSTGQVSVEIEWELQKENSKRWNPE  700
            ||||||||:||..|..:|..||||||||||||||||||||||||||||||
C11.12  648 IKNTPVPANPPEVFTPAKFASFITQYSTGQVSVEIEWELQKENSKRWNPE  697

AAV8    701 IQYTSNYYKSTSVDFAVNTEGVYSEPRPIGTRYLTRNL     738 (SEQ ID NO:64)
            |||||||.||.||||.|:|.||||||||||||||||||
C11.12  698 IQYTSNYNKSVSVDFTVDTNGVYSEPRPIGTRYLTRNL     735 (SEQ ID NO:13)
```

ADENO-ASSOCIATED VIRUS CAPSID POLYPEPTIDES AND VECTORS

RELATED APPLICATIONS

This application is a U.S. National Phase Application of PCT International Application Number PCT/AU2021/050158, filed on Feb. 25, 2021, designating the United States of America and published in the English language, which is an International Application of and claims the benefit of priority to Australian Patent Application No. 2020900529, filed on Feb. 25, 2020. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52 (e). The name of the ASCII text file for the Sequence Listing is SeqList-DAVI586-002APC.txt, the date of creation of the ASCII text file is Aug. 22, 2022, and the size of the ASCII text file is 322 KB.

FIELD OF THE DISCLOSURE

The present disclosure relates generally to adeno-associated virus (AAV) capsid polypeptides and encoding nucleic acid molecules. The disclosure also relates to AAV vectors comprising the capsid polypeptides, and nucleic acid vectors (e.g. plasmids) comprising the encoding nucleic acids molecules, as well as to host cells comprising the vectors. The disclosure also relates to methods and uses of the polypeptides, encoding nucleic acids molecules, vectors and host cells.

BACKGROUND OF THE DISCLOSURE

Gene therapy has most commonly been investigated and achieved using viral vectors, with notable recent advances being based on adeno-associated viral vectors. Adeno-associated virus (AAV) is a replication-deficient parvovirus, the single-stranded DNA genome of which is about 4.7 kb in length. The AAV genome includes inverted terminal repeat (ITRs) at both ends of the molecule, flanking two open reading frames: rep and cap. The cap gene encodes three structural capsid proteins: VP1, VP2 and VP3. The three capsid proteins typically assemble in a ratio of 1:1:8-10 to form the AAV capsid, although AAV capsids containing only VP3, or VP1 and VP3, or VP2 and VP3, have been produced. The cap gene also encodes the assembly activating protein (AAP) from an alternative open reading frame. AAP promotes capsid assembly, acting to target the capsid proteins to the nucleolus and promote capsid formation. The rep gene encodes four known regulatory proteins: Rep78, Rep68, Rep52 and Rep40. These Rep proteins are involved in AAV genome replication, packaging, genomic integration and other processes. More recently, an X gene has been identified in the 3' end of the AAV2 genome (Cao et al. PLoS One, 2014, 9:e104596). The encoded X protein appears to be involved in the AAV life cycle, including DNA replication.

The ITRs are involved in several functions, in particular integration of the AAV DNA into the host cell genome, as well as genome replication and packaging. When AAV infects a host cell, the viral genome can integrate into the host's chromosomal DNA resulting in latent infection of the cell. Thus, AAV can be exploited to introduce heterologous sequences into cells. In nature, a helper virus (for example, adenovirus or herpesvirus) provides protein factors that allow for replication of AAV virus in the infected cell and packaging of new virions. In the case of adenovirus, genes E1A, E16, E2A, E4 and VA provide helper functions. Upon infection with a helper virus, the AAV provirus is rescued and amplified, and both AAV and the helper virus are produced.

AAV vectors (also referred to as recombinant AAV, rAAV) that contain a genome that lacks some, most or all of the native AAV genome and instead contain one or more heterologous sequences flanked by the ITRs, have been successfully used in gene therapy settings. These AAV vectors are widely used to deliver heterologous nucleic acid to cells of a subject for therapeutic purposes, and in many instances, it is the expression of the heterologous nucleic acid that imparts the therapeutic effect. Although several AAV vectors have now been used in the clinic, there are a limited number that exhibit the required in vivo transduction efficiency of primary human cells/tissues to facilitate adequate expression of the heterologous nucleic acid for therapeutic applications. There is therefore a need to develop alternative AAV vectors that contain capsid proteins that facilitate efficient transduction of host cells in vivo.

SUMMARY OF THE DISCLOSURE

The present disclosure is predicated in part on the generation of novel AAV capsid polypeptides. In particular embodiments, the capsid polypeptides facilitate efficient transduction of human cells (such as human hepatocytes) when contained in an AAV vector. Typically, the in vivo transduction of AAV vectors comprising a capsid polypeptide of the present disclosure is improved compared to AAV vectors comprising other AAV capsid polypeptides (e.g. the prototypic AAV2 capsid set forth in SEQ ID NO:1). The capsids polypeptides of the present disclosure are therefore particularly useful in preparing AAV vectors, and in particular, AAV vectors for gene therapy uses. Similarly, AAV vectors comprising a capsid polypeptide of the present disclosure (i.e. having a capsid comprising or consisting of a capsid polypeptide of the present disclosure) are of particular use in gene therapy applications, such as for delivery of heterologous nucleic acids for the treatment of various diseases and conditions.

In one aspect, the disclosure provides a capsid polypeptide, comprising: (i) the sequence of amino acids set forth in any one of SEQ ID Nos:2-20 and 65-79 or a sequence having at least or about 90% or 95% sequence identity thereto; (ii) the sequence of amino acids at positions 138-735 of any one of SEQ ID NOs:2, 6, 7, 9, 10, 12-14, 16-20, 69, 71-74, 76 and 78, positions 138-734 of SEQ ID NO:5, 8 or 11, positions 138-736 of any one of SEQ ID NOs:3, 15, 65, 68, 75, 77 and 79, positions 138-737 of any one of SEQ ID NOs:4, 67 and 70, or positions 138-738 of SEQ ID NO:66; or a sequence having at least or about 90% or 95% sequence identity thereto; and/or (iii) the sequence of amino acids at positions 203-734 of any one of SEQ ID NOs:5, 8 and 11, positions 203-736 of SEQ ID NO:15, positions 204-735 of any one of SEQ ID NOs:2, 6, 7, 9, 10, 12-14, 16-20, 69, 71-74, 76 and 78, positions 204-736 of any one of SEQ ID NOs:3, 65, 68, 75, 77 and 79, positions 204-737 of any one of SEQ ID NOs: 4, 67 and 70, or positions 204-738 of SEQ ID NO:66; or a sequence having at least or about 90% or 95% sequence identity thereto.

In one embodiment, the capsid polypeptide comprises (i) the sequence of amino acids set forth in SEQ ID NO:13 or a sequence having at least or about 90%, 95%, 96%, 97%, 98% or 99% sequence identity thereto; (ii) the sequence of amino acids at positions 138-735 of SEQ ID NO:13 or a sequence having at least or about 90%, 95%, 96%, 97%, 98% or 99% sequence identity thereto; and/or (iii) the sequence of amino acids at positions 204-735 of SEQ ID NO:13 or a sequence having at least or about 90%, 95%, 96%, 97%, 98% or 99% sequence identity thereto.

In a particular examples, the capsid polypeptide comprises one or more of: a) amino acid residues S263, Q264, S265, S268 and H272, with numbering relative to SEQ ID NO:13; b) amino acid residues T546, G547, T549, N550, K551, T552, T553, L554, E555, N556, L558, M559, N561, R566 and P567, with numbering relative to SEQ ID NO:13; c) amino acid residues S580, S581, A585, A586, A590, T592, Q593, V594, and N597, with numbering relative to SEQ ID NO: 13; d) amino acid residues D532, S538 and V540, with numbering relative to SEQ ID NO:13; e) amino acid residues S451, Q456, G457, Q460, L462, A466, A469, N470, S472 and A473, with numbering relative to SEQ ID NO: 13; f) amino acid residues L493, S494, G505, A506, V518 and V522, with numbering relative to SEQ ID NO:13; g) the sequence of amino acids SQSGASNDNH (SEQ ID NO:58) at positions 263-272, with numbering relative to SEQ ID NO:13; h) the sequence of amino acids TGATNKTTLENVLMTNEEEIRP (SEQ ID NO:59) at positions 546-567, with numbering relative to SEQ ID NO:13; i) the sequence of amino acids SSNLQAANTAAQTQVVNN (SEQ ID NO:60) at positions 580-597, with numbering relative to SEQ ID NO:13; j) the sequence of amino acids DRFFPSSGV (SEQ ID NO:61) at positions 532-540, with numbering relative to SEQ ID NO:13; k) the sequence of amino acids STGGTQGTQQLLFSQAGPANMSA (SEQ ID NO:62) at positions 451-473, with numbering relative to SEQ ID NO:13; and/or 1) the sequence of amino acids LSQNNNSNFAWTGATKYHLNGRNSLVNPGV (SEQ ID NO:63) at positions 493-522, with numbering relative to SEQ ID NO:13.

Another aspect of the disclosure relates to a capsid polypeptide, comprising: (i) the sequence of amino acids set forth in SEQ ID NO:13 or a sequence having at least or about 85% sequence identity thereto; (ii) the sequence of amino acids at positions 138-735 of SEQ ID NO:13 or a sequence having at least or about 85% sequence identity thereto; and/or (iii) the sequence of amino acids at positions 204-735 of SEQ ID NO:13 or a sequence having at least or about 85% sequence identity thereto; wherein the capsid polypeptide comprises: a) amino acid residues S263, Q264, S265, S268 and H272, with numbering relative to SEQ ID NO:13; and b) amino acid residues T546, G547, T549, N550, K551, T552, T553, L554, E555, N556, L558, M559, N561, R566 and P567, with numbering relative to SEQ ID NO:13; and/or amino acid residues S580, S581, A585, A586, A590, T592, Q593, V594, and N597, with numbering relative to SEQ ID NO:13.

In some embodiments, the capsid polypeptide comprises a) the sequence of amino acids SQSGASNDNH (SEQ ID NO:58) at positions 263-272, with numbering relative to SEQ ID NO: 13; and b) the sequence of amino acids TGATNKTTLENVLMTNEEEIRP (SEQ ID NO:59) at positions 546-567, with numbering relative to SEQ ID NO:13 and/or the sequence of amino acids SSNLQAANTAAQTQVVNN (SEQ ID NO:60) at positions 580-597, with numbering relative to SEQ ID NO:13. In further embodiments, the capsid polypeptide comprises a) the sequence of amino acids ISSQSGASNDNH (SEQ ID NO:80) at positions 261-272, with numbering relative to SEQ ID NO:13; and b) the sequence of amino acids KTGATNKTTLENVLMTNEEEIRP (SEQ ID NO:81) at positions 545-567, with numbering relative to SEQ ID NO:13 and/or the sequence of amino acids SSNLQAANTAAQTQVVNN (SEQ ID NO:60) at positions 580-597, with numbering relative to SEQ ID NO:13.

The capsid polypeptide may comprise amino acid residues D532, S538 and V540, with numbering relative to SEQ ID NO:13. In some embodiments, the capsid polypeptide comprises the sequence of amino acids DRFFPSSGV (SEQ ID NO:61) at positions 532-540, with numbering relative to SEQ ID NO:13. In further embodiments, the capsid polypeptide comprises the sequence of amino acids AMATHKDDEDRFFPSSGV (SEQ ID NO:82) at positions 523-540, with numbering relative to SEQ ID NO:13.

In some examples, the capsid polypeptide comprises amino acid residues S451, Q456, G457, Q460, L462, A466, A469, N470, S472 and A473, with numbering relative to SEQ ID NO:13. In one embodiment, the capsid polypeptide comprises the sequence of amino acids STGGTQGTQQLLFSQAGPANMSA (SEQ ID NO:62) at positions 451-473, with numbering relative to SEQ ID NO:13. In further embodiments, the capsid polypeptide comprises the sequence of amino acids QSTGGTQGTQQLLFSQAGPANMSA (SEQ ID NO:83) at positions 450-473, with numbering relative to SEQ ID NO:13.

In further examples, the capsid polypeptide comprises amino acid residues L493, S494, G505, A506, V518 and V522, with numbering relative to SEQ ID NO:13. In some embodiments, the capsid polypeptide comprises the sequence of amino acids LSQNNNSNFAWTGATKYHLNGRNSLVNPGV (SEQ ID NO:63) at positions 493-522, with numbering relative to SEQ ID NO:13. In further embodiments, the capsid polypeptide comprises the sequence of amino acids RVSTTLSQNNNSNFAWTGATKYHLNGRNSLVNPGV (SEQ ID NO:84) at positions 488-522, with numbering relative to SEQ ID NO:13.

In another aspect, the disclosure provides a capsid polypeptide, comprising: (i) the sequence of amino acids set forth in SEQ ID NO:13 or a sequence having at least or about 85% sequence identity thereto; (ii) the sequence of amino acids at positions 138-735 of SEQ ID NO:13 or a sequence having at least or about 85% sequence identity thereto; and/or (iii) the sequence of amino acids at positions 204-735 of SEQ ID NO:13 or a sequence having at least or about 85% sequence identity thereto; wherein the capsid polypeptide comprises amino acid residues S451, Q456, G457, Q460, L462, A466, A469, N470, S472, A473, L493, S494, G505, A506, V518 V522, D532, S538 V540, T546, G547, T549, N550, K551, T552, T553, L554, E555, N556, L558, M559, N561, R566, P567, S580, S581, A585, A586, A590, T592, Q593, V594, and N597, with numbering relative to SEQ ID NO:13.

In some embodiments, the capsid polypeptide comprises the sequence of amino acids STGGTQGTQQLLFSQAGPANMSA (SEQ ID NO:62) at positions 451-473; the sequence of amino acids LSQNNNSNFAWTGATKYHLNGRNSLVNPGV (SEQ ID NO:63) at positions 493-522; the sequence of amino acids DRFFPSSGV (SEQ ID NO:61) at positions 532-540; the sequence of amino acids TGATNKTTLENVLMTNEEEIRP (SEQ ID NO:59) at positions 546-567; and the sequence of amino acids SSNLQAANTAAQTQVVNN (SEQ ID NO:60) at positions 580-597, with numbering relative to SEQ ID NO:13. In further embodiments, the capsid polypeptide comprises the sequence of amino acids QSTGGTQGTQQLLFSQAGPANMSA (SEQ ID NO: 83) at positions 450-473; the sequence of amino acids RVSTTLSQNNNSNFAWTGATKYHLNGRNSLVNPGV (SEQ ID NO:84) at positions 488-522; the sequence of amino acids AMATHKDDEDRFFPSSGV (SEQ ID NO:82) at positions 523-540; the sequence of amino acids KTGATNKTTLENVLMTNEEEIRP (SEQ ID NO:81) at positions 545-567, with numbering relative to SEQ ID NO:13; and the sequence of amino acids SSNLQAANTAAQTQVVNN (SEQ ID NO:60) at positions 580-597, with numbering relative to SEQ ID NO:13. In one example, the capsid polypeptide further comprises a) an insertion of NG after position 262 and residues T263, S264, G265, T268, and T272, with numbering relative to SEQ ID NO:13; or b) an insertion of NG after position 262 and the sequence of amino acids TSGGATNDNT at positions 263-272, with numbering relative to SEQ ID NO:13.

In one embodiment, the capsid polypeptide comprises at least or about 86%, 87%, 88%, 89%, 90%, 91%, 92%, 93%, 94%, 95%, 96% or 97% sequence identity to the sequence of amino acids set forth in SEQ ID NO:13, the sequence of amino acids at positions 138-735 of SEQ ID NO:13, or the sequence of amino acids at positions 204-735 of SEQ ID NO:13.

In another aspect, the disclosure provides an AAV vector, comprising a capsid polypeptide described herein.

In some examples, the vector exhibits increased in vivo transduction efficiency compared to an AAV vector comprising a capsid polypeptide comprising the sequence of amino acids set forth in SEQ ID NO:1. In particular examples, the vector exhibits increased in vivo transduction efficiency of human hepatocytes compared to an AAV vector comprising a capsid polypeptide comprising the sequence of amino acids set forth in SEQ ID NO:1. In one embodiment, transduction efficiency is increased by at least or about 10%, 20%, 30%, 40%, 50%, 60%, 70%, 80%, 90%, 100%, 200%, 300%, 400% or 500%.

In further examples, the AAV vector exhibits increased resistance to neutralization by pooled human immunoglobulins compared to an AAV vector comprising a capsid polypeptide comprising the sequence of amino acids set forth in SEQ ID NO:1. In one embodiment, resistance to neutralization is increased by at least or about 10%, 20%, 30%, 40%, 50%, 60%, 70%, 80%, 90%, 100%, 200%, 300%, 400% or 500%.

The AAV vector of the present disclosure may further include a heterologous coding sequence, such as one that encodes a peptide, polypeptide or polynucleotide. In some examples, the peptide, polypeptide or polynucleotide is a therapeutic peptide, polypeptide or polynucleotide.

In further aspects, provided is an isolated nucleic acid molecule encoding a capsid polypeptide described herein, and a vector comprising the nucleic acid molecule. In some examples, the vector is selected from among a plasmid, cosmid, phage and transposon. A host cell comprising an AAV vector, a nucleic acid molecule or a vector described above and herein is also provided.

Also provided is a method for introducing a heterologous coding sequence into a host cell, comprising contacting a host cell with an AAV vector of the present disclosure that comprises a heterologous coding sequence. In some examples, the host cell is a hepatocyte. In some embodiments of the method, contacting a host cell with the AAV vector comprises administering the AAV vector to a subject. In other embodiments, the method is in vitro or ex vivo.

In another aspect, provided is a method for producing an AAV vector, comprising culturing a host cell comprising a nucleic acid molecule encoding a capsid polypeptide of the present disclosure, an AAV rep gene, a heterologous coding sequence flanked by AAV inverted terminal repeats, and helper functions for generating a productive AAV infection, under conditions suitable to facilitate assembly of an AAV vector comprising a capsid comprising the capsid polypeptide, wherein the capsid encapsidates the heterologous coding sequence. In some examples, the host cell is a hepatocyte.

In a further aspect, provided is a method for enhancing the in vivo human hepatocyte transduction efficiency of an AAV vector, comprising:

a) identifying a reference capsid polypeptide for transducing human hepatocytes in vivo;
b) modifying the sequence of the reference capsid polypeptide at one or more of positions 263, 264, 265, 268, 272, 546, 547, 549, 550, 551, 552, 553, 554, 555, 556, 558, 559, 561, 566, 567, 580, 581, 585, 586, 590, 592, 593, 594 and 597, with numbering relative to SEQ ID NO:13, to thereby produce a modified capsid polypeptide that comprises: i) amino acid residues S263, Q264, S265, S268 and H272, with numbering relative to SEQ ID NO:13; and ii) amino acid residues T546, G547, T549, N550, K551, T552, T553, L554, E555, N556, L558, M559, N561, R566 and P567, with numbering relative to SEQ ID NO:13; and/or amino acid residues S580, S581, A585, A586, A590, T592, Q593, V594, and N597, with numbering relative to SEQ ID NO:13; and
c) vectorising the modified capsid polypeptide to thereby produce a modified AAV vector.

In some embodiments, the method further comprises modifying the sequence of the reference capsid polypeptide at one or more of positions 532, 538 and 540, with numbering relative to SEQ ID NO:13, wherein the modified capsid polypeptide comprises amino acid residues D532, S538 and V540, with numbering relative to SEQ ID NO:13. In further embodiments, the method further comprises modifying the sequence of the reference capsid polypeptide at one or more of positions 451, 456, 457, 460, 462, 466, 469, 470, 472 and 473, with numbering relative to SEQ ID NO:13, wherein the modified capsid polypeptide comprises amino acid residues S451, Q456, G457, Q460, L462, A466, A469, N470, S472 and A473, with numbering relative to SEQ ID NO:13. In other embodiments, the method further comprises modifying the sequence of the reference capsid polypeptide at one or more of positions 493, 494, 505, 506, 518 and 522, with numbering relative to SEQ ID NO:13, wherein the modified capsid polypeptide comprises amino acid residues L493, S494, G505, A506, V518 and V522, with numbering relative to SEQ ID NO:13.

In another aspect, provided is a method for enhancing the in vivo human hepatocyte transduction efficiency of an AAV vector, comprising:

a) identifying a reference capsid polypeptide for transducing human hepatocytes in vivo;
b) modifying the sequence of the reference capsid polypeptide at one or more of positions 263-272, 546-567 and 580-597 with numbering relative to SEQ ID NO: 13, to thereby produce a modified capsid polypeptide that comprises: i) the sequence of amino acids SQSGASNDNH (SEQ ID NO:58) at positions 263-272, with numbering relative to SEQ ID NO:13; and ii) the sequence of amino acids TGATNKTTLENVLMTNEEEIRP (SEQ ID NO:59) at positions 546-567, with numbering relative to SEQ ID NO:13 and/or the sequence of amino acids SSNLQAANTAAQTQVVNN (SEQ ID NO:60) at positions 580-597, with numbering relative to SEQ ID NO:13; and c) vectorising the modified capsid polypeptide to thereby produce a modified AAV vector.

In some embodiments, the method further comprises modifying the sequence of the reference capsid polypeptide at one or more of positions at positions 532-540, with numbering relative to SEQ ID NO:13, wherein the modified capsid polypeptide comprises the sequence of amino acids DRFFPSSGV (SEQ ID NO:61) at positions 532-540, with numbering relative to SEQ ID NO:13. In further embodiments, the method further comprises modifying the sequence of the reference capsid polypeptide at one or more of positions 451-473, with numbering relative to SEQ ID NO:13, wherein the modified capsid polypeptide comprises the sequence of amino acids STGGTQGTQQLLFSQAGPANMSA (SEQ ID NO:62) at positions 451-473, with numbering relative to SEQ ID NO:1. In other embodiments, the method further comprises modifying the sequence of the reference capsid polypeptide at one or more of positions 493-522, with numbering relative to SEQ ID NO:13, wherein the modified capsid polypeptide comprises the sequence of amino acids LSQNNNSNFAWTGATKYHLNGRNSLVNPGV (SEQ ID NO:63) at positions 493-522, with numbering relative to SEQ ID NO:13.

In some examples of the methods for enhancing the in vivo human hepatocyte transduction efficiency of an AAV vector, the reference capsid polypeptide comprises at least or about 85%, 86%, 87%, 88%, 89%, 90%, 91%, 92%, 93%, 94%, 95%, 96%, 97%, 98%, or 99% sequence identity to the sequence set forth in SEQ ID NO:13. In particular embodiments, the methods further comprise assessing the transduction efficiency of the modified AAV vector in vivo system that utilises human hepatocytes (e.g. an in vivo system that comprises a small animal (e.g. a mouse) with a chimeric liver comprising human hepatocytes, such as the hFRG mouse model. In particular examples, the modified AAV vector produced by the methods has an in vivo transduction efficiency that is enhanced by at least or about 10%, 20%, 30%, 40%, 50%, 60%, 70%, 80%, 90%, 100%, 150%, 200%, 300% or more compared to a reference AAV vector comprising the reference capsid polypeptide.

BRIEF DESCRIPTION OF THE DRAWINGS

Embodiments of the disclosure are described herein, by way of non-limiting example only, with reference to the following drawings.

FIG. 1 is an alignment of AAV capsid polypeptides.

FIG. 4 provides graphical representations of the transduction efficiency of AAV vectors in vivo in the presence of IVIg. Three hFRG mice were passively immunized with injections of 1, 5 mg or 20 mg of soluble IVIg, followed by injection with a mix of barcoded AAVC11.01, AAVC11.04, AAVC11.07, AAVC11.09, AAVC11.11-AAVC11.13 and AAVC11.15 vectors and assorted controls. A fourth hFRG mouse that did not receive IVIg injection (the hFRG mouse from FIG. 3) was used as control. DNA and RNA was extracted and NGS performed on the DNA and cDNA. (A) Percentage of NGS reads mapped to each barcode in human hepatocytes at the DNA level (cell entry, physical transduction) in control mouse (i.e. no IVIg). (B) Percentage of NGS reads mapped to each barcode in human hepatocytes at the cDNA level (expression, functional transduction) in control mouse. (C) Estimated reduction in vector genomes per AAV capsid in the presence of IVIg. Values express the logarithm of the quotient between vector genomes of the IVIg conditions (hFRGs #2-4) and the no-IVIG control (hFRG #1). (D) Quantification of the percentage of transduced human hepatocytes per human cluster, n=10 clusters/mouse. (A-B: Data are mean±SD. Statistical significance among means was calculated using the Kruskal-Wallis test, and Dunnett's multiple comparison test was used to compare AAV variants with control AAV-NP59 (*P≤0.05, P≤0.01, *P≤0.001, **P≤0.0001, n.s. P value>0.05). (D: Data are mean±SD. Statistical significance among means was calculated using one-way ANOVA, and Dunnett's multiple comparison test was used to compare AAV-SYDs with the control AAV-NP59 (** P≤0.0001, n.s. P value>0.05).

FIG. 8 provides graphical representations of the transduction efficiency of AAV vectors in vivo. A barcoded NGS comparison of AAVC11.12 with parental AAV2, AAV7, and AAV10 using two humanised FRG mice (hFRG #31 and hFRG #44) was performed. Percentage of NGS reads mapped to each barcode in human and murine hepatocytes at the DNA (cell entry, physical transduction) and cDNA (expression, functional transduction) level, normalized to the pre-injection mix, is shown. (A) Human hepatocyte entry (DNA). (B) Human hepatocyte expression (cDNA). (C) Mouse hepatocyte entry (DNA). (D) Mouse hepatocyte expression (cDNA). Data for hFRG #31 are on the left and data for hFRG #44 are on the right of each entry for each mouse on the graph. Data are mean±SD. Statistical significance among means was calculated using the Kruskal-Wallis test, and Dunnett's multiple comparison test was used to compare AAV-SYD12 and parental AAV variants with control AAV8 (*P≤0.01, P≤0.01, *P≤0.001, ****P≤0.0001, n.s. P value>0.05).

FIG. 10 is an alignment of the sequences of the AAV8 and AAVC11.12 capsid polypeptides. Variable region (VR)-I, VR-IV, VR-V, VR-VI, VR-VII and VR-III are shown, with residues making up those regions bolded and in italics in the AAV8 polypeptide. Residues from AAVC11.12 that were used to replace the corresponding residue in AAV8 are underlined, and the region spanning the first and last replacement for each variable region is shaded in grey.

DETAILED DESCRIPTION

Figure 2:
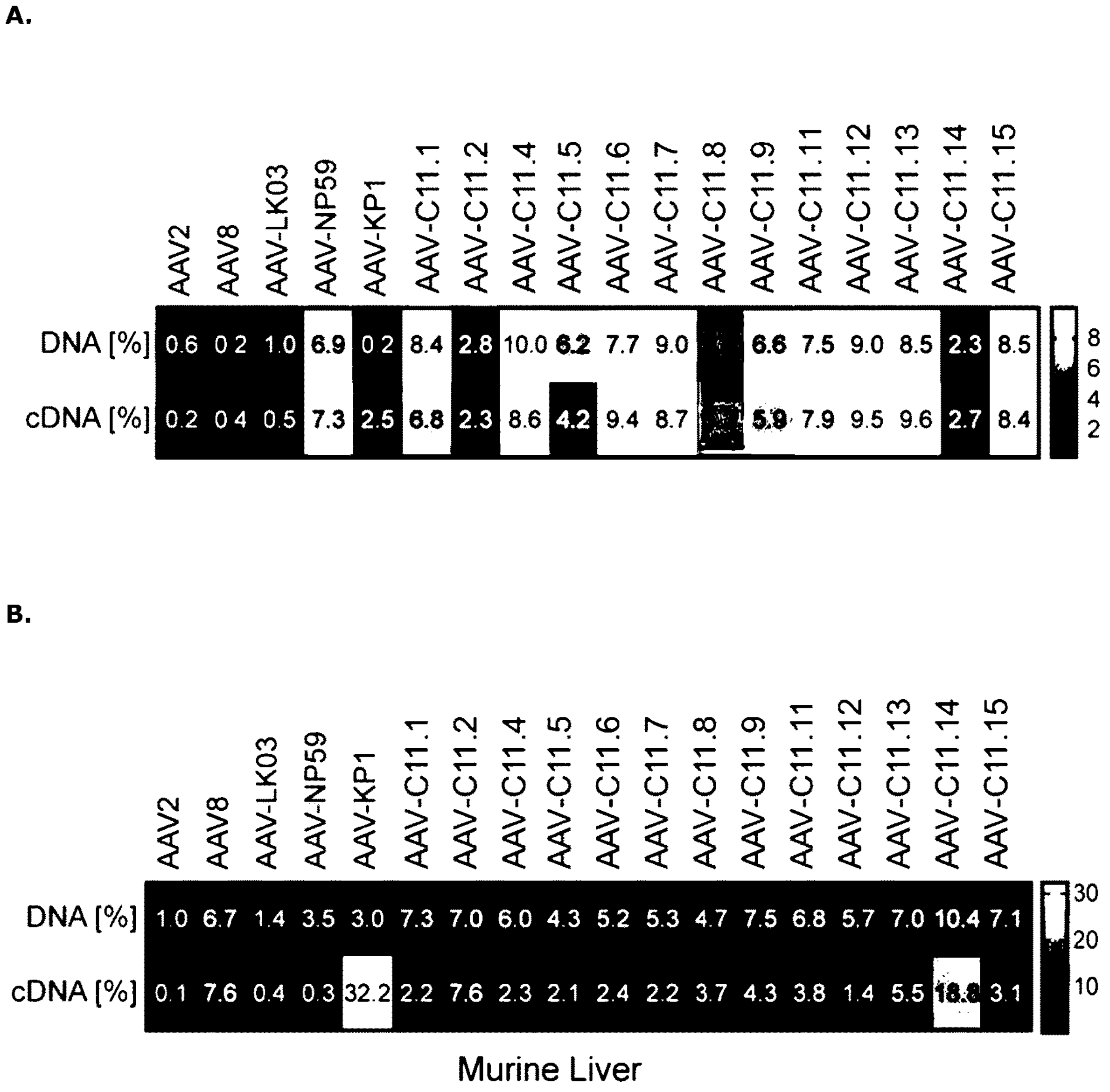
FIG. 2 is a representation of the in vivo performance of various AAV vectors. A humanised $Fah^{-/-}/Rag2^{-/-}/Il2rg^{-/-}$ (hFRG) mouse harbouring human primary and mouse primary hepatocytes in the liver was injected with $1.8\times10^{11}$ vg of each of the barcoded AAV vectors. Prototypic AAV2 and AAV8 vectors, as well as bioengineered LK03 and NP59 vectors, were also injected. One week after injection the chimeric liver of the mouse was perfused and human and murine hepatocytes were separated using cell sorting. DNA and RNA were recovered from the human population of hepatocytes and Illumina Next Generation Sequencing (NGS) of the barcoded transgene in each of the AAV vectors was performed. The number of NGS reads specific for the barcodes, and thus each vector, at the DNA and RNA (cDNA) levels were then quantified, and expressed as a proportion of the total reads. The DNA reads were also normalised to the preinjection mix, which was also quantified using NGS of the same barcode region. (A) DNA from human hepatocytes, normalised to pre-injection reads. (B) cDNA from human hepatocytes. (C) DNA from mouse hepatocytes, normalised to pre-injection reads. (D) cDNA from mouse hepatocytes.

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it is understood that such identifiers can change and particular information on the internet can come and go, but equivalent information can be found by searching the internet. Reference to the identifier evidences the availability and public dissemination of such information.

As used herein, the singular forms "a", "an" and "the" also include plural aspects (i.e. at least one or more than one) unless the context clearly dictates otherwise. Thus, for example, reference to "a polypeptide" includes a single polypeptide, as well as two or more polypeptides.

In the context of this specification, the term "about," is understood to refer to a range of numbers that a person of skill in the art would consider equivalent to the recited value in the context of achieving the same function or result.

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "vector" includes reference to both polynucleotide vectors and viral vectors, each of which are capable of delivering a transgene contained within the vector into a host cell. Vectors can be episomal, i.e., do not integrate into the genome of a host cell, or can integrate into the host cell genome. The vectors may also be replication competent or replication deficient. Exemplary polynucleotide vectors include, but are not limited to, plasmids, cosmids and transposons. Exemplary viral vectors include, for example, AAV, lentiviral, retroviral, adenoviral, herpes viral and hepatitis viral vectors.

As used herein, "adeno-associated viral vector" or "AAV vector" refers to a vector in which the capsid is derived from an adeno-associated virus, including without limitation, AAV1, AAV2, AAV3, AAV4, AAV5, AAV6, AAV7, AAV8, AAV9, AAV10, AAV11, AAV12 or AAV13, AAV from other clades or isolates, or is derived from synthetic, bioengineered or modified AAV capsid proteins, including chimeric capsid proteins. In particular embodiments, the AAV vector has a capsid comprising a capsid polypeptide of the present disclosure. When referring to AAV vectors, both the source of the genome and the source of the capsid can be identified, where the source of the genome is the first number designated and the source of the capsid is the second number designated. Thus, for example, a vector in which both the capsid and genome are derived from AAV2 is more accurately referred to as AAV2/2. A vector with an AAV6-derived capsid and an AAV2-derived genome is most accurately referred to as AAV2/6. A vector with the bioengineered DJ capsid and an AAV2-derived genome is most accurately referred to as AAV2/DJ. For simplicity, and because most vectors use an AAV2-derived genome, it is understood that reference to an AAV6 vector generally refers to an AAV2/6 vector, reference to an AAV2 vector generally refers to an AAV2/2 vector, etc. An AAV vector may also be referred to herein as "recombinant AAV", "rAAV", "recombinant AAV virion", "rAAV virion", "AAV variant", "recombinant AAV variant", and "rAAV variant" terms which are used interchangeably and refer to a replication-defective virus that includes an AAV capsid shell encapsidating an AAV genome. The AAV vector genome (also referred to as vector genome, recombinant AAV genome or rAAV genome) comprises a transgene flanked on both sides by functional AAV ITRs. Typically, one or more of the wild-type AAV genes have been deleted from the genome in whole or part, preferably the rep and/or cap genes. Functional ITR sequences are necessary for the rescue, replication and packaging of the vector genome into the rAAV virion.

The term "ITR" refers to an inverted terminal repeat at either end of the AAV genome. This sequence can form hairpin structures and is involved in AAV DNA replication and rescue, or excision, from prokaryotic plasmids. ITRs for use in the present disclosure need not be the wild-type nucleotide sequences, and may be altered, e.g., by the insertion, deletion or substitution of nucleotides, as long as the sequences provide for functional rescue, replication and packaging of rAAV.

As used herein, "functional" with reference to a capsid polypeptide means that the polypeptide can self-assemble or assemble with different capsid polypeptides to produce the proteinaceous shell (capsid) of an AAV virion. It is to be understood that not all capsid polypeptides in a given host cell assemble into AAV capsids. Preferably, at least 25%, at least 50%, at least 75%, at least 85%, at least 90%, at least 95% of all AAV capsid polypeptide molecules assemble into AAV capsids. Suitable assays for measuring this biological activity are described e.g. in Smith-Arica and Bartlett (2001), Curr Cardiol Rep 3(1): 43-49.

"AAV helper functions" or "helper functions" refer to functions that allow AAV to be replicated and packaged by a host cell. AAV helper functions can be provided in any of a number of forms, including, but not limited to, as a helper virus or as helper virus genes which aid in AAV replication and packaging. Helper virus genes include, but are not limited to, adenoviral helper genes such as E1A, E1B, E2A, E4 and VA. Helper viruses include, but are not limited to, adenoviruses, herpesviruses, poxviruses such as vaccinia, and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Baculoviruses available from depositories include *Autographa californica* nuclear polyhedrosis virus.

As used herein, the term "transduction" refers to entry of AAV vector into one or more particular cell types and transferal of the DNA contained within the AAV vector into the cell. Transduction can be assessed by measuring the amount of AAV DNA or RNA expressed from the AAV DNA in a cell or population of cells, and/or by assessing the number of cells in a population that contain AAV DNA or RNA expressed from the DNA. Where the presence or amount of RNA is assessed, the type of transduction assessed is referred to herein as "functional transduction", i.e. the ability of the AAV to transfer DNA to the cell and have that DNA expressed. The term "transduction efficiency" and grammatical variations thereof refers to the ability of an AAV vector to transduce host cells, and more particularly the efficiency with which an AAV vector transduces host cells. In particular embodiment, the transduction efficiency is in vivo transduction efficiency, and refers to the ability of an AAV vector to transduce host cells in vivo following administration of the vector to the subject. Transduction efficiency can be assessed in a number of ways known to those in the art, including assessing the number of host cells transduced following exposure to, or administration of, a given number of vector particles (e.g. as assessed by expression of a reporter gene from the vector genome, such as GFP or eGFP, using microscopy or flow cytometry techniques); the amount of vector DNA (e.g. number of vector genomes) in a population of host cells following exposure to a given number of vector particles; the amount of vector RNA in population of host cells following exposure to a given number of vector particles; and the level of protein expression from a reporter gene (e.g. GFP or eGFP) in the vector genome in a population of host cells following exposure to, or administration of, a given number of vector particles. The population of host cells can represent a particular number of host cells, a volume or weight of tissue, or an entire organ (e.g. liver). In vivo transduction efficiency can reflect the ability of an AAV vector to access host cells, such as hepatocytes in the liver; the ability of an AAV vector to enter host cells; and/or expression of a heterologous coding sequence contained in the vector genome upon host cell entry.

As used herein, "corresponding nucleotides", "corresponding amino acid residues" or "corresponding positions" refer to nucleotides, amino acids or positions that occur at aligned loci. The sequences of related or variant polynucleotides or polypeptides are aligned by any method known to those of skill in the art. Such methods typically maximize matches (e.g. identical nucleotides or amino acids at positions), and include methods such as using manual alignments and by using the numerous alignment programs available (for example, BLASTN, BLASTP, ClustlW, ClustlW2, EMBOSS, LALIGN, Kalign, etc) and others known to those of skill in the art. By aligning the sequences of polynucleotides, one skilled in the art can identify corresponding nucleotides. For example, by aligning the prototypic AAV2 capsid polypeptide set forth in SEQ ID NO:1 with another AAV capsid polypeptide (e.g. as shown in FIG. 1), one of skill in the art can identify regions or amino acids residues within the other AAV polypeptide that correspond to various regions or residues in the AAV polypeptide set forth in SEQ ID NO:1. For example, the methionine at position 204 of SEQ ID NO:2 is the corresponding amino acid of, or corresponds to, the methionine at position 203 of SEQ ID NO:1. In another example, and with reference to the alignment of the capsid polypeptides of AAV8 and AAVC11.12 in FIG. 10, position 262 of the serine at position 262 of the AAVC11.12 capsid polypeptide aligns with, or correspond to, position 264 of the AAV8 capsid polypeptide, and the serine at position 262 of the AAVC11.12 capsid polypeptide correspond to, or is the corresponding amino acid of, the threonine at position 264 of the AAV8 capsid polypeptide. Thus, when amino acid residues or positions are referred to herein with respect to a particular capsid polypeptide, it is understood that, where appropriate, the reference is also to the corresponding amino acid residue or position in another capsid polypeptide. For example, reference to a capsid polypeptide comprising "S264 with numbering relative to SEQ ID NO:13" encompasses not only the AAVC11.12 capsid polypeptide set forth in SEQ ID NO:13 having a serine at position 264, but also other capsid polypeptides having a serine at the position that corresponds to position 264 of SEQ ID NO:13. This includes, for example, capsid polypeptides such as the AAV8Swap1 (SEQ ID NO:65) capsid polypeptide, where the position in AAV8Swap1 that corresponds to position 264 of SEQ ID NO:13 is position 264 and is occupied by a serine; and the AAVC11.12 VP3 protein, where the position in the AAVC11.12 VP3 protein that corresponds to position 264 of SEQ ID NO:13 is position 60 (and is of course also occupied by a serine). In another example, reference to a capsid polypeptide comprising "S580 with numbering relative to SEQ ID NO:13" refers to the AAVC11.12 capsid polypeptide set forth in SEQ ID NO:13 having a serine at position 580 and to other capsid polypeptides having a serine at the position that corresponds to position 580 of SEQ ID NO:13, such as the AAV8Swap3 capsid polypeptide (SEQ ID NO:67), where the position in AAV8Swap3 that corresponds to position 580 of SEQ ID NO:13 is position 582 and is occupied by a serine.

A "heterologous coding sequence" as used herein refers to nucleic acid sequence present in a polynucleotide, vector, or host cell that is not naturally found in the polynucleotide, vector, or host cell or is not naturally found at the position that it is at in the polynucleotide, vector, or host cell, i.e. is non-native. A "heterologous coding sequence" can encode a peptide or polypeptide, or a polynucleotide that itself has a function or activity, such as an antisense or inhibitory oligonucleotide, including antisense DNA and RNA (e.g. miRNA, siRNA, and shRNA). In some examples, the heterologous coding sequence is a stretch of nucleic acids that is essentially homologous to a stretch of nucleic acids in the genomic DNA of an animal, such that when the heterologous coding sequence is introduced into a cell of the animal, homologous recombination between the heterologous sequence and the genomic DNA can occur. In one example, the heterologous coding sequence is a functional copy of a gene for introduction into a cell that has a defective/mutated copy.

As used herein, the term "operably-linked" with reference to a promoter and a coding sequence means that the transcription of the coding sequence is under the control of, or driven by, the promoter.

The term "host cell" refers to a cell, such as a mammalian cell, that has introduced into it the exogenous DNA, such as a vector or other polynucleotide. The term includes the progeny of the original cell into which the exogenous DNA has been introduced. Thus, a "host cell" as used herein generally refers to a cell that has been transfected or transduced with exogenous DNA.

As used herein, "isolated" with reference to a polynucleotide or polypeptide means that the polynucleotide or polypeptide is substantially free of cellular material or other contaminating proteins from the cells from which the polynucleotide or polypeptide is derived, or substantially free from chemical precursors or other chemicals when chemically synthesized.

The term "subject" as used herein refers to an animal, in particular a mammal and more particularly a primate including a lower primate and even more particularly, a human who can benefit from the present invention. A subject, regardless of whether a human or non-human animal or embryo, may be referred to as an individual, subject, animal, patient, host or recipient. The present disclosure has both human and veterinary applications. For convenience, an "animal" specifically includes livestock animals such as cattle, horses, sheep, pigs, camelids, goats and donkeys, as well as domestic animals, such as dogs and cats. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. In some embodiments, the subject is human.

As used herein, the term "conservative sequence modifications" or "conservative substitution" refers to amino acid modifications that do not significantly affect or alter the characteristics of a vector containing the amino acid sequence. Such conservative modifications include amino acid substitutions, additions and deletions. Modifications can be introduced into a vector that are compatible with various embodiments by standard techniques known in the art, such as site-directed mutagenesis and PCR-mediated mutagenesis. Conservative amino acid substitutions are ones in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a capsid can be replaced with other amino acid residues from the same side chain family and the altered capsid can be tested for tropism and/or the ability to deliver a payload using the functional assays described herein.

It will be appreciated that the above described terms and associated definitions are used for the purpose of explanation only and are not intended to be limiting.

TABLE 1

| Brief Description of the Sequences | |
|---|---|
| SEQ ID NO. | Description |
| 1 | Prototypic AAV2 capsid polypeptide |
| 2 | AAVC11.01 capsid polypeptide (VP1) |
| 3 | AAVC11.02 capsid polypeptide (VP1) |
| 4 | AAVC11.03 capsid polypeptide (VP1) |
| 5 | AAVC11.04 capsid polypeptide (VP1) |
| 6 | AAVC11.05 capsid polypeptide (VP1) |
| 7 | AAVC11.06 capsid polypeptide (VP1) |
| 8 | AAVC11.07 capsid polypeptide (VP1) |
| 9 | AAVC11.08 capsid polypeptide (VP1) |
| 10 | AAVC11.09 capsid polypeptide (VP1) |
| 11 | AAVC11.10 capsid polypeptide (VP1) |
| 12 | AAVC11.11 capsid polypeptide (VP1) |
| 13 | AAVC11.12 capsid polypeptide (VP1) |
| 14 | AAVC11.13 capsid polypeptide (VP1) |
| 15 | AAVC11.14 capsid polypeptide (VP1) |
| 16 | AAVC11.15 capsid polypeptide (VP1) |
| 17 | AAVC11.16 capsid polypeptide (VP1) |
| 18 | AAVC11.17 capsid polypeptide (VP1) |
| 19 | AAVC11.18 capsid polypeptide (VP1) |
| 20 | AAVC11.19 capsid polypeptide (VP1) |
| 21 | AAVC11.01 capsid polynucleotide |
| 22 | AAVC11.02 capsid polynucleotide |
| 23 | AAVC11.03 capsid polynucleotide |
| 24 | AAVC11.04 capsid polynucleotide |
| 25 | AAVC11.05 capsid polynucleotide |
| 26 | AAVC11.06 capsid polynucleotide |
| 27 | AAVC11.07 capsid polynucleotide |
| 28 | AAVC11.08 capsid polynucleotide |
| 29 | AAVC11.09 capsid polynucleotide |
| 30 | AAVC11.10 capsid polynucleotide |
| 31 | AAVC11.11 capsid polynucleotide |
| 32 | AAVC11.12 capsid polynucleotide |
| 33 | AAVC11.13 capsid polynucleotide |
| 34 | AAVC11.14 capsid polynucleotide |
| 35 | AAVC11.15 capsid polynucleotide |
| 36 | AAVC11.16 capsid polynucleotide |
| 37 | AAVC11.17 capsid polynucleotide |
| 38 | AAVC11.18 capsid polynucleotide |
| 39 | AAVC11.19 capsid polynucleotide |
| 40 | Shuffling_Rescue-F primer |
| 41 | Shuffling_Rescue-R primer |
| 42 | BB_GAR-F primer |
| 43 | BB_GAR-R primer |
| 44 | CapRescue-F primer |
| 45 | CapRescue-R primer |
| 46 | pHelperF primer |
| 47 | pHelperR primer |
| 48 | GFP-F1 primer |
| 49 | GFP-R1 primer |
| 50 | rep-F1 primer |
| 51 | rep-R2 primer |
| 52 | BC_F primer |
| 53 | BC_R primer |
| 54 | External_5_Seq primer |
| 55 | External_3_Seq primer |
| 56 | human_AAAVC._F primer |
| 57 | human_AAAVC._R primer |
| 58 | SQSGASNDNH (residues 263-272 of SEQ ID NO: 13) |
| 59 | TGATNKTTLENVLMTNEEEIRP (residues 546-567 of SEQ ID NO: 13) |
| 60 | SSNLQAANTAAQTQVVNN (residues 580-597 of SEQ ID NO: 13) |
| 61 | DRFFPSSGV (residues 532-540 of SEQ ID NO: 13) |
| 62 | STGGTQGTQQLLFSQAGPANMSA (residues 451-473 of SEQ ID NO: 13) |
| 63 | LSQNNNSNFAWTGATKYHLNGRNSLVNPGV (residues 493-522 of SEQ ID NO: 13) |
| 64 | AAV8 capsid polypeptide (VP1) |
| 65 | AAV8 Swap 1 capsid polypeptide |
| 66 | AAV8 Swap 2 capsid polypeptide |
| 67 | AAV8 Swap 3 capsid polypeptide |
| 68 | AAV8 Swap 4 capsid polypeptide |
| 69 | AAV8 Swap 5 capsid polypeptide |
| 70 | AAV8 Swap 6 capsid polypeptide |
| 71 | AAV8 Swap 7 capsid polypeptide |
| 72 | AAV8 Swap 8 capsid polypeptide |
| 73 | AAV8 Swap 9 capsid polypeptide |
| 74 | AAV8 Swap 10 capsid polypeptide |
| 75 | AAV8 Swap 11 capsid polypeptide |

TABLE 1-continued

| Brief Description of the Sequences | |
|---|---|
| SEQ ID NO. | Description |
| 76 | AAV8 Swap 12 capsid polypeptide |
| 77 | AAV8 Swap 13 capsid polypeptide |
| 78 | AAV8 Swap 14 capsid polypeptide |
| 79 | AAV8 Swap 15 capsid polypeptide |
| 80 | ISSQSGASNDNH (residues 261-272 of SEQ ID NO: 13) |
| 81 | KTGATNKTTLENVLMTNEEEIRP (residues 545-567 of SEQ ID NO: 13) |
| 82 | AMATHKDDEDRFFPSSGV (residues 523-540 of SEQ ID NO: 13) |
| 83 | QSTGGTQGTQQLLFSQAGPANMSA (residues 450-473 of SEQ ID NO: 13) |
| 84 | RVSTTLSQNNNSNFAWTGATKYHLNGRNSLVNPGV (residues 488-522 of SEQ ID NO: 13) |
| 85 | AAV8 Swap 1 capsid polynucleotide |
| 86 | AAV8 Swap 2 capsid polynucleotide |
| 87 | AAV8 Swap 3 capsid polynucleotide |
| 88 | AAV8 Swap 4 capsid polynucleotide |
| 89 | AAV8 Swap 5 capsid polynucleotide |
| 90 | AAV8 Swap 6 capsid polynucleotide |
| 91 | AAV8 Swap 7 capsid polynucleotide |
| 92 | AAV8 Swap 8 capsid polynucleotide |
| 93 | AAV8 Swap 9 capsid polynucleotide |
| 94 | AAV8 Swap 10 capsid polynucleotide |
| 95 | AAV8 Swap 11 capsid polynucleotide |
| 96 | AAV8 Swap 12 capsid polynucleotide |
| 97 | AAV8 Swap 13 capsid polynucleotide |
| 98 | AAV8 Swap 14 capsid polynucleotide |
| 99 | AAV8 Swap 15 capsid polynucleotide |

Capsid Polypeptides

The present disclosure is predicated in part on the identification of novel AAV capsid polypeptides. Typically, the capsid polypeptides, when present in the capsid of an AAV vector, facilitate efficient transduction of human cells (such as human hepatocytes). The in vivo transduction of cells by AAV vectors having a capsid comprising a capsid polypeptide of the present disclosure is generally increased or enhanced compared to AAV vectors comprising a reference AAV capsid polypeptide (e.g. the prototypic AAV2 capsid set forth in SEQ ID NO:1). Transduction or transduction efficiency of AAV vectors can be increased by at least or about 10%, 20%, 30%, 40%, 50%, 60%, 70%, 80%, 90%, 100%, 200%, 300%, 400%, 500%, 600%, 700%, 800%, 900%, 1000% or more, e.g. an AAV vector comprising a capsid polypeptide of the present disclosure can be at least or about 1.2×, 1.5×, 2×, 3×, 4×, 5×, 6×, 7×, 8×, 9×, 10×, 11×, 12×, 13×, 14×, 15×, 16×, 17×, 18×, 19×, 20×, 30×, 40×, 50×, 60×, 70×, 80×, 90×, 100× or more efficient at transducing cells in vivo compared to a reference AAV capsid polypeptide (e.g. one set forth in SEQ ID NO:1). In particular examples, the increased transduction or transduction efficiency is observed in human liver tissue or human hepatocytes.

AAV vectors comprising a capsid of the present disclosure may also exhibit enhanced or increased resistance to neutralization by pooled human immunoglobulins (also referred to as intravenous immunoglobulin or IVIg). The resistance to IVIg neutralization can be observed in vivo or in vitro using well-known assays, such as those described in the Examples below. The resistance to IVIg neutralization can be increased by at least or about 10%, 20%, 30%, 40%, 50%, 60%, 70%, 80%, 90%, 100%, 200%, 300%, 400%, 500%, 600%, 700%, 800%, 900%, 1000% or more, e.g. the resistance to IVIg neutralization of the AAV vector comprising a capsid polypeptide of the present disclosure can be at least or about 1.2×, 1.5×, 2×, 3×, 4×, 5×, 6×, 7×, 8×, 9×, 10×, 11×, 12×, 13×, 14×, 15×, 16×, 17×, 18×, 19×, 20×, 30×, 40×, 50×, 60×, 70×, 80×, 90×, 100× or more than the resistance to IVIg neutralization of an AAV vector comprising a reference AAV capsid polypeptide (e.g. one set forth in SEQ ID NO:1).

The capsid polypeptides of the present disclosure are therefore particularly useful in preparing AAV vectors, and in particular AAV vectors for gene therapy uses. In exemplary embodiments, the capsid polypeptides of the present disclosure are particularly useful in preparing AAV vectors that transduce hepatocytes, and in particular, human hepatocytes, and are thus useful for gene therapy applications targeting the liver.

Provided herein are polypeptides, including isolated polypeptides, comprising all or a portion of an AAV capsid polypeptide set forth in any one of SEQ ID Nos: 2-20 and 65-79, including all or a portion of the VP1 protein (comprising amino acid residues corresponding to those at positions 1-735 of SEQ ID NO:1), VP2 protein (comprising amino acid residues corresponding to those at positions 138-735 of SEQ ID NO:1) and/or the VP3 protein (comprising amino acid residues corresponding to those at positions 203-735 of SEQ ID NO:1), and variants thereof, including variants comprising at least or about 85%, 86%, 87%, 88%, 89%, 90%, 91%, 92%, 93%, 94%, 95%, 96%, 97%, 98%, or 99% sequence identity to the VP1, VP2 or VP3 proteins described herein.

Capsid polypeptides of the disclosure include those comprising all or a portion of the VP1 protein set forth in SEQ ID NO:2 (also referred to as AAVC11.01) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:2 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:2 or a functional fragment thereof; and capsid polypeptides comprising all or a portion of the VP3 protein set forth as amino acids 204-735 of SEQ ID NO:2 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:2 or a functional fragment thereof.

Capsid polypeptides of the disclosure also include those comprising all or a portion of the VP1 protein set forth in SEQ ID NO:3 (also referred to as AAVC11.02) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-736 of SEQ ID NO:3 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-736 of SEQ ID NO:3 or a functional fragment thereof; and capsid polypeptides comprising all or a portion of the VP3 protein set forth as amino acids 204-736 of SEQ ID NO:3 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-736 of SEQ ID NO:3 or a functional fragment thereof.

Exemplary capsid polypeptides of the disclosure also include those comprising all or a portion of the VP1 protein set forth in SEQ ID NO:4 (also referred to as AAVC11.03) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-737 of SEQ ID NO:4 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-737 of SEQ ID NO:4 or a functional fragment thereof; and capsid polypeptides comprising all or a portion of the VP3 protein set forth as amino acids 204-737 of SEQ ID NO:4 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-737 of SEQ ID NO:4 or a functional fragment thereof.

Also provided herein are capsid polypeptides comprising all or a portion of the VP1 protein set forth in SEQ ID NO:5 (also referred to as AAVC11.04) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-734 of SEQ ID NO:5 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-734 of SEQ ID NO:5 or a functional fragment thereof; and capsid polypeptides comprising all or a portion of the VP3 protein set forth as amino acids 203-734 of SEQ ID NO:5 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 203-734 of SEQ ID NO:5 or a functional fragment thereof.

Capsid polypeptides of the disclosure also include those comprising all or a portion of the VP1 protein set forth in SEQ ID NO:6 (also referred to as AAVC11.05) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:6 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:6 or a functional fragment thereof; and capsid polypeptides comprising all or a portion of the VP3 protein set forth as amino acids 204-735 of SEQ ID NO:6 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:6 or a functional fragment thereof.

Capsid polypeptides of the disclosure also include those comprising all or a portion of the VP1 protein set forth in SEQ ID NO:7 (also referred to AAVC11.06) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:7 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:7 or a functional fragment thereof; and capsid polypeptides comprising all or a portion of the VP3 protein set forth as amino acids 204-735 of SEQ ID NO:7 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:7 or a functional fragment thereof.

Other exemplary capsid polypeptides of the disclosure include those comprising all or a portion of the VP1 protein set forth in SEQ ID NO:8 (also referred to as AAVC11.07) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-734 of SEQ ID NO:8 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-734 of SEQ ID NO:8 or a functional fragment thereof; and capsid polypeptides comprising all or a portion of the VP3 protein set forth as amino acids 203-734 of SEQ ID NO:8 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 203-734 of SEQ ID NO:8 or a functional fragment thereof.

Further exemplary capsid polypeptides of the disclosure include those comprising all or a portion of the VP1 protein set forth in SEQ ID NO:9 (also referred to as AAVC11.08) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:9 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:9 or a functional fragment thereof; and capsid polypeptides comprising all or a portion of the VP3 protein set forth as amino acids 204-735 of SEQ ID NO:9 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:9 or a functional fragment thereof.

Capsid polypeptides of the present disclosure also include those comprising all or a portion of the VP1 protein set forth in SEQ ID NO:10 (also referred to as AAVC11.09) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:10 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:10 or a functional fragment thereof; and capsid polypeptides comprising all or a portion of the VP3 protein set forth as amino acids 204-735 of SEQ ID NO:10 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:10 or a functional fragment thereof.

Capsid polypeptides of the present disclosure also include those comprising all or a portion of the VP1 protein set forth in SEQ ID NO:11 (also referred to as AAVC11.10) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-734 of SEQ ID NO:11 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-734 of SEQ ID NO:11 or a functional fragment thereof; and capsid polypeptides comprising all or a portion of the VP3 protein set forth as amino acids 203-734 of SEQ ID NO:11 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 203-734 of SEQ ID NO:11 or a functional fragment thereof.

Exemplary capsid polypeptides of the present disclosure also include those comprising all or a portion of the VP1 protein set forth in SEQ ID NO: 12 (also referred to as AAVC11.11) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO: 12 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO: 12 or a functional fragment thereof; and capsid polypeptides comprising all or a portion of the VP3 protein set forth as amino acids 204-735 of SEQ ID NO: 12 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO: 12 or a functional fragment thereof.

Further exemplary capsid polypeptides of the present disclosure include those comprising all or a portion of the VP1 protein set forth in SEQ ID NO:13 (also referred to as AAVC11.12) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:13 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:13 or a functional fragment thereof; and capsid polypeptides comprising all or a portion of the VP3 protein set forth as amino acids 204-735 of SEQ ID NO:13 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:13 or a functional fragment thereof.

Also provided are capsid polypeptides that comprise all or a portion of the VP1 protein set forth in SEQ ID NO:14 (also referred to as AAVC11.13) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:14 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:14 or a functional fragment thereof; and capsid polypeptides comprising all or a portion of the VP3 protein set forth as amino acids 204-735 of SEQ ID NO:14 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:14 or a functional fragment thereof.

Capsid polypeptides of the present disclosure also include those that comprise all or a portion of the VP1 protein set forth in SEQ ID NO:15 (also referred to as AAVC11.14) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-736 of SEQ ID NO:15 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-736 of SEQ ID NO:15 or a functional fragment thereof; and capsid polypeptides comprising all or a portion of the VP3 protein set forth as amino acids 203-736 of SEQ ID NO:15 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 203-736 of SEQ ID NO:15 or a functional fragment thereof.

Capsid polypeptides of the present disclosure also include those that comprise all or a portion of the VP1 protein set forth in SEQ ID NO:16 (also referred to as AAVC11.15) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:16 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:16 or a functional fragment thereof; and capsid polypeptides comprising all or a portion of the VP3 protein set forth as amino acids 204-735 of SEQ ID NO:16 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:16 or a functional fragment thereof.

Exemplary capsid polypeptides of the present disclosure also include those that comprise all or a portion of the VP1 protein set forth in SEQ ID NO:17 (also referred to as AAVC11.16) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:17 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:17 or a functional fragment thereof; and capsid polypeptides comprising all or a portion of the VP3 protein set forth as amino acids 204-735 of SEQ ID NO:17 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:17 or a functional fragment thereof.

Exemplary capsid polypeptides also include those comprising all or a portion of the VP1 protein set forth in SEQ ID NO:18 (also referred to as AAVC11.17) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:18 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:18 or a functional fragment thereof; and capsid polypeptides comprising all or a portion of the VP3 protein set forth as amino acids 204-735 of SEQ ID NO:18 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:18 or a functional fragment thereof.

Further exemplary capsid polypeptides of the present disclosure include those comprising all or a portion of the VP1 protein set forth in SEQ ID NO:19 (also referred to as AAVC11.18) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:19 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:19 or a functional fragment thereof; and capsid polypeptides comprising all or a portion of the VP3 protein set forth as amino acids 204-735 of SEQ ID NO:19 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:19 or a functional fragment thereof.

Capsid polypeptides of the present disclosure also include those comprising all or a portion of the VP1 protein set forth in SEQ ID NO:20 (also referred to as AAVC11.19) or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of SEQ ID NO:20 or comprising a sequence having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:20 or a functional fragment thereof; and capsid polypeptides comprising all or a portion of the VP3 protein set forth as amino acids 204-735 of SEQ ID NO:20 or comprising a sequence having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:20 or a functional fragment thereof.

Capsid polypeptides of the present disclosure also include those comprising all or a portion of the VP1 protein set forth in any one of SEQ ID NOs:65-79 or a polypeptide having at least or about 85%, 86%, 87%, 88%, 89%, 90%, 91%, 92%, 93%, 94%, 95%, 96%, 97%, 98%, or 99% sequence identity thereto. Thus, also included in the present disclosure are capsid polypeptides comprising all or a portion of the VP2 protein set forth as amino acids 138-735 of any one of SEQ ID NOs: 69, 71-74, 76 and 78, amino acids 138-736 of any one of SEQ ID NOs: 65, 68, 75, 77 and 79, amino acids 138-737 of SEQ ID NOs: 67 or 70, or amino acids 138-738 of SEQ ID NO:66; or comprising a sequence having at least or about 85%, 86%, 87%, 88%, 89%, 90%, 91%, 92%, 93%, 94%, 95%, 96%, 97%, 98%, or 99% sequence identity to the aforementioned VP2 protein or a functional fragment thereof. Also included in the present disclosure are capsid polypeptides comprising all or a portion of the VP3 protein set forth as amino acids 204-735 of any one of SEQ ID NOs: 69, 71-74, 76 and 78, amino acids 204-736 of any one of SEQ ID NOs: 65, 68, 75, 77 and 79, amino acids 204-737 of SEQ ID NO: 67 or 70, or amino acids 204-738 of SEQ ID NO:66; or comprising a sequence having at least or about 85%, 86%, 87%, 88%, 89%, 90%, 91%, 92%, 93%, 94%, 95%, 96%, 97%, 98%, or 99% sequence identity to the aforementioned VP3 protein or a functional fragment thereof.

In some examples, the capsid polypeptides described above and herein comprise all or a portion of one or more variable regions having a sequence that is the same as the sequence of the corresponding variable region present in the AAVC11.12 polypeptide (SEQ ID NO:13). The variable regions of AAV capsid polypeptides have been described (see e.g. Drouin and Agbandje-McKenna, 2013, Future Virol. 8(12): 1183-1199) and include VR-I, spanning positions 260-267; VR-II, spanning positions 326-330; VR-III, spanning positions 380-384; VR-IV, spanning positions 449-467; VR-V, spanning positions 487-504; VR-VI, spanning positions 522-538; VR-VII, spanning positions 544-557; VR-VIII, spanning positions 580-592; and VR-IX, spanning positions 703-711 with numbering relative to AAV2. The AAVC11.12 polypeptide, which was generated from a DNA shuffled library, contains a VR-I of AAV2 origin, VR-IV and VR-V of AAV10 origin, and VR-VI, VR-VII, and VR-VIII of AAV7 origin (when using the VR regions as defined above and in Drouin and Agbandje-McKenna, 2013, the VR-I spans positions 261-268; the VR-IV spans positions 450-468; the VR-V spans positions 488-505; the VR-VI spans positions 523-539; the VR-VII spans positions 545-557; and the VR-VIII spans positions 580-592 of the AAVC11.12 polypeptide set forth in SEQ ID NO:13). Thus, in some examples, the capsid polypeptides of the present disclosure comprise all or a portion of one or more of the VR-I, VR-IV, VR-V, VR-VI, VR-VII and VR-VIII of the AAVC11.12 polypeptide. In some embodiments, capsid polypeptides have at least 85%, 86%, 87%, 88%, 89%, 90%, 91%, 92%, 93%, 94%, 95%, 96%, 97%, 98%, or 99% sequence identity to all or a portion of one or more of the VR-I, VR-IV, VR-V, VR-VI, VR-VII and VR-VIII of the AAVC11.12 polypeptide In one example, the capsid polypeptides of the present disclosure (e.g. a capsid polypeptide comprising a sequence having at least 85%, 86%, 87%, 88%, 89%, 90%, 91%, 92%, 93%, 94%, 95%, 96%, 97%, 98%, or 99% sequence identity to the VP1, VP2 or VP3 protein of any one of SEQ ID NOs: 2-20 or 65-79) comprise amino acid residues S263, Q264, S265, S268 and H272 (i.e. including residues in or near the VR-I of AAVC11.12); amino acid residues S451, Q456, G457, Q460, L462, A466, A469, N470, S472 and A473 (i.e. including residues in and/or near the VR-IV of AAVC11.12); amino acid residues L493, S494, G505, A506, V518 and V522 (i.e. including residues in or near the VR-V of AAVC11.12); amino acid residues D532, S538 and V540 (i.e. including residues in or near the VR-VI of AAVC11.12); amino acid residues T546, G547, T549, N550, K551, T552, T553, L554, E555, N556, L558, M559, N561, R566 and P567 (i.e. including residues in or near the VR-VII of AAVC11.12); and/or amino acid residues S580, S581, A585, A586, A590, T592, Q593, V594, and N597 (i.e. including residues in or near the VR-VIII of AAVC11.12); with numbering relative to SEQ ID NO:13.

In further examples, the capsid polypeptides comprise the sequence of amino acids SQSGASNDNH (SEQ ID NO:58) at positions 263-272; the sequence of amino acids ISSQSGASNDNH (SEQ ID NO:80) at positions 261-272; the sequence of amino acids STGGTQGTQQLLESQAGPANMSA (SEQ ID NO:62) at positions 451-473; the sequence of amino acids QSTGGTQGTQQLLFSQAGPANMSA (SEQ ID NO:83) at positions 450-473; the sequence of amino acids LSQNNNSNFAWTGATKYHLNGRNSLVNPGV (SEQ ID NO:63) at positions 493-522; the sequence of amino acids RVSTTLSQNNNSNFAWTGATKYHLNGRNSLVNPGV (SEQ ID NO:84) at positions 488-522; the sequence of amino acids DRFFPSSGV (SEQ ID NO:61) at positions 532-540; the sequence of amino acids AMATHKDDEDRFFPSSGV (SEQ ID NO:82) at positions 523-540; the sequence of amino acids TGATNKTTLENVLMTNEEEIRP (SEQ ID NO:59) at positions 546-567; the sequence of amino acids KTGATNKTTLENVLMTNEEEIRP (SEQ ID NO:81) at positions 545-567; and/or the sequence of amino acids SSNLQAANTAAQTQVVNN (SEQ ID NO: 60) at positions 580-597; with numbering relative to SEQ ID NO:13.

In a particular example, the capsid polypeptides of the present disclosure (e.g. a capsid polypeptide comprising a sequence having at least 85%, 86%, 87%, 88%, 89%, 90%, 91%, 92%, 93%, 94%, 95%, 96%, 97%, 98%, or 99% sequence identity to the VP1, VP2 or VP3 protein of any one of SEQ ID NOs: 2-20 or 65-79) comprise all or a portion of the VR-I of AAVC11.12, and all or a portion of the VR-VII and/or VR-VIII of AAVC11.12. Thus, in one example, the polypeptides comprise a) amino acid residues S263, Q264, S265, S268 and H272; and b) amino acid residues T546, G547, T549, N550, K551, T552, T553, L554, E555, N556, L558, M559, N561, R566 and P567; and/or amino acid residues S580, S581, A585, A586, A590, T592, Q593, V594, and N597, with numbering relative to SEQ ID NO:13. In further examples, the capsid polypeptides comprise a) the sequence of amino acids SQSGASNDNH (SEQ ID NO:58) at positions 263-272; and b) the sequence of amino acids TGATNKTTLENVLMTNEEEIRP (SEQ ID NO: 59) at positions 546-567 and/or the sequence of amino acids SSNLQAANTAAQTQVVNN (SEQ ID NO:60) at positions 580-597, with numbering relative to SEQ ID NO:13. In other examples, the capsid polypeptides comprise the sequence of amino acids ISSQSGASNDNH (SEQ ID NO:80) at positions 261-272; and b) the sequence of amino acids KTGATNKTTLENVLMTNEEEIRP (SEQ ID NO:81) at positions 545-567 and/or the sequence of amino acids SSNLQAANTAAQTQVVNN (SEQ ID NO:60) at positions 580-597, with numbering relative to SEQ ID NO:13. Such capsid polypeptides can further include all or a portion of the VR-VI of AAVC11.12 (e.g. amino acid residues D532, S538 and V540; the sequence of amino acids DRFFPSSGV (SEQ ID NO:61) at positions 532-540; and/or the sequence of amino acids AMATHKDDEDRFFPSSGV (SEQ ID NO:82) at positions 523-540), all or a portion of the VR-IV of AAVC11.12 (e.g. comprising amino acid residues S451, Q456, G457, Q460, L462, A466, A469, N470, S472 and A473; the sequence of amino acids STGGTQGTQQLLESQAGPANMSA (SEQ ID NO:62) at positions 451-473, and/or the sequence of amino acids QSTGGTQGTQQLLFSQAGPANMSA (SEQ ID NO:83) at positions 450-473), and/or all or a portion of the VR-V of AAVC11.12 (e.g. comprising amino acid residues L493, S494, G505, A506, V518 and V522, the sequence of amino acids LSQNNNSNFAWTGATKYHLNGRNSLVNPGV (SEQ ID NO:63) at positions 493-522, and/or the sequence of amino acids RVSTTLSQNNNSNFAWTGATKYHLNGRNSLVNPGV (SEQ ID NO: 84) at positions 488-522), with numbering relative to SEQ ID NO:13.

In some embodiments, capsid polypeptides of the present disclosure comprise a sequence of amino acids having at least about 50%, 60%, 70%, 80%, or 90% sequence identity to SEQ ID NO: 58 and include at least one substitution at any of positions 264-272 (e.g., at least one conservative substitution, e.g., at least two, three, four, or five substitutions). In some embodiments, capsid polypeptides of the present disclosure comprise a sequence of amino acids having at least about 50%, 60%, 70%, 80%, or 90% sequence identity to SEQ ID NO: 58 (e.g., at least one conservative substitution, e.g., at least two, three, four, or five substitutions) and include at least one substitution at any of positions 266, 267, 269, 270, and 271. In some embodiments, capsid polypeptides of the present disclosure comprise a sequence of amino acids having at least about 50%, 60%, 70%, 80%, or 90% sequence identity to SEQ ID NO: 58 and include at least one deletion or insertion. In some embodiments, capsid polypeptides may comprise S at position 263, or a conservative substitution thereof. In some embodiments, capsid polypeptides may comprise Q at position 264, or a conservative substitution thereof. In some embodiments, capsid polypeptides may comprise S at position 265, or a conservative substitution thereof. In some embodiments, capsid polypeptides may comprise S at position 268, or a conservative substitution thereof. In some embodiments, capsid polypeptides may comprise H at position 272, or a conservative substitution thereof.

In some embodiments, capsid polypeptides of the present disclosure comprise a sequence of amino acids having at least about 65%, 70%, 75%, 80%, 85%, 90%, or 95% sequence identity to SEQ ID NO: 59 and include at least one substitution at any of positions 545-567 (e.g., at least one conservative substitution, e.g., at least two, three, four, five, six, or seven substitutions). In some embodiments, capsid polypeptides of the present disclosure comprise a sequence of amino acids having at least about 65%, 70%, 75%, 80%, 85%, 90%, or 95% sequence identity to SEQ ID NO: 59 (e.g., at least one conservative substitution, e.g., at least two, three, four, five, six, or seven substitutions) and include at least one substitution at any of positions 545, 548, 557, 560, 562, 563, 564, or 565. In some embodiments, capsid polypeptides of the present disclosure comprise a sequence of amino acids having at least about 65%, 70%, 75%, 80%, 85%, 90%, or 95% sequence identity to SEQ ID NO: 59 and include at least one deletion or insertion. In some embodiments, capsid polypeptides may comprise T at position 546, or a conservative substitution thereof. In some embodiments, capsid polypeptides may comprise G at position 547, or a conservative substitution thereof. In some embodiments, capsid polypeptides may comprise T at position 549, or a conservative substitution thereof. In some embodiments, capsid polypeptides may comprise N at position 550, or a conservative substitution thereof. In some embodiments, capsid polypeptides may comprise K at position 551, or a conservative substitution thereof. In some embodiments, capsid polypeptides may comprise T at position 552, or a conservative substitution thereof. In some embodiments, capsid polypeptides may comprise T at position 553, or a conservative substitution thereof. In some embodiments, capsid polypeptides may comprise L at position 554, or a conservative substitution thereof. In some embodiments, capsid polypeptides may comprise E at position 555, or a conservative substitution thereof. In some embodiments, capsid polypeptides may comprise N at position 556, or a conservative substitution thereof. In some embodiments, capsid polypeptides may comprise L at position 558, or a conservative substitution thereof. In some embodiments, capsid polypeptides may comprise M at position 559, or a conservative substitution thereof. In some embodiments, capsid polypeptides may comprise N at position 561, or a conservative substitution thereof. In some embodiments, capsid polypeptides may comprise R at position 566, or a conservative substitution thereof. In some embodiments, capsid polypeptides may comprise P at position 567, or a conservative substitution thereof.

In some embodiments, capsid polypeptides of the present disclosure comprise a sequence of amino acids having at least about 50%, 55%, 60%, 65%, 70%, 75%, 80%, 85%, 90%, or 95% sequence identity to SEQ ID NO: 60 (e.g., at least one conservative substitution, e.g., at least two, three, four, five, six, seven, eight, or nine substitutions) and include at least one substitution at any of positions 581-597. In some embodiments, capsid polypeptides of the present disclosure comprise a sequence of amino acids having at least about 50%, 55%, 60%, 65%, 70%, 75%, 80%, 85%, 90%, or 95% sequence identity to SEQ ID NO: 60 (e.g., at least one conservative substitution, e.g., at least two, three, four, five, six, seven, eight, or nine substitutions) and include at least one substitution at any of positions 582, 583, 584, 587, 588, 589, 591, 595, or 596. In some embodiments, capsid polypeptides of the present disclosure comprise a sequence of amino acids having at least about 50%, 55%, 60%, 65%, 70%, 75%, 80%, 85%, 90%, or 95% sequence identity to SEQ ID NO: 60 and include at least one deletion or insertion. In some embodiments, capsid polypeptides may comprise S at position 580, or a conservative substitution thereof. In some embodiments, capsid polypeptides may comprise S at position 581, or a conservative substitution thereof. In some embodiments, capsid polypeptides may comprise A at position 585, or a conservative substitution thereof. In some embodiments, capsid polypeptides may comprise A at position 586, or a conservative substitution thereof. In some embodiments, capsid polypeptides may comprise A at position 590, or a conservative substitution thereof. In some embodiments, capsid polypeptides may comprise T at position 592, or a conservative substitution thereof. In some embodiments, capsid polypeptides may comprise O at position 593, or a conservative substitution thereof. In some embodiments, capsid polypeptides may comprise V at position 594, or a conservative substitution thereof. In some embodiments, capsid polypeptides may comprise N at position 597, or a conservative substitution thereof.

In some embodiments, capsid polypeptides of the present disclosure comprise a sequence of amino acids having at least about 30%, 40%, 50%, 60%, 70%, 80%, or 90% sequence identity to SEQ ID NO: 61 (e.g., at least one conservative substitution, e.g., at least two, three, four, five, or six substitutions) and include at least one substitution at any of positions 532-540. In some embodiments, capsid polypeptides of the present disclosure comprise a sequence of amino acids having at least about 30%, 40%, 50%, 60%, 70%, 80%, or 90% sequence identity to SEQ ID NO: 61 (e.g., at least one conservative substitution, e.g., at least two, three, four, five, or six substitutions) and include at least one substitution at any of positions 533, 534, 535, 536, 537, or 539. In some embodiments, capsid polypeptides of the present disclosure comprise a sequence of amino acids having at least about 30%, 40%, 50%, 60%, 70%, 80%, or 90% sequence identity to SEQ ID NO: 61 and include at least one deletion or insertion. In some embodiments, capsid polypeptides may comprise D at position 532, or a conservative substitution thereof. In some embodiments, capsid polypeptides may comprise S at position 538, or a conservative substitution thereof. In some embodiments, capsid polypeptides may comprise V at position 540, or a conservative substitution thereof.

In some embodiments, capsid polypeptides of the present disclosure comprise a sequence of amino acids having at least about 40%, 45%, 50%, 55%, 60%, 65%, 70%, 75%, 80%, 85%, 90%, or 95% sequence identity to SEQ ID NO: 62 (e.g., at least one conservative substitution, e.g., at least two, three, four, five, six, seven, eight, nine, ten, eleven, twelve, or thirteen substitutions) and include at least one substitution at any of positions 451-473. In some embodiments, capsid polypeptides of the present disclosure comprise a sequence of amino acids having at least about 40%, 45%, 50%, 55%, 60%, 65%, 70%, 75%, 80%, 85%, 90%, or 95% sequence identity to SEQ ID NO: 62 (e.g., at least one conservative substitution, e.g., at least two, three, four, five, six, seven, eight, nine, ten, eleven, twelve, or thirteen substitutions) and include at least one substitution at any of positions 452. 453. 454. 455. 458, 459, 461, 463, 464, 465, 467, 468, or 471. In some embodiments, capsid polypeptides of the present disclosure comprise a sequence of amino acids having at least about 40%, 45%, 50%, 55%, 60%, 65%, 70%, 75%, 80%, 85%, 90%, or 95% sequence identity to SEQ ID NO: 62 and include at least one deletion or insertion. In some embodiments, capsid polypeptides may comprise S at position 451, or a conservative substitution thereof. In some embodiments, capsid polypeptides may comprise Q at position 456, or a conservative substitution thereof. In some embodiments, capsid polypeptides may comprise G at position 457, or a conservative substitution thereof. In some embodiments, capsid polypeptides may comprise Q at position 460, or a conservative substitution thereof. In some embodiments, capsid polypeptides may comprise L at position 462, or a conservative substitution thereof. In some embodiments, capsid polypeptides may comprise A at position 466, or a conservative substitution thereof. In some embodiments, capsid polypeptides may comprise A at position 469, or a conservative substitution thereof. In some embodiments, capsid polypeptides may comprise N at position 470, or a conservative substitution thereof. In some embodiments, capsid polypeptides may comprise S at position 472, or a conservative substitution thereof. In some embodiments, capsid polypeptides may comprise A at position 473, or a conservative substitution thereof.

In some embodiments, capsid polypeptides of the present disclosure comprise a sequence of amino acids having at least about 20%, 25%, 30%, 35%, 40%, 45%, 50%, 55%, 60%, 65%, 70%, 75%, 80%, 85%, 90%, or 95% sequence identity to SEQ ID NO: 63 (e.g., at least one conservative substitution, e.g., at least two, three, four, five, six, seven, eight, nine, ten, eleven, twelve, thirteen, fourteen, fifteen, sixteen, seventeen, eighteen, nineteen, twenty, twenty one, twenty two, twenty three, or twenty four substitutions) and include at least one substitution at any of positions 493-522. In some embodiments, capsid polypeptides of the present disclosure comprise a sequence of amino acids having at least about 20%, 25%, 30%, 35%, 40%, 45%, 50%, 55%, 60%, 65%, 70%, 75%, 80%, 85%, 90%, or 95% sequence identity to SEQ ID NO: 63 (e.g., at least one conservative substitution, e.g., at least two, three, four, five, six, seven, eight, nine, ten, eleven, twelve, thirteen, fourteen, fifteen, sixteen, seventeen, eighteen, nineteen, twenty, twenty one, twenty two, twenty three, or twenty four substitutions) and include at least one substitution at any of positions 495, 496, 497, 498, 499, 500, 501, 502, 503, 504, 507, 508, 509, 510, 511, 512, 513, 514, 515, 516, 517, 519, 520, or 521. In some embodiments, capsid polypeptides of the present disclosure comprise a sequence of amino acids having at least about 20%, 25%, 30%, 35%, 40%, 45%, 50%, 55%, 60%, 65%, 70%, 75%, 80%, 85%, 90%, or 95% sequence identity to SEQ ID NO: 63 and include at least one deletion or insertion. In some embodiments, capsid polypeptides may comprise L at position 493, or a conservative substitution thereof. In some embodiments, capsid polypeptides may comprise S at position 494, or a conservative substitution thereof. In some embodiments, capsid polypeptides may comprise G at position 505, or a conservative substitution thereof. In some embodiments, capsid polypeptides may comprise A at position 506, or a conservative substitution thereof. In some embodiments, capsid polypeptides may comprise V at position 518, or a conservative substitution thereof. In some embodiments, capsid polypeptides may comprise V at position 522, or a conservative substitution thereof.

In a particular example, the capsid polypeptides of the present disclosure (e.g. a capsid polypeptide comprising a sequence having at least 85%, 86%, 87%, 88%, 89%, 90%, 91%, 92%, 93%, 94%, 95%, 96%, 97%, 98%, or 99% sequence identity to the VP1, VP2 or VP3 protein of any one of SEQ ID NOs: 2-20 or 65-79) comprise all or a portion of the VR-IV, VR-V, VR-VI, VR-VII and VR-VIII of AAVC11.12. Thus, in one example, the polypeptides comprise amino acid residues S451, Q456, G457, Q460, L462, A466, A469, N470, S472, A473, L493, S494, G505, A506, V518 V522, D532, S538 V540, T546, G547, T549, N550, K551, T552, T553, L554, E555, N556, L558, M559, N561, R566, P567, S580, S581, A585, A586, A590, T592, Q593, V594, and N597, with numbering relative to SEQ ID NO:13. In particular examples, the capsid polypeptides comprise the sequence of amino acids STGGTQGTQQLLFSQAGPANMSA (SEQ ID NO:62) at positions 451-473; the sequence of amino acids LSQNNNSNFAWTGATKYHLNGRNSLVNPGV (SEQ ID NO:63) at positions 493-522; the sequence of amino acids DRFFPSSGV (SEQ ID NO:61) at positions 532-540; the sequence of amino acids TGATNKTTLENVLMTNEEEIRP (SEQ ID NO:59) at positions 546-567; and the sequence of amino acids SSNLQAANTAAQTQVVNN (SEQ ID NO:60) at positions 580-597, with numbering relative to SEQ ID NO:13. In still further examples, the polypeptides comprise the sequence of amino acids QSTGGTQGTQQLLFSQAGPANMSA (SEQ ID NO:83) at positions 450-473; the sequence of amino acids RVSTTLSQNNNSNFAWTGATKYHLNGRNSLVNPGV (SEQ ID NO:84) at positions 488-522; the sequence of amino acids AMATHKDDEDRFFPSSGV (SEQ ID NO:82) at positions 523-540; the sequence of amino acids KTGATNKTTLENVLMTNEEEIRP (SEQ ID NO:81) at positions 545-567, with numbering relative to SEQ ID NO:13; and the sequence of amino acids SSNLQAANTAAQTQVVNN (SEQ ID NO:60) at positions 580-597, with numbering relative to SEQ ID NO:13. Typically, such polypeptides do not have the VR-I from AAVC11.12 (i.e. do not have the AAV2 VR-I). These polypeptides may have a VR-I from AAV8. For example, the polypeptides may have an insertion of NG after position 262, and contain residues T263, S264, G265, T268, and T272, with numbering relative to SEQ ID NO:13. In particular examples, the polypeptide contains an insertion of NG after position 262 and the sequence of amino acids TSGGATNDNT at positions 263-272, with numbering relative to SEQ ID NO:13.

Also provided are nucleic acid molecules, including isolated nucleic acid molecules, encoding a capsid polypeptide described herein. Thus, for example, amongst the nucleic acid molecules provided herein are those encoding the VP1, VP2 and/or VP3 of any one of the capsid polypeptides described herein. Non-limiting examples of nucleic acid molecules therefore include those set forth in SEQ ID NOs:21-39 and 85-99, those having at least or about 85%, 86%, 87%, 88%, 89%, 90%, 91%, 92%, 93%, 94%, 95%, 96%, 97%, 98%, or 99% sequence identity thereto, and those that hybridize with medium or high stringency to nucleic acid molecules comprising a sequence set forth in any one of SEQ ID NOs:21-39 and 85-99.

Vectors

The present disclosure also provides vectors comprising a nucleic acid molecule that encodes a capsid polypeptide described herein, and vectors comprising a capsid polypeptide described herein. The vectors include nucleic acid vectors that comprise a nucleic acid molecule that encodes a capsid polypeptide described herein, and AAV vectors that have a capsid comprising a capsid polypeptide described herein.

Nucleic Acid Vectors

Vectors of the present disclosure include nucleic acid vectors that comprise a polynucleotide that encodes all or a portion of a capsid polypeptide described herein, e.g. that encodes a polypeptide comprising an amino acid sequence set forth in any one of SEQ ID NOs:2-20 or an amino acid sequence having at least or about 85%, 86%, 87%, 88%, 89%, 90%, 91%, 92%, 93%, 94%, 95%, 96%, 97%, 98% or 99% sequence identity to a sequence set forth in any one of SEQ ID NOs:2-20, or a fragment thereof (e.g. all or a portion of the VP2 or VP3 protein), as described above. The vectors can be episomal vectors (i.e., that do not integrate into the genome of a host cell) or can be vectors that integrate into the host cell genome. Exemplary vectors that comprise a nucleic acid molecule encoding a capsid polypeptide include, but are not limited to, plasmids, cosmids, transposons and artificial chromosomes. In particular examples, the vectors are plasmids.

Vectors, such as plasmids, suitable for use in bacterial, insect and mammalian cells are widely described and well-known in the art. Those skilled in the art would appreciate that vectors of the present disclosure may also contain additional sequences and elements useful for the replication of the vector in prokaryotic and/or eukaryotic cells, selection of the vector and the expression of a heterologous sequence in a variety of host cells. For example, the vectors of the present disclosure can include a prokaryotic replicon (that is, a sequence having the ability to direct autonomous replication and maintenance of the vector extra-chromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein. The nucleic acid vectors will likely also comprise other elements, including any one or more of those described below. Most typically, the vectors will comprise a promoter operably linked to the nucleic acid encoding the capsid protein.

The nucleic acid vectors of the present disclosure can be constructed using known techniques, including, without limitation, the standard techniques of restriction endonuclease digestion, ligation, transformation, plasmid purification, in vitro or chemical synthesis of DNA, and DNA sequencing. The vectors of the present disclosure may be introduced into a host cell using any method known in the art. Accordingly, the present disclosure is also directed to host cells comprising a vector or nucleic acid described herein.

AAV Vectors

Provided herein are AAV vectors comprising a capsid polypeptide described herein, such as a polypeptide comprising all or a portion of an AAV capsid protein (e.g. a polypeptide comprising the amino acid sequence set forth in any one of SEQ ID NOs:2-20 or an amino acid sequence having at least or about 85%, 86%, 87%, 88%, 89%, 90%, 91%, 92%, 93%, 94%, 95%, 96%, 97%, 98% or 99% sequence identity to a sequence set forth in any one of SEQ ID NOs:2-20, or a fragment thereof (e.g. all or a portion of the VP2 or VP3 protein).

Methods for vectorizing a capsid protein are well known in the art and any suitable method can be employed for the purposes of the present disclosure. For example, the cap gene can be recovered (e.g. by PCR or digest with enzymes that cut upstream and downstream of cap) and cloned into a packaging construct containing rep. Any AAV rep gene may be used, including, for example, a rep gene is from AAV1, AAV2, AAV3, AAV4, AAV5, AAV6, AAV7, AAV8, AAV9, AAV10, AAV11, AAV12 or AAV13 and any variants thereof. Typically, the cap gene is cloned downstream of rep so the rep p40 promoter can drive cap expression. This construct does not contain ITRs. This construct is then introduced into a packaging cell line with a second construct containing ITRs, typically flanking a heterologous coding sequence. Helper function or a helper virus are also introduced, and recombinant AAV comprising a capsid generated from capsid proteins expressed from the cap gene, and encapsidating a genome comprising the transgene flanked by the ITRs, is recovered from the supernatant of the packaging cell line. Various types of cells can be used as the packaging cell line. For example, packaging cell lines that can be used include, but are not limited to, HEK293 cells, HeLa cells, and Vero cells, for example as disclosed in US20110201088. The helper functions may be provided by one or more helper plasmids or helper viruses comprising adenoviral helper genes. Non-limiting examples of the adenoviral helper genes include E1A, E1B, E2A, E4 and VA, which can provide helper functions to AAV packaging. Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

In some instances, rAAV virions are produced using a cell line that stably expresses some of the necessary components for AAV virion production. For example, a plasmid (or multiple plasmids) comprising the nucleic acid containing a cap gene identified as described herein and a rep gene, and a selectable marker, such as a neomycin resistance gene, can be integrated into the genome of a cell (the packaging cells). The packaging cell line can then be transfected with an AAV vector and a helper plasmid or transfected with an AAV vector and co-infected with a helper virus (e.g., adenovirus providing the helper functions). The advantages of this method are that the cells are selectable and are suitable for large-scale production of the recombinant AAV. As another non-limiting example, adenovirus or baculovirus rather than plasmids can be used to introduce the nucleic acid encoding the capsid polypeptide, and optionally the rep gene, into packaging cells. As yet another non-limiting example, the AAV vector is also stably integrated into the DNA of producer cells, and the helper functions can be provided by a wild-type adenovirus to produce the recombinant AAV.

In still further instances, the AAV vectors are produced synthetically, by synthesising AAV capsid proteins and assembling and packaging the capsids in vitro.

Typically, the AAV vectors of the present disclosure also comprise a heterologous coding sequence. The heterologous coding sequence may be operably linked to a promoter to facilitate expression of the sequence. The heterologous coding sequence can encode a peptide or polypeptide, such as a therapeutic peptide or polypeptide, or can encode a polynucleotide or transcript that itself has a function or activity, such as an antisense or inhibitory oligonucleotide, including antisense DNA and RNA (e.g. miRNA, siRNA, and shRNA). In some examples, the heterologous coding sequence is a stretch of nucleic acids that is essentially homologous to a stretch of nucleic acids in the genomic DNA of an animal, such that when the heterologous coding sequence is introduced into a cell of the animal, homologous recombination between the heterologous coding sequence and the genomic DNA can occur. As would be appreciated, the nature of the heterologous coding sequence is not essential to the present disclosure. In particular embodiments, the vectors comprising the heterologous coding sequence(s) will be used in gene therapy.

In particular examples, the heterologous coding sequence encodes a peptide or polypeptide, or polynucleotide, whose expression is of therapeutic use, such as, for example, for the treatment of a disease or disorder. For example, expression of a therapeutic peptide or polypeptide may serve to restore or replace the function of the endogenous form of the peptide or polypeptide that is defective (i.e. gene replacement therapy). In other examples, expression of a therapeutic peptide or polypeptide, or polynucleotide, from the heterologous sequence serves to alter the levels and/or activity of one or more other peptides, polypeptides or polynucleotides in the host cell. Thus, according to particular embodiments, the expression of a heterologous coding sequence introduced by a vector described herein into a host cell can be used to provide a therapeutic amount of a peptide, polypeptide or polynucleotide to ameliorate the symptoms of a disease or disorder. In other instance, the heterologous coding sequence is a stretch of nucleic acids that is essentially homologous to a stretch of nucleic acids in the genomic DNA of an animal, such that when the heterologous sequence is introduced into a cell of the animal, homologous recombination between the heterologous coding sequence and the genomic DNA can occur. Accordingly, the introduction of a heterologous sequence by an AAV vector described herein into a host cell can be used to correct mutations in genomic DNA, which in turn can ameliorate the symptoms of a disease or disorder.

In non-limiting examples, the heterologous coding sequence encodes an expression product that, when delivered to a subject, and in particular the liver of a subject, treats a liver-associated disease or condition. In illustrative embodiments, the liver-associated disease or condition is selected from among a urea cycle disorder (UCD; including N-acetylglutamate synthase deficiency (NAGSD), carbamylphosphate synthetase 1 deficiency (CPS1D), ornithine transcarbamylase deficiency (OTCD), argininosuccinate synthetase deficiency (ASSD), argininosuccinate lyase (ASLD), arginase 1 deficiency (ARG1D), citrin or aspartate/glutamate carrier deficiency and the mitochondrial ornithine transporter 1 deficiency causing hyperornithinemia-hyperammonemia-homocitrullinuria syndrome (HHH syndrome)), organic acidopathy (or organic academia, including methylmalonic acidemia, propionic acidemia, isovaleric acidemia, and maple syrup urine disease), aminoacidopathy, glycogenoses (Types I, III and IV), Wilson's disease, Progressive Familial Intrahepatic Cholestasis, primary hyperoxaluria, complementopathy, coagulopathy (e.g. hemophilia A, hemophilia B, von Willebrand disease (VWD)), Crigler Najjar syndrome, familial hypercholesterolaemia, α-1-antitrypsin deficiency, mitochondria respiratory chain hepatopathy, and citrin deficiency. Those skilled in the art would readily be able to select an appropriate heterologous coding sequence useful for treating such diseases. In some examples, the heterologous coding sequence comprises all or a part of a gene that is associated with the disease, such as all or a part of a gene set forth in Table 2. Introduction of such a sequence to the liver can be used for gene replacement or gene editing/correction, e.g. using CRISPR-Cas9. In particular examples, the heterologous coding sequence encodes a protein encoded by a gene that is associated with the disease, such as a gene set forth in Table 2.

TABLE 2

| Exemplary liver-associated diseases | Exemplary associated genes |
|---|---|
| Urea cycle disorders (UCDs) | OTC, ASS, CPS1, ASL, ARG1 |
| Organic acidopathies | PCCA, PCCB, MMUT |
| Aminoacidopathies | PAH, FAH |
| Glycogenoses (Types I, III and IV) | SLC37A4 |
| Wilson's Disease | ATP7B |
| Progressive Familial Intrahepatic Cholestasis | ABCB4, ABCB11, ATP8B1 |
| Primary Hyperoxaluria | AGXT |
| Complementopathies | CFH, CFI |
| Coagulopathies | F8, F9, VWF |
| Crigler Najjar syndrome | UGT1A1 |
| Familial Hypercholesterolaemia | LDLR |
| α-1-antitrypsin Deficiency | SERPINA1 |
| Mitochondria Respiratory Chain Hepatopathies | POLG |
| Citrin Deficiency | SLC25A13 |

The heterologous coding sequence in the AAV vector is flanked by 3' and 5' AAV ITRs. AAV ITRs used in the vectors of the disclosure need not have a wild-type nucleotide sequence, and may be altered, e.g., by the insertion, deletion or substitution of nucleotides. Additionally, AAV ITRs may be derived from any of several AAV serotypes, including without limitation, AAV1, AAV2, AAV3, AAV4, AAV5, AAV6, AAV7, AAV8, AAV9, AAV10, AAV11, AAV12 or AAV13. Such ITRs are well known in the art.

As will be appreciated by a skilled artisan, any method suitable for purifying AAV can be used in the embodiments described herein to purify the AAV vectors, and such methods are well known in the art. For example, the AAV vectors can be isolated and purified from packaging cells and/or the supernatant of the packaging cells. In some embodiments, the AAV is purified by separation method using a CsCl or iodixanol gradient centrifugation. In other embodiments, AAV is purified as described in US20020136710 using a solid support that includes a matrix to which an artificial receptor or receptor-like molecule that mediates AAV attachment is immobilized.

Additional Elements in the Vectors

The vectors of the present disclosure can comprise promoters. In instances where the vector is a nucleic acid vector comprising nucleic acid encoding the capsid polypeptide, the promoter may facilitate expression of the nucleic acid encoding the capsid polypeptide. In instances where the vector is an AAV vector, the promoter may facilitate expression of a heterologous coding sequence, as described above.

In some examples, the promoters are AAV promoters, such as the p5, p19 or p40 promoter. In other examples, the promoters are derived from other sources. Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the 8-actin promoter, the phosphoglycerol kinase (PGK) promoter, and the EF1α promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Non-limiting examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In some embodiments, tissue specific promoters are used. Non-limiting examples of such promoters include the liver-specific thyroxin binding globulin (TBG) promoter, insulin promoter, glucagon promoter, somatostatin promoter, pancreatic polypeptide (PPY) promoter, synapsin-1 (Syn) promoter, creatine kinase (MCK) promoter, mammalian desmin (DES) promoter, a α-myosin heavy chain (a-MHC) promoter, a cardiac Troponin T (cTnT) promoter, beta-actin promoter, and hepatitis B virus core promoter. The selection of an appropriate promoter is well within the ability of one of ordinary skill in the art.

The vectors can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly (A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence.

The vectors can include various posttranscriptional regulatory elements. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element, and any variants thereof. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to, Mason-Pfizer Monkey Virus CTE and Avian Leukemia Virus CTE.

A signal peptide sequence can also be included in the vector to provide for secretion of a polypeptide from a mammalian cell. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. Typically, the nucleotide sequence of the signal peptide is located immediately upstream of the heterologous sequence (e.g., fused at the 5' of the coding region of the protein of interest) in the vector.

In further examples, the vectors can contain a regulatory sequence that allows, for example, the translation of multiple proteins from a single mRNA. Non-limiting examples of such regulatory sequences include internal ribosome entry site (IRES) and 2A self-processing sequence, such as a 2A peptide site from foot-and-mouth disease virus (F2A sequence).

Host Cells

Also provided herein are host cells comprising a nucleic acid molecule or vector or of the present disclosure. In some instances, the host cells are used to amplify, replicate, package and/or purify a polynucleotide or vector. In other examples, the host cells are used to express a heterologous sequence, such as one packaged within AAV vector. Exemplary host cells include prokaryotic and eukaryotic cells. In some instances, the host cell is a mammalian host cell. It is well within the skill of a skilled artisan to select an appropriate host cell for the expression, amplification, replication, packaging and/or purification of a polynucleotide, vector or rAAV virion of the present disclosure. Exemplary mammalian host cells include, but are not limited to, HEK293 cells, HeLa cells, Vero cells, HuH-7 cells, and HepG2 cells. In particular examples, the host cell is a hepatocyte or cell-line derived from a hepatocyte.

Compositions

Also provided are compositions comprising the nucleic acid molecules, polypeptides and/or vectors of the present disclosure. In particular examples, provided are pharmaceutical compositions comprising the AAV vectors disclosed herein and a pharmaceutically acceptable carrier. The compositions can also comprise additional ingredients such as diluents, stabilizers, excipients, and adjuvants.

The carriers, diluents and adjuvants can include buffers such as phosphate, citrate, or other organic acids; antioxidants such as ascorbic acid; low molecular weight polypeptides (e.g., less than about 10 residues); proteins such as serum aAAVC.umin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Methods

The AAV vectors of the present disclosure, and compositions containing the AAV vectors, may be used in methods for the introduction of a heterologous coding sequence into a host cell. Such methods involve contacting the host cell with the AAV vector. This may be performed in vitro, ex vivo or in vivo. In particular embodiments, the host cell is a hepatocyte (e.g. a human hepatocyte).

When the methods are performed ex vivo or in vivo, typically the introduction of the heterologous sequence into the host cell is for therapeutic purposes, whereby expression of the heterologous sequence results in the treatment of a disease or condition. Thus, the AAV vectors disclosed herein can be administered to a subject (e.g., a human) in need thereof, such as subject with a disease or condition amendable to treatment with a protein, peptide or polynucleotide encoded by a heterologous sequence described herein.

When used in vivo, titers of AAV vectors to be administered to a subject will vary depending on, for example, the particular recombinant virus, the disease or disorder to be treated, the mode of administration, the treatment goal, the individual to be treated, and the cell type(s) being targeted, and can be determined by methods well known to those skilled in the art. Although the exact dosage will be determined on an individual basis, in most cases, typically, recombinant viruses of the present disclosure can be administered to a subject at a dose of between $1\times10^{10}$ genome copies of the recombinant virus per kg of the subject and $1\times10^{14}$ genome copies per kg. In other examples, less than $1\times10^{10}$ genome copies may be sufficient for a therapeutic effect. In other examples, more than $1\times10^{14}$ genome copies may be required for a therapeutic effect.

The route of the administration is not particularly limited. For example, a therapeutically effective amount of the AAV vector can be administered to the subject via, for example, intramuscular, intravaginal, intravenous, intraperitoneal, subcutaneous, epicutaneous, intradermal, rectal, intraocular, pulmonary, intracranial, intraosseous, oral, buccal, or nasal routes. The AAV vector can be administrated as a single dose or multiple doses, and at varying intervals.

Also provided are methods for producing an AAV vector described above and herein, i.e. one comprising a capsid polypeptide of the present disclosure. Such methods comprise culturing a host cell comprising a nucleic acid molecule encoding a capsid polypeptide the present disclosure, an AAV rep gene, a heterologous coding sequence flanked by AAV inverted terminal repeats, and helper functions for generating a productive AAV infection, under conditions suitable to facilitate assembly of an AAV vector comprising a capsid polypeptide of the present disclosure, wherein the capsid encapsidates the heterologous coding sequence.

In further aspects, provided are methods for enhancing the in vivo human hepatocyte transduction efficiency of an AAV vector. As demonstrated herein, some variable regions, and combinations of capsid variable regions, are important for efficient transduction of human hepatocytes by an AAV vector. In particular, the presence of all or a part of VR-VII and/or VR-VIII from AAV7 in a capsid polypeptide imparts enhanced transduction by AAV vectors of a human hepatocyte in vivo. VR-I from AAV2 can also enhance the transduction by AAV vectors of a human hepatocyte in vivo.

Thus, provided herein are methods for enhancing the in vivo human hepatocyte transduction efficiency of an AAV vector (or producing an AAV vector with enhanced in vivo human hepatocyte transduction efficiency), which include the steps of modifying the sequence of a reference capsid polypeptide at one or more of positions 263, 264, 265, 268, 272, 546, 547, 549, 550, 551, 552, 553, 554, 555, 556, 558, 559, 561, 566, 567, 580, 581, 585, 586, 590, 592, 593, 594 and 597, with numbering relative to SEQ ID NO:13, to thereby produce a modified capsid polypeptide that comprises: i) amino acid residues S263, Q264, S265, S268 and H272, with numbering relative to SEQ ID NO:13; and ii) amino acid residues T546, G547, T549, N550, K551, T552, T553, L554, E555, N556, L558, M559, N561, R566 and P567, with numbering relative to SEQ ID NO:13; and/or amino acid residues S580, S581, A585, A586, A590, T592, Q593, V594, and N597, with numbering relative to SEQ ID NO:13. Additional modifications can optionally be made at or adjacent to one or more other variable regions, such as VR-IV, VR-V and VR-VI. For example, modifications can be made at one or more of positions 532, 538 and 540, with numbering relative to SEQ ID NO:13, wherein the modified capsid polypeptide comprises amino acid residues D532, S538 and V540, with numbering relative to SEQ ID NO:13. In another example, modifications can be at one or more of positions 451, 456, 457, 460, 462, 466, 469, 470, 472 and 473, with numbering relative to SEQ ID NO:13, wherein the modified capsid polypeptide comprises amino acid residues S451, Q456, G457, Q460, L462, A466, A469, N470, S472 and A473, with numbering relative to SEQ ID NO:13. In a further example, modifications can be made at one or more of positions 493, 494, 505, 506, 518 and 522, with numbering relative to SEQ ID NO:13, wherein the modified capsid polypeptide comprises amino acid residues L493, S494, G505, A506, V518 and V522, with numbering relative to SEQ ID NO:13.

Methods for enhancing the in vivo human hepatocyte transduction efficiency of an AAV vector (or producing an AAV vector with enhanced in vivo human hepatocyte transduction efficiency) also include those methods that include the steps of modifying the sequence of a reference capsid polypeptide at one or more of positions 263-272, 546-567 and 580-597 with numbering relative to SEQ ID NO:13, to thereby produce a modified capsid polypeptide that comprises: i) the sequence of amino acids SQSGASNDNH (SEQ ID NO:58) at positions 263-272, with numbering relative to SEQ ID NO:13; and ii) the sequence of amino acids TGATNKTTLENVLMTNEEEIRP (SEQ ID NO:59) at positions 546-567, with numbering relative to SEQ ID NO:13 and/or the sequence of amino acids SSNLQAANTAAQTQVVNN (SEQ ID NO:60) at positions 580-597, with numbering relative to SEQ ID NO:13.

Methods for enhancing the in vivo human hepatocyte transduction efficiency of an AAV vector (or producing an AAV vector with enhanced in vivo human hepatocyte transduction efficiency) also include those methods that include the steps of modifying the sequence of a reference capsid polypeptide at one or more of positions 261-272, 545-567 and 580-597 with numbering relative to SEQ ID NO:13, to thereby produce a modified capsid polypeptide that comprises: i) the sequence of amino acids ISSQSGASNDNH (SEQ ID NO:80) at positions 261-272, with numbering relative to SEQ ID NO:13; and ii) the sequence of amino acids KTGATNKTTLENVLMTNEEEIRP (SEQ ID NO:81) at positions 545-567, with numbering relative to SEQ ID NO:13 and/or the sequence of amino acids SSNLQAANTAAQTQVVNN (SEQ ID NO:60) at positions 580-597, with numbering relative to SEQ ID NO:13.

Additional modifications can optionally be made at or adjacent to one or more other variable regions, such as VR-IV, VR-V and VR-VI. For example, modifications can be made at one or more of positions 532-540, with numbering relative to SEQ ID NO:13, wherein the modified capsid polypeptide comprises the sequence of amino acids DRFFPSSGV (SEQ ID NO:61) at positions 532-540, with numbering relative to SEQ ID NO:13; at one or more of positions 523-540, with numbering relative to SEQ ID NO:13, wherein the modified capsid polypeptide comprises the sequence of amino acids AMATHKDDEDRFFPSSGV (SEQ ID NO:82) at positions 523-540, with numbering relative to SEQ ID NO:13; at one or more of positions 451-473, with numbering relative to SEQ ID NO:13, wherein the modified capsid polypeptide comprises the sequence of amino acids STGGTQGTQQLLFSQAGPANMSA (SEQ ID NO:62) at positions 451-473, with numbering relative to SEQ ID NO:1; at one or more of positions 450-473, with numbering relative to SEQ ID NO:13, wherein the modified capsid polypeptide comprises the sequence of amino acids QSTGGTQGTQQLLFSQAGPANMSA (SEQ ID NO:83) at positions 450-473, with numbering relative to SEQ ID NO:1; at one or more of positions 493-522, with numbering relative to SEQ ID NO:13, wherein the modified capsid polypeptide comprises the sequence of amino acids LSQNNNSNFAWTGATKYHLNGRNSLVNPGV (SEQ ID NO:63) at positions 493-522, with numbering relative to SEQ ID NO:13; and/or at one or more of positions 488-522, with numbering relative to SEQ ID NO:13, wherein the modified capsid polypeptide comprises the sequence of amino acids RVST- TLSQNNNSNFAWTGATKYHLNGRNSLVNPGV (SEQ ID NO:84) at positions 488-522, with numbering relative to SEQ ID NO:13.

It will be understood that any modification or combination of modifications, e.g. amino acid replacement or substitution, amino acid deletion and/or amino acid insertion, will result in a change of amino acid sequence in the modified capsid polypeptide compared to the reference capsid polypeptide. Thus, for example, reference to modification does not include within its scope amino acid substitutions where one amino acid residue is substituted with the same amino acid residue, or modifications when an amino acid deletion is accompanied by an insertion of that deleted amino acid, such that there is no difference in the amino acid sequence of the modified capsid polypeptide compared to the reference capsid polypeptide sequence, i.e. the amino acid sequence of the modified capsid polypeptide can not be the same as (or must be different to) the amino acid sequence of the reference capsid polypeptide sequence.

Typically, the methods include an initial step of first identifying a reference capsid polypeptide for transducing human hepatocytes in vivo. The reference capsid polypeptide may be any AAV polypeptide, such as an AAV1, AAV2, AAV3, AAV3B, AAV4, AAV5, AAV6, AAV7, AAV8, AAV9, AAV10, AAV11, AAV12 or AAV13 capsid polypeptide, or a synthetic or chimeric capsid polypeptide. In illustrative embodiments, the reference polypeptide comprises at least or about 85%, 86%, 87%, 88%, 89%, 90%, 91%, 92%, 93%, 94%, 95%, 96%, 97%, 98%, or 99% sequence identity to the sequence set forth in SEQ ID NO:13. Reference capsid polypeptides include those comprising all or a portion of the VP1 protein, VP2 protein or VP3 protein. Thus, in some embodiments, the reference capsid polypeptide comprises all or a portion of a VP1 protein having at least or about 85%, 86%, 87%, 88%, 89%, 90%, 91%, 92%, 93%, 94%, 95%, 96%, 97%, 98%, or 99% sequence identity to the sequence set forth in SEQ ID NO:13 (also referred to as AAVC11.12); all or a portion of a VP2 protein having at least or about 85%, 86%, 87%, 88%, 89%, 90%, 91%, 92%, 93%, 94%, 95%, 96%, 97%, 98%, or 99% sequence identity to the VP2 protein set forth as amino acids 138-735 of SEQ ID NO:13; and all or a portion of a VP3 protein having at least or about 85%, 86%, 87%, 88%, 89%, 90%, 91%, 92%, 93%, 94%, 95%, 96%, 97%, 98%, or 99% sequence identity to the VP3 protein set forth as amino acids 204-735 of SEQ ID NO:13.

Methods for modifying the sequence of a reference capsid polypeptide or polynucleotide so as to produce a modified capsid polypeptide or polynucleotide are well known in the art, and any such method can be utilised so as to perform the methods of the present disclosure. For example, the modification of the sequence of the reference capsid polynucleotide to produce a modified capsid polynucleotide can be performed using any method known in the art, including recombinant and synthetic methods, performed (either in part or in whole) in silico and/or in vitro. In a particular example, the modification of the sequence is performed in silico, followed by de novo synthesis of the modified capsid polynucleotide having the modified sequence (e.g. by gene synthesis methods such as those involving the chemical synthesis of overlapping oligonucleotides following by gene assembly).

The modified capsid polynucleotides may be contained in nucleic acid vector, such as a plasmid, for subsequent expression, replication, amplification and/or manipulation. Vectors suitable for use in bacterial, insect and mammalian cells are widely described and well-known in the art. Those skilled in the art would appreciate that the vectors may also contain additional sequences and elements useful for the replication of the vector in prokaryotic and/or eukaryotic cells, selection of the vector and the expression of a heterologous sequence in a variety of host cells. For example, the vectors can include a prokaryotic replicon, which is a sequence having the ability to direct autonomous replication and maintenance of the vector extrachromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein. The nucleic acid vectors will likely also comprise other elements, including any one or more of those described below. Most typically, the vectors will comprise a promoter operably linked to the nucleic acid encoding the capsid protein.

The nucleic acid vectors can be constructed using known techniques, including, without limitation, the standard techniques of restriction endonuclease digestion, ligation, transformation, plasmid purification, in vitro or chemical synthesis of DNA, and DNA sequencing. The vectors comprising a modified capsid polynucleotide may be introduced into a host cell using any method known in the art.

Following modification, the modified capsid are then vectorised. Methods for vectorising a capsid polypeptide are well known in the art and non-limiting examples are described above.

The AAV vector produced by these methods typically has an in vivo transduction efficiency that is enhanced compared to a reference AAV vector having a capsid comprising the reference capsid polypeptide. The transduction efficiency can be enhanced by at least or about, 10%, 20%, 30%, 40%, 50%, 60%, 70%, 80%, 90%, 100%, 200%, 300%, 400%, 500%, 600%, 700%, 800%, 900% 1000%, or more, e.g. the transduction efficiency of the AAV vector can be at least or about 2×, 3×, 4×, 5×, 6×, 7×, 8×, 9×, 10×, 12×, 13×, 14×, 15×, 16×, 17×, 18×, 19×, 20×, 30×, 40×, 50×, 60×, 70×, 80×, 90×, 100× or more efficient at transducing cells in vivo.

Thus, also provided are AAV vectors produced by the methods of the present disclosure.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1. Materials and Methods

Shuffled AAV Capsid Plasmid Library Generation

Parental AAV cap genes (AAV1 through 12, AAV-mAAV1 (WO2019227168) and AAV-EVE1 (WO2017192699) were cloned into the plasmid p-RescueVector (pRV 1-12), a construct based on the pGEM-T Easy Vector System (catalog [Cat] #A1360; Promega) modified to harbor trimethoprim resistance and randomized ends flanking the capsids, for optimal Gibson Assembly (GA). Individual clones were Sanger sequenced (Garvan Molecular Genetics). Capsid genes (serotypes 1-12) were excised using SwaI and NsiI (NEB), mixed at 1:1 molar ratio, and digested with 1:10 prediluted DNaseI (Cat #M030S; NEB) for 2-5 min. The pool of fragments was separated on a 1% (w/v) agarose gel and fragments ranging from 200 to 1,000 bp were recovered using the Zymoclean Gel DNA Recovery Kit (Cat #D4001T; Zymogen). For each primer-less PCR reassembly reaction, 500 ng of gel-extracted fragments was used, and fully reassembled capsids were amplified in a second PCR with primers (Shuffling Rescue-F/R, Table 3) binding the cap gene and carrying overlapping ends to pRV plasmids. A GA reaction was performed by mixing an equal volume of 2 GA Master Mix (Cat #E2611L; NEB) with 1 pmoL PCR-amplified and DpnI-treated pRV (BB GAR-F/R, Table 3) and 1 pmol of the recovered shuffled capsids, at 50° C. for 30 min. DNA was ethanol precipitated and electroporated into SS320 electrocompetent *E. coli* (Cat #60512-2; Lucigen). The total number of transformants was calculated by preparing and plating five 10-fold serial dilutions of the electroporated bacteria. The pool of transformants was grown overnight in 250 mL of Luria-Bertani media supplemented with trimethoprim (10 mg/mL). Total pRV library plasmids were purified with an EndoFree Maxiprep Kit (Cat #12362; QIAGEN). pRV-based libraries were then digested overnight with SwaI and NsiI, and 1.4 μg of insert was ligated at 16° C. with T4 DNA ligase (Cat #M0202; NEB) for 16 hr into 1 μg of a replication-competent AAV2-based plasmid platform (p-Replication-Competent [p-RC]) containing ITR-2 and rep2, and unique SwaI and NsiI sites flanking a 1-kb randomized stuffer [ITR2-rep2-(SwaI)-stuffer-(NsiI)-ITR2]. Ligation reactions were concentrated by using ethanol precipitation, electroporated into SS320 electro-competent bacteria, and grown as described above. Total pRC library plasmids were purified with an EndoFreeMaxiprep Kit (Cat #12362; QIAGEN).

In Vivo Selection of AAV Library

A humanised FRG (hFRG) mouse was injected with $1\times10^{11}$ vg of replication-competent RC-AAVC11 by i.v. tail vein administration. $5\times10^{9}$ PFUs of wild-type human adenovirus-5 (ATCC, VR-5, Lot #70010153) were administered intraperitoneally (i.p.) 24 hr later. The xenograft liver was harvested 72 hr after hAd5 administration, homogenised and snap frozen in liquid nitrogen. To extract AAV particles, approximately 0.3 g fragment of liver was subjected to three freeze-thaw cycles and mechanical homogenisation in the presence of 2× w/v of PBS. Sample was subsequently centrifuged for 30 min at 4° C. at top speed in a table-top centrifuge to separate the virus-containing supernatant from cellular debris. To inactivate wtAd5, the virus-containing supernatant was incubated at 65° C. for 30 min. Following titration by qPCR, 200 μL of the virus-containing supernatant was administrated i.p. into hFRG mouse for subsequent round of selection. A total of 5 rounds of selection were performed for this selection.

Vectorisation of AAV Cap Candidates

After round five of selection, AAV capsid sequences were recovered from the supernatant by PCR using primers flanking the capsid region (CapRescue-F/R, Table 3). PCR-amplified cap genes were cloned by GA in-frame downstream of the rep2 gene in a recipient pHelper packaging plasmid opened by PCR amplification using the following primers (pHelper-F/R) and DpnI treated. Individual clones containing full-length cap candidates were then Sanger sequenced.

AAV Vector Packaging and Viral Production

AAV constructs were packaged into AAV capsids using HEK293 cells and a helper-virus-free system as previously described (Xiao et al, 1998 J Virol, 1998. 72(3): 2224-32). Genomes were packaged in capsid serotypes AAV2, AAV8, LK03 and NP59 using packaging plasmid constructs pAAV2, pAAV8, pLK03 and pAAVNP59, respectively. Replication-competent (RC) library AAVC11 was packaged by co-transfection of a corresponding plasmid containing the full-length AAV genome (ITR2-rep2-cap-ITR2) and pAd5 into HEK-293T cells.

All vector/virus were purified using iodixanol gradient ultracentrifugation as previously described (Khan et al. 2011. Nat Protoc, 2011. 6(4): p. 482-501). AAV preparations were titred using real-time quantitative PCR (qPCR) using eGFP-specific qPCR primers GFP-qPCR-For/Rev or AAV2-rep-specific qPCR primers Rep-qPCR-For/Rev (Table 3). For in vivo testing of capsid candidates (Example 2), n=4 independent barcoded transgenes were packaged per capsid using two different concentrations (n=2 barcoded transgenes at high dose: 10 μg/transgene per preparation, and n=2 barcoded transgenes at low dose: 1 μg/transgene per preparation). The presence of the two distinct populations was confirmed by next-generation sequencing of the pre-injection mix. For further comparisons, n=5 barcoded transgenes were packaged at increasing concentration by co-transfecting 2, 4, 8, 12 and 16 μg per barcode per preparation. NGS analysis of vector mix confirmed presence of the five barcoded populations per capsid.

Mouse Studies

All animal care and experimental procedures were approved by the joint Children's Medical Research Institute (CMRI) and The Children's Hospital at Westmead Animal Care and Ethics Committee. CMRI's established $Fah^{-/-}$/$Rag2^{-/-}$/$Il2rg^{-/-}$ (FRG) mouse colony was used to breed recipient animals. FRG mice were housed in individually ventilated cages with 2-(2-nitro-4-trifluoro-methyAAVC.enzoyl)-1,3-cyclohexanedione (NTBC)-supplemented in drinking water. FRG mice, 6 to 8 weeks old, were engrafted with human hepatocytes (Lonza Group Ltd., Basel, Switzerland) as described previously (Azuma et al., 2007, Nat Biotechnol. 25(8):903-10). Humanised FRG (hFRG) mice were placed on 10% NTBC 1 week prior to transduction with vectors and were maintained on 10% NTBC until harvest.

The vector for injection was made up to a final volume of 150 μL using saline. Mice were randomly selected and transduced by intravenous injection (lateral tail vein) with the indicated vectors at a dose of $1\times10^{10}$ vg/vector for NGS comparison, and at a dose of $2\times10^{11}$ vg/vector for immunohistochemistry. For in vivo IVIg screening, 5 mg or 20 mg of IVIg (Intragam 10, CSL Behring) were injected into hFRG (i.v.) 24 h prior to vector injection. Mice were euthanized by $CO_2$ inhalation 2 weeks after transduction for immunohistochemistry and 1 week after transduction for barcoded Next-Generation Sequencing (NGS) analysis. Hepatocytes for flow cytometry analysis were obtained by collagenase perfusion of the liver (see below).

Isolation of Human Hepatocytes by Collagenase Perfusion

To perfuse mouse liver and obtain single-cell suspension, the inferior vena cava (IVC) was cannulated, and the solutions were pumped with an osmotic minipump (Gilson Minipuls 3) in the following order: 25 mL of Hank's balanced salt solution (−/−) (−/−) (cat #H9394; Sigma), 25 mL of HBSS (–/–) supplemented with 0.5 mM EDTA, 25 ml HBSS (–/–), and 25 mL of HBSS (–/–) supplemented with 5 mM $CaCl_2$), 0.05% wt/vol collagenase IV (Sigma) and 0.01% wt/vol DNase I (Sigma).

Following perfusion, the liver was carefully removed and placed in a Petri dish containing 25 ml of DuAAVC.ecco's modified Eagle's medium (DMEM) supplemented with 10% foetal bovine serum (FBS). The blunt end of a scalpel blade was used to break the liver capsule to release the cells into the medium. After collection, the cells were spun down at 50× g for 3 min at 4° C. The pellet was resuspended in 21 mL of DMEM and passed through a 100-μm nylon cell strainer. Isotonic Percoll (9 mL) (1 part of 10×PBS (–/–) with 9 parts of Percoll; GE Healthcare) was added to the cell suspension to separate live and dead cells. Live cells were pelleted at 650× g for 10 min at 4° C. and the pellet was resuspended in FACS buffer (PBS (–/–) with 5% FBS and 5 mM EDTA). To delineate between mouse liver cells and human hepatocytes, cells were labelled with phycoerythrin (PE)-conjugated anti-human-HLA-ABC (clone W6/32; Invitrogen 12-9983-42; 1:20), biotin-conjugated anti-mouse-H2Kb (clone AF6-88.5, BD Pharmigen 553568; 1:100) and allophycocyanin (APC)-conjugated streptavidin (eBioscience 17-4317-82; 1:500). GFP-positive labelled samples were sorted to a minimal 95% purity using a BD Influx cell sorter. Sorting of the GFP-positive population was included to enrich for murine hepatocytes among non-parenchymal cells, given the hepatocyte-restricted expression of the pLSP1-GFP-WPRE-BGHpA AAV construct. Flow cytometry was performed in the Flow Cytometry Facility, Westmead Institute for Medical Research, Westmead, NSW, Australia. The data were analysed using FlowJo 7.6.1 (Flow®), LLC).

Human AAAVC.umin ELISA

Levels of human cell engraftment in chimeric mice were assessed by measuring presence of human aAAVC.umin on peripheral blood, using the Human AAAVC.umin ELISA Quantitation Kit (Bethyl, cat #E80-129) as previously reported (Azuma et al., 2007, Nat Biotechnol. 25(8):903-10).

Adeno-Associated Virus Transgene Constructs

AAV transgene constructs were cloned using standard molecular biological techniques. All of the vectors used in the study contain AAV2 ITR sequences. The AAV construct pLSP1-eGFP-WPRE-BGHpA, which encodes eGFP under the transcriptional control of a heterologous promoter containing one copy of the SERPINA1 (hAAT) promoter and two copies of the APOE enhancer element, has been previously reported (Dane et al., 2009, Mol Ther, 2009. 17(9): 1548-54). Eighty four (n=84) versions of the pLSP1-eGFP-BC-WPRE-BGHpA construct were produced by cloning n=84 unique 6-nucleotide-long barcodes (BC) downstream of eGFP.

DNA and RNA Isolation

To extract DNA from sorted cells, the cells were resuspended in 200 μL lysis buffer (100 mM Tris-HCl pH 8.5 (Astral Scientific, BioSD8141-450ML), 5 mM EDTA (ThermoFisher), 0.2% (w/v) sodium dodecyl sulphate (Sigma-Aldrich), 200 mM NaCl (Sigma-Aldrich) containing 50 μg/mL of proteinase K (Bioline). Samples were incubated overnight at 56° C. degrees. DNA was extracted using a standard phenol:chloroform protocol using phenol:chloroform:isoamyl alcohol (25:24:1) (Sigma-Aldrich), followed by DNA ethanol precipitation.

RNA from sorted cells was extracted using the Direct-Zol kit (Zymogen Cat #R2062) and treated with TURBO DNase (ThermoFisher, Cat #AM2238). cDNA was synthesised using the SuperScript IV First-Strand Synthesis System, following manufacturer's instructions (ThermoFisher, Cat #18091050).

Cell Culture, Vector Transduction and Heparin Competition Assay

HEK293 cells were validated and provided by ATCC. HuH-7 cells were provided by Dr Jerome Laurence (The University of Sydney). All cells were cultured in DuAAVC.ecco's Modified Eagle Medium (DMEM) (Gibco, 11965-092) supplemented with 10% FBS (Sigma Aldrich, F9423-500 mL, Lot #16K598), 100 Units/mL Penicillin, 100 μg/mL Streptomycin (Sigma Aldrich, P4458) and passaged using TrypLE Express Enzyme (Gibco, 12604-21). For HuH-7 cultures, media were supplemented also with non-essential amino acids (Gibco, 11140-050). All cells were tested for mycoplasma and were mycoplasma-free. For transduction studies, cells were plated into 24-well plates in complete DMEM at $2\times10^5$ cells per well and incubated overnight in a tissue-culture incubator at 37° C./5% $CO_2$. 16 hrs later, the vector stock was diluted in 1 ml of complete DMEM and added to cells (at the indicated vector genome copies per cell (vac/cell). When indicated, serial 2-fold dilutions of intravenous immunoglobulin (IVIg) (Intragam 10, CSL Behring) were mixed with vectors for 1 h at 37° C. prior to cell transduction.

After a 72-h incubation, the cells were harvested using TrypLE Express (Gibco) and analysed for GFP using BD LSRFortessa cell analyser. The data were analysed using FlowJo 7.6.1.

Barcode Amplification, Next-Generation Sequencing and Distribution Analysis

The 150 base pair region surrounding the 6-mer barcode was amplified with Q5 High-Fidelity DNA Polymerase (NEB, Cat #M0491L) using BC_F and BC_R primers (Table 3). Next-generation sequencing library preparations and sequencing using a 2×150 paired-end (PE) configuration were performed by Genewiz (Suzhou, China) using an Illumina MiSeq instrument. A workflow was written in Snakemake (5.6) (Koster et al. 2012 Bioinformatics 28:2520-2522) to process reads and count barcodes. Paired reads were merged using BBMerge and then filtered for reads of the expected length in a second pass through BBDuk, both from BBTools 38.68. The merged, filtered fastq files were passed to a Perl (5.26) script that identified barcodes corresponding to AAV variants.

Immunohistochemical Analysis of Mouse Livers

Mouse livers were fixed with 4% (w/v) paraformaldehyde, cryo-protected in 10-30% (w/v) sucrose before freezing in O.C.T. (Tissue-Tek; Sakura Finetek USA, Torrance, California). Frozen liver sections (5 μm) were permeabilised in –20° C. methanol, then room temperature 0.1% Triton X-100, and then reacted with anti-human GAPDH antibody (Abcam, Cat #ab215227, Clone AF674), and DAPI (Invitrogen, D1306) at 0.08 ng/mL. After immunolabelling, the images were captured and analysed on a Zeiss Axio Imager.M1 using ZEN 2 software. The percentage of transduced human hepatocytes per field of view was determined by counting total human GAPDH-positive cells and eGFP/human GAPDH double-positive cells.

Sanger Sequencing

When specified, clones were Sanger-sequenced at the Garvan Molecular Genetics facility of the Garvan Institute of Medical Research (Darlinghurst, NSW, Australia) with External_Seq_F/R primers (Table 3).

Vector DNA Copy Number Per Cell

Vector copy numbers were measured with primers GFP-qPCR-For/Rev using Droplet Digital (dd)PCR (Bio-Rad, Berkeley, US) with QX200 ddPCR EvaGreen Supermix (Bio-Rad, Cat #1864034) and following manufacturer's instructions. Vector genomes were normalised to human aAAVC.umin copy number using primers human_AAAVC._F/R_ddPCR.

TABLE 3

| Primer sequences | | |
|---|---|---|
| SEQ ID NO | Name | Sequence |
| 40 | Shuffling_Rescue-F | GTCGGAAAGCATATGCCGCG |
| 41 | Shuffling_Rescue-R | GACGTCGCATGCAACTAGTAT |
| 42 | BB_GAR-F | ACTTGTTCACTTTGATGGCGAGG |
| 43 | BB_GAR-R | CTGCACACGACATGACA TCACG |
| 44 | CapRescue-F | CCCTGCAGACAATGCGAGAGAATGAATCAGAATTCAAATATCTGC |
| 45 | CapRescue-R | ATGCATATGGAAACTAGATAAGAAAGAAATACG |
| 46 | pHelperF | CGCATTGTCTGCAGGGAAACAGCATC |
| 47 | pHelperR | TTTCTTTCTTATCTAGTTTCCA TATGCATGTAGATAAGTAGCATGGCGGG |
| 48 | GFP-F1 | TCAAGATCCGCCACAACATC |
| 49 | GFP-R1 | TTCTCGTTGGGGTCTTTGCT |
| 50 | rep-F1 | CTCAACCCGTTTCTGTCGTC |
| 51 | rep-R2 | CACATTGACCAGATCGCAGG |
| 52 | BC_F | GCTGGAGTTCGTGACCGCCG |
| 53 | BC_R | CAACATAGTTAAGAATACCAGTCAATCTTTCACAAATTTTGTAATCCAGAGG |
| 54 | External_5_Seq | TGTGGATTTGGATGACTGC |
| 55 | External_3_Seq | GACCAAAGTTCAACTGAAACG |
| 56 | human_AAAVC._F | TGCTGTCATCTCTTGTGGGCTG |
| 57 | human_AAAVC._R | AACTCATGGGAGCTGCTGGTTC |

Example 2. Generation and Assessment of Novel Capsids

A shuffled DNA library was generated as described in Example 1. Replication-competent virus produced with the library were produced and injected into a hFRG mouse, and 5 rounds of selection were performed as described above to identify sixteen AAV capsid polypeptides: AAVC11.01 (SEQ ID NO:2), AAVC11.02 (SEQ ID NO:3), AAVC11.03 (SEQ ID NO:4), AAVC11.04 (SEQ ID NO:5), AAVC11.05 (SEQ ID NO:6), AAVC11.06 (SEQ ID NO:7), AAVC11.07 (SEQ ID NO:8), AAVC11.8 (SEQ ID NO:9), AAVC11.09 (SEQ ID NO:10), AAVC11.10 (SEQ ID NO:11), AAVC11.11 (SEQ ID NO: 12), AAVC11.12 (SEQ ID NO:13), AAVC11.13 (SEQ ID NO:14), AAVC11.14 (SEQ ID NO:15), AAVC11.15 (SEQ ID NO:16), and AAVC11.16 (SEQ ID NO:17) (Table 4).

Four barcoded AAV transgenes (Liver Specific Promoter (LSP)-GFP-Barcode-WPRE-BGHpA) were packaged into each capsid (AAVC11.01-AAVC11.16 capsid, AAV2, AAV8, LK03 and NP59) to produce vectors. As the yield from AAVC11.03, AAVC11.10 and AAVC11.16 vectors was lower than that of AAV2, these were excluded from further testing. The remaining vectors were co-injected ($1\times10^{10}$ vg/capsid; a total of $1.8\times10^{11}$ vg/capsid) into a hFRG mouse for comparison of function. One week after injection the chimeric liver from the mouse was perfused and human and murine hepatocytes were single cell sorted. DNA and RNA were recovered from the mouse and human populations of hepatocytes and NGS of the barcoded transgene was performed on the DNA and RNA (cDNA).

As shown in FIG. 2, the majority of the novel vectors, including AAVC11.01, AAVC11.04, AAVC11.05, AAVC11.06, AAVC11.07, AAVC11.09, AAVC11.11, AAVC11.12, AAVC11.13 and AAVC11.15, were every effective at entering human hepatocytes and expressing the transgene, and these vectors were selected for further analysis.

AAVC11.01, AAVC11.04, AAVC11.05, AAVC11.06, AAVC11.07, AAVC11.09, AAVC11.11, AAVC11.12, AAVC11.13 and AAVC11.15, as well as AAV2, AAV8, LK03 and NP59, were re-packaged with 5× barcoded transgene/capsid at increasing barcode concentration with the aim of studying the ratio of DNA to RNA conversion. The AAV-DJ vector was also included as a titer control. For each capsid, 5×15 cm HEK293T plates (~20M cells−15 mL media) were independently transfected, processed and titered.

Figure 3:
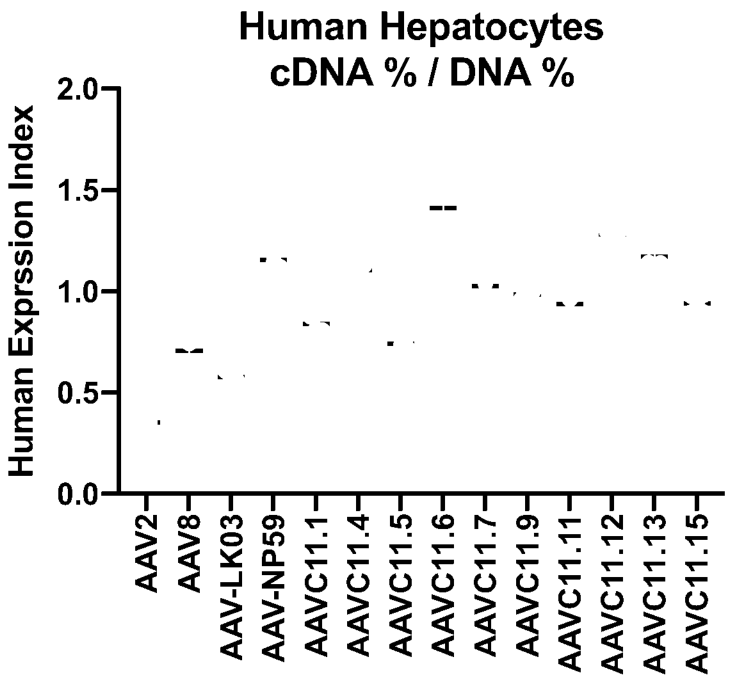
FIG. 3 is a graphical representation of the in vivo transduction of hepatocytes of select AAV vectors. AAVC11.01, AAVC11.04, AAVC11.05, AAVC11.06, AAVC11.07, AAVC11.09, AAVC11.11, AAVC11.12, AAVC11.13 and AAVC11.15, AAV2, AAV8, LK03, NP59, packaged with 5×barcoded transgene/capsid (BC A-E) were mixed at equal ratio ($1\times10^{10}$ vg/capsid) and injected into a single hFRG mouse. Human and murine hepatocytes were isolated and sorted after one week. DNA and RNA was extracted and NGS performed on the DNA and cDNA. The graph shows Human Expression Index (HEXI), representing cDNA reads normalized to DNA reads.

The vectors (excluding AAV-DJ) were then mixed at equal ratio ($1\times10^{10}$ vg/capsid) and injected into a single hFRG mouse. Human and murine hepatocytes were isolated and sorted after one week. DNA and RNA were extracted and NGS performed on the DNA and cDNA. NGS of the pre-injection mix was also performed for validation, and the DNA and RNA (cDNA) reads from hepatocytes were normalized to pre-injection reads. This normalization is expressed as 'Human Entry Index' (HEI), which is a constant for each capsid on a determined experiment and expresses how efficient a given capsid is at physically transducing human hepatocytes in relation to the other capsids included in the experiment. It was observed that regardless of initial barcode concentration, the HEI for each capsid remained constant (data not shown).

cDNA reads were then normalized to DNA reads. This normalization is expressed as 'Human Expression Index' (HEXI), which is a constant for each capsid on a determined experiment and indicated how efficient a given capsid is at functionally transducing human hepatocytes, i.e. converting DNA reads into RNA reads. This is an important property, as some AAV capsids (e.g. AAV2) are relatively efficient at entering the hepatocytes but relatively deficient at functional transduction (i.e. transgene expression). FIG. 3 shows the HEXI for each vector.

The HEI and HEXI were converted into a normalized percentage read to analyze the overall functional transduction power of the tested capsids. This data is shown in FIGS. 4A and B.

It has been observed that the rate of DNA to RNA conversion follows a linear trend, with a slope corresponding to each specific HEXI (RNA/DNA). Non-normalized DNA reads vs non-normalized RNA reads were plotted, where the x-axis extension gives an estimate of how efficient a capsid is at human entry, and the slope gives the approximate ratio of DNA to RNA conversion. When doing such an analysis, it becomes apparent that AAV2 is relatively better than AAV8 at human entry, but AAV8 is relatively better than AAV2 at expression (functional transduction) (data not shown). This analysis was performed with NP59 and AAVC11.04, AAVC11.06, AAVC11.11, AAVC11.12 and AAVC11.13, and demonstrated that each of AAVC11.04, AAVC11.06, AAVC11.11, AAVC11.12 and AAVC11.13 is comparable to NP59, a highly efficient capsid described previously (Paulk et al., 2018, Mol Ther 26:289-303).

Example 3. IVIg Neutralization Resistance

Having identified the most functional AAVC11 variants, their relative in vivo performance in human hepatocytes in the presence of pooled human immunoglobulins was investigated. To do so, following a method recently reported (Cabanes-Creus et al. 2020, Mol Ther Methods Clin Dev, 17:1139-1154), five barcoded AAV-LSP1-eGFP cassettes were packaged at increasing concentrations in the selected AAV variant capsids. AAV2, AAV8, AAV-LK03, and AAV-NP59 were included as controls. Three hFRG animals were passively immunized by intravenous administration of increasing doses of pooled human IgGs 24 h before AAV administration ($1\times10^{10}$ vgs/capsid). A control hFRG animal that received no IVIg was also included (the same animal as used for the study shown in FIG. 3). One week later, human hepatocytes were sorted and the vector copy number per diploid genome determined. An IVIg dose-dependent reduction of vector genomes per cell was observed, leading to a >500-fold difference between the no-IVIg control (hFRG #1=321.25 vc/dc) and the hFRG mouse pre-injected with 20 mg of human immunoglobulin (hFRG #4=0.63 vc/dc). hFRG mice pre-injected with 1 mg (hFRG #2) or 5 mg (hFRG #3) of human immunoglobulin also showed reduced vector genomes (hFRG #2=81.16 vc/dc; hFRG #3=10.62 vc/dc.

The relative performance of the individual AAV variants in the human hepatocytes harvested from hFRG #1 (the no-IVIg control) was then analysed. As shown in FIG. 4, all AAV variants, except for AAVC11.09, transduced hepatocytes with high efficiency compared to benchmark AAV-NP59, as measured at the DNA (cell entry) and RNA/cDNA (transgene expression) levels. Since the percentage of DNA reads ultimately indicates the contribution of each AAV variant to the final vector copy number per cell, it is possible to empirically estimate the IVIg neutralization effect for each capsid (FIG. 4C). The reduction in vector genome copies per capsid was calculated and expressed as a logarithm of the quotient between the IVIg and the no-IVIg control (i.e., a value of −1 indicates a 10-fold reduction on vector genomes/capsid, FIG. 4C). AAV8 was found to be the most resistant to neutralization by human IVIg. Interestingly, in contrast to previous reports (Lisowski et al. 2014, Nature, 506(7488):382-6; Cabanes-Creus et al. 2020, Mol Ther Methods Clin Dev, 17:1139-1154), bioengineered AAV-LK03 and AAV-NP59 (AAV3b- and AAV2-like, respectively) were also strongly neutralized at the IVIg concentrations tested in this in vivo model. All AAVC11 variants presented intermediate resistance between AAV8 and AAV-NP59 at all IVIg doses tested.

As a final validation, the top three performers (AAVC11.06, AAVC11.11, and AAVC11. 12) were injected into individual humanised FRG mice, using AAV-NP59 as a control ($2\times10^{11}$ vgs/hFRG). As shown in FIG. 4D, AAVC11.12 was found to be significantly more functional than the AAV-NP59 control. Based on these results, AAVC11.12 was evaluated further. Because the ability to study vector function in preclinical models can have a substantial influence on its clinical development, the performance of AAVC11.12 in non-engrafted FRG using the same dose as in hFRG studies ($2\times10^{11}$ vector genomes/mouse) was evaluated. It was observed that AAVC11.12 can functionally transduce murine liver cells, although with substantially lower efficiency than the human hepatocytes (data not shown), consistent with the observations shown in FIG. 2 and described in Example 4.

Example 4. Immunohistochemical Analysis

AAVC11.12 and AAVC11.13 were injected into individual hFRG mice at $2\times10^{11}$ vg/mouse. Livers were harvested two weeks after injection and processed for immunohistochemistry. DAPI (blue) was used to stain all cells (murine/human) and an antibody against human GAPDH (hGAPDH, red) was used to stain only human cells. eGFP (green) expressed from the AAV indicated cells that were functionally-transduced with rAAV. It was observed that AAVC11.12 and AAVC11.13 preferentially transduced human hepatocytes (data not shown).

Example 5. Further Assessment of AAVC11.12

Figure 5:
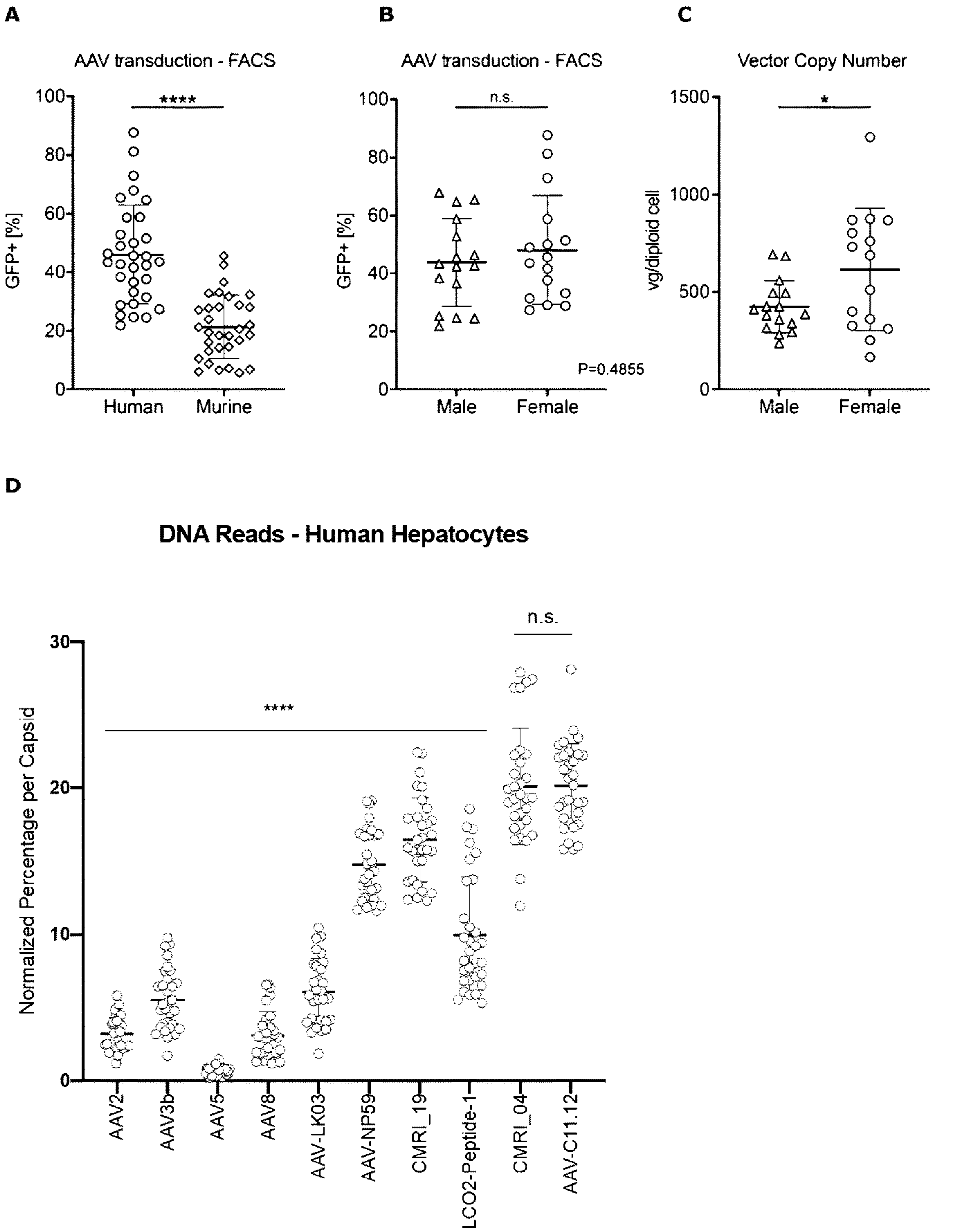
FIG. 5 provides graphical representations of the transduction efficiency of AAV vectors in vivo. An NGS-based comparison of AAVC11.12 and relevant AAV variants in FRG mice engrafted with hepatocytes from different human donors was performed. (A-C) Combined transduction of the barcoded AAV-mix englobing the ten serotypes in N=32 hFRGs (N=31 for vector copy number). Each data point represents an independent mouse. (A) Percentage of GFP+ cells on FAC-sorted human hepatocytes and murine liver cells. (B) Percentage of GFP+ cells on FAC-sorted human hepatocytes engrafted with male and female donors. (C) Vector copy number per diploid human hepatocyte on FAC-sorted human hepatocytes. For (A-C), data are mean±SD. Statistical significance among means was calculated using a paired t-test, an unpaired t-test and an unpaired t-test with Welch's correction, respectively (* P≤0.05, ** P≤0.0001, n.s. P value>0.05). (D) Percentage of NGS reads mapped to each AAV capsid (sum of n=5 barcodes/capsid) in human hepatocytes at the DNA (cell entry, physical transduction) level, normalized to the pre-injection mix, is shown. (E) Percentage of NGS reads mapped to each AAV capsid (sum of n=5 barcodes/capsid) in human hepatocytes at the cDNA (expression, functional transduction) level, normalized to the pre-injection mix, is shown. For (D-E), each data point represents percentage in an independent mouse (N=31 hFRGs analysed for DNA and N=32 for cDNA). Data are mean±SD. Statistical significance among means was calculated using one-way ANOVA, and Dunnett's multiple comparison test was used to compare AAV-SYD12 with all other AAV variants (** P≤0.0001, n.s. P value>0.05). (F) Average percentage of mapped NGS reads per AAV capsid in FAC-sorted human hepatocytes at the DNA (N=31 hFRGs) and cDNA (N=32 hFRGs) level. The expression index is defined as the quotient between average cDNA and DNA percentual reads.

The inventors then investigated whether relative transduction efficiency among AAV variants is dependent on the origin of the engrafted human hepatocytes. To do so, an equimolar mix was produced of barcoded AAVs that, in addition to AAVC11.12, contained prototypical variants (AAV2, AAV3b, AAV5, AAV8), bioengineered variants (AAV-LK03, AAV-NP59, AAV2-N496D (Cabanes-Creus et al. 2020, Mol Ther Methods Clin Dev, 17:1139-1154), AAV2-RC01 as well as the naturally occurring human variant AAV-hu.Lvr02 (Australian provisional patent no. 2020904687 and Cabanes-Creus et al. 2020, Sci Transl Med, 12(560):eaba3312). FRG mice were engrafted with hepatocytes from seventeen different human donors, varying in age, gender, and ethnicity (n=2 hFRGs per donor, n=1 for donor 13 and 16). The level of liver repopulation was assessed by measuring the concentration of human albumin in the blood, with the aim of performing the barcoded NGS-based comparison at mid-levels of engraftment (average of 3.6 mg human albumin/mL blood, which corresponds to a 20-60% level of human engraftment). Although there was an evident variability in the engraftment rate between donors, a positive correlation between the concentration of human albumin and the percentage of human hepatocytes in harvested livers was observed (data not shown). Each animal was injected i.v. with $1\times10^{11}$ vg, which corresponds to a dose of $1\times10^{10}$ vg per capsid variant. One-week post-injection, the chimeric livers were perfused, human GFP positive hepatocytes were sorted, and the vector copy number per cell and the barcode composition for each sample was analysed. It was observed that the AAV vector mix transduces human hepatocytes more efficiently than murine cells, as estimated by the respective GFP positive population in live cells (FIG. 5A). No significant difference in AAV transduction between male and female human donors was found when assessed based on the percentage of GFP+ cells (FIG. 5B), although the vector copy number per diploid cell was found to be marginally higher in female hepatocytes (FIG. 5C, which is in agreement with recently published data from Zou et al. 2020, Mol Ther Methods Clin Dev 18:189-198). The normalized percentages corresponding to the overall share of NGS reads per AAV capsid are shown in FIGS. 5D-F. The relative performance of the AAV vectors analysed appeared unaffected by the source of primary human hepatocytes in this model. More specifically, bioengineered variants AAV-NP59, AAV2-N496D, AAV2-RC01 and AAVC11.12, and the naturally occurring AAV-hu.Lvr02, entered human hepatocytes, as measured at the DNA level, more efficiently than vectors based on prototypical capsids (AAV2/3b/5/8) and bioengineered AAV-LK03 (FIG. 5D). The average physical transduction was higher for AAV-hu.Lvr02 and AAVC11.12, and these differences were significant when compared to the other variants (FIG. 5D). Analysis of the barcoded transgenes at the cDNA level, which estimates the functional performance, revealed substantial differences between individual variants with AAVC11.12 emerging as the most functional variant among the cohort tested (FIG. 5E). To gain a better understanding of relative vector fitness, the relative differences between cell entry (DNA, FIG. 5D) and expression (RNA/cDNA, FIG. 5E) were analysed and indicated an expression index (FIG. 5F). Interestingly, the analysis revealed that while AAVC11.12 had an expression index>1, and thus accounted for a larger fraction of RNA/cDNA reads than DNA reads, the other vectors, especially AAV2, AAV3b, and AAV-hu.Lvr02, lost relative share of reads at the RNA/cDNA level (FIG. 5F), highlighting differences between physical transduction and vector function (transgene expression). Consistent with previous reports, AAV-NP59 functionally transduced human hepatocytes with high efficiency. Of interest, AAV8 also had an expression index>1, suggesting that the relatively inferior performance of this variant in human hepatocytes may be caused by suboptimal cell entry (FIG. 5F).

Example 6. Identification of Additional Capsids

It was observed that the three top capsids based on RNA reads (AAVC11.06, AAVC11.12, AAVC11.13) were part of a phylogenetic cluster. Four additional clones from the same selection that clustered with AAVC11.06, AAVC11.12 and AAVC11.13 were sequenced and named AAVC11.17 (SEQ ID NO:18), AAVC11.18 (SEQ ID NO:19), and AAVC11.19 (SEQ ID NO:20) (Table 5).

Example 7. Phylogenetic Analysis of Capsids

Figure 6:
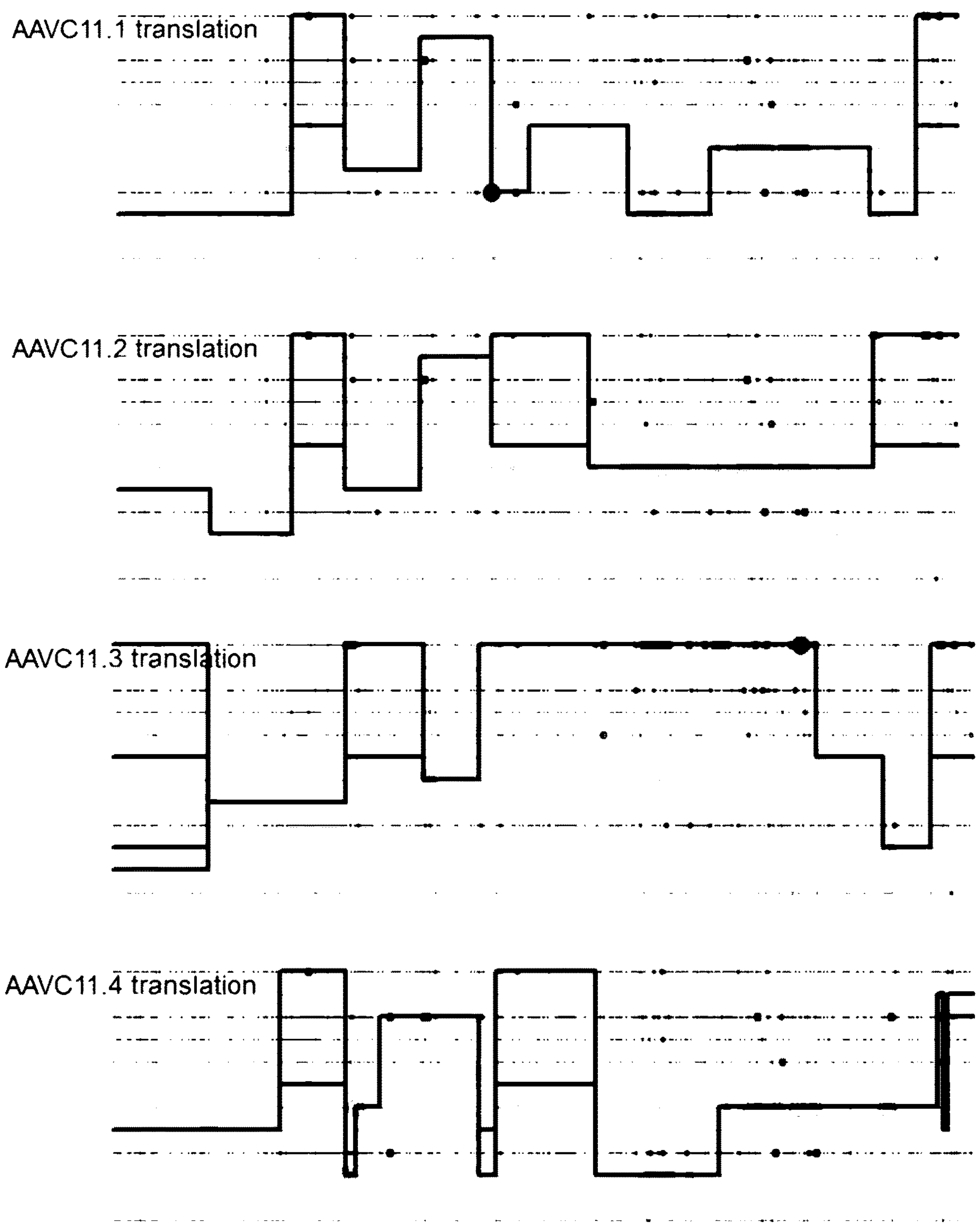
FIG. 6 is a schematic representation of analysis of the parental contribution to the AAV capsid protein sequences. Library parents are depicted as horizontal dotted lines (from top to bottom: AAV1, AAV2, AAV3b, AAV4, AAV5, AAV6, AAV7, AAV8, AAV9, AAV10, AAV11 and AAV12). Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability.
Figure 6:
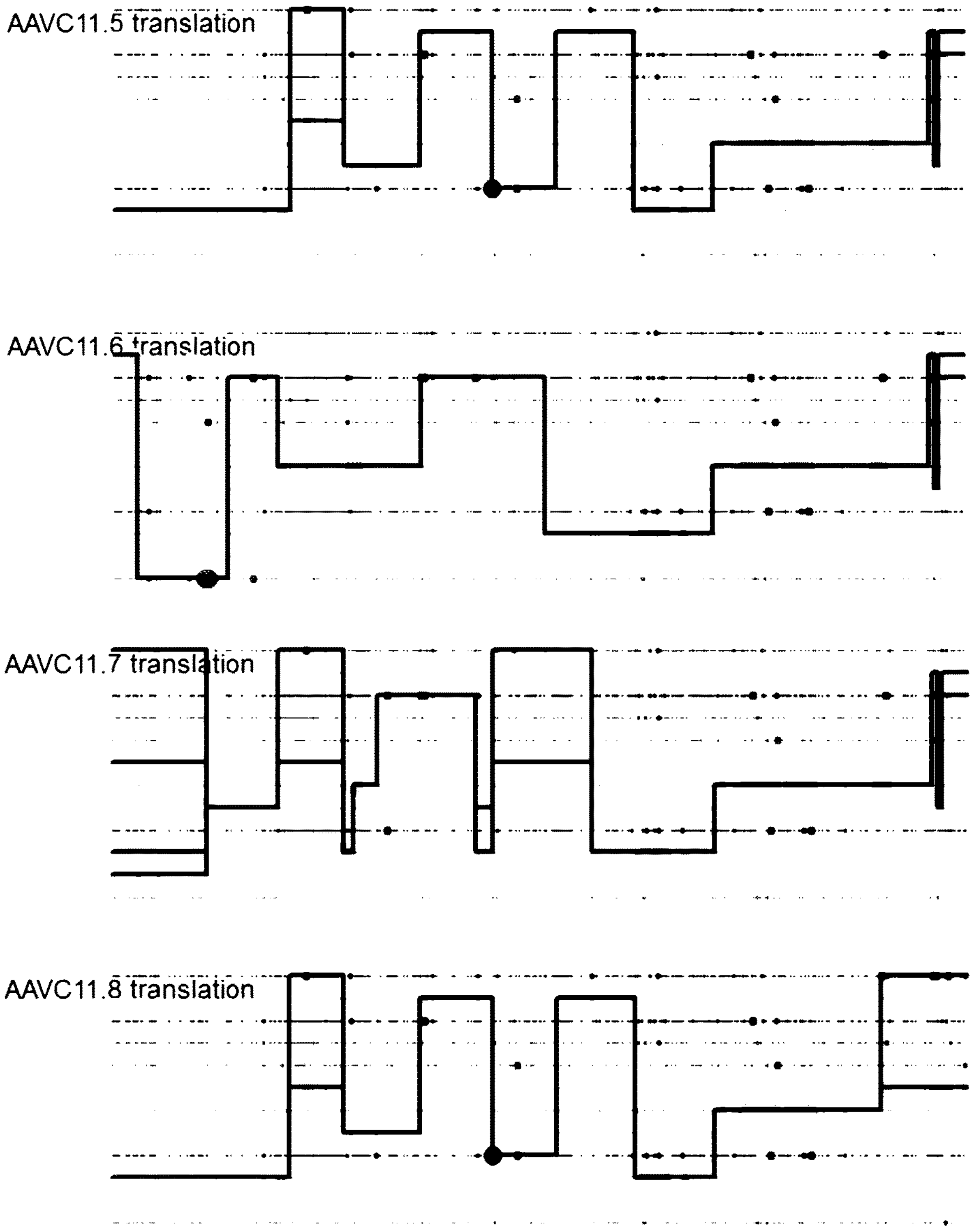
Figure 6:
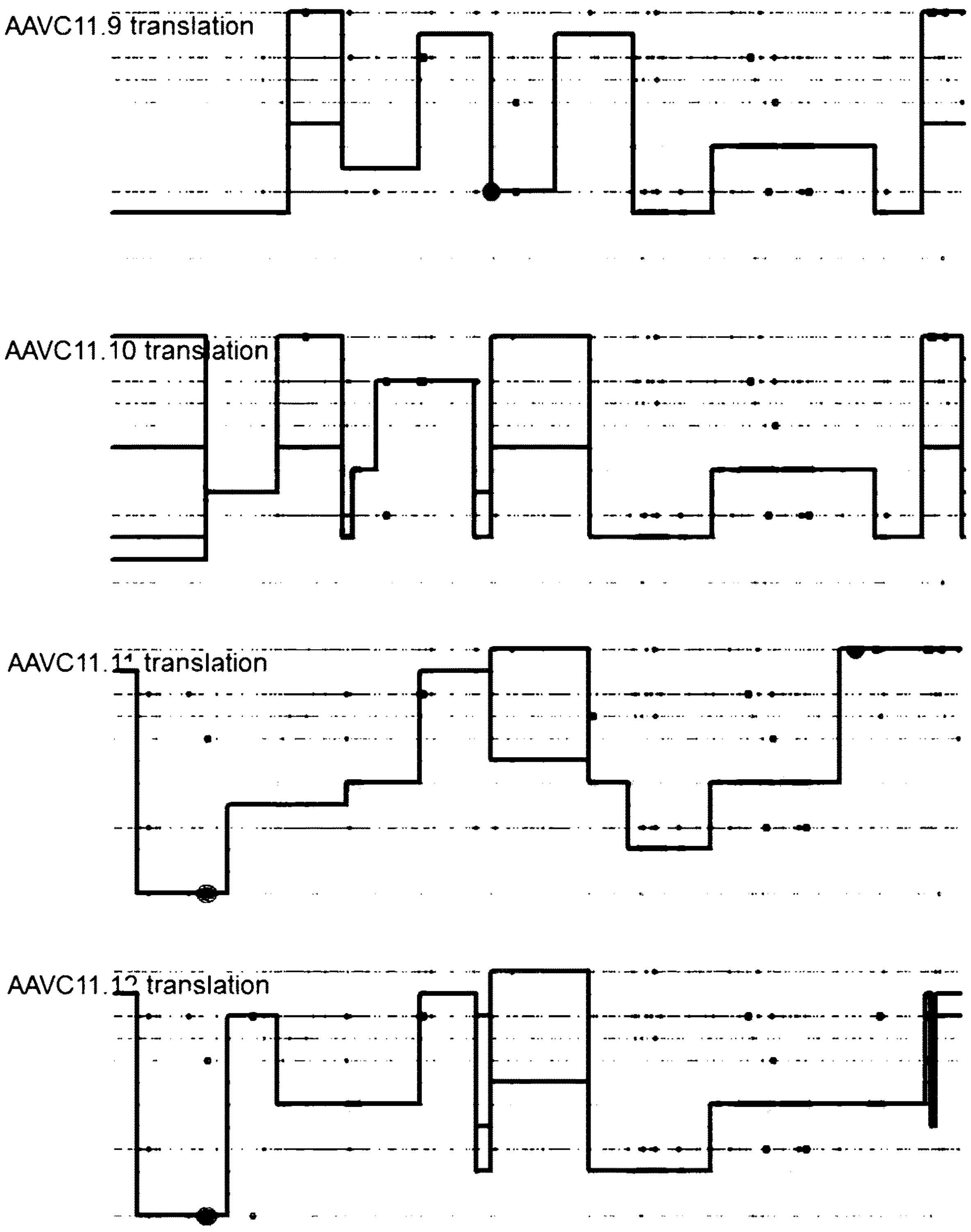
Figure 6:
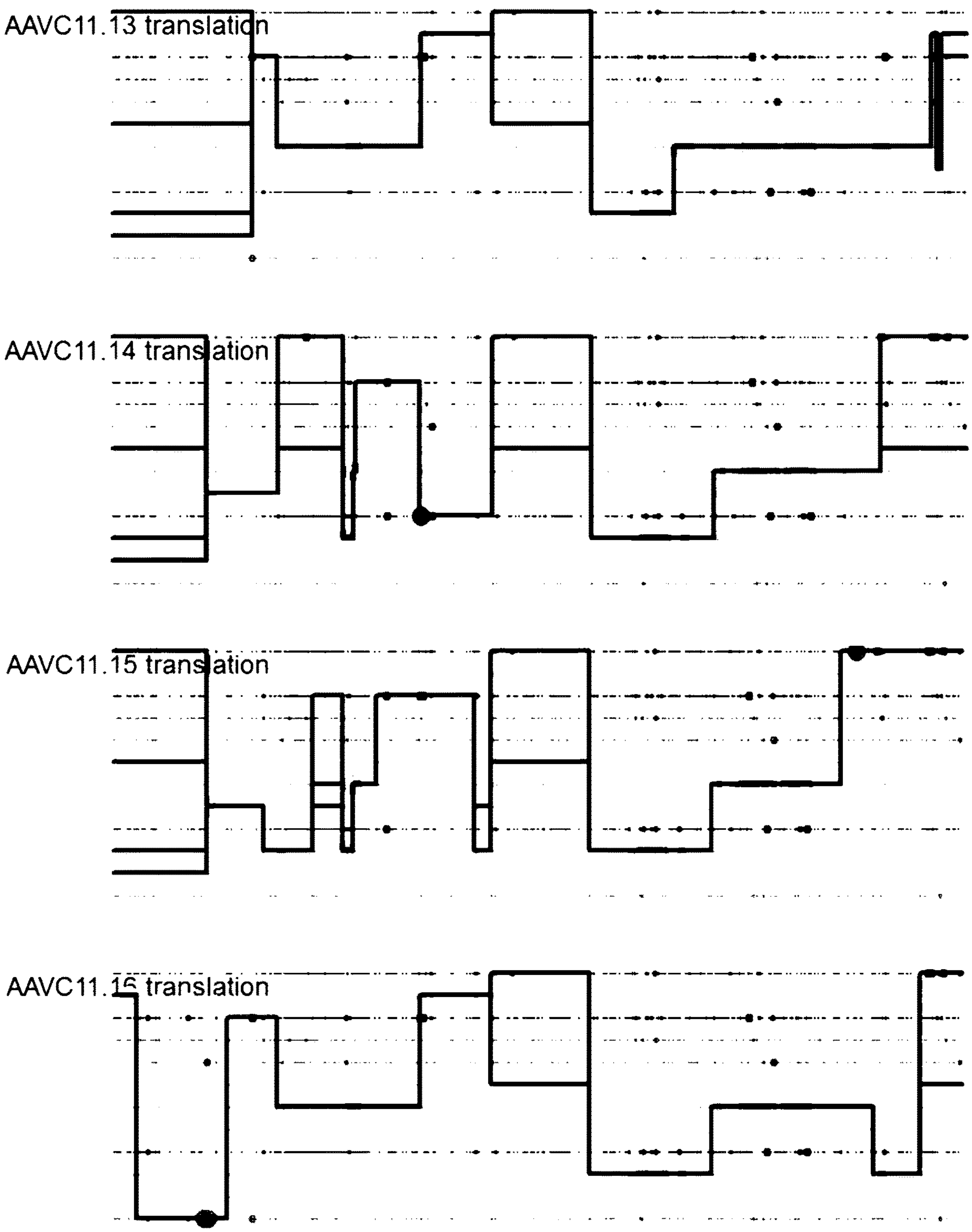
Figure 6:
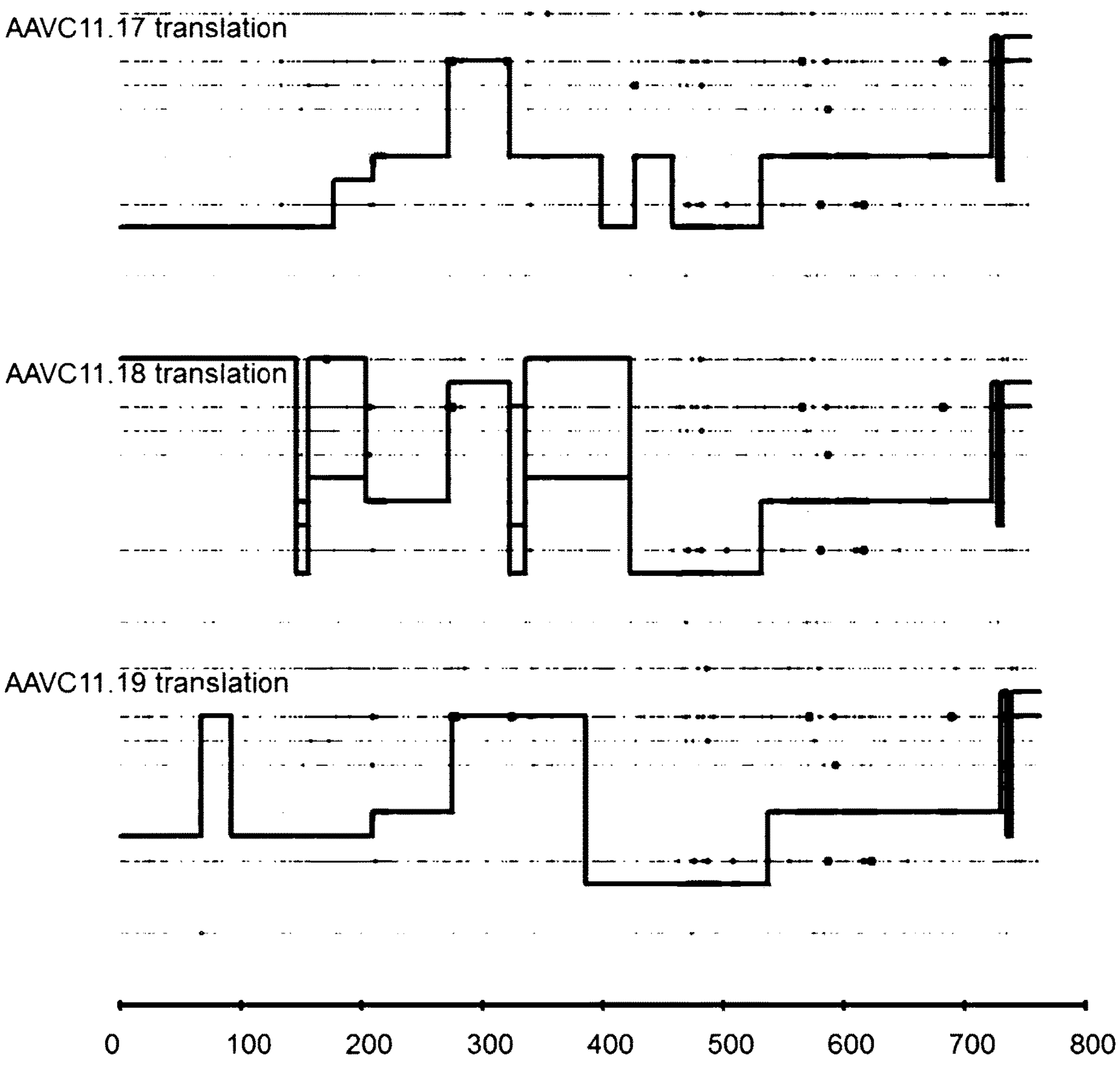

Phylogenetic analysis and analysis of the parental contribution was performed. As shown in FIG. 6, multiple parental capsids contributed to the sequence of each of the new capsids (see FIG. 6A of Australian Provisional Application No. 2020900529 for phylogenetic analysis).

Example 8. In Vivo Functional Comparison of AAVC11.12 to Parental Variants

Figure 7:
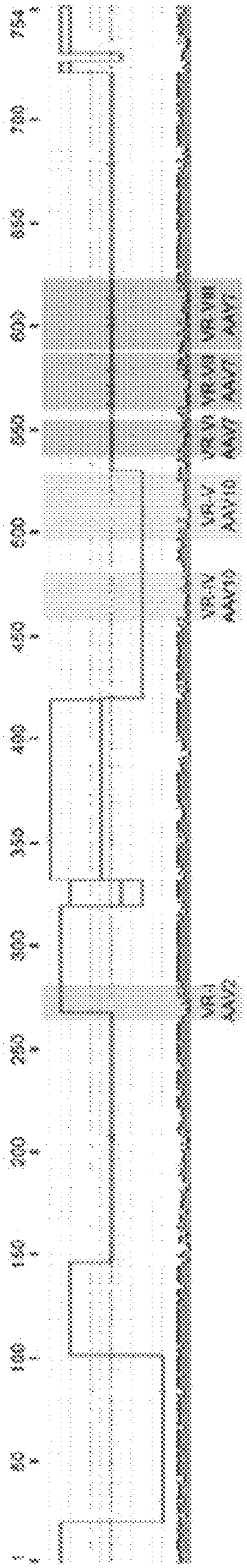
FIG. 7 is a schematic representation of analysis of the parental contribution to the AAVC11.12 capsid protein sequence. The thick solid line represents the most probable parental origin of each region based on the longest sequence of identity to parental variants in a 5' to 3' direction. Parental AAVs are in horizontal dotted lines (AAV1-12, from top to bottom) VR-I and VRs-IV to VIII from AAVC11.12 are shown in blocks with an indication of parental origin (AAV2, AAV10, or AAV7).

Given the substantially superior performance of AAVC11.12 when compared to other liver-tropic vectors, studies to investigate which capsid regions were the main determinants of human hepatocyte tropism in the hFRG model were performed. Due to the fact that AAVC11.12 was selected from a DNA-family shuffled library, it harbours regions of multiple parental variants (AAV1/AAV6, AAV2, AAV3b, AAV7, AAV10, and AAV12) as depicted in detail in FIG. 7. Interestingly, all of the functional AAVC11 variants described herein share high sequence identity and common parental capsid regions for Variable Region (VR) I (AAV2), VRs IV and V (AAV10), and VRs VI to VIII (AAV7), except for AAVC11.13 in which the region from parental AAV7 extended to VR-V (FIGS. 1 and 5B). A barcoded NGS comparison of AAVC11.12 with parental AAV2, AAV7, and AAV10 using two humanised FRG mice was performed. AAV8 was included as a positive control for the transduction of murine cells. As shown in FIG. 8, AAVC11.12 was found to significantly outperform all parental variants at human hepatocyte physical (DNA) and functional (RNA/cDNA) transduction. Of interest, AAVC11.12 was observed to physically transduce the murine liver at an efficiency similar to AAV7, AAV8, and AAV10. However, as observed before, this physical transduction was associated with relatively weak functional transduction of murine cells when compared to the parental variants. These data suggest that the superior function of AAVC11.12 in human hepatocytes results from a unique combination of parental features that in isolation are not sufficient to provide the benefit to any of the parental AAVs.

Figure 9:
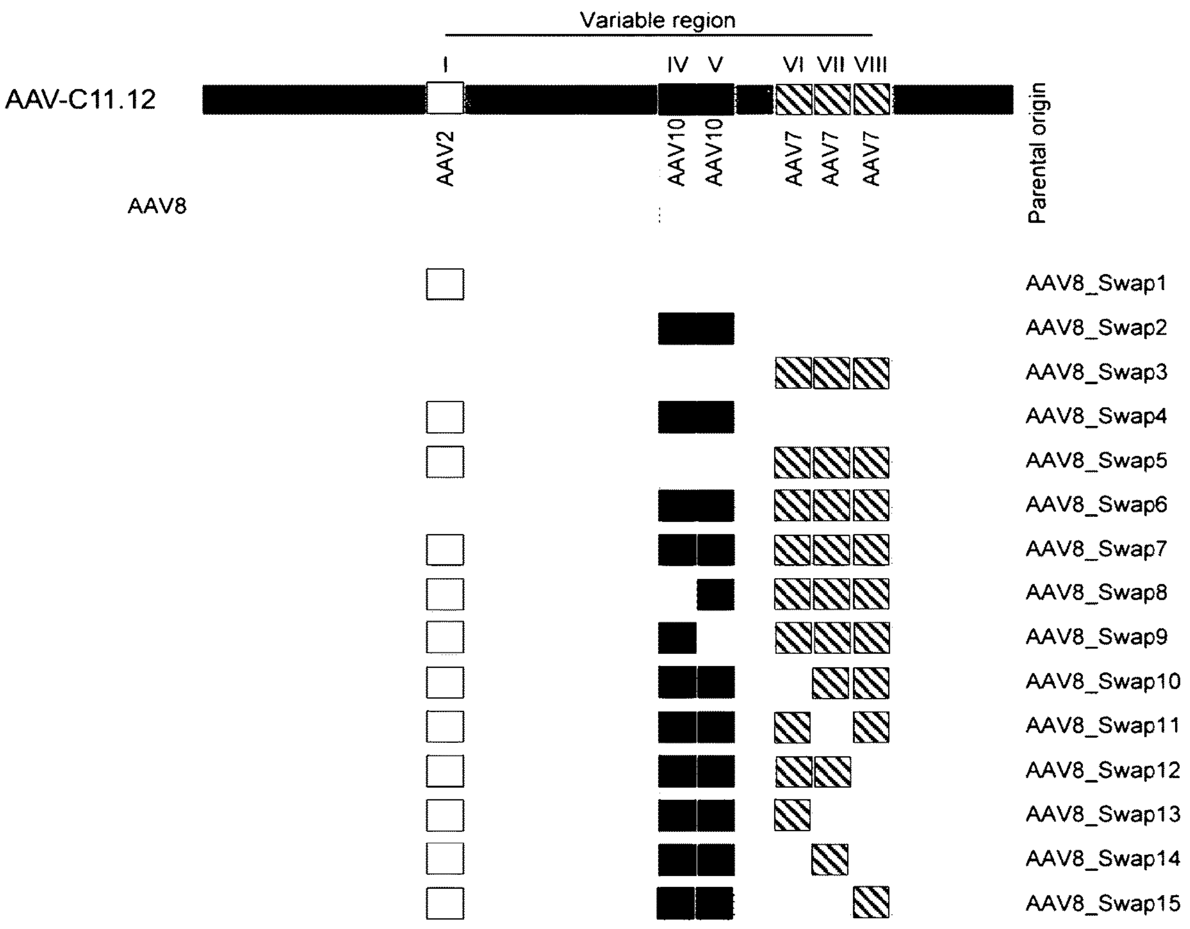
FIG. 9 is a schematic representation of AAV variable regions swapped into the AAV8 capsid scaffold.

Example 9. Identification of Variable Regions Important for Human Hepatocyte Tropism Given the differential performance of AAVC11.12 (SEQ ID NO:13) and AAV8 (SEQ ID NO:64) in human and murine cells and so as to understand which functional capsid domains are responsible for the superior function of AAVC11.12, a series of domain swaps between the two AAV was generated. As schematically shown in FIG. 9, combinations of variables regions I (AAV2 origin), IV-V (AAV10 origin), and VI-VIII (AAV7 origin) from AAVC11.12 were systematically cloned into the AAV8 capsid scaffold. Specific amino acid changes between AAV8 and the swapped variants are shown in Table 4. FIG. 10 provides an alignment between AAVC11.12 (SEQ ID NO:13) and AAV8 (SEQ ID NO:64), also showing the residues from AAVC11.12 that were substituted into AAV8. The amino acid and nucleic acid sequences of the resulting capsid polypeptides (i.e. Swap1-Swap15) are provided in Table 5, below.

TABLE 4

Amino acid changes between AAV8 and the Variable region swaps.

| Changes = 7 | AAV8 | Swap1 | Changes = 45 | AAV8 | Swap9 |
|---|---|---|---|---|---|
| 1 | N263 | del | 1 | N263 | del |
| 2 | G264 | del | 2 | G264 | del |
| 3 | T265 | S | 3 | T265 | S |
| 4 | S266 | Q | 4 | S266 | Q |
| 5 | G267 | S | 5 | G267 | S |
| 6 | T270 | S | 6 | T270 | S |
| 7 | T274 | H | 7 | T274 | H |
| Changes = 16 | AAV8 | Swap2 | 8 | T453 | S |
| 1 | T453 | S | 9 | A458 | Q |
| 2 | A458 | Q | 10 | N459 | G |
| 3 | N459 | G | 11 | T462 | Q |
| 4 | T462 | Q | 12 | G464 | L |
| 5 | G464 | L | 13 | G468 | A |
| 6 | G468 | A | 14 | N471 | A |
| 7 | N471 | A | 15 | T472 | N |
| 8 | T472 | N | 16 | A474 | S |
| 9 | A474 | S | 17 | N475 | A |
| 10 | N475 | A | 18 | E534 | D |
| 11 | T495 | L | 19 | N540 | S |
| 12 | G496 | S | 20 | I542 | V |
| 13 | A507 | G | 21 | Q548 | T |
| 14 | G508 | A | 22 | N549 | G |
| 15 | A520 | V | 23 | A551 | T |
| 16 | I524 | V | 24 | R552 | del |
| Changes = 28 | AAV8 | Swap3 | 25 | D553 | N |
| 1 | E534 | D | 26 | N554 | K |
| 2 | N540 | S | 27 | A555 | T |
| 3 | I542 | V | 28 | D556 | T |
| 4 | Q548 | T | 29 | Y557 | L |
| 5 | N549 | G | 30 | S558 | E |
| 6 | A551 | T | 31 | D559 | N |
| 7 | R552 | del | 32 | M561 | L |
| 8 | D553 | N | 33 | L562 | M |
| 9 | N554 | K | 34 | S564 | N |
| 10 | A555 | T | 35 | K569 | R |
| 11 | D556 | T | 36 | T570 | P |
| 12 | Y557 | L | 37 | A583 | S |
| 13 | S558 | E | 38 | D584 | S |
| 14 | D559 | N | 39 | Q588 | A |
| 15 | M561 | L | 40 | Q589 | A |
| 16 | L562 | M | 41 | P593 | A |
| 17 | S564 | N | 42 | I595 | T |
| 18 | K569 | R | 43 | G596 | Q |
| 19 | T570 | P | 44 | T597 | V |
| 20 | A583 | S | 45 | S600 | N |
| 21 | D584 | S | Changes = 48 | AAV8 | Swap10 |
| 22 | Q588 | A | 1 | N263 | del |
| 23 | Q589 | A | 2 | G264 | del |
| 24 | P593 | A | 3 | T265 | S |
| 25 | I595 | T | 4 | S266 | Q |
| 26 | G596 | Q | 5 | G267 | S |
| 27 | T597 | V | 6 | T270 | S |
| 28 | S600 | N | 7 | T274 | H |
| Changes = 23 | AAV8 | Swap4 | 8 | T453 | S |
| 1 | N263 | del | 9 | A458 | Q |
| 2 | G264 | del | 10 | N459 | G |
| 3 | T265 | S | 11 | T462 | Q |
| 4 | S266 | Q | 12 | G464 | L |
| 5 | G267 | S | 13 | G468 | A |
| 6 | T270 | S | 14 | N471 | A |
| 7 | T274 | H | 15 | T472 | N |
| 8 | T453 | S | 16 | A474 | S |
| 9 | A458 | Q | 17 | N475 | A |
| 10 | N459 | G | 18 | T495 | L |
| 11 | T462 | Q | 19 | G496 | S |
| 12 | G464 | L | 20 | A507 | G |
| 13 | G468 | A | 21 | G508 | A |
| 14 | N471 | A | 22 | A520 | V |
| 15 | T472 | N | 23 | I524 | V |
| 16 | A474 | S | 24 | Q548 | T |
| 17 | N475 | A | 25 | N549 | G |
| 18 | T495 | L | 26 | A551 | T |
| 19 | G496 | S | 27 | R552 | del |
| 20 | A507 | G | 28 | D553 | N |
| 21 | G508 | A | 29 | N554 | K |
| 22 | A520 | V | 30 | A555 | T |
| 23 | I524 | V | 31 | D556 | T |

TABLE 4-continued

Amino acid changes between AAV8 and the Variable region swaps.

| Changes = 35 | AAV8 | Swap5 | 32 | Y557 | L |
|---|---|---|---|---|---|
| 1 | N263 | del | 33 | S558 | E |
| 2 | G264 | del | 34 | D559 | N |
| 3 | T265 | S | 35 | M561 | L |
| 4 | S266 | Q | 36 | L562 | M |
| 5 | G267 | S | 37 | S564 | N |
| 6 | T270 | S | 38 | K569 | R |
| 7 | T274 | H | 39 | T570 | P |
| 8 | E534 | D | 40 | A583 | S |
| 9 | N540 | S | 41 | D584 | S |
| 10 | I542 | V | 42 | Q588 | A |
| 11 | Q548 | T | 43 | Q589 | A |
| 12 | N549 | G | 44 | P593 | A |
| 13 | A551 | T | 45 | I595 | T |
| 14 | R552 | del | 46 | G596 | Q |
| 15 | D553 | N | 47 | T597 | V |
| 16 | N554 | K | 48 | S600 | N |
| 17 | A555 | T | Changes = 35 | AAV8 | Swap11 |
| 18 | D556 | T | 1 | N263 | del |
| 19 | Y557 | L | 2 | G264 | del |
| 20 | S558 | E | 3 | T265 | S |
| 21 | D559 | N | 4 | S266 | Q |
| 22 | M561 | L | 5 | G267 | S |
| 23 | L562 | M | 6 | T270 | S |
| 24 | S564 | N | 7 | T274 | H |
| 25 | K569 | R | 8 | T453 | S |
| 26 | T570 | P | 9 | A458 | Q |
| 27 | A583 | S | 10 | N459 | G |
| 28 | D584 | S | 11 | T462 | Q |
| 29 | Q588 | A | 12 | G464 | L |
| 30 | Q589 | A | 13 | G468 | A |
| 31 | P593 | A | 14 | N471 | A |
| 32 | I595 | T | 15 | T472 | N |
| 33 | G596 | Q | 16 | A474 | S |
| 34 | T597 | V | 17 | N475 | A |
| Changes = 44 | AAV8 | Swap6 | 18 | T495 | L |
| 1 | T453 | S | 19 | G496 | S |
| 2 | A458 | Q | 20 | A507 | G |
| 3 | N459 | G | 21 | G508 | A |
| 4 | T462 | Q | 22 | A520 | V |
| 5 | G464 | L | 23 | I524 | V |
| 6 | G468 | A | 24 | E534 | D |
| 7 | N471 | A | 25 | N540 | S |
| 8 | T472 | N | 26 | I542 | V |
| 9 | A474 | S | 27 | A583 | S |
| 10 | N475 | A | 28 | D584 | S |
| 11 | T495 | L | 29 | Q588 | A |
| 12 | G496 | S | 30 | Q589 | A |
| 13 | A507 | G | 31 | P593 | A |
| 14 | G508 | A | 32 | I595 | T |
| 15 | A520 | V | 33 | G596 | Q |
| 16 | I524 | V | 34 | T597 | V |
| 17 | E534 | D | 35 | S600 | N |
| 18 | N540 | S | Changes = 42 | AAV8 | Swap12 |
| 19 | I542 | V | 1 | N263 | del |
| 20 | Q548 | T | 2 | G264 | del |
| 21 | N549 | G | 3 | T265 | S |
| 22 | A551 | T | 4 | S266 | Q |
| 23 | R552 | del | 5 | G267 | S |
| 24 | D553 | N | 6 | T270 | S |
| 25 | N554 | K | 7 | T274 | H |
| 26 | A555 | T | 8 | T453 | S |
| 27 | D556 | T | 9 | A458 | Q |
| 28 | Y557 | L | 10 | N459 | G |
| 29 | S558 | E | 11 | T462 | Q |
| 30 | D559 | N | 12 | G464 | L |
| 31 | M561 | L | 13 | G468 | A |
| 32 | L562 | M | 14 | N471 | A |
| 33 | S564 | N | 15 | T472 | N |
| 34 | K569 | R | 16 | A474 | S |
| 35 | T570 | P | 17 | N475 | A |
| 36 | A583 | S | 18 | T495 | L |
| 37 | D584 | S | 19 | G496 | S |
| 38 | Q588 | A | 20 | A507 | G |
| 39 | Q589 | A | 21 | G508 | A |
| 40 | P593 | A | 22 | A520 | V |
| 41 | I595 | T | 23 | I524 | V |
| 42 | G596 | Q | 24 | E534 | D |

TABLE 4-continued

Amino acid changes between AAV8 and the Variable region swaps.

| | | | | | |
|---|---|---|---|---|---|
| 43 | T597 | V | 25 | N540 | S |
| 44 | S600 | N | 26 | 1542 | V |
| Changes = 51 | AAV8 | Swap7 | 27 | 0548 | T |
| 1 | N263 | del | 28 | N549 | G |
| 2 | G264 | del | 29 | A551 | T |
| 3 | T265 | S | 30 | R552 | del |
| 4 | S266 | Q | 31 | D553 | N |
| 5 | G267 | S | 32 | N554 | K |
| 6 | T270 | S | 33 | A555 | T |
| 7 | T274 | H | 34 | D556 | T |
| 8 | T453 | S | 35 | Y557 | L |
| 9 | A458 | Q | 36 | S558 | E |
| 10 | N459 | G | 37 | D559 | N |
| 11 | T462 | Q | 38 | M561 | L |
| 12 | G464 | L | 39 | L562 | M |
| 13 | G468 | A | 40 | S564 | N |
| 14 | N471 | A | 41 | K569 | R |
| 15 | T472 | N | 42 | T570 | P |
| 16 | A474 | S | Changes = 26 | AAV8 | Swap13 |
| 17 | N475 | A | 1 | N263 | del |
| 18 | T495 | L | 2 | G264 | del |
| 19 | G496 | S | 3 | T265 | S |
| 20 | A507 | G | 4 | S266 | Q |
| 21 | G508 | A | 5 | G267 | S |
| 22 | A520 | V | 6 | T270 | S |
| 23 | 1524 | V | 7 | T274 | H |
| 24 | E534 | D | 8 | T453 | S |
| 25 | N540 | S | 9 | A458 | Q |
| 26 | I542 | V | 10 | N459 | G |
| 27 | Q548 | T | 11 | T462 | Q |
| 28 | N549 | G | 12 | G464 | L |
| 29 | A551 | T | 13 | G468 | A |
| 30 | R552 | del | 14 | N471 | A |
| 31 | D553 | N | 15 | T472 | N |
| 32 | N554 | K | 16 | A474 | S |
| 33 | A555 | T | 17 | N475 | A |
| 34 | D556 | T | 18 | T495 | L |
| 35 | Y557 | L | 19 | G496 | S |
| 36 | S558 | E | 20 | A507 | G |
| 37 | D559 | N | 21 | G508 | A |
| 38 | M561 | L | 22 | A520 | V |
| 39 | L562 | M | 23 | I524 | V |
| 40 | S564 | N | 24 | E534 | D |
| 41 | K569 | R | 25 | N540 | S |
| 42 | T570 | P | 26 | 1542 | V |
| 43 | A583 | S | Changes = 39 | AAV8 | Swap14 |
| 44 | D584 | S | 1 | N263 | del |
| 45 | Q588 | A | 2 | G264 | del |
| 46 | Q589 | A | 3 | T265 | S |
| 47 | P593 | A | 4 | S266 | Q |
| 48 | I595 | T | 5 | G267 | S |
| 49 | G596 | Q | 6 | T270 | S |
| 50 | T597 | V | 7 | T274 | H |
| 51 | S600 | N | 8 | T453 | S |
| Changes = 41 | AAV8 | Swap8 | 9 | A458 | Q |
| 1 | N263 | del | 10 | N459 | G |
| 2 | G264 | del | 11 | T462 | Q |
| 3 | T265 | S | 12 | G464 | L |
| 4 | S266 | Q | 13 | G468 | A |
| 5 | G267 | S | 14 | N471 | A |
| 6 | T270 | S | 15 | T472 | N |
| 7 | T274 | H | 16 | A474 | S |
| 8 | T495 | L | 17 | N475 | A |
| 9 | G496 | S | 18 | T495 | L |
| 10 | A507 | G | 19 | G496 | S |
| 11 | G508 | A | 20 | A507 | G |
| 12 | A520 | V | 21 | G508 | A |
| 13 | I524 | V | 22 | A520 | V |
| 14 | E534 | D | 23 | I524 | V |
| 15 | N540 | S | 24 | Q548 | T |
| 16 | I542 | V | 25 | N549 | G |
| 17 | Q548 | T | 26 | A551 | T |
| 18 | N549 | G | 27 | R552 | del |
| 19 | A551 | T | 28 | D553 | N |
| 20 | R552 | del | 29 | N554 | K |
| 21 | D553 | N | 30 | A555 | T |
| 22 | N554 | K | 31 | D556 | T |
| 23 | A555 | T | 32 | Y557 | L |

TABLE 4-continued

Amino acid changes between AAV8 and the Variable region swaps.

| | | | | | |
|---|---|---|---|---|---|
| 24 | D556 | T | 33 | S558 | E |
| 25 | Y557 | L | 34 | D559 | N |
| 26 | S558 | E | 35 | M561 | L |
| 27 | D559 | N | 36 | L562 | M |
| 28 | M561 | L | 37 | S564 | N |
| 29 | L562 | M | 38 | K569 | R |
| 30 | S564 | N | 39 | T570 | P |
| 31 | K569 | R | Changes = 32 | AAV8 | Swap15 |
| 32 | T570 | P | 1 | N263 | del |
| 33 | A583 | S | 2 | G264 | del |
| 34 | D584 | S | 3 | T265 | S |
| 35 | Q588 | A | 4 | S266 | Q |
| 36 | Q589 | A | 5 | G267 | S |
| 37 | P593 | A | 6 | T270 | S |
| 38 | I595 | T | 7 | T274 | H |
| 39 | G596 | Q | 8 | T453 | S |
| 40 | T597 | V | 9 | A458 | Q |
| 41 | S600 | N | 10 | N459 | G |
| | | | 11 | T462 | Q |
| | | | 12 | G464 | L |
| | | | 13 | G468 | A |
| | | | 14 | N471 | A |
| | | | 15 | T472 | N |
| | | | 16 | A474 | S |
| | | | 17 | N475 | A |
| | | | 18 | T495 | L |
| | | | 19 | G496 | S |
| | | | 20 | A507 | G |
| | | | 21 | G508 | A |
| | | | 22 | A520 | V |
| | | | 23 | I524 | V |
| | | | 24 | A583 | S |
| | | | 25 | D584 | S |
| | | | 26 | Q588 | A |
| | | | 27 | Q589 | A |
| | | | 28 | P593 | A |
| | | | 29 | I595 | T |
| | | | 30 | G596 | Q |
| | | | 31 | T597 | V |
| | | | 32 | S600 | N |

Figure 11:
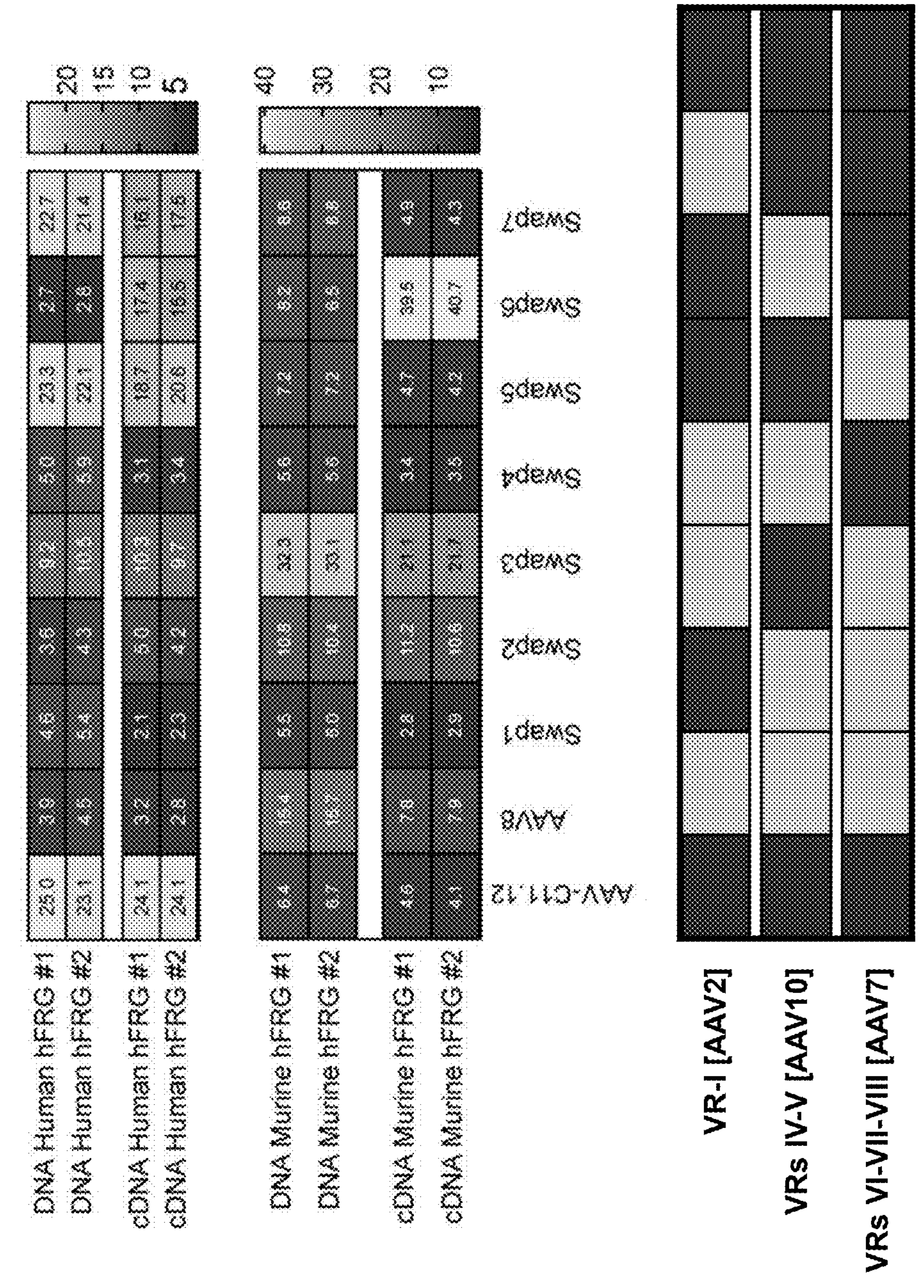
FIG. 11 is a representation of the in vivo performance of AAVC11.12, AAV8 and Swaps 1-7 in hFRG mice (N=2). The percentage of NGS reads mapped to each AAV capsid (sum of n=5 barcodes/capsid) in human hepatocytes and in the murine liver at the DNA (cell entry, physical transduction) and cDNA (expression, functional transduction) level, normalized to the pre-injection mix, is shown. Variable region origin for each capsid is shown for reference in the bottom panel, with variable regions of AAVC11.12 origin in dark grey and variable regions of AAV8 origin in light grey.

Two independent barcoded-AAV NGS comparisons among these variants were then performed. In the first experiment (N=2 hFRGs, hFRG #1 and #2), AAVC11.12 and AAV8 were included as controls, as well as AAV8-Swaps1-7. As shown in FIG. 11, the introduction of AAV2's VR-I and AAV7's VR-VI to VR-VIII was sufficient to significantly enhance the performance of AAV8 in human hepatocytes (AAV8-Swap-5, FIG. 11). In contrast, VRs IV-V from AAV10 appeared not to have any substantial effect on the transduction of human cells (compare Swap-5 and Swap-7, FIG. 10). AAV8-Swap6, which maintained AAV8's VR-I origin, displayed a lower human entry performance as AAV8, although the substantial read share increase on the cDNA population suggests an outstanding performance at DNA to RNA conversion (FIG. 11). The phenotype of AAV8-Swap6 was even more pronounced in murine hepatocytes (FIG. 11). In these cells, the inclusion of VRs VI-VIII from AAV7 enhanced entry and expression of AAV8 (AAV8-Swap3, FIG. 11).

Figure 12:
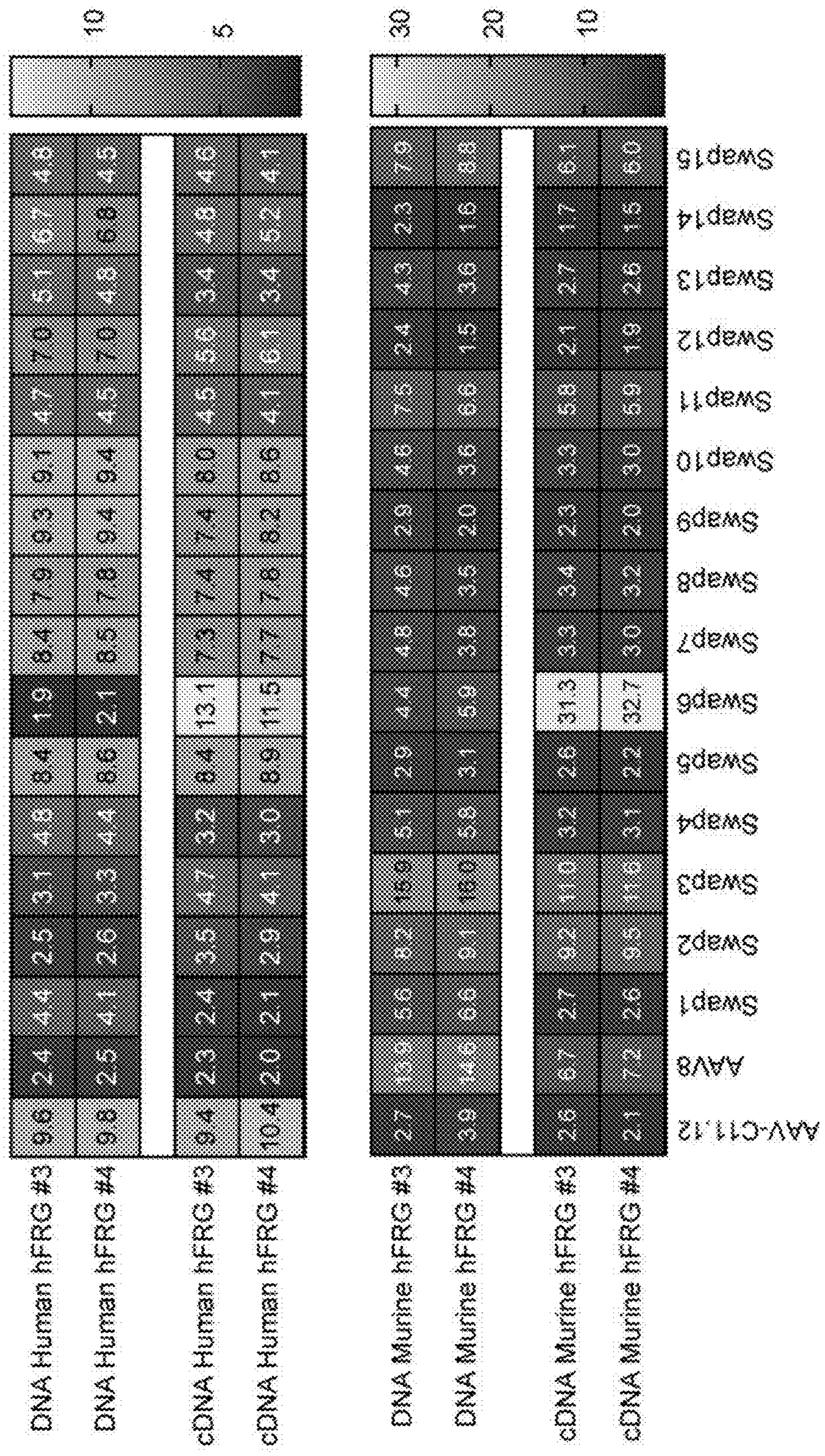
FIG. 12 is a representation of the in vivo performance of AAVC11.12, AAV8 and Swaps 1-15 in hFRG mice (N=2). The percentage of NGS reads mapped to each AAV capsid (sum of n=5 barcodes/capsid) in human hepatocytes and in the murine liver at the DNA (cell entry, physical transduction) and cDNA (expression, functional transduction) level, normalized to the pre-injection mix, is shown. Variable region origin for each capsid is shown for reference in the bottom panel, with variable regions of AAVC11.12 origin in dark grey and variable regions of AAV8 origin in light grey.

In the second comparison (N=2 hFRGs, hFRGs #3 and #4, FIG. 12), the inventors extended the barcoded-AAV to include fifteen AAV8 swaps. The same relative trend was confirmed as in study #1 for Swap5, Swap6, and Swap7. Additionally, the analysis of results from systematic reversion of variable regions back to AAV8 (Swap8 to Swap15) suggested that VR-VI (AAV7's origin) was not essential for enhancing human performance (compare Swap7 and Swap10). In contrast, the reversion of VR-VII and VR-VIII affected both entry and expression in human cells. Regarding the murine sample, the highly efficient DNA to RNA transcription for AAV8-Swap6 was confirmed in this larger comparison pool.

To validate these results, a multiplexed immunofluorescence comparison of AAV8+Swap5 and AAV8+Swap6 was performed in two independent hFRGs. Briefly, to allow visualisation of transduction patterns of two AAVs in the same animal, two AAV cassettes expressing the Cerulean or the Venus fluorescent reporters under the control of a liver-specific promoter were cloned. $1\times10^{11}$ vg of AAV8-Cerulean with Swap5-Venus was mixed with AAV8-Cerulean with Swap6-Venus and injected into two independent hFRG mice. The immunofluorescence experiments confirmed the NGS results, with Swap5 transducing human hepatocytes substantially better than AAV8, and Swap6 displaying poor cell entry and strong expression in both human and murine hepatocytes (data not shown).

Figure 13:
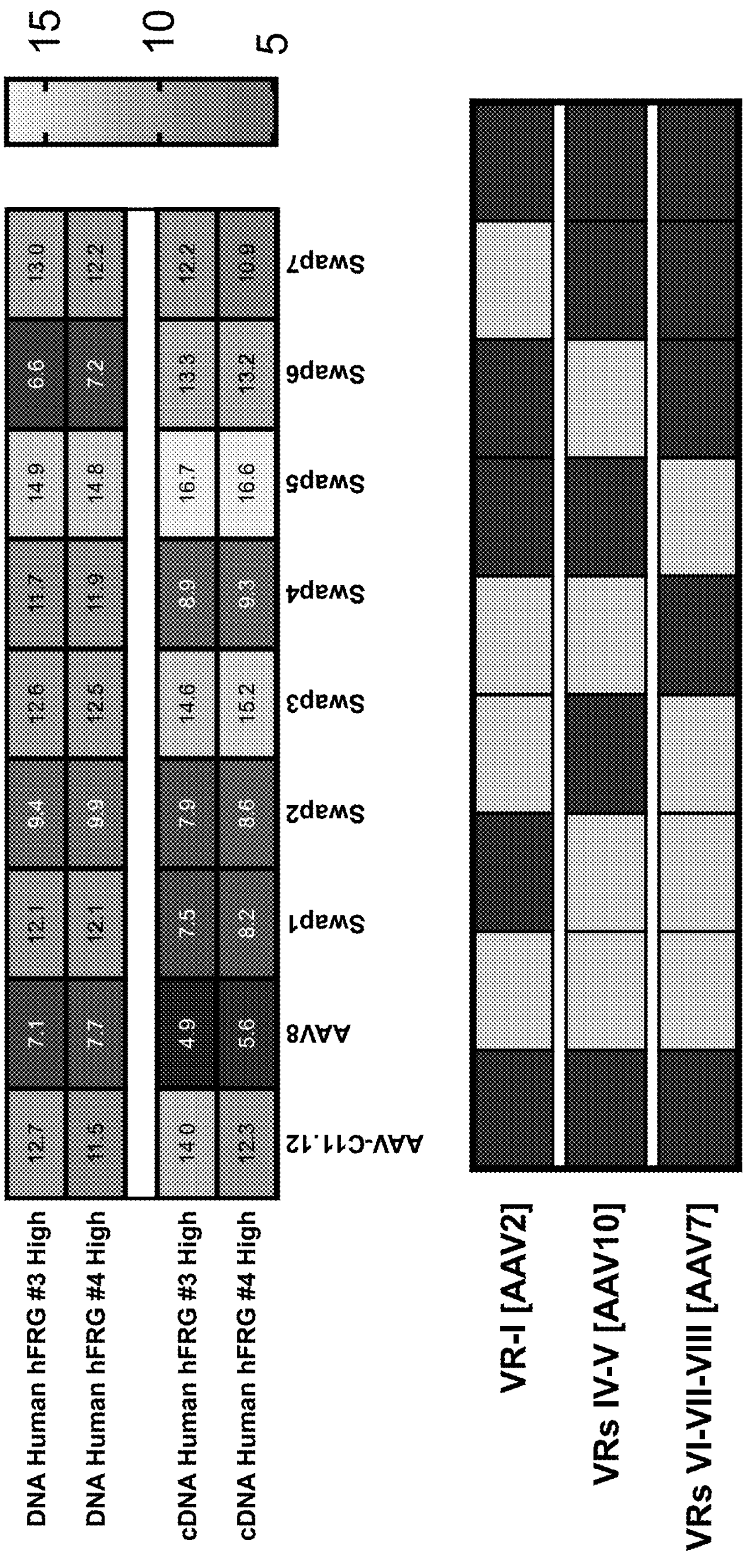
FIG. 13 is a representation of the in vivo performance of AAVC11.12, AAV8 and Swaps 1-7 in highly engrafted hFRG mice (N=2). The percentage of NGS reads mapped to each AAV capsid (sum of n=5 barcodes/capsid) in human hepatocytes at the DNA (cell entry, physical transduction) and cDNA (expression, functional transduction) level, normalized to the pre-injection mix, is shown. Variable region origin for each capsid is shown for reference in the bottom panel, with variable regions of AAVC11.12 origin in dark grey and variable regions of AAV8 origin in light grey.

In a further validation of the results, the same barcoded mix from the first experiment (i.e. AAVC11.12 and AAV8, as well as AAV8-Swaps1-7) was injected in two highly engrafted mice. The highly engrafted mice had an average of 11 mg human albumin per mL blood, compared to the "low engraftment" mice from the previous experiments, which had an average of 1.8 mg human albumin per mL blood. The relative NGS reads mapped to each capsid were analyzed as previously for DNA and cDNA populations. As shown in FIG. 13, the overall trend was similar to that observed with the low engraftment mice, although the percentages flattened. This might reflect an increase in vector availability for AAV8, Swap3 and Swap6, which each contain VR-I from AAV8. The VR-I from AAV8 appears to impart a preference for murine hepatocytes, such that when murine hepatocytes are present, a portion of the vectors enter murine hepatocytes rather than human hepatocytes. When fewer murine hepatocytes are present, such as in the high engraftment mice, there is greater observed entry of these vectors into the human hepatocytes.

In summary, it appears that VR-VII (in particular) and VR-VIII, both from AAV7, alone or in combination, are important for efficient transduction of human hepatocytes (as evidenced by the reduction in transduction for Swap11 and Swap12 compared to Swap7). Conversely, it appears that VR-VI (also from AAV7) is dispensable for improving AAV8 performance in humans (see Swap5 compared to Swap10). VR-I, which is from AAV2, may be important for entry of human hepatocytes, such that the combination of the AAVC11.12 VR-I and VR-VII and/or VR-VIII appears to impart good entry of human hepatocytes and also good expression. In contrast, the combination present in Swap6, i.e. VR-I from AAV8, VR-IV and V from AAV10, and VR-VI, VR-VII and VR-VIII from AAV7, appears to impart much poorer entry into human hepatocytes but strong expression nonetheless, a phenotype that may have some advantages in the context of gene therapy (e.g. comparable expression with less physical transduction, potentially lessening concerns around DNA integration).

TABLE 5

Capsid Sequences

| SEQ ID NO | Name | Sequence |
|---|---|---|
| 1 | AAV2 prototypic capsid-VP1 (protein) | MAADGYLPDWLEDTLSEGIRQWWKLKPGPPPPKPAERHKDDSRGLVLPGYKYLGPFNGLD KGEPVNEADAAALEHDKAYDRQLDSGDNPYLKYNHADAEFQERLKEDTSFGGNLGRAVFQ AKKRVLEPLGLVEEPVKTAPGKKRPVEHSPVEPDSSSGTGKAGQQPARKRLNFGQTGDAD SVPDPQPLGQPPAAPSGLGTNTMATGSGAPMADNNEGADGVGNSSGNWHCDSTWMGD RVITTSTRTWALPTYNNHLYKQISSQSGASNDNHYFGYSTPWGYFDFNRFHCHFSPRDWQ RLINNNWGFRPKRLNFKLFNIQVKEVTQNDGTTTIANNLTSTVQVFTDSEYQLPYVLGSAHQ GCLPPFPADVFMVPQYGYLTLNNGSQAVGRSSFYCLEYFPSQMLRTGNNFTFSYTFEDVPFH SSYAHSQSLDRLMNPLIDQYLYYLSRTNTPSGTTTQSRLQFSQAGASDIRDQSRNWLPGPC YRQQRVSKTSADNNNSEYSWTGATKYHLNGRDSLVNPGPAMASHKDDEEKFFPQSGVLIF GKQGSEKTNVDIEKVMITDEEEIRTTNPVATEQYGSVSTNLQRGNRQAATADVNTQGVLPG MVWQDRDVYLQGPIWAKIPHTDGHFHPSPLMGGFGLKHPPPQILIKNTPVPANPSTTFSAA KFASFITQYSTGQVSVEIEWELQKENSKRWNPEIQYTSNYNKSVNVDFTVDTNGVYSEPRP IGTRYLTRNL |
| 2 | AAVC11.01 (protein) | MAADGYLPDWLEDNLSEGIREWWDLKPGAPKPKANQQKQDDGRGLVLPGYKYLGPFNGL DKGEPVNAADAAALEHDKAYDQQLKAGDNPYLRYNHADAEFQERLQEDTSFGGNLGRAVF QAKKRVLEPLGLVEEAAKTAPGKKRPVEPSPQRSPDSSSGIGKTGQQPAKKRLNFGQTGDS ESVPDPQPLGEPPAAPSGVGPNTMAAGGGAPMADNNEGADGVGSSSGNWHCDSTWLGD RVITTSTRTWALPTYNNHLYKQISSQSGASNDNHYFGYSTPWGYFDFNRFHCHFSPRDWQ RLINNNWGFRPKRLNFKLFNIQVKEVTDNNGVKTIANNLTSTVQVFTDSDYQLPYVLGSAH QGCLPPFPADVFMIPQYGYLTLNNGSQAVGRSSFYCLEYFPSQMLRTGNNFTFSYTFEDVPF HSSYAHSQSLDRLMNPLIDQYLYYLSRTQSTGGTQGTQQLLFSQAGPANMSAQAKNWLPG PCYRQQRVSTTLSQNNNSNFAWTGATKYHLNGRNSLVNPGVAMATHKDDEDRFFPSSGV LIFGKTGATNKTTLENVLMTNEEEIRPTNPVATEEYGIVSSNLQAANTAAQTQVVNNQGALP GMVWQNRDVYLQGPIWAKIPHTDGNFHPSPLMGGFGLKHPPPQILIKNTPVPADPPTTFSQ AKLASFITQYSTGQVSVEIEWELQKENSKRWNPEVQYTSNYAKSANVDFTVDNNGLYTEPR PIGTRYLTRPL |
| 3 | AAVC11.02 (protein) | MAADGYLPDWLEDNLSEGIREWWALKPGAPKPKANQQKQDDGRGLVLPGYKYLGPFNGL DKGEPVNAADAAALEHDKAYDQQLKAGDNPYLRYNHADAEFQERLQEDTSFGGNLGRAVF QAKKRVLEPLGLVEEAAKTAPGKKRPVEPSPQRSPDSSSGIGKTGQQPAKKRLNFGQTGDS ESVPDPQPLGEPPAAPSGVGPNTMAAGGGAPMADNNEGADGVGSSSGNWHCDSTWLGD RVITTSTRTWALPTYNNHLYKQISSQSGASNDNHYFGYSTPWGYFDFNRFHCHFSPRDWQ RLINNNWGFRPKRLNFKLFNIQVKEVTTNDGVTTIANNLTSTVQVFSDSEYQLPYVLGSAHQ GCLPPFPADVFMIPQYGYLTLNNGSQAVGRSSFYCLEYFPSQMLRTGNNFEFSYSFEDVPFH SSYAHSQSLDRLMNPLIDQYLYYLARTQSNPGGTAGNRELQFYQGGPSTMAEQAKNWLPG PCFRQQRVSKTLDQNNNSNFAWTGATKYHLNGRNSLVNPGVAMATHKDDEDRFFPSSGV LIFGKTGATNKTTLENVLMTNEEEIRPTNPVATEEYGIVSSNLQAANTAAQTQVVNNQGALP |

TABLE 5-continued

Capsid Sequences

| SEQ ID NO | Name | Sequence |
|---|---|---|
| | | GMVWQNRDVYLQGPIWAKIPHTDGNFHPSPLMGGFGLKHPPPQILIKNTPVPANPPAEFSA<br>TKFASFITQYSTGQVSVEIEWELQKENSKRWNPEVQYTSNYAKSANVDFTVDNNGLYTEPR<br>PIGTRYLTRPL |
| 4 | AAVC11.03 (protein) | MAADGYLPDWLEDNLSEGIREWWDLKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPATPAAVGPTTMASGGGAPMADNNEGADGVGNASGNWHCDSTWLGD<br>RVITTSTRTWALPTYNNHLYKQISSETAGSTNDNTYFGYSTPWGYFDFNRFHCHFSPRDWQ<br>RLINNNWGFRPKRLNFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFTFSYTFEEVPFH<br>SSYAHSQSLDRLMNPLIDQYLYYLNRTQNQSGSAQNKDLLFSRGSPAGMSVQPKNWLPGP<br>CYRQQRVSKTKTDNNNSNFTWTGASKYNLNGRESIINPGTAMASHKDDEDKFFPMSGVMI<br>FGKESAGASNTALDNVMITDEEEIKATNPVATERFGTVAVNFQSSSTDPATGDVHVMGALP<br>GMVWQDRDVYLQGPIWAKIPHTDGHFHPSPLMGGFGLKHPPPQILIKNTPVPADPPTTFSQ<br>AKLASFITQYSTGQVSVEIEWELQKENSKRWNPEVQYTSNYAKSANVDFTVDNNGLYTEPR<br>PIGTRYLTRPL |
| 5 | AAVC11.04 (protein) | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEQSPQEPDSSSGIGKTGQQPAKKRLNFGQTGDS<br>ESVPDPQPLGEPPAGPSGLGSGTVAAGGGAPMADNNEGADGVGNSSGNWHCDSQWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |
| 6 | AAVC11.05 (protein) | MAADGYLPDWLEDNLSEGIREWWDLKPGAPKPKANQQKQDDGRGLVLPGYKYLGPFNGL<br>DKGEPVNAADAAALEHDKAYDQQLKAGDNPYLRYNHADAEFQERLQEDTSFGGNLGRAVF<br>QAKKRVLEPLGLVEEAAKTAPGKKRPVEPSPQRSPDSSSGIGKTGQQPAKKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLNFKLFNIQVKEVTDNNGVKTIANNLTSTVQVFTDSDYQLPYVLGSAH<br>EGCLPPFPADVFMIPQYGYLTLNNGSQAVGRSSFYCLEYFPSQMLRTGNNFTFSYTFEDVPF<br>HSSYAHSQSLDRLMNPLIDQYLYYLSRTQSTGGTQGTQQLLFSQAGPANMSAQAKNWLPG<br>PCYRQQRVSTTLSQNNNSNFAWTGATKYHLNGRNSLVNPGVAMATHKDDEDRFFPSSGV<br>LIFGKTGATNKTTLENVLMTNEEEIRPTNPVATEEYGIVSSNLQAANTAAQTQVVNNQGALP<br>GMVWQNRDVYLQGPIWAKIPHTDGNFHPSPLMGGFGLKHPPPQILIKNTPVPANPPEVFTP<br>AKFASFITQYSTGQVSVEIEWELQKENSKRWNPEIQYTSNYNKSVSVDFTVDTNGVYSEPR<br>PIGTRYLTRNL |
| 7 | AAVC11.06 (protein) | MAADGYLPDWLEDTLSEGIREWWALKPGAPQPKANQQHQDNGRGLVLPGYKYLGPFNGL<br>DKGEPVNEADAAALEHDKAYDKQLEQGDNPYLKYNHADAEFQERLQEDTSFGGNLGRAVF<br>QAKKRILEPLGLVEEAAKTAPGKKRPVEPSPQRSPDSSTGIGKKGQQPARKRLNFGQTGDS<br>ESVPDPQPLGEPPAAPSSVGSGTVAAGGGAPMADNNEGADGVGNASGNWHCDSTWLGD<br>RVITTSTRTWALPTYNNHLYKQISSQSGASNDNHYFGYSTPWGYFDFNRFHCHFSPRDWQ<br>RLINNNWGFRPKKLSFKLFNIQVKEVTQNDGTTTIANNLTSTVQVFTDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |
| 8 | AAVC11.07 (protein) | MAADGYLPDWLEDNLSEGIREWWDLKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEQSPQEPDSSSGIGKTGQQPAKKRLNFGQTGDS<br>ESVPDPQPLGEPPAGPSGLGSGTVAAGGGAPMADNNEGADGVGNSSGNWHCDSQWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |

TABLE 5-continued

Capsid Sequences

| SEQ ID NO | Name | Sequence |
|---|---|---|
| 9 | AAVC11.08 (protein) | MAADGYLPDWLEDNLSEGIREWWDLKPGAPKPKANQQKQDDGRGLVLPGYKYLGPFNGL DKGEPVNAADAAALEHDKAYDQQLKAGDNPYLRYNHADAEFQERLQEDTSFGGNLGRAVF QAKKRVLEPLGLVEEAAKTAPGKKRPVEPSPQRSPDSSSGIGKTGQQPAKKRLNFGQTGDS ESVPDPQPLGEPPAAPSGVGPNTMAAGGGAPMADNNEGADGVGSSSGNWHCDSTWLGD RVITTSTRTWALPTYNNHLYKQISSQSGASNDNHYFGYSTPWGYFDFNRFHCHFSPRDWQ RLINNNWGFRPKRLNFKLFNIQVKEVTDNNGVKTIANNLTSTVQVFTDSDYQLPYVLGSAH EGCLPPFPADVFMIPQYGYLTLNNGSQAVGRSSFYCLEYFPSQMLRTGNNFTFSYTFEDVPF HSSYAHSQSLDRLMNPLIDQYLYYLSRTQSTGGTQGTQQLLFSQAGPANMSAQAKNWLPG PCYRQQRVSTTLSQNNNSNFAWTGATKYHLNGRNSLVNPGVAMATHKDDEDRFFPSSGV LIFGKTGATNKTTLENVLMTNEEEIRPTNPVATEEYGIVSSNLQAANTAAQTQVVNNQGALP GMVWQNRDVYLQGPIWAKIPHTDGNFHPSPLMGGFGLKHPPPQILIKNTPVPANPPAEFSA TKFASFITQYSTGQVSVEIEWELQKENSKRWNPEVQYTSNYAKSANVDFTVDNNGLYTEPR PIGTRYLTRPL |
| 10 | AAVC11.09 (protein) | MAADGYLPDWLEDNLSEGIREWWDLKPGAPKPKANQQKQDDGRGLVLPGYKYLGPFNGL DKGEPVNAADAAALEHDKAYDQQLKAGDNPYLRYNHADAEFQERLQEDTSFGGNLGRAVF QAKKRVLEPLGLVEEAAKTAPGKKRPVEPSPQRSPDSSSGIGKTGQQPAKKRLNFGQTGDS ESVPDPQPLGEPPAAPSGVGPNTMAAGGGAPMADNNEGADGVGSSSGNWHCDSTWLGD RVITTSTRTWALPTYNNHLYKQISSQSGASNDNHYFGYSTPWGYFDFNRFHCHFSPRDWQ RLINNNWGFRPKRLNFKLFNIQVKEVTDNNGVKTIANNLTSTVQVFTDSDYQLPYVLGSAH EGCLPPFPADVFMIPQYGYLTLNNGSQAVGRSSFYCLEYFPSQMLRTGNNFTFSYTFEDVPF HSSYAHSQSLDRLMNPLIDQYLYYLSRTQSTGGTQGTQQLLFSQAGPANMSAQAKNWLPG PCYRQQRVSTTLSQNNNSNFAWTGATKYHLNGRNSLVNPGVAMATHKDDEDRFFPSSGV LIFGKTGATNKTTLENVLMTNEEEIRPTNPVATEEYGIVSSNLQAANTAAQTQVVNNQGALP GMVWQNRDVYLQGPIWAKIPHTDGNFHPSPLMGGFGLKHPPPQILIKNTPVPADPPTTFSQ AKLASFITQYSTGQVSVEIEWELQKENSKRWNPEVQYTSNYAKSANVDFTVDNNGLYTEPR PIGTRYLTRPL |
| 11 | AAVC11.10 (protein) | MAADGYLPDWLEDNLSEGIREWWDLKPGAPKPKANQQKQDDGRGLVLPGYKYLGPFNGL DKGEPVNAADAAALEHDKAYDQQLQAGDNPYLRYNHADAEFQERLQEDTSFGGNLGRAVF QAKKRVLEPLGLVEEGAKTAPGKKRPVEQSPQEPDSSSGIGKTGQQPAKKRLNFGQTGDS ESVPDPQPLGEPPAGPSGLGSGTVAAGGGAPMADNNEGADGVGNSSGNWHCDSQWLGD RVITTSTRTWALPTYNNHLYKQISSQSGASNDNHYFGYSTPWGYFDFNRFHCHFSPRDWQ RLINNNWGFRPKRLSFKLFNIQVKEVTTNDGVTTIANNLTSTVQVFSDSEYQLPYVLGSAHQ GCLPPFPADVFMIPQYGYLTLNNGSQAVGRSSFYCLEYFPSQMLRTGNNFEFSYTFEDVPFH SSYAHSQSLDRLMNPLIDQYLYYLSRTQSTGGTQGTQQLLFSQAGPANMSAQAKNWLPGP CYRQQRVSTTLSQNNNSNFAWTGATKYHLNGRNSLVNPGVAMATHKDDEDRFFPSSGVLI FGKTGATNKTTLENVLMTNEEEIRPTNPVATEEYGIVSSNLQAANTAAQTQVVNNQGALPG MVWQNRDVYLQGPIWAKIPHTDGNFHPSPLMGGFGLKHPPPQILIKNTPVPADPPTTFSQA KLASFITQYSTGQVSVEIEWELQKENSKRWNPEVQYTSNYAKSANVDFTVDNNGLYTEPRP IGTRYLTRNL |
| 12 | AAVC11.11 (protein) | MAADGYLPDWLEDTLSEGIREWWALKPGAPQPKANQQHQDNGRGLVLPGYKYLGPFNGL DKGEPVNEADAAALEHDKAYDKQLEQGDNPYLKYNHADAEFQERLQEDTSFGGNLGRAVF QAKKRVLEPLGLVEEGAKTAPGKKRPVEPSPQRSPDSSTGIGKKGQQPARKRLNFGQTGDS ESVPDPQPLGEPPAAPSSVGSGTVAAGGGAPMADNNEGADGVGNASGNWHCDSTWLGD RVITTSTRTWALPTYNNHLYKQISSQSGASNDNHYFGYSTPWGYFDFNRFHCHFSPRDWQ RLINNNWGFRPKRLNFKLFNIQVKEVTTNDGVTTIANNLTSTVQVFSDSEYQLPYVLGSAHQ GCLPPFPADVFMIPQYGYLTLNNGSQAVGRSSFYCLEYFPSQMLRTGNNFEFSYSFEDVPFH SSYAHSQSLDRLMNPLIDQYLYYLSRTQSTGGTQGTQQLLFSQAGPANMSAQAKNWLPGP CYRQQRVSTTLSQNNNSNFAWTGATKYHLNGRNSLVNPGVAMATHKDDEDRFFPSSGVLI FGKTGATNKTTLENVLMTNEEEIRPTNPVATEEYGIVSSNLQAANTAAQTQVVNNQGALPG MVWQNRDVYLQGPIWAKIPHTDGHFHPSPLMGGFGLKNPPPQILIKNTPVPANPPAEFSAT KFASFITQYSTGQVSVEIEWELQKENSKRWNPEVQYTSNYAKSANVDFTVDNNGLYTEPRP IGTRYLTRPL |
| 13 | AAVC11.12 (protein) | MAADGYLPDWLEDTLSEGIREWWALKPGAPQPKANQQHQDNGRGLVLPGYKYLGPFNGL DKGEPVNEADAAALEHDKAYDKQLEQGDNPYLKYNHADAEFQERLQEDTSFGGNLGRAVF QAKKRILEPLGLVEEAAKTAPGKKRPVEPSPQRSPDSSTGIGKKGQQPARKRLNFGQTGDS ESVPDPQPLGEPPAAPSSVGSGTVAAGGGAPMADNNEGADGVGNASGNWHCDSTWLGD RVITTSTRTWALPTYNNHLYKQISSQSGASNDNHYFGYSTPWGYFDFNRFHCHFSPRDWQ RLINNNWGFRPKRLSFKLFNIQVKEVTTNDGVTTIANNLTSTVQVFSDSEYQLPYVLGSAHQ GCLPPFPADVFMIPQYGYLTLNNGSQAVGRSSFYCLEYFPSQMLRTGNNFEFSYTFEDVPFH SSYAHSQSLDRLMNPLIDQYLYYLSRTQSTGGTQGTQQLLFSQAGPANMSAQAKNWLPGP CYRQQRVSTTLSQNNNSNFAWTGATKYHLNGRNSLVNPGVAMATHKDDEDRFFPSSGVLI FGKTGATNKTTLENVLMTNEEEIRPTNPVATEEYGIVSSNLQAANTAAQTQVVNNQGALPG MVWQNRDVYLQGPIWAKIPHTDGNFHPSPLMGGFGLKHPPPQILIKNTPVPANPPEVFTPA KFASFITQYSTGQVSVEIEWELQKENSKRWNPEIQYTSNYNKSVSVDFTVDTNGVYSEPRP IGTRYLTRNL |
| 14 | AAVC11.13 (protein) | MAADGYLPDWLEDNLSEGIREWWDLKPGAPKPKANQQKQDDGRGLVLPGYKYLGPFNGL DKGEPVNAADAAALEHDKAYDQQLKAGDNPYLRYNHADAEFQERLQEDTSFGGNLGRAVF QAKKRILEPLGLVEEAAKTAPGKKRPVEPSPQRSPDSSTGIGKKGQQPARKRLNFGQTGDS ESVPDPQPLGEPPAAPSSVGSGTVAAGGGAPMADNNEGADGVGNASGNWHCDSTWLGD |

TABLE 5-continued

| Capsid Sequences | | |
|---|---|---|
| SEQ ID NO | Name | Sequence |
| | | RVITTSTRTWALPTYNNHLYKQISSQSGASNDNHYFGYSTPWGYFDFNRFHCHFSPRDWQ<br>RLINNNWGFRPKRLNFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CFRQQRVSKTLDQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |
| 15 | AAVC11.14 (protein) | MAADGYLPDWLEDNLSEGIREWWDLKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEQSPQEPDSSSGIGKTGQQPAKKRLNFGQTGDS<br>ESVPDPQPLGEPPAGPSGLGSGTVASGGGAPMADNNEGADGVGNSSGNWHCDSQWLGD<br>RVITTSTRTWALPTYNNHLYKQISNSTSGGSSNDNAYFGYSTPWGYFDFNRFHCHFSPRD<br>WQRLINNNWGFRPKRLNFKLFNIQVKEVTTNDGVTTIANNLTSTVQVFSDSEYQLPYVLGS<br>AHQGCLPPFPADVFMIPQYGYLTLNNGSQAVGRSSFYCLEYFPSQMLRTGNNFEFSYTFEDV<br>PFHSSYAHSQSLDRLMNPLIDQYLYYLSRTQSTGGTQGTQQLLFSQAGPANMSAQAKNWL<br>PGPCYRQQRVSTTLSQNNNSNFAWTGATKYHLNGRNSLVNPGVAMATHKDDEDRFFPSS<br>GVLIFGKTGATNKTTLENVLMTNEEEIRPTNPVATEEYGIVSSNLQAANTAAQTQVVNNQGA<br>LPGMVWQNRDVYLQGPIWAKIPHTDGNFHPSPLMGGFGLKHPPPQILIKNTPVPANPPAEF<br>SATKFASFITQYSTGQVSVEIEWELQKENSKRWNPEVQYTSNYAKSANVDFTVDNNGLYTE<br>PRPIGTRYLTRPL |
| 16 | AAVC11.15 (protein) | MAADGYLPDWLEDNLSEGIREWWDLKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEAAKTAPGKKRPVEPSPQRSPDSSTGIGKKGQQPARKRLNFGQTGDS<br>ESVPDPQPLGEPPAGPSGLGSGTVAAGGGAPMADNNEGADGVGNSSGNWHCDSQWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGHFHPSPLMGGFGLKNPPPQILIKNTPVPANPPAEFSAT<br>KFASFITQYSTGQVSVEIEWELQKENSKRWNPEVQYTSNYAKSANVDFTVDNNGLYTEPRP<br>IGTRYLTRPL |
| 17 | AAVC11.16 (protein) | MAADGYLPDWLEDTLSEGIREWWALKPGAPQPKANQQHQDNGRGLVLPGYKYLGPFNGL<br>DKGEPVNEADAAALEHDKAYDKQLEQGDNPYLKYNHADAEFQERLQEDTSFGGNLGRAVF<br>QAKKRILEPLGLVEEAAKTAPGKKRPVEPSPQRSPDSSTGIGKKGQQPARKRLNFGQTGDS<br>ESVPDPQPLGEPPAAPSSVGSGTVAAGGGAPMADNNEGADGVGNASGNWHCDSTWLGD<br>RVITTSTRTWALPTYNNHLYKQISSQSGASNDNHYFGYSTPWGYFDFNRFHCHFSPRDWQ<br>RLINNNWGFRPKRLNFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPADPPTTFSQA<br>KLASFITQYSTGQVSVEIEWELQKENSKRWNPEVQYTSNYAKSANVDFTVDNNGLYTEPRP<br>IGTRYLTRPL |
| 18 | AAVC11.17 (protein) | MAADGYLPDWLEDNLSEGIREWWDLKPGAPKPKANQQKQDDGRGLVLPGYKYLGPFNGL<br>DKGEPVNAADAAALEHDKAYDQQLKAGDNPYLRYNHADAEFQERLQEDTSFGGNLGRAVF<br>QAKKRVLEPLGLVEEAAKTAPGKKRPVEPSPQRSPDSSTGIGKKGQQPARKRLNFGQTGDS<br>ESVPDPQPLGEPPAAPSGVGSGTVAAGGGAPMADNNEGADGVGNASGNWHCDSTWLGD<br>RVITTSTRTWALPTYNNHLYKQISSQSGASNDNHYFGYSTPWGYFDFNRFHCHFSPRDWQ<br>RLINNNWGFRPKKLRFKLFNIQVKEVTTNDGVTTIANNLTSTIQVFSDSEYQLPYVLGSAHQ<br>GCLPPFPADVFMIPQYGYLTLNNGSQAVGRSSFYCLEYFPSQMLRTGNNFEFSYSFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |
| 19 | AAVC11.18 (protein) | MAADGYLPDWLEDNLSEGIREWWDLKPGAPKPKANQQKQDDGRGLVLPGYKYLGPFNGL<br>DKGEPVNAADAAALEHDKAYDQQLKAGDNPYLRYNHADAEFQERLQEDTSFGGNLGRAVF<br>QAKKRVLEPLGLVEEGAKTAPGKKRPVEPSPQRSPDSSSGIGKTGQQPAKKRLNFGQTGDS<br>ESVPDPQPLGEPPAAPSSVGSGTVAAGGGAPMADNNEGADGVGNASGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP |

TABLE 5-continued

| Capsid Sequences | | |
|---|---|---|
| SEQ ID NO | Name | Sequence |
| | | CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |
| 20 | AAVC11.19 (protein) | MAADGYLPDWLEDNLSEGIREWWALKPGAPKPKANQQKQDDGRGLVLPGYKYLGPFNGL<br>DKGEPVNEADAAALEHDKAYDQQLKAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSSVGSGTVAAGGGAPMADNNEGADGVGNASGNWHCDSTWLGD<br>RVITTSTRTWALPTYNNHLYKQISSQSGASNDNHYFGYSTPWGYFDFNRFHCHFSPRDWQ<br>RLINNNWGFRPKKLSFKLFNIQVKEVTQNDGTTTIANNLTSTVQVFTDSEYQLPYVLGSAHQ<br>GCLPPFPADVFMIPQYGYLTLNNGSQAVGRSSFYCLEYFPSQMLRTGNNFEFSYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPANPPEVFTPA<br>KFASFITQYSTGQVSVEIEWELQKENSKRWNPEIQYTSNYNKSVSVDFTVDTNGVYSEPRP<br>IGTRYLTRNL |
| 21 | AAVC11.01 (nucleic acid) | ATGGCTGCTGACGGTTATCTTCCAGATTGGCTCGAGGACAACCTCTCTGAGGGCATTCG<br>CGAGTGGTGGGACCTGAAACCTGGAGCCCCGAAGCCCAAGGCCAACCAGCAGAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTCAAAGCGGGTGACAATCCGTACCTGCGGTATAACCACGCCGACG<br>CCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGCTGCTA<br>AGACGGCTCCTGGAAAGAAGAGACCGGTAGAACCGTCACCTCAGCGTTCCCCAGACTCC<br>TCCTCGGGCATCGGCAAGACAGGCCAGCAGCCCGCTAAAAAGAGACTCAATTTTGGTCA<br>GACTGGCGACTCAGAGTCAGTTCCAGACCCTCAACCTCTCGGAGAACCTCCAGCAGCGC<br>CCTCTGGTGTGGGACCTAATACAATGGCTGCAGGCGGTGGCGCACCAATGGCAGACAA<br>TAACGAAGGCGCCGACGGAGTGGGTAGTTCCTCGGGAAATTGGCATTGCGATTCCACAT<br>GGCTGGGCGACAGAGTCATCACCACCAGCACCCGAACCTGGGCCCTGCCCACTTACAA<br>CAACCATCTCTACAAGCAAATCTCCAGCCAATCAGGAGCTTCAAACGACAACCACTACTT<br>TGGCTACAGCACCCCTTGGGGGTATTTTGACTTCAACAGATTCCACTGCCACTTCTCACC<br>ACGTGACTGGCAGCGACTCATCAACAACAACTGGGGATTCCGGCCTAAGCGACTCAACT<br>TCAAGCTCTTCAACATTCAGGTCAAAGAGGTTACGGACAACAATGGAGTCAAGACCATC<br>GCCAATAACCTTACCAGCACGGTCCAGGTCTTCACGGACTCAGACTATCAGCTCCCGTA<br>CGTGCTCGGGTCGGCTCACCAGGGCTGCCTCCCGCCGTTCCCAGCGGACGTCTTCATG<br>ATTCCTCAGTACGGCTACCTAACGCTCAACAATGGCAGCCAGGCAGTGGGACGGTCATC<br>CTTTTACTGCCTGGAATATTTCCCATCGCAGATGCTGAGAACGGGCAATAACTTTACCTT<br>CAGCTACACCTTCGAGGACGTGCCTTTCCACAGCAGCTACGCTCACAGCCAGAGTTTGG<br>ACCGACTGATGAATCCTCTCATTGACCAGTACCTGTACTACTTATCCAGAACTCAGTCCA<br>CAGGAGGAACTCAAGGTACCCAGCAATTGTTATTTTCTCAAGCTGGGCCTGCAAACATG<br>TCGGCTCAGGCCAAGAACTGGCTGCCTGGACCTTGCTACCGGCAGCAGCGAGTCTCCA<br>CGACACTGTCGCAAAACAACAACAGCAACTTTGCTTGGACTGGTGCCACCAAATATCACC<br>TGAACGGCAGAAACTCGTTGGTTAATCCCGGCGTCGCCATGGCAACTCACAAGGACGAC<br>GAGGACCGCTTTTTCCCATCCAGCGGAGTCCTGATTTTTGGAAAAACTGGAGCAACTAA<br>CAAAACTACATTGGAAAATGTGTTAATGACAAATGAAGAAGAAATTCGTCCTACTAATCC<br>TGTAGCCACGGAAGAATACGGGATAGTCAGCAGCAACTTACAAGCGGCTAATACTGCAG<br>CCCAGACACAAGTTGTCAACAACCAGGGAGCCTTACCTGGCATGGTCTGGCAGAACCGA<br>GACGTGTACCTGCAGGGTCCCATCTGGGCCAAGATTCCTCACACGGACGGCAACTTTCA<br>CCCGTCTCCTCTGATGGGCGGCTTTGGACTTAAACACCCGCCTCCACAGATCCTGATCA<br>AGAACACGCCGGTACCTGCGGATCCTCCAACAACGTTCAGCCAGGCGAAATTGGCTTCC<br>TTCATCACGCAGTACAGCACCGGACAGGTCAGCGTGGAGATCGAGTGGGAGCTGCAGA<br>AGGAAAACAGCAAGCGCTGGAATCCCGAAGTGCAGTACACATCCAATTATGCAAAATCT<br>GCCAACGTTGATTTTACTGTGGACAACAATGGACTTTATACTGAGCCTCGCCCCATTGGC<br>ACCCGTTACCTTACCCGTCCCCTGTAA |
| 22 | AAVC11.02 (nucleic acid) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAGAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTCAAAGCGGGTGACAATCCGTACCTGCGGTATAACCACGCCGACG<br>CCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGCTGCTA<br>AGACGGCTCCTGGAAAGAAGAGACCGGTAGAACCGTCACCTCAGCGTTCCCCAGACTCC<br>TCCTCGGGCATCGGCAAGACAGGCCAGCAGCCCGCTAAAAAGAGACTCAATTTTGGTCA<br>GACTGGCGACTCAGAGTCAGTTCCAGACCCTCAACCTCTCGGAGAACCTCCAGCAGCGC<br>CCTCTGGTGTGGGACCTAATACAATGGCTGCAGGCGGTGGCGCACCAATGGCAGACAA<br>TAACGAAGGCGCCGACGGAGTGGGTAGTTCCTCGGGAAATTGGCATTGCGATTCCACAT<br>GGCTGGGCGACAGAGTCATCACCACCAGCACCCGAACCTGGGCCCTGCCCACTTACAA<br>CAACCATCTCTACAAGCAAATCTCCAGCCAATCAGGAGCTTCAAACGACAACCACTACTT<br>TGGCTACAGCACCCCTTGGGGGTATTTTGACTTCAACAGATTCCACTGCCACTTCTCACC |

TABLE 5-continued

Capsid Sequences

| SEQ ID NO | Name | Sequence |
|---|---|---|
| | | ACGTGACTGGCAGCGACTCATCAACAACAACTGGGGATTCCGGCCCAAGAGACTCAACT<br>TCAAGCTCTTCAACATCCAAGTCAAGGAGGTCACGACGAATGATGGCGTCACGACCATC<br>GCTAATAACCTTACCAGCACGGTTCAAGTCTTCTCGGACTCGGAGTACCAGTTGCCGTAC<br>GTCCTCGGCTCTGCGCACCAGGGCTGCCTCCCTCCGTTCCCGGCGGACGTGTTCATGAT<br>TCCCCAGTACGGCTACCTAACACTCAACAACGGTAGTCAGGCCGTGGGACGCTCCTCCT<br>TTTACTGCCTGGAATATTTCCCATCGCAGATGCTGAGAACGGGCAATAACTTTGAGTTCA<br>GCTACAGCTTCGAGGACGTGCCTTTCCACAGCAGCTACGCACACAGCCAGAGCCTGGAC<br>CGGCTGATGAATCCCCTCATCGACCAGTACTTGTACTACCTGGCCAGAACACAGAGTAA<br>CCCAGGAGGCACAGCTGGCAATCGGGAACTGCAGTTTTACCAGGGCGGGCCTTCAACT<br>ATGGCCGAACAAGCCAAGAATTGGTTACCTGGACCTTGCTTCCGGCAACAAAGAGTCTC<br>CAAAACGCTGGATCAAAACAACAACAGCAACTTTGCTTGGACTGGTGCCACCAAATATCA<br>CCTGAACGGCAGAAACTCGTTGGTTAATCCCGGCGTCGCCATGGCAACTCACAAGGACG<br>ACGAGGACCGCTTTTTCCCATCCAGCGGAGTCCTGATTTTTGGAAAAACTGGAGCAACT<br>AACAAAACTACATTGGAAAATGTGTTAATGACAAATGAAGAAGAAATTCGTCCTACTAAT<br>CCTGTAGCCACGGAAGAATACGGGATAGTCAGCAGCAACTTACAAGCGGCTAATACTGC<br>AGCCCAGACACAAGTTGTCAACAACCAGGGAGCCTTACCTGGCATGGTCTGGCAGAACC<br>GGGACGTGTACCTGCAGGGTCCCATCTGGGCCAAGATTCCTCACACGGATGGCAACTTT<br>CACCCGTCTCCTTTGATGGGCGGCTTTGGACTTAAACATCCGCCTCCTCAGATCCTCATC<br>AAAAACACGCCTGTTCCTGCGAATCCTCCGGCGGAGTTTTCAGCTACAAAGTTTGCTTCA<br>TTCATCACCCAATACTCCACAGGACAAGTGAGCGTGGAGATTGAATGGGAGCTGCAGAA<br>AGAAAACAGCAAACGCTGGAATCCCGAAGTGCAGTATACATCTAACTATGCAAAATCTG<br>CCAACGTTGATTTCACTGTGGACAACAATGGACTTTATACTGAGCCTCGCCCCATTGGCA<br>CCCGTTACCTCACCCGTCCCCTGTAA |
| 23 | AAVC11.03 (nucleic acid) | ATGGCTGCTGACGGTTATCTTCCAGATTGGCTCGAGGACAACCTCTCTGAAGGCATTCG<br>CGAGTGGTGGGACCTGAAACCTGGAGCCCCCAAGCCCAAGGCCAACCAGCAGAAGCAG<br>GACGACGGTCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTAAATTTCGGTC<br>AGACTGGCGACTCAGAGTCAGTCCCAGACCCTCAACCTCTCGGAGAACCTCCAGCAACC<br>CCCGCTGCTGTGGGACCTACTACAATGGCTTCAGGCGGTGGCGCACCAATGGCAGACA<br>ATAACGAAGGCGCCGACGGAGTGGGTAATGCCTCAGGAAATTGGCATTGCGATTCCACA<br>TGGCTGGGCGACAGAGTCATCACCACCAGCACCCGCACCTGGGCCTTGCCCACCTACAA<br>CAACCACCTCTACAAGCAAATCTCCAGTGAAACTGCAGGTAGTACCAACGACAACACCTA<br>CTTCGGCTACAGCACCCCCTGGGGGTATTTTGACTTCAACAGATTCCACTGCCACTTTTC<br>ACCACGTGACTGGCAAAGACTCATCAACAACAACTGGGGATTCCGGCCCAAGAGGCTCA<br>ACTTCAAACTCTTCAACATCCAAGTCAAGGAGGTCACGACGAATGATGGCGTCACAACC<br>ATCGCTAATAACCTTACCAGCACGGTTCAAGTCTTCTCGGACTCGGAGTACCAGCTTCCG<br>TACGTCCTCGGCTCTGCGCACCAGGGCTGCCTCCCTCCGTTCCCGGCGGACGTGTTCAT<br>GATTCCGCAATACGGCTACCTGACGCTCAACAATGGCAGCCAAGCCGTGGGACGTTCAT<br>CCTTTTACTGCCTGGAATATTTCCCATCGCAGATGCTGAGAACGGGCAACAACTTTACCT<br>TCAGCTACACCTTTGAGGAAGTGCCTTTCCACAGCAGCTACGCGCACAGCCAGAGCCTG<br>GACCGGCTGATGAATCCTCTCATCGACCAATACCTGTATTACCTGAACAGAACTCAAAAT<br>CAGTCCGGAAGTGCCCAAAACAAGGACTTGCTGTTTAGCCGTGGGTCTCCAGCTGGCAT<br>GTCTGTTCAGCCCAAAAACTGGCTACCTGGACCCTGTTATCGGCAGCAGCGCGTTTCTA<br>AAACAAAAACAGACAACAACAACAGCAATTTTACCTGGACTGGTGCTTCAAAATATAACC<br>TTAATGGGCGTGAATCTATAATCAACCCTGGCACTGCTATGGCCTCACACAAAGACGAC<br>GAAGACAAGTTCTTTCCCATGAGCGGTGTCATGATTTTTGGAAAAGAGAGCGCCGGAGC<br>TTCAAACACTGCATTGGACAATGTCATGATTACAGACGAAGAGGAAATTAAAGCCACTAA<br>CCCTGTGGCCACCGAAAGATTTGGGACCGTGGCAGTCAATTTCCAGAGCAGCAGCACAG<br>ACCCTGCGACCGGAGATGTGCATGTTATGGGAGCCTTACCTGGAATGGTGTGGCAAGA<br>CAGAGACGTATACCTGCAGGGTCCTATTTGGGCCAAAATTCCTCACACGGATGGACACT<br>TTCACCCGTCTCCTCTCATGGGCGGCTTTGGACTTAAGCACCCGCCTCCTCAGATCCTCA<br>TCAAAAACACGCCGGTACCTGCGGATCCTCCAACAACGTTCAGCCAGGCGAAATTGGCT<br>TCCTTCATCACGCAGTACAGCACCGGACAGGTCAGCGTGGAGATCGAGTGGGAGCTGC<br>AGAAGGAAAACAGCAAGCGCTGGAATCCCGAAGTGCAGTACACATCCAATTATGCAAAA<br>TCTGCCAACGTTGATTTTACTGTGGACAACAATGGACTTTATACTGAGCCTCGCCCCATT<br>GGCACCCGTTACCTTACCCGTCCCCTGTAA |
| 24 | AAVC11.04 (nucleic acid) | ATGGCTGCCGATGGTTATCTTCCAGATTGGCTCGAGGACAACCTTTCTGAAGGCATTCGT<br>GAGTGGTGGGCGCTGAAACCTGGAGCCCCGAAGCCCAAAGCCAACCAGCAAAAGCAGG<br>ACGACGGCCGGGGTCTGGTGCTTCCTGGCTACAAGTACCTCGGACCCTTCAACGGACTC<br>GACAAGGGGGAGCCCGTCAACGCGGCGGACGCAGCGGCCCTCGAGCACGACAAGGCC<br>TACGACCAGCAGCTGCAGGCGGGTGACAATCCGTACCTGCGGTATAACCACGCCGACG<br>CCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTA<br>AGACGGCTCCTGGAAAGAAACGTCCGGTAGAGCAGTCGCCACAAGAGCCAGACTCCTC<br>CTCGGGCATTGGCAAGACAGGCCAGCAGCCCGCTAAAAAGAGACTCAATTTTGGTCAGA<br>CTGGCGACTCAGAGTCAGTCCCCGACCCACAACCTCTCGGAGAACCACCAGCAGGCCC<br>CTCTGGTCTGGGATCTGGTACAGTGGCTGCAGGCGGTGGCGCACCAATGGCAGACAAT |

TABLE 5-continued

Capsid Sequences

| SEQ ID NO | Name | Sequence |
|---|---|---|
| | | AACGAGGGTGCCGATGGAGTGGGTAATTCCTCAGGAAATTGGCATTGCGATTCCCAATG<br>GCTGGGCGACAGAGTCATCACCACCAGCACCAGAACCTGGGCCCTGCCCACTTACAACA<br>ACCATCTCTACAAGCAAATCTCCAGCCAATCAGGAGCTTCAAACGACAACCACTACTTCG<br>GCTACAGCACCCCCTGGGGGTATTTTGACTTTAACAGATTCCACTGCCACTTTTCACCAC<br>GTGACTGGCAGCGACTCATCAACAACAACTGGGGATTCCGGCCCAAGAGACTCAGCTTC<br>AAGCTCTTCAACATCCAAGTCAAGGAGGTCACGACGAATGATGGCGTCACGACCATCGC<br>TAATAACCTTACCAGCACGGTTCAAGTCTTCTCGGACTCGGAGTACCAGCTTCCGTACGT<br>CCTCGGCTCTGCGCACCAGGGCTGCCTCCCTCCGTTCCCGGCGGACGTGTTCATGATTC<br>CGCAGTACGGCTACCTAACGCTCAACAATGGCAGCCAGGCAGTGGGACGGTCATCCTTT<br>TACTGCCTGGAATATTTTCCATCTCAAATGCTGCGAACTGGAAACAATTTTGAATTCAGCT<br>ACACCTTCGAGGACGTGCCTTTCCACAGCAGCTACGCACACAGCCAGAGCTTGGACCGA<br>CTGATGAATCCTCTCATTGACCAGTACCTGTACTACTTATCCAGAACTCAGTCCACAGGA<br>GGAACTCAAGGTACCCAGCAATTGTTATTTTCTCAAGCTGGGCCTGCAAACATGTCGGCT<br>CAGGCCAAGAACTGGCTGCCTGGACCTTGCTACCGGCAGCAGCGAGTCTCCACGACAC<br>TGTCGCAAAACAACAACAGCAACTTTGCTTGGACTGGTGCCACCAAATATCACCTGAACG<br>GCAGAAACTCGTTGGTTAATCCCGGCGTCGCCATGGCAACTCACAAGGACGACGAGGA<br>CCGCTTTTTCCCATCCAGCGGAGTCCTGATTTTTGGAAAAACTGGAGCAACTAACAAAAC<br>TACATTGGAAAATGTGTTAATGACAAATGAAGAAGAAATTCGTCCTACTAATCCTGTAGC<br>CACGGAAGAATACGGGATAGTCAGCAGCAACTTACAAGCGGCTAATACTGCAGCCCAGA<br>CACAAGTTGTCAACAACCAGGGAGCCTTACCTGGCATGGTCTGGCAGAACCGGGACGT<br>GTACCTGCAGGGTCCCATCTGGGCCAAGATTCCTCACACGGATGGCAACTTTCACCCGT<br>CTCCTTTGATGGGCGGCTTTGGACTTAAACATCCGCCTCCTCAGATCCTGATCAAGAACA<br>CTCCCGTTCCCGCTAATCCTCCGGAGGTGTTTACTCCTGCCAAGTTTGCTTCGTTCATCA<br>CACAGTACAGCACCGGACAAGTCAGCGTGGAAATCGAGTGGGAGCTGCAGAAGGAAAA<br>CAGCAAGCGCTGGAACCCGGAGATTCAGTACACTTCAAACTACAACAAGTCTGTTAGTG<br>TGGACTTTACTGTAGACACTAATGGCGTGTATTCAGAGCCTCGCCCCATTGGCACCAGAT<br>ACCTGACTCGTAATCTGTAA |
| 25 | AAVC11.05 (nucleic acid) | ATGGCTGCTGACGGTTATCTTCCAGATTGGCTCGAGGACAACCTCTCTGAGGGCATTCG<br>CGAGTGGTGGGACCTGAAACCTGGAGCCCCCAAGCCCAAGGCCAACCAGCAGAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTCAAAGCGGGTGACAATCCGTACCTGCGGTATAACCACGCCGACG<br>CCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGCTGCTA<br>AGACGGCTCCTGGAAAGAAGAGACCGGTAGAACCGTCACCTCAGCGTTCCCCAGACTCC<br>TCCTCGGGCATCGGCAAGACAGGCCAGCAGCCCGCTAAAAAGAGACTCAATTTTGGTCA<br>GACTGGCGACTCAGAGTCAGTTCCAGACCCTCAACCTCTCGGAGAACCTCCAGCAGCGC<br>CCTCTGGTGTGGGACCTAATACAATGGCTGCAGGCGGTGGCGCACCAATGGCAGACAA<br>TAACGAAGGCGCCGACGGAGTGGGTAGTTCCTCGGGAAATTGGCATTGCGATTCCACAT<br>GGCTGGGCGACAGAGTCATCACCACCAGCACCCGAACCTGGGCCCTGCCCACTTACAA<br>CAACCATCTCTACAAGCAAATCTCCAGCCAATCAGGAGCTTCAAACGACAACCACTACTT<br>TGGCTACAGCACCCCTTGGGGGTATTTTGACTTCAACAGATTCCACTGCCACTTCTCACC<br>ACGTGACTGGCAGCGACTCATCAACAACAACTGGGGATTCCGGCCTAAGCGACTCAACT<br>TCAAGCTCTTCAACATTCAGGTCAAAGAGGTTACGGACAACAATGGAGTCAAGACCATC<br>GCCAATAACCTTACCAGCACGGTCCAGGTCTTCACGGACTCAGACTATCAGCTCCCGTA<br>CGTGCTCGGGTCGGCTCACGAGGGCTGCCTCCCGCCGTTCCCAGCGGACGTCTTCATG<br>ATTCCTCAGTACGGCTACCTAACGCTCAACAATGGCAGCCAGGCAGTGGGACGGTCATC<br>CTTTTACTGCCTGGAATATTTCCCATCGCAGATGCTGAGAACGGGCAATAACTTTACCTT<br>CAGCTACACCTTCGAGGACGTGCCTTTCCACAGCAGCTACGCTCACAGCCAGAGTTTGG<br>ACCGACTGATGAATCCTCTCATTGACCAGTACCTGTACTACTTATCCAGAACTCAGTCCA<br>CAGGAGGAACTCAAGGTACCCAGCAATTGTTATTTTCTCAAGCTGGGCCTGCAAACATG<br>TCGGCTCAGGCCAAGAACTGGCTGCCTGGACCTTGCTACCGGCAGCAGCGAGTCTCCA<br>CGACACTGTCGCAAAACAACAACAGCAACTTTGCTTGGACTGGTGCCACCAAATATCACC<br>TGAACGGCAGAAACTCGTTGGTTAATCCCGGCGTCGCCATGGCAACTCACAAGGACGAC<br>GAGGACCGCTTTTTCCCATCCAGCGGAGTCCTGATTTTTGGAAAAACTGGAGCAACTAA<br>CAAAACTACATTGGAAAATGTGTTAATGACAAATGAAGAAGAAATTCGTCCTACTAATCC<br>TGTAGCCACGGAAGAATACGGGATAGTCAGCAGCAACTTACAAGCGGCTAATACTGCAG<br>CCCAGACACAAGTTGTCAACAACCAGGGAGCCTTACCTGGCATGGTCTGGCAGAACCGG<br>GACGTGTACCTGCAGGGTCCCATCTGGGCCAAGATTCCTCACACGGATGGCAACTTTCA<br>CCCGTCTCCTTTGATGGGCGGCTTTGGACTTAAACATCCGCCTCCTCAGATCCTGATCAA<br>GAACACTCCCGTTCCCGCTAATCCTCCGGAGGTTTTTACTCCTGCCAAGTTTGCTTCGTT<br>CATCACACAGTACAGCACCGGACAAGTCAGCGTGGAAATCGAGTGGGAGCTGCAGAAG<br>GAAAACAGCAAGCGCTGGAACCCGGAGATTCAGTACACTTCAAACTACAACAAGTCTGT<br>TAGTGTGGACTTTACTGTAGACACTAATGGCGTGTATTCAGAGCCTCGCCCCATTGGCAC<br>CAGATACCTGACTCGTAATCTGTAA |
| 26 | AAVC11.06 (nucleic acid) | ATGGCTGCCGATGGTTATCTTCCAGATTGGCTCGAGGACACTCTCTCTGAAGGCATTCG<br>CGAGTGGTGGGCGCTGAAACCTGGAGCTCCACAACCCAAGGCCAACCAACAGCATCAG<br>GACAACGGCAGGGGTCTTGTGCTTCCTGGCTACAAGTACCTCGGACCCTTCAACGGACT<br>CGACAAGGGAGAGCCGGTCAACGAGGCAGACGCCGCGGCCCTCGAGCACGACAAGGC<br>CTACGACAAGCAGCTCGAGCAGGGGGACAACCCGTACCTCAAGTACAACCACGCCGAC<br>GCCGAGTTTCAGGAGCGTCTTCAAGAAGATACGTCTTTTGGGGGCAACCTTGGCAGAGC<br>AGTCTTCCAGGCCAAAAAGAGGATCCTTGAGCCTCTTGGTCTGGTTGAGGAAGCTGCTA |

TABLE 5-continued

Capsid Sequences

| SEQ ID NO | Name | Sequence |
|---|---|---|
| | | AGACGGCTCCTGGAAAGAAGAGACCGGTAGAGCCGTCACCTCAGCGTTCCCCCGACTC<br>CTCCACGGGCATCGGCAAGAAAGGCCAGCAGCCCGCCAGAAAGAGACTCAATTTCGGT<br>CAGACTGGCGACTCAGAGTCAGTCCCCGACCCTCAACCTCTCGGAGAACCTCCAGCAGC<br>GCCCTCTAGTGTGGGATCTGGTACAGTGGCTGCAGGCGGTGGCGCACCAATGGCAGAC<br>AATAACGAAGGTGCCGACGGAGTGGGTAATGCCTCAGGAAATTGGCATTGCGATTCCAC<br>ATGGCTGGGCGACAGAGTCATCACCACCAGCACCAGAACCTGGGCCCTGCCCACTTACA<br>ACAACCATCTCTACAAGCAAATCTCCAGCCAATCAGGAGCTTCAAACGACAACCACTACT<br>TTGGCTACAGCACCCCTTGGGGGTATTTTGACTTTAACAGATTCCACTGCCATTTCTCAC<br>CACGTGACTGGCAGCGACTCATTAACAACAACTGGGGATTCCGGCCCAAGAAACTCAGC<br>TTCAAGCTCTTCAACATCCAAGTTAAAGAGGTCACGCAGAACGATGGCACGACGACTATT<br>GCCAATAACCTTACCAGCACGGTTCAAGTGTTTACGGACTCGGAATACCAGCTGCCGTA<br>CGTCCTCGGCTCCGCGCACCAGGGCTGCCTGCCTCCGTTCCCGGCGGATGTCTTCATGA<br>TTCCCCAGTACGGCTACCTGACACTGAACAATGGAAGTCAAGCCGTAGGCCGTTCCTCC<br>TTCTACTGCCTGGAATATTTTCCATCTCAAATGCTGCGAACTGGAAACAATTTTGAATTCA<br>GCTACACCTTCGAGGACGTGCCTTTCCACAGCAGCTACGCACACAGCCAGAGCTTGGAC<br>CGACTGATGAATCCTCTCATTGACCAGTACCTGTACTACTTATCCAGAACTCAGTCCACA<br>GGAGGAACTCAAGGTACCCAGCAATGTTATTTTCTCAAGCTGGGCCTGCAAACATGTC<br>GGCTCAGGCCAAGAACTGGCTGCCTGGACCTTGCTACCGGCAGCAGCGAGTCTCCACG<br>ACACTGTCGCAAAACAACAACAGCAACTTTGCTTGGACTGGTGCCACCAAATATCACCTG<br>AACGGCAGAAACTCGTTGGTTAATCCCGGCGTCGCCATGGCAACTCACAAGGACGACGA<br>GGACCGCTTTTTCCCATCCAGCGGAGTCCTGATTTTTGGAAAAACTGGAGCAACTAACAA<br>AACTACATTGGAAAATGTGTTAATGACAAATGAGGAAGAAATTCGTCCTACTAATCCTGT<br>AGCCACGGAAGAATACGGGATAGTCAGCAGCAACTTACAAGCGGCTAATACTGCAGCCC<br>AGACACAAGTTGTCAACAACCAGGGAGCCTTACCTGGCATGGTCTGGCAGAACCGGGA<br>CGTGTACCTGCAGGGTCCCATCTGGGCCAAGATTCCTCACACGGATGGCAACTTTCACC<br>CGTCTCCTTTGATGGGCGGCTTTGGACTTAAACATCCGCCTCCTCAGATCCTGATCAAGA<br>ACACTCCCGTTCCCGCTAATCCTCCGGAGGTGTTTACTCCTGCCAAGTTTGCTTCGTTCA<br>TCACACAGTACAGCACCGGACAAGTCAGCGTGGAAATCGAGTGGGAGCTGCAGAAGGA<br>AAACAGCAAGCGCTGGAACCCGGAGATTCAGTACACTTCAAACTACAACAAGTCTGTTA<br>GTGTGGACTTTACTGTAGACACTAATGGCGTGTATTCAGAGCCTCGCCCCATTGGCACC<br>AGATACCTGACTCGTAATCTGTAA |
| 27 | AAVC11.07 (nucleic acid) | ATGGCTGCTGACGGTTATCTTCCAGATTGGCTCGAGGACAACCTCTCTGAAGGCATTCG<br>CGAGTGGTGGGACCTGAAACCTGGAGCCCCCAAGCCCAAGGCCAACCAGCAGAAGCAG<br>GACGACGGTCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAACGTCCGGTAGAGCAGTCGCCACAAGAGCCAGACTCCT<br>CCTCGGGCATTGGCAAGACAGGCCAGCAGCCCGCTAAAAAGAGACTCAATTTTGGTCAG<br>ACTGGCGACTCAGAGTCAGTCCCCGACCCACAACCTCTCGGAGAACCACCAGCAGGCC<br>CCTCTGGTCTGGGATCTGGTACAGTGGCTGCAGGCGGTGGCGCACCAATGGCAGACAA<br>TAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAAGTCAAGGAGGTCACGACGAATGATGGCGTCACGACCATC<br>GCTAATAACCTTACCAGCACGGTTCAAGTCTTCTCGGACTCGGAGTACCAGCTTCCGTAC<br>GTCCTCGGCTCTGCGCACCAGGGCTGCCTCCCTCCGTTCCCGGCGGATGTCTTCATGAT<br>TCCCCAGTACGGCTACCTGACACTGAACAATGGAAGTCAAGCCGTAGGCCGTTCCTCCT<br>TCTACTGCCTGGAATATTTTCCATCTCAAATGCTGCGAACTGGAAACAATTTTGAATTCAG<br>CTACACCTTCGAGGACGTGCCTTTCCACAGCAGCTACGCACACAGCCAGAGCTTGGACC<br>GACTGATGAATCCTCTCATTGACCAGTACCTGTACTACTTATCCAGAACTCAGTCCACAG<br>GAGGAACTCAAGGTACCCAGCAATTGTTATTTTCTCAAGCTGGGCCTGCAAACATGTCG<br>GCTCAGGCCAAGAACTGGCTGCCTGGACCTTGCTACCGGCAGCAGCGAGTCTCCACGA<br>CACTGTCGCAAAACAACAACAGCAACTTTGCTTGGACTGGTGCCACCAAATATCACCTGA<br>ACGGCAGAAACTCGTTGGTTAATCCCGGCGTCGCCATGGCAACTCACAAGGACGACGA<br>GGACCGCTTTTTCCCATCCAGCGGAGTCCTGATTTTTGGAAAAACTGGAGCAACTAACAA<br>AACTACATTGGAAAATGTGTTAATGACAAATGAGGAAGAAATTCGTCCTACTAATCCTGT<br>AGCCACGGAAGAATACGGGATAGTCAGCAGCAACTTACAAGCGGCTAATACTGCAGCCC<br>AGACACAAGTTGTCAACAACCAGGGAGCCTTACCTGGCATGGTCTGGCAGAACCGGGA<br>CGTGTACCTGCAGGGTCCCATCTGGGCCAAGATTCCTCACACGGATGGCAACTTTCACC<br>CGTCTCCTTTGATGGGCGGCTTTGGACTTAAACATCCGCCTCCTCAGATCCTGATCAAGA<br>ACACTCCTGTTCCTGCGAATCCTCCGGAGGTGTTTACTCCTGCCAAGTTTGCTTCGTTCA<br>TCACACAGTACAGCACCGGACAAGTCAGCGTGGAAATCGAGTGGGAGCTGCAGAAGGA<br>AAACAGCAAGCGCTGGAACCCGGAGATTCAGTACACTTCAAACTACAACAAGTCTGTTA<br>GTGTGGACTTTACTGTAGACACTAATGGCGTGTATTCAGAGCCTCGCCCCATTGGCACC<br>AGATACCTGACTCGTAATCTGTAA |
| 28 | AAVC11.08 (nucleic acid) | ATGGCTGCTGACGGTTATCTTCCAGATTGGCTCGAGGACAACCTCTCTGAGGGCATTCG<br>CGAGTGGTGGGACCTGAAACCTGGAGCCCCGAAGCCCAAGGCCAACCAGCAGAAGCAG<br>GACGACGGCCGGGGTCTGGTGCTTCCTGGCTACAAGTACCTCGGACCCTTCAACGGACT |

TABLE 5-continued

Capsid Sequences

| SEQ ID NO | Name | Sequence |
|---|---|---|
| | | CGACAAGGGGGAGCCCGTCAACGCGGCGGACGCAGCGGCCCTCGAGCACGACAAGGC |
| | | CTACGACCAGCAGCTCAAAGCGGGTGACAATCCGTACCTGCGGTATAACCACGCCGACG |
| | | CCGAGTTTCAGGAGCGTCTGCAAGAAGATACGTCTTTTGGGGGCAACCTCGGGCGAGC |
| | | AGTCTTCCAGGCCAAGAAGCGGGTTCTCGAACCTCTCGGTCTGGTTGAGGAAGCTGCTA |
| | | AGACGGCTCCTGGAAAGAAGAGACCGGTAGAACCGTCACCTCAGCGTTCCCCAGACTCC |
| | | TCCTCGGGCATCGGCAAGACAGGCCAGCAGCCCGCTAAAAAGAGACTCAATTTTGGTCA |
| | | GACTGGCGACTCAGAGTCAGTTCCAGACCCTCAACCTCTCGGAGAACCTCCAGCAGCGC |
| | | CCTCTGGTGTGGGACCTAATACAATGGCTGCAGGCGGTGGCGCACCAATGGCAGACAA |
| | | TAACGAAGGCGCCGACGGAGTGGGTAGTTCCTCGGGAAATTGGCATTGCGATTCCACAT |
| | | GGCTGGGCGACAGAGTCATCACCACCAGCACCCGAACCTGGGCCCTGCCCACTTACAA |
| | | CAACCATCTCTACAAGCAAATCTCCAGCCAATCAGGAGCTTCAAACGACAACCACTACTT |
| | | TGGCTACAGCACCCCTTGGGGGTATTTTGACTTCAACAGATTCCACTGCCACTTCTCACC |
| | | ACGTGACTGGCAGCGACTCATCAACAACAACTGGGGATTCCGGCCTAAGCGACTCAACT |
| | | TCAAGCTCTTCAACATTCAGGTCAAAGAGGTTACGGACAACAATGGAGTCAAGACCATC |
| | | GCCAATAACCTTACCAGCACGGTCCAGGTCTTCACGGACTCAGACTATCAGCTCCCGTA |
| | | CGTGCTCGGGTCGGCTCACGAGGGCTGCCTCCCGCCGTTCCCAGCGGATGTCTTCATG |
| | | ATTCCTCAGTACGGCTACCTAACGCTCAACAATGGCAGCCAGGCAGTGGGACGGTCATC |
| | | CTTTTACTGCCTGGAATATTTCCCATCGCAGATGCTGAGAACGGGCAATAACTTTACCTT |
| | | CAGCTACACCTTCGAGGACGTGCCTTTCCACAGCAGCTACGCTCACAGCCAGAGTTTGG |
| | | ACCGACTGATGAATCCTCTCATTGACCAGTACCTGTACTACTTATCCAGAACTCAGTCCA |
| | | CAGGAGGAACTCAAGGTACCCAGCAATTGTTATTTTCTCAAGCTGGGCCTGCAAACATG |
| | | TCGGCTCAGGCCAAGAACTGGCTGCCTGGACCTTGCTACCGGCAGCAGCGAGTCTCCA |
| | | CGACACTGTCGCAAAACAACAACAGCAACTTTGCTTGGACTGGTGCCACCAAATATCACC |
| | | TGAACGGCAGAAACTCGTTGGTTAATCCCGGCGTCGCCATGGCAACTCACAAGGACGAC |
| | | GAGGACCGCTTTTTCCCATCCAGCGGAGTCCTGATTTTTGGAAAAACTGGAGCAACTAA |
| | | CAAAACTACATTGGAAAATGTGTTAATGACAAATGAAGAAGAAATTCGTCCTACTAATCC |
| | | TGTAGCCACGGAAGAATACGGGATAGTCAGCAGCAACTTACAAGCGGCTAATACTGCAG |
| | | CCCAGACACAAGTTGTCAACAACCAGGGAGCCTTACCTGGCATGGTCTGGCAGAACCGA |
| | | GACGTGTACCTGCAGGGTCCCATCTGGGCCAAGATTCCTCACACGGACGGCAACTTTCA |
| | | CCCGTCTCCTCTGATGGGCGGCTTTGGACTTAAACACCCGCCTCCACAGATCCTCATCAA |
| | | AAACACGCCTGTTCCTGCGAATCCTCCGGCGGAGTTTTCAGCTACAAAGTTTGCTTCATT |
| | | CATCACCCAATACTCCACAGGACAAGTGAGTGTGGAAATTGAATGGGAGCTGCAGAAAG |
| | | AAAACAGCAAGCGCTGGAATCCCGAAGTGCAGTACACATCCAATTATGCAAAATCTGCC |
| | | AACGTTGATTTTACTGTGGACAACAATGGACTTTATACTGAGCCTCGCCCCATTGGCACC |
| | | CGTTACCTCACCCGTCCCCTGTAA |
| 29 | AAVC11.09 (nucleic acid) | ATGGCTGCTGACGGTTATCTTCCAGATTGGCTCGAGGACAACCTCTCTGAGGGCATTCG |
| | | CGAGTGGTGGGACCTGAAACCTGGAGCCCCGAAGCCCAAGGCCAACCAGCAGAAGCAG |
| | | GACGACGGCCGGGGTCTGGTGCTTCCTGGCTACAAGTACCTCGGACCCTTCAACGGACT |
| | | CGACAAGGGGGAGCCCGTCAACGCGGCGGACGCAGCGGCCCTCGAGCACGACAAGGC |
| | | CTACGACCAGCAGCTCAAAGCGGGTGACAATCCGTACCTGCGGTATAACCACGCCGACG |
| | | CCGAGTTTCAGGAGCGTCTGCAAGAAGATACGTCTTTTGGGGGCAACCTCGGGCGAGC |
| | | AGTCTTCCAGGCCAAGAAGCGGGTTCTCGAACCTCTCGGTCTGGTTGAGGAAGCTGCTA |
| | | AGACGGCTCCTGGAAAGAAGAGACCGGTAGAACCGTCACCTCAGCGTTCCCCAGACTCC |
| | | TCCTCGGGCATCGGCAAGACAGGCCAGCAGCCCGCTAAAAAGAGACTCAATTTTGGTCA |
| | | GACTGGCGACTCAGAGTCAGTTCCAGACCCTCAACCTCTCGGAGAACCTCCAGCAGCGC |
| | | CCTCTGGTGTGGGACCTAATACAATGGCTGCAGGCGGTGGCGCACCAATGGCAGACAA |
| | | TAACGAAGGCGCCGACGGAGTGGGTAGTTCCTCGGGAAATTGGCATTGCGATTCCACAT |
| | | GGCTGGGCGACAGAGTCATCACCACCAGCACCCGAACCTGGGCCCTGCCCACTTACAA |
| | | CAACCATCTCTACAAGCAAATCTCCAGCCAATCAGGAGCTTCAAACGACAACCACTACTT |
| | | TGGCTACAGCACCCCTTGGGGGTATTTTGACTTCAACAGATTCCACTGCCACTTCTCACC |
| | | ACGTGACTGGCAGCGACTCATCAACAACAACTGGGGATTCCGGCCTAAGCGACTCAACT |
| | | TCAAGCTCTTCAACATTCAGGTCAAAGAGGTTACGGACAACAATGGAGTCAAGACCATC |
| | | GCCAATAACCTTACCAGCACGGTCCAGGTCTTCACGGACTCAGACTATCAGCTCCCGTA |
| | | CGTGCTCGGGTCGGCTCACGAGGGCTGCCTCCCGCCGTTCCCAGCGGACGTCTTCATG |
| | | ATTCCTCAGTACGGCTACCTAACGCTCAACAATGGCAGCCAGGCAGTGGGACGGTCATC |
| | | CTTTTACTGCCTGGAATATTTCCCATCGCAGATGCTGAGAACGGGCAATAACTTTACCTT |
| | | CAGCTACACCTTCGAGGACGTGCCTTTCCACAGCAGCTACGCTCACAGCCAGAGTTTGG |
| | | ACCGACTGATGAATCCTCTCATTGACCAGTACCTGTACTACTTATCCAGAACTCAGTCCA |
| | | CAGGAGGAACTCAAGGTACCCAGCAATTGTTATTTTCTCAAGCTGGGCCTGCAAACATG |
| | | TCGGCTCAGGCCAAGAACTGGCTGCCTGGACCTTGCTACCGGCAGCAGCGAGTCTCCA |
| | | CGACACTGTCGCAAAACAACAACAGCAACTTTGCTTGGACTGGTGCCACCAAATATCACC |
| | | TGAACGGCAGAAACTCGTTGGTTAATCCCGGCGTCGCCATGGCAACTCACAAGGACGAC |
| | | GAGGACCGCTTTTTCCCATCCAGCGGAGTCCTGATTTTTGGAAAAACTGGAGCAACTAA |
| | | CAAAACTACATTGGAAAATGTGTTAATGACAAATGAAGAAGAAATTCGTCCTACTAATCC |
| | | TGTAGCCACGGAAGAATACGGGATAGTCAGCAGCAACTTACAAGCGGCTAATACTGCAG |
| | | CCCAGACACAAGTTGTCAACAACCAGGGAGCCTTACCTGGCATGGTCTGGCAGAACCGA |
| | | GACGTGTACCTGCAGGGTCCCATCTGGGCCAAGATTCCTCACACGGACGGCAACTTTCA |
| | | CCCGTCTCCTCTGATGGGCGGCTTTGGACTTAAACACCCGCCTCCACAGATCCTGATCA |
| | | AGAACACGCCGGTACCTGCGGATCCTCCAACAACGTTCAGCCAGGCGAAATTGGCTTCC |
| | | TTCATCACGCAGTACAGCACCGGACAGGTCAGCGTGGAGATCGAGTGGGAGCTGCAGA |
| | | AGGAAAACAGCAAGCGCTGGAATCCCGAAGTGCAGTACACATCCAATTATGCAAAATCT |
| | | GCCAACGTTGATTTTACTGTGGACAACAATGGACTTTATACTGAGCCTCGCCCCATTGGC |
| | | ACCCGTTACCTTACCCGTCCCCTGTAA |

TABLE 5-continued

| Capsid Sequences | | |
|---|---|---|
| SEQ ID NO | Name | Sequence |
| 30 | AAVC11.10 (nucleic acid) | ATGGCTGCCGATGGTTATCTTCCAGATTGGCTCGAGGACAACCTCTCTGAGGGCATTCG<br>CGAGTGGTGGGACTTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAACGTCCGGTAGAGCAGTCGCCACAAGAGCCAGACTCCT<br>CCTCGGGCATTGGCAAGACAGGCCAGCAGCCCGCTAAAAAGAGACTCAATTTTGGTCAG<br>ACTGGCGACTCAGAGTCAGTCCCCGACCCACAACCTCTCGGAGAACCACCAGCAGGCC<br>CCTCTGGTCTGGGATCTGGTACAGTGGCTGCAGGCGGTGGCGCACCAATGGCAGACAA<br>TAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAAGTCAAGGAGGTCACGACGAATGATGGCGTCACGACCATC<br>GCTAATAACCTTACCAGCACGGTTCAAGTCTTCTCGGACTCGGAGTACCAGCTTCCGTAC<br>GTCCTCGGCTCTGCGCACCAGGGCTGCCTCCCTCCGTTCCCGGCGGACGTGTTCATGAT<br>TCCGCAGTACGGCTACCTAACGCTCAACAATGGCAGCCAGGCAGTGGGACGGTCATCCT<br>TTTACTGCCTGGAATATTTTCCATCTCAAATGCTGCGAACTGGAAACAATTTTGAATTCAG<br>CTACACCTTCGAGGACGTGCCTTTCCACAGCAGCTACGCACACAGCCAGAGCTTGGACC<br>GACTGATGAATCCTCTCATTGACCAGTACCTGTACTACTTATCCAGAACTCAGTCCACAG<br>GAGGAACTCAAGGTACCCAGCAATTGTTATTTTCTCAAGCTGGGCCTGCAAACATGTCG<br>GCTCAGGCCAAGAACTGGCTGCCTGGACCTTGCTACCGGCAGCAGCGAGTCTCCACGA<br>CACTGTCGCAAAACAACAACAGCAACTTTGCTTGGACTGGTGCCACCAAATATCACCTGA<br>ACGGCAGAAACTCGTTGGTTAATCCCGGCGTCGCCATGGCAACTCACAAGGACGACGA<br>GGACCGCTTTTTCCCATCCAGCGGAGTCCTGATTTTTGGAAAAACTGGAGCAACTAACAA<br>AACTACATTGGAAAATGTGTTAATGACAAATGAAGAAGAAATTCGTCCTACTAATCCTGT<br>AGCCACGGAAGAATACGGGATAGTCAGCAGCAACTTACAAGCGGCTAATACTGCAGCCC<br>AGACACAAGTTGTCAACAACCAGGGAGCCTTACCTGGCATGGTCTGGCAGAACCGAGAC<br>GTGTACCTGCAGGGTCCCATCTGGGCCAAGATTCCTCACACGGACGGCAACTTTCACCC<br>GTCTCCTCTGATGGGCGGCTTTGGACTTAAACACCCGCCTCCACAGATCCTGATCAAGA<br>ACACGCCGGTACCTGCGGATCCTCCAACAACGTTCAGCCAGGCGAAATTGGCTTCCTTC<br>ATCACGCAGTACAGCACCGGACAGGTCAGCGTGGAGATCGAGTGGGAGCTGCAGAAGG<br>AAAACAGCAAGCGCTGGAATCCCGAAGTGCAGTACACATCCAATTATGCAAAATCTGCC<br>AACGTTGATTTTACTGTGGACAACAATGGACTTTATACTGAGCCTCGCCCCATTGGCACC<br>AGATACCTGACTCGTAATCTGTAA |
| 31 | AAVC11.11 (nucleic acid) | ATGGCTGCCGATGGTTATCTTCCAGATTGGCTCGAGGACACTCTCTCTGAAGGCATTCG<br>CGAGTGGTGGGCGCTGAAACCTGGAGCTCCACAACCCAAGGCCAACCAACAGCATCAG<br>GACAACGGCAGGGGTCTTGTGCTTCCTGGGTACAAGTACCTCGGACCCTTCAACGGACT<br>CGACAAGGGAGAGCCGGTCAACGAGGCAGACGCCGCGGCCCTCGAGCACGACAAGGC<br>CTACGACAAGCAGCTCGAGCAGGGGGACAACCCGTACCTCAAGTACAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCGTCACCTCAGCGTTCCCCCGACT<br>CCTCCACGGGCATCGGCAAGAAAGGCCAGCAGCCCGCCAGAAAGAGACTCAATTTCGG<br>TCAGACTGGCGACTCAGAGTCAGTCCCCGACCCTCAACCTCTCGGAGAACCTCCAGCAG<br>CGCCCTCTAGTGTGGGATCTGGTACAGTGGCTGCAGGCGGTGGCGCACCAATGGCAGA<br>CAATAACGAAGGTGCCGACGGAGTGGGTAATGCCTCAGGAAATTGGCATTGCGATTCCA<br>CATGGCTGGGCGACAGAGTCATTACCACCAGCACCCGAACCTGGGCCCTGCCCACCTAC<br>AACAACCACCTCTACAAGCAAATCTCCAGCCAATCAGGAGCTTCAAACGACAACCACTAC<br>TTTGGCTACAGCACCCCTTGGGGGTATTTTGACTTTAACAGATTCCACTGCCACTTCTCA<br>CCACGTGACTGGCAGCGACTCATTAACAACAACTGGGGATTCCGGCCCAAGAGACTCAA<br>CTTCAAGCTCTTCAACATCCAAGTCAAGGAGGTCACGACGAATGATGGCGTCACGACCA<br>TCGCTAATAACCTTACCAGCACGGTTCAAGTCTTCTCGGACTCGGAGTACCAGTTGCCGT<br>ACGTCCTCGGCTCTGCGCACCAGGGCTGCCTCCCTCCGTTCCCGGCGGACGTGTTCATG<br>ATTCCCCAGTACGGCTACCTAACACTCAACAACGGTAGTCAGGCCGTGGGACGCTCCTC<br>CTTTTACTGCCTGGAATATTTCCCATCGCAGATGCTGAGAACGGGCAATAACTTTGAGTT<br>CAGCTACAGCTTCGAGGACGTGCCTTTCCACAGCAGCTACGCACACAGCCAGAGCTTGG<br>ACCGACTGATGAATCCTCTCATTGACCAGTACCTGTACTACTTATCCAGAACTCAGTCCA<br>CAGGAGGAACTCAAGGTACCCAGCAATGTTATTTTCTCAAGCTGGGCCTGCAAACATG<br>TCGGCTCAGGCCAAGAACTGGCTGCCTGGACCTTGCTACCGGCAGCAGCGAGTCTCCA<br>CGACACTGTCGCAAAACAACAACAGCAACTTTGCTTGGACTGGTGCCACCAAATATCACC<br>TGAACGGCAGAAACTCGTTGGTTAATCCCGGCGTCGCCATGGCAACTCACAAGGACGAC<br>GAGGACCGCTTTTTCCCATCCAGCGGAGTCCTGATTTTTGGAAAAACTGGAGCAACTAA<br>CAAAACTACATTGGAAAATGTGTTAATGACAAATGAAGAAGAAATTCGTCCTACTAATCC<br>TGTAGCCACGGAAGAATACGGGATAGTCAGCAGCAACTTACAAGCGGCTAATACTGCAG<br>CCCAGACACAAGTTGTCAACAACCAGGGAGCCTTACCTGGCATGGTCTGGCAGAACCGG<br>GACGTGTACCTGCAGGGTCCCATTTGGGCCAAAATTCCTCACACAGATGGACACTTTCA<br>CCCGTCTCCTCTTATGGGCGGCTTTGGACTCAAGAACCCGCCTCCTCAGATCCTCATCAA<br>AAACACGCCTGTTCCTGCGAATCCTCCGGCGGAGTTTTCAGCTACAAAGTTTGCTTCATT |

TABLE 5-continued

| Capsid Sequences | | |
|---|---|---|
| SEQ ID NO | Name | Sequence |
| | | CATCACCCAGTATTCCACAGGACAAGTGAGCGTGGAGATTGAATGGGAGCTGCAGAAA<br>GAAAACAGCAAACGCTGGAATCCCGAAGTGCAGTATACATCTAACTATGCAAAATCTGC<br>CAACGTTGATTTCACTGTGGACAACAATGGACTTTATACTGAGCCTCGCCCCATTGGCAC<br>CCGTTACCTTACCCGTCCCCTGTAA |
| 32 | AAVC11.12 (nucleic acid) | ATGGCTGCCGATGGTTATCTTCCAGATTGGCTCGAGGACACTCTCTCTGAAGGCATTCG<br>CGAGTGGTGGGCGCTGAAACCTGGAGCTCCACAACCCAAGGCCAACCAACAGCATCAG<br>GACAACGGCAGGGGTCTTGTGCTTCCTGGGTACAAGTACCTCGGACCCTTCAACGGACT<br>CGACAAGGGAGAGCCGGTCAACGAGGCAGACGCCGCGGCCCTCGAGCACGACAAGGC<br>CTACGACAAGCAGCTCGAGCAGGGGGACAACCCGTACCTCAAGTACAACCACGCCGAC<br>GCCGAGTTTCAGGAGCGTCTTCAAGAAGATACGTCTTTTGGGGGCAACCTTGGCAGAGC<br>AGTCTTCCAGGCCAAAAAGAGGATCCTTGAGCCTCTTGGTCTGGTTGAGGAAGCTGCTA<br>AGACGGCTCCTGGAAAGAAGAGACCGGTAGAACCGTCACCTCAGCGTTCCCCCGACTCC<br>TCCACGGGCATCGGCAAGAAAGGCCAGCAGCCCGCCAGAAAGAGACTCAATTTCGGTC<br>AGACTGGCGACTCAGAGTCAGTCCCCGACCCTCAACCTCTCGGAGAACCTCCAGCAGCG<br>CCCTCTAGTGTGGGATCTGGTACAGTGGCTGCAGGCGGTGGCGCACCAATGGCAGACA<br>ATAACGAAGGTGCCGACGGAGTGGGTAATGCCTCAGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAAGTCAAGGAGGTCACGACGAATGATGGCGTCACGACCATC<br>GCTAATAACCTTACCAGCACGGTTCAAGTCTTCTCGGACTCGGAGTACCAGCTTCCGTAC<br>GTCCTCGGCTCTGCGCACCAGGGCTGCCTCCCTCCGTTCCCGGCGGACCTCTTCATGAT<br>TCCGCAGTACGGCTACCTAACGCTCAACAATGGCAGCCAGGCAGTGGGACGGTCATCCT<br>TTTACTGCCTGGAATATTTTCCATCTCAAATGCTGCGAACTGGAAACAATTTTGAATTCAG<br>CTACACCTTCGAGGACGTGCCTTTCCACAGCAGCTACGCACACAGCCAGAGCTTGGACC<br>GACTGATGAATCCTCTCATTGACCAGTACCTGTACTACTTATCCAGAACTCAGTCCACAG<br>GAGGAACTCAAGGTACCCAGCAATGTTATTTTCTCAAGCTGGGCCTGCAAACATGTCG<br>GCTCAGGCCAAGAACTGGCTGCCTGGACCTTGCTACCGGCAGCAGCGAGTCTCCACGA<br>CACTGTCGCAAAACAACAACAGCAACTTTGCTTGGACTGGTGCCACCAAATATCACCTGA<br>ACGGCAGAAACTCGTTGGTTAATCCCGGCGTCGCCATGGCAACTCACAAGGACGACGA<br>GGACCGCTTTTTCCCATCCAGCGGAGTCCTGATTTTTGGAAAAACTGGAGCAACTAACAA<br>AACTACATTGGAAAATGTGTTAATGACAAATGAAGAAGAAATTCGTCCTACTAATCCTGT<br>AGCCACGGAAGAATACGGGATAGTCAGCAGCAACTTACAAGCGGCTAATACTGCAGCCC<br>AGACACAAGTTGTCAACAACCAGGGAGCCTTACCTGGCATGGTCTGGCAGAACCGGGA<br>CGTGTACCTGCAGGGTCCCATCTGGGCCAAGATTCCTCACACGGATGGCAACTTTCACC<br>CGTCTCCTTTGATGGGCGGCTTTGGACTTAAACATCCGCCTCCTCAGATCCTGATCAAGA<br>ACACTCCCGTTCCCGCTAATCCTCCGGAGGTGTTTACTCCTGCCAAGTTTGCTTCGTTCA<br>TCACACAGTACAGCACCGGACAAGTCAGCGTGGAAATCGAGTGGGAGCTGCAGAAGGA<br>AAACAGCAAGCGCTGGAACCCGGAGATTCAGTACACTTCAAACTACAACAAGTCTGTTA<br>GTGTGGACTTTACTGTAGACACTAATGGCGTGTATTCAGAGCCTCGCCCCATTGGCACC<br>AGATACCTGACTCGTAATCTGTAA |
| 33 | AAVC11.13 (nucleic acid) | ATGGCTGCTGACGGTTATCTTCCAGATTGGCTCGAGGACAACCTCTCTGAGGGCATTCG<br>CGAGTGGTGGGACCTGAAACCTGGAGCCCCGAAGCCCAAGGCCAACCAGCAGAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTCAAAGCGGGTGACAATCCGTACCTGCGGTATAACCACGCCGACG<br>CCGAGTTTCAGGAGCGTCTGCAAGAAGATACGTCTTTTGGGGGCAACCTTGGCAGAGCA<br>GTCTTCCAGGCCAAAAAGAGGATCCTTGAGCCTCTTGGTCTGGTTGAGGAAGCTGCTAA<br>GACGGCTCCTGGAAAGAAGAGACCGGTAGAACCGTCACCTCAGCGTTCCCCCGACTCCT<br>CCACGGGCATCGGCAAGAAAGGCCAGCAGCCCGCCAGAAAGAGACTCAATTTCGGTCA<br>GACTGGCGACTCAGAGTCAGTCCCCGACCCTCAACCTCTCGGAGAACCTCCAGCAGCGC<br>CCTCTAGTGTGGGATCTGGTACAGTGGCTGCAGGCGGTGGCGCACCAATGGCAGACAA<br>TAACGAAGGTGCCGACGGAGTGGGTAATGCCTCAGGAAATTGGCATTGCGATTCCACAT<br>GGCTGGGCGACAGAGTCATTACCACCAGCACCCGAACCTGGGCCCTGCCCACCTACAA<br>CAACCACCTCTACAAGCAAATCTCCAGCCAATCAGGAGCTTCAAACGACAACCACTACTT<br>TGGCTACAGCACCCCTTGGGGGTATTTTGACTTTAACAGATTCCACTGCCACTTCTCACC<br>ACGTGACTGGCAGCGACTCATTAACAACAACTGGGGATTCCGGCCCAAGAGACTCAACT<br>TCAAGCTCTTCAACATCCAAGTCAAGGAGGTCACGACGAATGATGGCGTCACGACCATC<br>GCTAATAACCTTACCAGCACGGTTCAAGTCTTCTCGGACTCGGAGTACCAGCTTCCGTAC<br>GTCCTCGGCTCTGCGCACCAGGGCTGCCTCCCTCCGTTCCCGGCGGACGTGTTCATGAT<br>TCCGCAGTACGGCTACCTAACGCTCAACAATGGCAGCCAGGCAGTGGGACGGTCATCCT<br>TTTACTGCCTGGAATATTTCCCATCGCAGATGCTGAGAACGGGCAATAACTTTGAGTTCA<br>GCTACACCTTCGAGGACGTGCCTTTCCACAGCAGCTACGCACACAGCCAGAGCTTGGAC<br>CGACTGATGAATCCTCTCATTGACCAGTACCTGTACTACTTATCCAGAACTCAGTCCACA<br>GGAGGAACTCAAGGTACCCAGCAATTGTTATTTTCTCAAGCTGGGCCTGCAAACATGTC<br>GGCTCAGGCCAAGAACTGGCTGCCTGGACCTTGCTTCCGGCAACAAAGAGTCTCCAAAA<br>CGCTGGATCAAAACAACAACAGCAACTTTGCTTGGACTGGTGCCACCAAATATCACCTGA<br>ACGGCAGAAACTCGTTGGTTAATCCCGGCGTCGCCATGGCAACTCACAAGGACGACGA<br>GGACCGCTTTTTCCCATCCAGCGGAGTCCTGATTTTTGGAAAAACTGGAGCAACTAACAA<br>AACTACATTGGAAAATGTGTTAATGACAAATGAAGAAGAAATTCGTCCTACTAATCCTGT<br>AGCCACGGAAGAATACGGGATAGTCAGCAGCAACTTACAAGCGGCTAATACTGCAGCCC |

TABLE 5-continued

Capsid Sequences

| SEQ ID NO | Name | Sequence |
|---|---|---|
| | | AGACACAAGTTGTCAACAACCAGGGAGCCTTACCTGGCATGGTCTGGCAGAACCGGGA<br>CGTGTACCTGCAGGGTCCCATCTGGGCCAAGATTCCTCACACGGATGGCAACTTTCACC<br>CGTCTCCTTTGATGGGCGGCTTTGGACTTAAACATCCGCCTCCTCAGATCCTGATCAAGA<br>ACACTCCCGTTCCCGCTAATCCTCCGGAGGTGTTTACTCCTGCCAAGTTTGCTTCGTTCA<br>TCACACAGTACAGCACCGGACAAGTCAGCGTGGAAATCGAGTGGGAGCTGCAGAAGGA<br>AAACAGCAAGCGCTGGAACCCGGAGATTCAGTACACTTCAAACTACAACAAGTCTGTTA<br>GTGTGGACTTTACTGTAGACACTAATGGCGTGTATTCAGAGCCTCGCCCCATTGGCACC<br>AGATACCTGACTCGTAATCTGTAA |
| 34 | AAVC11.14 (nucleic acid) | ATGGCTGCTGACGGTTATCTTCCAGATTGGCTCGAGGACAACCTCTCTGAAGGCATTCG<br>CGAGTGGTGGGACCTGAAACCTGGAGCCCCCAAGCCCAAGGCCAACCAGCAGAAGCAG<br>GACGACGGTCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAACGTCCGGTAGAGCAGTCGCCACAAGAGCCAGACTCCT<br>CCTCGGGCATTGGCAAGACAGGCCAGCAGCCCGCTAAAAAGAGACTCAATTTTGGTCAG<br>ACTGGCGACTCAGAGTCAGTCCCCGACCCACAACCTCTCGGAGAACCACCAGCAGGCC<br>CCTCTGGTCTGGGATCTGGTACAGTGGCTTCAGGCGGTGGCGCACCAATGGCAGACAA<br>TAACGAGGGTGCCGATGGAGTGGGTAATTCCTCAGGAAATTGGCATTGCGATTCCCAAT<br>GGCTGGGCGACAGAGTCATCACCACCAGCACCCGAACCTGGGCCCTGCCCACCTACAA<br>CAATCACCTCTACAAGCAAATCTCCAACAGCACATCTGGAGGATCTTCAAATGACAACGC<br>CTACTTCGGCTACAGCACCCCCTGGGGGTATTTTGACTTCAACAGATTCCACTGCCATTT<br>CTCACCACGTGACTGGCAGCGACTCATCAACAACAATTGGGGATTCCGGCCCAAGAGAC<br>TCAACTTCAAGCTCTTCAACATCCAAGTCAAGGAGGTCACGACGAATGATGGCGTCACG<br>ACCATCGCTAATAACCTTACCAGCACGGTTCAAGTCTTCTCGGACTCGGAGTACCAGTTG<br>CCGTACGTCCTCGGCTCTGCGCACCAGGGCTGCCTCCCTCCGTTCCCGGCGGACGTGTT<br>CATGATTCCCCAGTACGGCTACCTAACACTCAACAACGGTAGTCAGGCCGTGGGACGCT<br>CCTCCTTTTACTGCCTGGAATATTTCCCATCTCAAATGCTGCGAACTGGAAACAATTTTGA<br>ATTCAGCTACACCTTCGAGGACGTGCCTTTCCACAGCAGCTACGCACACAGCCAGAGCT<br>TGGACCGACTGATGAATCCTCTCATTGACCAGTACCTGTACTACTTATCCAGAACTCAGT<br>CCACAGGAGGAACTCAAGGTACCCAGCAATTGTTATTTTCTCAAGCTGGGCCTGCAAAC<br>ATGTCGGCTCAGGCCAAGAACTGGCTGCCTGGACCTTGCTACCGGCAGCAGCGAGTCT<br>CCACGACACTGTCGCAAAACAACAACAGCAACTTTGCTTGGACTGGTGCCACCAAATATC<br>ACCTGAACGGCAGAAACTCGTTGGTTAATCCCGGCGTCGCCATGGCAACTCACAAGGAC<br>GACGAGGACCGCTTTTTCCCATCCAGCGGAGTCCTGATTTTTGGAAAAACTGGAGCAAC<br>TAACAAAACTACATTGGAAAATGTGTTAATGACAAATGAGGAAGAAATTCGTCCTACTAA<br>TCCTGTAGCCACGGAAGAATACGGGATAGTCAGCAGCAACTTACAAGCGGCTAATACTG<br>CAGCCCAGACACAAGTTGTCAACAACCAGGGAGCCTTACCTGGCATGGTCTGGCAGAAC<br>CGGGACGTGTACCTGCAGGGTCCCATCTGGGCCAAGATTCCTCACACGGATGGCAACTT<br>TCACCCGTCTCCTTTGATGGGCGGCTTTGGACTTAAACATCCGCCTCCTCAGATCCTGAT<br>CAAGAACACTCCTGTTCCTGCGAATCCTCCGGCAGAGTTTTCGGCTACAAAGTTTGCTTC<br>ATTCATCACCCAATACTCCACAGGACAAGTGAGTGTGGAAATTGAATGGGAGCTGCAGA<br>AAGAAAACAGCAAGCGCTGGAATCCCGAAGTGCAGTATACATCTAACTATGCAAAATCT<br>GCCAACGTTGATTTTACTGTGGACAACAATGGACTTTATACTGAGCCTCGCCCCATTGGC<br>ACCCGTTACCTTACCCGTCCCCTGTAA |
| 35 | AAVC11.15 (nucleic acid) | ATGGCTGCCGATGGTTATCTTCCAGATTGGCTCGAGGACAACCTCTCTGAGGGCATTCG<br>CGAGTGGTGGGACTTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGCTGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTCCCCGACCCACAACCTCTCGGAGAACCACCAGCAGG<br>CCCCTCTGGTCTGGGATCTGGTACAGTGGCTGCAGGCGGTGGCGCACCAATGGCAGAC<br>AATAACGAGGGTGCCGATGGAGTGGGTAATTCCTCAGGAAATTGGCATTGCGATTCCCA<br>ATGGCTGGGCGACAGAGTCATCACCACCAGCACCAGAACCTGGGCCCTGCCCACTTACA<br>ACAACCATCTCTACAAGCAAATCTCCAGCCAATCAGGAGCTTCAAACGACAACCACTACT<br>TCGGCTACAGCACCCCCTGGGGGTATTTTGACTTTAACAGATTCCACTGCCACTTTTCAC<br>CACGTGACTGGCAGCGACTCATCAACAACAACTGGGGATTCCGGCCCAAGAGACTCAGC<br>TTCAAGCTCTTCAACATCCAAGTCAAGGAGGTCACGACGAATGATGGCGTCACGACCAT<br>CGCTAATAACCTTACCAGCACGGTTCAAGTCTTCTCGGACTCGGAGTACCAGCTTCCGTA<br>CGTCCTCGGCTCTGCGCACCAGGGCTGCCTCCCTCCGTTCCCGGCGGACGTGTTCATGA<br>TTCCGCAGTACGGCTACCTAACGCTCAACAATGGCAGCCAGGCAGTGGGACGGTCATCC<br>TTTTACTGCCTGGAATATTTTCCATCTCAAATGCTGCGAACTGGAAACAATTTTGAATTCA<br>GCTACACCTTCGAGGACGTGCCTTTCCACAGCAGCTACGCACACAGCCAGAGCTTGGAC<br>CGACTGATGAATCCTCTCATTGACCAGTACCTGTACTACTTATCCAGAACTCAGTCCACA<br>GGAGGAACTCAAGGTACCCAGCAATTGTTATTTTCTCAAGCTGGGCCTGCAAACATGTC<br>GGCTCAGGCCAAGAACTGGCTGCCTGGACCTTGCTACCGGCAGCAGCGAGTCTCCACG<br>ACACTGTCGCAAAACAACAACAGCAACTTTGCTTGGACTGGTGCCACCAAATATCACCTG |

TABLE 5-continued

| Capsid Sequences | | |
|---|---|---|
| SEQ ID NO | Name | Sequence |
| | | AACGGCAGAAACTCGTTGGTTAATCCCGGCGTCGCCATGGCAACTCACAAGGACGACGA GGACCGCTTTTTCCCATCCAGCGGAGTCCTGATTTTTGGAAAAACTGGAGCAACTAACAA AACTACATTGGAAAATGTGTTAATGACAAATGAAGAAGAAATTCGTCCTACTAATCCTGT AGCCACGGAAGAATACGGGATAGTCAGCAGCAACTTACAAGCGGCTAATACTGCAGCCC AGACACAAGTTGTCAACAACCAGGGAGCCTTACCTGGCATGGTCTGGCAGAACCGGGA CGTGTACCTGCAGGGTCCCATTTGGGCCAAAATTCCTCACACAGATGGACACTTTCACCC GTCTCCTCTTATGGGCGGCTTTGGACTCAAGAACCCGCCTCCTCAGATCCTCATCAAAAA CACGCCTGTTCCTGCGAATCCTCCGGCGGAGTTTTCAGCTACAAAGTTTGCTTCATTCAT CACCCAGTATTCCACAGGACAAGTGAGCGTGGAGATTGAATGGGAGCTGCAGAAAGAA AACAGCAAACGCTGGAATCCCGAAGTGCAGTATACATCTAACTATGCAAAATCTGCCAAC GTTGATTTCACTGTGGACAACAATGGACTTTATACTGAGCCTCGCCCCATTGGCACCCGT TACCTTACCCGTCCCCTGTAA |
| 36 | AAVC11.16 (nucleic acid) | ATGGCTGCCGATGGTTATCTTCCAGATTGGCTCGAGGACACTCTCTCTGAAGGCATTCG CGAGTGGTGGGCGCTGAAACCTGGAGCTCCACAACCCAAGGCCAACCAACAGCATCAG GACAACGGCAGGGGTCTTGTGCTTCCTGGGTACAAGTACCTCGGACCCTTCAACGGACT CGACAAGGGAGAGCCGGTCAACGAGGCAGACGCCGCGGCCCTCGAGCACGACAAGGC CTACGACAAGCAGCTCGAGCAGGGGGACAACCCGTACCTCAAGTACAACCACGCCGAC GCCGAGTTTCAGGAGCGTCTTCAAGAAGATACGTCTTTTGGGGGCAACCTTGGCAGAGC AGTCTTCCAGGCCAAAAAGAGGATCCTTGAGCCTCTTGGTCTGGTTGAGGAAGCTGCTA AGACGGCTCCTGGAAAGAAGAGACCGGTAGAACCGTCACCTCAGCGTTCCCCCGACTCC TCCACGGGCATCGGCAAGAAAGGCCAGCAGCCCGCCAGAAAGAGACTCAATTTCGGTC AGACTGGCGACTCAGAGTCAGTCCCCGACCCTCAACCTCTCGGAGAACCTCCAGCAGCG CCCTCTAGTGTGGGATCTGGTACAGTGGCTGCAGGCGGTGGCGCACCAATGGCAGACA ATAACGAAGGTGCCGACGGAGTGGGTAATGCCTCAGGAAATTGGCATTGCGATTCCACA TGGCTGGGCGACAGAGTCATTACCACCAGCACCCGAACCTGGGCCCTGCCCACCTACAA CAACCACCTCTACAAGCAAATCTCCAGCCAATCAGGAGCTTCAAACGACAACCACTACTT TGGCTACAGCACCCCTTGGGGGTATTTTGACTTTAACAGATTCCACTGCCACTTCTCACC ACGTGACTGGCAGCGACTCATTAACAACAACTGGGGATTCCGGCCCAAGAGACTCAACT TCAAGCTCTTCAACATCCAAGTCAAGGAGGTCACGACGAATGATGGCGTCACGACCATC GCTAATAACCTTACCAGCACGGTTCAAGTCTTCTCGGACTCGGAGTACCAGCTTCCGTAC GTCCTCGGCTCTGCGCACCAGGGCTGCCTCCCTCCGTTCCCGGCGGACGTGTTCATGAT TCCGCAGTACGGCTACCTAACGCTCAACAATGGCAGCCAGGCAGTGGGACGGTCATCCT TTTACTGCCTGGAATATTTCCCATCGCAGATGCTGAGAACGGGCAATAACTTTGAGTTCA GCTACACCTTCGAGGACGTGCCTTTCCACAGCAGCTACGCACACAGCCAGAGCTTGGAC CGACTGATGAATCCTCTCATTGACCAGTACCTGTACTACTTATCCAGAACTCAGTCCACA GGAGGAACTCAAGGTACCCAGCAATTGTTATTTTCTCAAGCTGGGCCTGCAAACATGTC GGCTCAGGCCAAGAACTGGCTGCCTGGACCTTGCTACCGGCAGCAGCGAGTCTCCACG ACACTGTCGCAAAACAACAACAGCAACTTTGCTTGGACTGGTGCCACCAAATATCACCTG AACGGCAGAAACTCGTTGGTTAATCCCGGCGTCGCCATGGCAACTCACAAGGACGACGA GGACCGCTTTTTCCCATCCAGCGGAGTCCTGATTTTTGGAAAAACTGGAGCAACTAACAA AACTACATTGGAAAATGTGTTAATGACAAATGAAGAAGAAATTCGTCCTACTAATCCTGT AGCCACGGAAGAATACGGGATAGTCAGCAGCAACTTACAAGCGGCTAATACTGCAGCCC AGACACAAGTTGTCAACAACCAGGGAGCCTTACCTGGCATGGTCTGGCAGAACCGAGAC GTGTACCTGCAGGGTCCCATCTGGGCCAAGATTCCTCACACGGACGGCAACTTTCACCC GTCTCCTCTGATGGGCGGCTTTGGACTTAAACACCCGCCTCCACAGATCCTGATCAAGA ACACGCCGGTACCTGCGGATCCTCCAACAACGTTCAGCCAGGCGAAATTGGCTTCCTTC ATCACGCAGTACAGCACCGGACAGGTCAGCGTGGAGATCGAGTGGGAGCTGCAGAAGG AAAACAGCAAGCGCTGGAATCCCGAAGTGCAGTACACATCCAATTATGCAAAATCTGCC AACGTTGATTTTACTGTGGACAACAATGGACTTTATACTGAGCCTCGCCCCATTGGCACC CGTTACCTTACCCGTCCCCTGTAA |
| 37 | AAVC11.17 (nucleic acid) | ATGGCTGCTGACGGTTATCTTCCAGATTGGCTCGAGGACAACCTCTCTGAAGGCATTCG CGAGTGGTGGGACCTGAAACCTGGAGCCCCCAAGCCCAAGGCCAACCAGCAGAAGCAG GACGACGGTCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTCAAAGCGGGTGACAATCCGTACCTGCGGTATAACCACGCCGACG CCGAGTTTCAGGAGCGTCTGCAAGAAGATACGTCTTTTGGGGGCAACCTCGGGCGAGC AGTCTTCCAGGCCAAGAAGCGGGTTCTCGAACCTCTCGGTCTGGTTGAGGAAGCTGCTA AGACGGCTCCTGGAAAGAAGAGACCGGTAGAGCCATCACCCCAGCGTTCTCCAGACTCC TCTACGGGCATCGGCAAGAAAGGCCAACAGCCCGCCAGAAAAAGACTCAATTTTGGTCA GACTGGCGACTCAGAGTCAGTTCCAGACCCTCAACCTCTCGGAGAACCTCCAGCAGCGC CCTCTGGTGTGGGATCTGGTACAGTGGCTGCAGGCGGTGGCGCACCAATGGCAGACAA TAACGAAGGTGCCGACGGAGTGGGTAATGCCTCAGGAAATTGGCATTGCGATTCCACAT GGCTGGGCGACAGAGTCATTACCACCAGCACCCGAACCTGGGCCCTGCCCACTTACAAC AACCATCTCTACAAGCAAATCTCCAGCCAATCAGGAGCTTCAAACGACAACCACTACTTT GGCTACAGCACCCCTTGGGGGTATTTTGACTTTAACAGATTCCACTGCCACTTCTCACCA CGTGACTGGCAGCGACTCATCAACAACAACTGGGGATTCCGGCCCAAGAAGCTGCGGTT CAAGCTCTTCAACATCCAGGTCAAGGAGGTCACGACGAATGACGGCGTTACGACCATCG CTAATAACCTTACCAGCACGATTCAGGTATTCTCGGACTCGGAATACCAGCTGCCGTACG TCCTCGGCTCTGCGCACCAGGGCTGCCTCCCTCCGTTCCCGGCGGACGTGTTCATGATT CCGCAGTACGGCTACCTAACACTCAACAACGGTAGTCAGGCCGTGGGACGCTCATCCTT TTACTGCCTGGAGTACTTCCCCTCTCAGATGCTGAGAACGGGCAACAACTTTGAGTTCAG CTACAGCTTCGAGGACGTGCCTTTCCACAGCAGCTACGCACACAGCCAGAGCTTGGACC |

TABLE 5-continued

Capsid Sequences

| SEQ ID NO | Name | Sequence |
|---|---|---|
| | | GACTGATGAATCCTCTCATTGACCAGTACCTGTACTACTTATCCAGAACTCAGTCCACAG |
| | | GAGGAACTCAAGGTACCCAGCAATTGTTATTTTCTCAAGCTGGGCCTGCAAACATGTCG |
| | | GCTCAGGCCAAGAACTGGCTGCCTGGACCTTGCTACCGGCAGCAGCGAGTCTCCACGA |
| | | CACTGTCGCAAAACAACAACAGCAACTTTGCTTGGACTGGTGCCACCAAATATCACCTGA |
| | | ACGGCAGAAACTCGTTGGTTAATCCCGGCGTCGCCATGGCAACTCACAAGGACGACGA |
| | | GGACCGCTTTTTCCCATCCAGCGGAGTCCTGATTTTTGGAAAAACTGGAGCAACTAACAA |
| | | AACTACATTGGAAAATGTGTTAATGACAAATGAAGAAGAAATTCGTCCTACTAATCCTGT |
| | | AGCCACGGAAGAATACGGGATAGTCAGCAGCAACTTACAAGCGGCTAATACTGCAGCCC |
| | | AGACACAAGTTGTCAACAACCAGGGAGCCTTACCTGGCATGGTCTGGCAGAACCGGGA |
| | | CGTGTACCTGCAGGGTCCCATCTGGGCCAAGATTCCTCACACGGATGGCAACTTTCACC |
| | | CGTCTCCTTTGATGGGCGGCTTTGGACTTAAACATCCGCCTCCTCAGATCCTGATCAAGA |
| | | ACACTCCCGTTCCCGCTAATCCTCCGGAGGTGTTTACTCCTGCCAAGTTTGCTTCGTTCA |
| | | TCACACAGTACAGCACCGGACAAGTCAGCGTGGAAATCGAGTGGGAGCTGCAGAAGGA |
| | | AAACAGCAAGCGCTGGAACCCGGAGATTCAGTACACTTCAAACTACAACAAGTCTGTTA |
| | | GTGTGGACTTTACTGTAGACACTAATGGCGTGTATTCAGAGCCTCGCCCCATTGGCACC |
| | | AGATACCTGACTCGTAATCTGTAA |
| 38 | AAVC11.18 (nucleic acid) | ATGGCTGCCGATGGTTATCTTCCAGATTGGCTCGAGGACAACCTCTCTGAGGGCATTCG |
| | | CGAGTGGTGGGACCTGAAACCTGGAGCCCCGAAGCCCAAGGCCAACCAGCAGAAGCAG |
| | | GACGACGGCCGGGGTCTGGTGCTTCCTGGCTACAAGTACCTCGGACCCTTCAACGGACT |
| | | CGACAAGGGGGAGCCCGTCAACGCGGCGGACGCAGCGGCCCTCGAGCACGACAAGGC |
| | | CTACGACCAGCAGCTCAAAGCGGGTGACAATCCGTACCTGCGGTATAACCACGCCGACG |
| | | CCGAGTTTCAGGAGCGTCTGCAAGAAGATACGTCTTTTGGGGGCAACCTCGGGCGAGC |
| | | AGTCTTCCAGGCCAAGAAGCGGGTTCTCGAACCTCTCGGTCTGGTTGAGGAAGGCGCTA |
| | | AGACGGCTCCTGGAAAGAAGAGACCGGTAGAGCCATCACCCCAGCGTTCTCCAGACTCC |
| | | TCCTCGGGCATTGGCAAGACAGGCCAGCAGCCCGCTAAAAAGAGACTCAATTTCGGTCA |
| | | GACTGGCGACTCAGAGTCAGTCCCCGACCCTCAACCTCTCGGAGAACCTCCAGCAGCGC |
| | | CCTCTAGTGTGGGATCTGGTACAGTGGCTGCAGGCGGTGGCGCACCAATGGCAGACAA |
| | | TAACGAAGGTGCCGACGGAGTGGGTAATGCCTCAGGAAATTGGCATTGCGATTCCACAT |
| | | GGCTGGGCGACAGAGTCATCACCACCAGCACCAGAACCTGGGCCCTGCCCACTTACAA |
| | | CAACCATCTCTACAAGCAAATCTCCAGCCAATCAGGAGCTTCAAACGACAACCACTACTT |
| | | CGGCTACAGCACCCCCTGGGGGTATTTTGACTTTAACAGATTCCACTGCCACTTTTCACC |
| | | ACGTGACTGGCAGCGACTCATCAACAACAACTGGGGATTCCGGCCCAAGAGACTCAGCT |
| | | TCAAGCTCTTCAACATCCAAGTCAAGGAGGTCACGACGAATGATGGCGTCACGACCATC |
| | | GCTAATAACCTTACCAGCACGGTTCAAGTCTTCTCGGACTCGGAGTACCAGCTTCCGTAC |
| | | GTCCTCGGCTCTGCGCACCAGGGCTGCCTCCCTCCGTTCCCGGCGGACGTGTTCATGAT |
| | | TCCGCAGTACGGCTACCTAACGCTCAACAATGGCAGCCAGGCAGTGGGACGGTCATCCT |
| | | TTTACTGCCTGGAATATTTTCCATCTCAAATGCTGCGAACTGGAAACAATTTTGAATTCAG |
| | | CTACACCTTCGAGGACGTGCCTTTCCACAGCAGCTACGCACACAGCCAGAGCTTGGACC |
| | | GACTGATGAATCCTCTCATTGACCAGTACCTGTACTACTTATCCAGAACTCAGTCCACAG |
| | | GAGGAACTCAAGGTACCCAGCAATTGTTATTTTCTCAAGCTGGGCCTGCAAACATGTCG |
| | | GCTCAGGCCAAGAACTGGCTGCCTGGACCTTGCTACCGGCAGCAGCGAGTCTCCACGA |
| | | CACTGTCGCAAAACAACAACAGCAACTTTGCTTGGACTGGTGCCACCAAATATCACCTGA |
| | | ACGGCAGAAACTCGTTGGTTAATCCCGGCGTCGCCATGGCAACTCACAAGGACGACGA |
| | | GGACCGCTTTTTCCCATCCAGCGGAGTCCTGATTTTTGGAAAAACTGGAGCAACTAACAA |
| | | AACTACATTGGAAAATGTGTTAATGACAAATGAAGAAGAAATTCGTCCTACTAATCCTGT |
| | | AGCCACGGAAGAATACGGGATAGTCAGCAGCAACTTACAAGCGGCTAATACTGCAGCCC |
| | | AGACACAAGTTGTCAACAACCAGGGAGCCTTACCTGGCATGGTCTGGCAGAACCGGGA |
| | | CGTGTACCTGCAGGGTCCCATCTGGGCCAAGATTCCTCACACGGATGGCAACTTTCACC |
| | | CGTCTCCTTTGATGGGCGGCTTTGGACTTAAACATCCGCCTCCTCAGATCCTGATCAAGA |
| | | ACACTCCCGTTCCCGCTAATCCTCCGGAGGTGTTTACTCCTGCCAAGTTTGCTTCGTTCA |
| | | TCACACAGTACAGCACCGGACAAGTCAGCGTGGAAATCGAGTGGGAGCTGCAGAAGGA |
| | | AAACAGCAAGCGCTGGAACCCGGAGATTCAGTACACTTCAAACTACAACAAGTCTGTTA |
| | | GTGTGGACTTTACTGTAGACACTAATGGCGTGTATTCAGAGCCTCGCCCCATTGGCACC |
| | | AGATACCTGACTCGTAATCTGTAA |
| 39 | AAVC11.19 (nucleic acid) | ATGGCTGCCGATGGTTATCTTCCAGATTGGCTCGAGGACAACCTCTCTGAGGGCATTCG |
| | | CGAGTGGTGGGCGCTGAAACCTGGAGCCCCGAAGCCCAAAGCCAACCAGCAGAAGCAG |
| | | GACGACGGCCGGGGTCTGGTGCTTCCTGGCTACAAGTACCTCGGACCCTTCAACGGACT |
| | | CGACAAGGGAGAGCCGGTCAACGAGGCAGACGCCGCGGCCCTCGAGCACGACAAAGC |
| | | CTACGACCAGCAGCTCAAAGCGGGTGACAATCCGTACCTGCGGTATAACCACGCCGACG |
| | | CCGAGTTTCAGGAGCGTCTGCAAGAAGATACGTCATTTGGGGGCAACCTCGGGCGAGC |
| | | AGTCTTCCAGGCCAAGAAGCGGGTTCTCGAACCTCTCGGTCTGGTTGAGGAAGGCGCTA |
| | | AGACGGCTCCTGGAAAGAAGAGACCGGTAGAGCCGTCACCTCAGCGTTCCCCCGACTC |
| | | CTCCACGGGCATCGGCAAGAAAGGCCAGCAGCCCGCCAGAAAGAGACTCAATTTCGGT |
| | | CAGACTGGCGACTCAGAGTCAGTCCCCGACCCTCAACCTCTCGGAGAACCTCCAGCAGC |
| | | GCCCTCTAGTGTGGGATCTGGTACAGTGGCTGCAGGCGGTGGCGCACCAATGGCAGAC |
| | | AATAACGAAGGTGCCGACGGAGTGGGTAATGCCTCAGGAAATTGGCATTGCGATTCCAC |
| | | ATGGCTGGGCGACAGAGTCATCACCACCAGCACCAGAACCTGGGCCCTGCCCACTTACA |
| | | ACAACCATCTCTACAAGCAAATCTCCAGCCAATCAGGAGCTTCAAACGACAACCACTACT |
| | | TTGGCTACAGCACCCCTTGGGGGTATTTTGACTTTAACAGATTCCACTGCCATTTCTCAC |
| | | CACGTGACTGGCAGCGACTCATTAACAACAACTGGGGATTCCGGCCCAAGAAACTCAGC |
| | | TTCAAGCTCTTCAACATCCAAGTTAAAGAGGTCACGCAGAACGATGGCACGACGACTATT |
| | | GCCAATAACCTTACCAGCACGGTTCAAGTGTTTACGGACTCGGAATACCAGCTGCCGTA |

TABLE 5-continued

Capsid Sequences

| SEQ ID NO | Name | Sequence |
|---|---|---|
| | | CGTCCTCGGCTCCGCGCACCAGGGCTGCCTGCCTCCGTTCCCGGCGGATGTCTTCATGA TTCCCCAGTACGGCTACCTGACACTGAACAATGGAAGTCAAGCCGTAGGCCGTTCCTCC TTCTACTGCCTGGAATATTTTCCATCTCAAATGCTGCGAACTGGAAACAATTTTGAATTCA GCTACACCTTCGAGGACGTGCCTTTCCACAGCAGCTACGCACACAGCCAGAGCTTGGAC CGACTGATGAATCCTCTCATTGACCAGTACCTGTACTACTTATCCAGAACTCAGTCCACA GGAGGAACTCAAGGTACCCAGCAATTGTTATTTTCTCAAGCTGGGCCTGCAAACATGTC GGCTCAGGCCAAGAACTGGCTGCCTGGACCTTGCTACCGGCAGCAGCGAGTCTCCACG ACACTGTCGCAAAACAACAACAGCAACTTTGCTTGGACTGGTGCCACCAAATATCACCTG AACGGCAGAAACTCGTTGGTTAATCCCGGCGTCGCCATGGCAACTCACAAGGACGACGA GGACCGCTTTTTCCCATCCAGCGGAGTCCTGATTTTTGGAAAAACTGGAGCAACTAACAA AACTACATTGGAAAATGTGTTAATGACAAATGAAGAAGAAATTCGTCCTACTAATCCTGT AGCCACGGAAGAATACGGGATAGTCAGCAGCAACTTACAAGCGGCTAATACTGCAGCCC AGACACAAGTTGTCAACAACCAGGGAGCCTTACCTGGCATGGTCTGGCAGAACCGGGA CGTGTACCTGCAGGGTCCCATCTGGGCCAAGATTCCTCACACGGATGGCAACTTTCACC CGTCTCCTTTGATGGGCGGCTTTGGACTTAAACATCCGCCTCCTCAGATCCTGATCAAGA ACACTCCCGTTCCCGCTAATCCTCCGGAGGTGTTTACTCCTGCCAAGTTTGCTTCGTTCA TCACACAGTACAGCACCGGACAAGTCAGCGTGGAAATCGAGTGGGAGCTGCAGAAGGA AAACAGCAAGCGCTGGAACCCGGAGATTCAGTACACTTCAAACTACAACAAGTCTGTTA GTGTGGACTTTACTGTAGACACTAATGGCGTGTATTCAGAGCCTCGCCCCATTGGCACC AGATACCTGACTCGTAATCTGTAA |
| 64 | AAV8 | MAADGYLPDWLEDNLSEGIREWWALKPGAPKPKANQQKQDDGRGLVLPGYKYLGPFNGL DKGEPVNAADAAALEHDKAYDQQLQAGDNPYLRYNHADAEFQERLQEDTSFGGNLGRAVF QAKKRVLEPLGLVEEGAKTAPGKKRPVEPSPQRSPDSSTGIGKKGQQPARKRLNFGQTGDS ESVPDPQPLGEPPAAPSGVGPNTMAAGGGAPMADNNEGADGVGSSSGNWHCDSTWLGD RVITTSTRTWALPTYNNHLYKQISNGTSGGATNDNTYFGYSTPWGYFDFNRFHCHFSPRD WQRLINNNWGFRPKRLSFKLFNIQVKEVTQNEGTKTIANNLTSTIQVFTDSEYQLPYVLGSA HQGCLPPFPADVFMIPQYGYLTLNNGSQAVGRSSFYCLEYFPSQMLRTGNNFQFTYTFEDVP FHSSYAHSQSLDRLMNPLIDQYLYYLSRTQTTGGTANTQTLGFSQGGPNTMANQAKNWLP GPCYRQQRVSTTTGQNNNSNFAWTAGTKYHLNGRNSLANPGIAMATHKDDEERFFPSNGI LIFGKQNAARDNADYSDVMLTSEEEIKTTNPVATEEYGIVADNLQQQNTAPQIGTVNSQGA LPGMVWQNRDVYLQGPIWAKIPHTDGNFHPSPLMGGFGLKHPPPQILIKNTPVPADPPTTF NQSKLNSFITQYSTGQVSVEIEWELQKENSKRWNPEIQYTSNYYKSTSVDFAVNTEGVYSE PRPIGTRYLTRNL |
| 65 | AAV8 Swap 1 | MAADGYLPDWLEDNLSEGIREWWALKPGAPKPKANQQKQDDGRGLVLPGYKYLGPFNGL DKGEPVNAADAAALEHDKAYDQQLQAGDNPYLRYNHADAEFQERLQEDTSFGGNLGRAVF QAKKRVLEPLGLVEEGAKTAPGKKRPVEPSPQRSPDSSTGIGKKGQQPARKRLNFGQTGDS ESVPDPQPLGEPPAAPSGVGPNTMAAGGGAPMADNNEGADGVGSSSGNWHCDSTWLGD RVITTSTRTWALPTYNNHLYKQISSQSGASNDNHYFGYSTPWGYFDFNRFHCHFSPRDWQ RLINNNWGFRPKRLSFKLFNIQVKEVTQNEGTKTIANNLTSTIQVFTDSEYQLPYVLGSAHQ GCLPPFPADVFMIPQYGYLTLNNGSQAVGRSSFYCLEYFPSQMLRTGNNFQFTYTFEDVPFH SSYAHSQSLDRLMNPLIDQYLYYLSRTQTTGGTANTQTLGFSQGGPNTMANQAKNWLPGP CYRQQRVSTTTGQNNNSNFAWTAGTKYHLNGRNSLANPGIAMATHKDDEERFFPSNGILIF GKQNAARDNADYSDVMLTSEEEIKTTNPVATEEYGIVADNLQQQNTAPQIGTVNSQGALP GMVWQNRDVYLQGPIWAKIPHTDGNFHPSPLMGGFGLKHPPPQILIKNTPVPADPPTTFNQ SKLNSFITQYSTGQVSVEIEWELQKENSKRWNPEIQYTSNYYKSTSVDFAVNTEGVYSEPR PIGTRYLTRNL |
| 66 | AAV8 Swap 2 | MAADGYLPDWLEDNLSEGIREWWALKPGAPKPKANQQKQDDGRGLVLPGYKYLGPFNGL DKGEPVNAADAAALEHDKAYDQQLQAGDNPYLRYNHADAEFQERLQEDTSFGGNLGRAVF QAKKRVLEPLGLVEEGAKTAPGKKRPVEPSPQRSPDSSTGIGKKGQQPARKRLNFGQTGDS ESVPDPQPLGEPPAAPSGVGPNTMAAGGGAPMADNNEGADGVGSSSGNWHCDSTWLGD RVITTSTRTWALPTYNNHLYKQISNGTSGGATNDNTYFGYSTPWGYFDFNRFHCHFSPRD WQRLINNNWGFRPKRLSFKLFNIQVKEVTQNEGTKTIANNLTSTIQVFTDSEYQLPYVLGSA HQGCLPPFPADVFMIPQYGYLTLNNGSQAVGRSSFYCLEYFPSQMLRTGNNFQFTYTFEDVP FHSSYAHSQSLDRLMNPLIDQYLYYLSRTQSTGGTQGTQQLLFSQAGPANMSAQAKNWLP GPCYRQQRVSTTLSQNNNSNFAWTGATKYHLNGRNSLVNPGVAMATHKDDEERFFPSNGI LIFGKQNAARDNADYSDVMLTSEEEIKTTNPVATEEYGIVADNLQQQNTAPQIGTVNSQGA LPGMVWQNRDVYLQGPIWAKIPHTDGNFHPSPLMGGFGLKHPPPQILIKNTPVPADPPTTF NQSKLNSFITQYSTGQVSVEIEWELQKENSKRWNPEIQYTSNYYKSTSVDFAVNTEGVYSE PRPIGTRYLTRNL |
| 67 | AAV8 Swap 3 | MAADGYLPDWLEDNLSEGIREWWALKPGAPKPKANQQKQDDGRGLVLPGYKYLGPFNGL DKGEPVNAADAAALEHDKAYDQQLQAGDNPYLRYNHADAEFQERLQEDTSFGGNLGRAVF QAKKRVLEPLGLVEEGAKTAPGKKRPVEPSPQRSPDSSTGIGKKGQQPARKRLNFGQTGDS ESVPDPQPLGEPPAAPSGVGPNTMAAGGGAPMADNNEGADGVGSSSGNWHCDSTWLGD RVITTSTRTWALPTYNNHLYKQISNGTSGGATNDNTYFGYSTPWGYFDFNRFHCHFSPRD WQRLINNNWGFRPKRLSFKLFNIQVKEVTQNEGTKTIANNLTSTIQVFTDSEYQLPYVLGSA HQGCLPPFPADVFMIPQYGYLTLNNGSQAVGRSSFYCLEYFPSQMLRTGNNFQFTYTFEDVP FHSSYAHSQSLDRLMNPLIDQYLYYLSRTQTTGGTANTQTLGFSQGGPNTMANQAKNWLP GPCYRQQRVSTTTGQNNNSNFAWTAGTKYHLNGRNSLANPGIAMATHKDDEDRFFPSSG VLIFGKTGATNKTTLENVLMTNEEEIRPTNPVATEEYGIVSSNLQAANTAAQTQVVNNQGAL PGMVWQNRDVYLQGPIWAKIPHTDGNFHPSPLMGGFGLKHPPPQILIKNTPVPADPPTTFN |

TABLE 5-continued

Capsid Sequences

| SEQ ID NO | Name | Sequence |
| --- | --- | --- |
| | | QSKLNSFITQYSTGQVSVEIEWELQKENSKRWNPEIQYTSNYYKSTSVDFAVNTEGVYSEP<br>RPIGTRYLTRNL |
| 68 | AAV8 Swap 4 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEERFFPSNGILI<br>FGKQNAARDNADYSDVMLTSEEEIKTTNPVATEEYGIVADNLQQQNTAPQIGTVNSQGALP<br>GMVWQNRDVYLQGPIWAKIPHTDGNFHPSPLMGGFGLKHPPPQILIKNTPVPADPPTTFNQ<br>SKLNSFITQYSTGQVSVEIEWELQKENSKRWNPEIQYTSNYYKSTSVDFAVNTEGVYSEPR<br>PIGTRYLTRNL |
| 69 | AAV8 Swap 5 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQTTGGTANTQTLGFSQGGPNTMANQAKNWLPGP<br>CYRQQRVSTTTGQNNNSNFAWTAGTKYHLNGRNSLANPGIAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |
| 70 | AAV8 Swap 6 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISNGTSGGATNDNTYFGYSTPWGYFDFNRFHCHFSPRD<br>WQRLINNNWGFRPKRLSFKLFNIQVKEVTQNEGTKTIANNLTSTIQVFTDSEYQLPYVLGSA<br>HQGCLPPFPADVFMIPQYGYLTLNNGSQAVGRSSFYCLEYFPSQMLRTGNNFQFTYTFEDVP<br>FHSSYAHSQSLDRLMNPLIDQYLYYLSRTQSTGGTQGTQQLLFSQAGPANMSAQAKNWLP<br>GPCYRQQRVSTTLSQNNNSNFAWTGATKYHLNGRNSLVNPGVAMATHKDDEDRFFPSSG<br>VLIFGKTGATNKTTLENVLMTNEEEIRPTNPVATEEYGIVSSNLQAANTAAQTQVVNNQGAL<br>PGMVWQNRDVYLQGPIWAKIPHTDGNFHPSPLMGGFGLKHPPPQILIKNTPVPADPPTTFN<br>QSKLNSFITQYSTGQVSVEIEWELQKENSKRWNPEIQYTSNYYKSTSVDFAVNTEGVYSEP<br>RPIGTRYLTRNL |
| 71 | AAV8 Swap 7 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |
| 72 | AAV8 Swap 8 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQTTGGTANTQTLGFSQGGPNTMANQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |

TABLE 5-continued

| Capsid Sequences | | |
|---|---|---|
| SEQ ID NO | Name | Sequence |
| 73 | AAV8 Swap 9 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTTGQNNNSNFAWTAGTKYHLNGRNSLANPGIAMATHKDDEDRFFPSSGVLI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |
| 74 | AAV8 Swap 10 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEERFFPSNGILI<br>FGKTGATNKTTLENVLMTNEEEIRPTNPVATEEYGIVSSNLQAANTAAQTQVVNNQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |
| 75 | AAV8 Swap 11 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKQNAARDNADYSDVMLTSEEEIKTTNPVATEEYGIVSSNLQAANTAAQTQVVNNQGALP<br>GMVWQNRDVYLQGPIWAKIPHTDGNFHPSPLMGGFGLKHPPPQILIKNTPVPADPPTTFNQ<br>SKLNSFITQYSTGQVSVEIEWELQKENSKRWNPEIQYTSNYYKSTSVDFAVNTEGVYSEPR<br>PIGTRYLTRNL |
| 76 | AAV8 Swap 12 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKTGATNKTTLENVLMTNEEEIRPTNPVATEEYGIVADNLQQQNTAPQIGTVNSQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |
| 77 | AAV8 Swap 13 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEDRFFPSSGVLI<br>FGKQNAARDNADYSDVMLTSEEEIKTTNPVATEEYGIVADNLQQQNTAPQIGTVNSQGALP<br>GMVWQNRDVYLQGPIWAKIPHTDGNFHPSPLMGGFGLKHPPPQILIKNTPVPADPPTTFNQ<br>SKLNSFITQYSTGQVSVEIEWELQKENSKRWNPEIQYTSNYYKSTSVDFAVNTEGVYSEPR<br>PIGTRYLTRNL |
| 78 | AAV8 Swap 14 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS |

TABLE 5-continued

Capsid Sequences

| SEQ ID NO | Name | Sequence |
|---|---|---|
| | | ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEERFFPSNGILI<br>FGKTGATNKTTLENVLMTNEEEIRPTNPVATEEYGIVADNLQQQNTAPQIGTVNSQGALPG<br>MVWQNRDVYLQGPIWAKIPHTDGNFHPSPLMGGFGLKHPPPQILIKNTPVPADPPTTFNQS<br>KLNSFITQYSTGQVSVEIEWELQKENSKRWNPEIQYTSNYYKSTSVDFAVNTEGVYSEPRPI<br>GTRYLTRNL |
| 79 | AAV8 Swap 15 | MAADGYLPDWLEDNLSEGIREWWALKPGAPKPKANQQKQDDGRGLVLPGYKYLGPFNGL<br>DKGEPVNAADAAALEHDKAYDQQLQAGDNPYLRYNHADAEFQERLQEDTSFGGNLGRAVF<br>QAKKRVLEPLGLVEEGAKTAPGKKRPVEPSPQRSPDSSTGIGKKGQQPARKRLNFGQTGDS<br>ESVPDPQPLGEPPAAPSGVGPNTMAAGGGAPMADNNEGADGVGSSSGNWHCDSTWLGD<br>RVITTSTRTWALPTYNNHLYKQISSQSGASNDNHYFGYSTPWGYFDFNRFHCHFSPRDWQ<br>RLINNNWGFRPKRLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVPFH<br>SSYAHSQSLDRLMNPLIDQYLYYLSRTQSTGGTQGTQQLLFSQAGPANMSAQAKNWLPGP<br>CYRQQRVSTTLSQNNNSNFAWTGATKYHLNGRNSLVNPGVAMATHKDDEERFFPSNGILI<br>FGKQNAARDNADYSDVMLTSEEEIKTTNPVATEEYGIVSSNLQAANTAAQTQVVNNQGALP<br>GMVWQNRDVYLQGPIWAKIPHTDGNFHPSPLMGGFGLKHPPPQILIKNTPVPADPPTTFNQ<br>SKLNSFITQYSTGQVSVEIEWELQKENSKRWNPEIQYTSNYYKSTSVDFAVNTEGVYSEPR<br>PIGTRYLTRNL |
| 85 | AAV8 Swap 1 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTGTCTCGGACTCAAACAAC<br>AGGAGGCACGGCAAATACGCAGACTCTGGGCTTCAGCCAAGGTGGGCCTAATACAATG<br>GCCAATCAGGCAAAGAACTGGCTGCCAGGACCCTGTTACCGCCAACAACGCGTCTCAAC<br>GACAACCGGGCAAAACAACAATAGCAACTTTGCCTGGACTGCTGGGACCAAATACCATC<br>TGAATGGAAGAAATTCATTGGCTAATCCTGGCATCGCTATGGCAACACACAAGGACGAC<br>GAGGAGCGTTTTTTTCCCAGTAACGGGATCCTGATTTTTGGCAAACAAAATGCTGCCAGA<br>GACAATGCGGATTACAGCGATGTCATGCTCACCAGCGAGGAAGAAATCAAAACCACTAA<br>CCCTGTGGCTACAGAGGAATACGGTATCGTGGCAGATAACTTGCAGCAGCAAAACACGG<br>CTCCTCAAATTGGAACTGTCAACAGCCAGGGGGCCTTACCCGGTATGGTCTGGCAGAAC<br>CGGGACGTGTACCTGCAGGGTCCCATCTGGGCCAAGATTCCTCACACGGACGGCAACTT<br>CCACCCGTCTCCGCTGATGGGCGGCTTTGGCCTGAAACATCCTCCGCCTCAGATCCTGA<br>TCAAGAACACGCCTGTACCTGCGGATCCTCCGACCACCTTCAACCAGTCAAAGCTGAAC<br>TCTTTCATCACGCAATACAGCACCGGACAGGTCAGCGTGGAAATTGAATGGGAGCTGCA<br>GAAGGAAAACAGCAAGCGCTGGAACCCCGAGATCCAGTACACCTCCAACTACTACAAAT<br>CTACAAGTGTGGACTTTGCTGTTAATACAGAAGGCGTGTACTCTGAACCCCGCCCCATTG<br>GCACCCGTTACCTCACCCGTAATCTGTAA |
| 86 | AAV8 Swap 2 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG |

TABLE 5-continued

| Capsid Sequences | | |
|---|---|---|
| SEQ ID NO | Name | Sequence |
| | | CCCTCTGGTGTGGGACCTAATACAATGGCTGCAGGCGGTGGCGCACCAATGGCAGACA ATAACGAAGGCGCCGACGGAGTGGGTAGTTCCTCGGGAAATTGGCATTGCGATTCCACA TGGCTGGGCGACAGAGTCATCACCACCAGCACCCGAACCTGGGCCCTGCCCACCTACA ACAACCACCTCTACAAGCAAATCTCCAACGGGACATCGGGAGGAGCCACCAACGACAAC ACCTACTTCGGCTACAGCACCCCCTGGGGGTATTTTGACTTTAACAGATTCCACTGCCAC TTTTCACCACGTGACTGGCAGCGACTCATCAACAACAACTGGGGATTCCGGCCCAAGAG ACTCAGCTTCAAGCTCTTCAACATCCAGGTCAAGGAGGTCACGCAGAATGAAGGCACCA AGACCATCGCCAATAACCTCACCAGCACCATCCAGGTGTTTACGGACTCGGAGTACCAG CTGCCGTACGTTCTCGGCTCTGCCCACCAGGGCTGCCTGCCTCCGTTCCCGGCGGACGT GTTCATGATTCCCCAGTACGGCTACCTAACACTCAACAACGGTAGTCAGGCCGTGGGAC GCTCCTCCTTCTACTGCCTGGAATACTTTCCTTCGCAGATGCTGAGAACCGGCAACAACT TCCAGTTTACTTACACCTTCGAGGACGTGCCTTTCCACAGCAGCTACGCCCACAGCCAGA GCTTGGACCGGCTGATGAATCCTCTGATTGACCAGTACCTGTACTACTTATCCAGAACTC AGTCCACAGGAGGAACTCAAGGTACCCAGCAATTGTTATTTTCTCAAGCTGGGCCTGCA AACATGTCGGCTCAGGCCAAGAACTGGCTGCCTGGACCTTGCTACCGGCAGCAGCGAG TCTCCACGACACTGTCGCAAAACAACAACAGCAACTTTGCTTGGACTGGTGCCACCAAAT ATCACCTGAACGGCAGAAACTCGTTGGTTAATCCCGGCGTCGCCATGGCAACACACAAG GACGACGAGGAGCGTTTTTTTCCCAGTAACGGGATCCTGATTTTTGGCAAACAAAATGCT GCCAGAGACAATGCGGATTACAGCGATGTCATGCTCACCAGCGAGGAAGAAATCAAAAC CACTAACCCTGTGGCTACAGAGGAATACGGTATCGTGGCAGATAACTTGCAGCAGCAAA ACACGGCTCCTCAAATTGGAACTGTCAACAGCCAGGGGGCCTTACCCGGTATGGTCTGG CAGAACCGGGACGTGTACCTGCAGGGTCCCATCTGGGCCAAGATTCCTCACACGGACG GCAACTTCCACCCGTCTCCGCTGATGGGCGGCTTTGGCCTGAAACATCCTCCGCCTCAG ATCCTGATCAAGAACACGCCTGTACCTGCGGATCCTCCGACCACCTTCAACCAGTCAAA GCTGAACTCTTTCATCACGCAATACAGCACCGGACAGGTCAGCGTGGAAATTGAATGGG AGCTGCAGAAGGAAAACAGCAAGCGCTGGAACCCCGAGATCCAGTACACCTCCAACTAC TACAAATCTACAAGTGTGGACTTTGCTGTTAATACAGAAGGCGTGTACTCTGAACCCCGC CCCATTGGCACCCGTTACCTCACCCGTAATCTGTAA |
| 87 | AAV8 Swap 3 (nt) | ATGGCTGCCGATGGTTATCTTCCAGATTGGCTCGAGGACAACCTCTCTGAGGGCATTCG CGAGTGGTGGGCGCTGAAACCTGGAGCCCCGAAGCCCAAAGCCAACCAGCAAAAGCAG GACGACGGCCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTGCAGGCGGGTGACAATCCGTACCTGCGGTATAACCACGCCGAC GCCGAGTTTCAGGAGCGTCTGCAAGAAGATACGTCTTTTGGGGGCAACCTCGGGCGAG CAGTCTTCCAGGCCAAGAAGCGGGTTCTCGAACCTCTCGGTCTGGTTGAGGAAGGCGCT AAGACGGCTCCTGGAAAGAAGAGACCGGTAGAGCCATCACCCCAGCGTTCTCCAGACTC CTCTACGGGCATCGGCAAGAAAGGCCAACAGCCCGCCAGAAAAAGACTCAATTTTGGTC AGACTGGCGACTCAGAGTCAGTTCCAGACCCTCAACCTCTCGGAGAACCTCCAGCAGCG CCCTCTGGTGTGGGACCTAATACAATGGCTGCAGGCGGTGGCGCACCAATGGCAGACA ATAACGAAGGCGCCGACGGAGTGGGTAGTTCCTCGGGAAATTGGCATTGCGATTCCACA TGGCTGGGCGACAGAGTCATCACCACCAGCACCCGAACCTGGGCCCTGCCCACCTACA ACAACCACCTCTACAAGCAAATCTCCAACGGGACATCGGGAGGAGCCACCAACGACAAC ACCTACTTCGGCTACAGCACCCCCTGGGGGTATTTTGACTTTAACAGATTCCACTGCCAC TTTTCACCACGTGACTGGCAGCGACTCATCAACAACAACTGGGGATTCCGGCCCAAGAG ACTCAGCTTCAAGCTCTTCAACATCCAGGTCAAGGAGGTCACGCAGAATGAAGGCACCA AGACCATCGCCAATAACCTCACCAGCACCATCCAGGTGTTTACGGACTCGGAGTACCAG CTGCCGTACGTTCTCGGCTCTGCCCACCAGGGCTGCCTGCCTCCGTTCCCGGCGGACGT GTTCATGATTCCCCAGTACGGCTACCTAACACTCAACAACGGTAGTCAGGCCGTGGGAC GCTCCTCCTTCTACTGCCTGGAATACTTTCCTTCGCAGATGCTGAGAACCGGCAACAACT TCCAGTTTACTTACACCTTCGAGGACGTGCCTTTCCACAGCAGCTACGCCCACAGCCAGA GCTTGGACCGGCTGATGAATCCTCTGATTGACCAGTACCTGTACTACTTGTCTCGGACTC AAACAACAGGAGGCACGGCAAATACGCAGACTCTGGGCTTCAGCCAAGGTGGGCCTAA TACAATGGCCAATCAGGCAAAGAACTGGCTGCCAGGACCCTGTTACCGCCAACAACGCG TCTCAACGACAACCGGGCAAAACAACAATAGCAACTTTGCCTGGACTGCTGGGACCAAA TACCATCTGAATGGAAGAAATTCATTGGCTAATCCTGGCATCGCTATGGCAACACACAAG GACGACGAGGACCGCTTTTTCCCATCCAGCGGAGTCCTGATTTTTGGAAAAACTGGAGC AACTAACAAAACTACATTGGAAAATGTGTTAATGACAAATGAAGAAGAAATTCGTCCTAC TAATCCTGTAGCCACGGAAGAATACGGGATAGTCAGCAGCAACTTACAAGCGGCTAATA CTGCAGCCCAGACACAAGTTGTCAACAACCAGGGAGCCTTACCTGGCATGGTCTGGCAG AACCGGGACGTGTACCTGCAGGGTCCCATCTGGGCCAAGATTCCTCACACGGACGGCA ACTTCCACCCGTCTCCGCTGATGGGCGGCTTTGGCCTGAAACATCCTCCGCCTCAGATC CTGATCAAGAACACGCCTGTACCTGCGGATCCTCCGACCACCTTCAACCAGTCAAAGCT GAACTCTTTCATCACGCAATACAGCACCGGACAGGTCAGCGTGGAAATTGAATGGGAGC TGCAGAAGGAAAACAGCAAGCGCTGGAACCCCGAGATCCAGTACACCTCCAACTACTAC AAATCTACAAGTGTGGACTTTGCTGTTAATACAGAAGGCGTGTACTCTGAACCCCGCCCC ATTGGCACCCGTTACCTCACCCGTAATCTGTAA |
| 88 | AAV8 Swap 4 (nt) | ATGGCTGCCGATGGTTATCTTCCAGATTGGCTCGAGGACAACCTCTCTGAGGGCATTCG CGAGTGGTGGGCGCTGAAACCTGGAGCCCCGAAGCCCAAAGCCAACCAGCAAAAGCAG GACGACGGCCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTGCAGGCGGGTGACAATCCGTACCTGCGGTATAACCACGCCGAC GCCGAGTTTCAGGAGCGTCTGCAAGAAGATACGTCTTTTGGGGGCAACCTCGGGCGAG |

TABLE 5-continued

Capsid Sequences

| SEQ ID NO | Name | Sequence |
|---|---|---|
| | | CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTATCCAGAACTCAGTCCAC<br>AGGAGGAACTCAAGGTACCCAGCAATTGTTATTTTCTCAAGCTGGGCCTGCAAACATGT<br>CGGCTCAGGCCAAGAACTGGCTGCCTGGACCTTGCTACCGGCAGCAGCGAGTCTCCAC<br>GACACTGTCGCAAAACAACAACAGCAACTTTGCTTGGACTGGTGCCACCAAATATCACCT<br>GAACGGCAGAAACTCGTTGGTTAATCCCGGCGTCGCCATGGCAACACACAAGGACGAC<br>GAGGAGCGTTTTTTTCCCAGTAACGGGATCCTGATTTTTGGCAAACAAAATGCTGCCAGA<br>GACAATGCGGATTACAGCGATGTCATGCTCACCAGCGAGGAAGAAATCAAAACCACTAA<br>CCCTGTGGCTACAGAGGAATACGGTATCGTGGCAGATAACTTGCAGCAGCAAAACACGG<br>CTCCTCAAATTGGAACTGTCAACAGCCAGGGGGCCTTACCCGGTATGGTCTGGCAGAAC<br>CGGGACGTGTACCTGCAGGGTCCCATCTGGGCCAAGATTCCTCACACGGACGGCAACTT<br>CCACCCGTCTCCGCTGATGGGCGGCTTTGGCCTGAAACATCCTCCGCCTCAGATCCTGA<br>TCAAGAACACGCCTGTACCTGCGGATCCTCCGACCACCTTCAACCAGTCAAAGCTGAAC<br>TCTTTCATCACGCAATACAGCACCGGACAGGTCAGCGTGGAAATTGAATGGGAGCTGCA<br>GAAGGAAAACAGCAAGCGCTGGAACCCCGAGATCCAGTACACCTCCAACTACTACAAAT<br>CTACAAGTGTGGACTTTGCnCTTAATACAGAAGGCGTGTACTCTGAACCCCGCCCCATTG<br>GCACCCGTTACCTCACCCGTAATCTGTAA |
| 89 | AAV8 Swap 5 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTGTCTCGGACTCAAACAAC<br>AGGAGGCACGGCAAATACGCAGACTCTGGGCTTCAGCCAAGGTGGGCCTAATACAATG<br>GCCAATCAGGCAAAGAACTGGCTGCCAGGACCCTGTTACCGCCAACAACGCGTCTCAAC<br>GACAACCGGGCAAAACAACAATAGCAACTTTGCCTGGACTGCTGGGACCAAATACCATC<br>TGAATGGAAGAAATTCATTGGCTAATCCTGGCATCGCTATGGCAACACACAAGGACGAC<br>GAGGACCGCTTTTTCCCATCCAGCGGAGTCCTGATTTTTGGAAAAACTGGAGCAACTAA<br>CAAAACTACATTGGAAAATGTGTTAATGACAAATGAAGAAGAAATTCGTCCTACTAATCC<br>TGTAGCCACGGAAGAATACGGGATAGTCAGCAGCAACTTACAAGCGGCTAATACTGCAG<br>CCCAGACACAAGTTGTCAACAACCAGGGAGCCTTACCTGGCATGGTCTGGCAGAACCGG<br>GACGTGTACCTGCAGGGTCCCATCTGGGCCAAGATTCCTCACACGGACGGCAACTTCCA<br>CCCGTCTCCGCTGATGGGCGGCTTTGGCCTGAAACATCCTCCGCCTCAGATCCTGATCA<br>AGAACACGCCTGTACCTGCGGATCCTCCGACCACCTTCAACCAGTCAAAGCTGAACTCTT<br>TCATCACGCAATACAGCACCGGACAGGTCAGCGTGGAAATTGAATGGGAGCTGCAGAA<br>GGAAAACAGCAAGCGCTGGAACCCCGAGATCCAGTACACCTCCAACTACTACAAATCTA<br>CAAGTGTGGACTTTGCTTGTTAATACAGAAGGCGTGTACTCTGAACCCCGCCCCATTGGC<br>ACCCGTTACCTCACCCGTAATCTGTAA |

TABLE 5-continued

| Capsid Sequences | | |
|---|---|---|
| SEQ ID NO | Name | Sequence |
| 90 | AAV8 Swap 6 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCCGAACCTGGGCCCTGCCCACCTACA<br>ACAACCACCTCTACAAGCAAATCTCCAACGGGACATCGGGAGGAGCCACCAACGACAAC<br>ACCTACTTCGGCTACAGCACCCCCTGGGGGTATTTTGACTTTAACAGATTCCACTGCCAC<br>TTTTCACCACGTGACTGGCAGCGACTCATCAACAACAACTGGGGATTCCGGCCCAAGAG<br>ACTCAGCTTCAAGCTCTTCAACATCCAGGTCAAGGAGGTCACGCAGAATGAAGGCACCA<br>AGACCATCGCCAATAACCTCACCAGCACCATCCAGGTGTTTACGGACTCGGAGTACCAG<br>CTGCCGTACGTTCTCGGCTCTGCCCACCAGGGCTGCCTGCCTCCGTTCCCGGCGGACGT<br>GTTCATGATTCCCCAGTACGGCTACCTAACACTCAACAACGGTAGTCAGGCCGTGGGAC<br>GCTCCTCCTTCTACTGCCTGGAATACTTTCCTTCGCAGATGCTGAGAACCGGCAACAACT<br>TCCAGTTTACTTACACCTTCGAGGACGTGCCTTTCCACAGCAGCTACGCCCACAGCCAGA<br>GCTTGGACCGGCTGATGAATCCTCTGATTGACCAGTACCTGTACTACTTATCCAGAACTC<br>AGTCCACAGGAGGAACTCAAGGTACCCAGCAATTGTTATTTTCTCAAGCTGGGCCTGCA<br>AACATGTCGGCTCAGGCCAAGAACTGGCTGCCTGGACCTTGCTACCGGCAGCAGCGAG<br>TCTCCACGACACTGTCGCAAAACAACAACAGCAACTTTGCTTGGACTGGTGCCACCAAAT<br>ATCACCTGAACGGCAGAAACTCGTTGGTTAATCCCGGCGTCGCCATGGCAACACACAAG<br>GACGACGAGGACCGCTTTTTCCCATCCAGCGGAGTCCTGATTTTTGGAAAAACTGGAGC<br>AACTAACAAAACTACATTGGAAAATGTGTTAATGACAAATGAAGAAGAAATTCGTCCTAC<br>TAATCCTGTAGCCACGGAAGAATACGGGATAGTCAGCAGCAACTTACAAGCGGCTAATA<br>CTGCAGCCCAGACACAAGTTGTCAACAACCAGGGAGCCTTACCTGGCATGGTCTGGCAG<br>AACCGGGACGTGTACCTGCAGGGTCCCATCTGGGCCAAGATTCCTCACACGGACGGCA<br>ACTTCCACCCGTCTCCGCTGATGGGCGGCTTTGGCCTGAAACATCCTCCGCCTCAGATC<br>CTGATCAAGAACACGCCTGTACCTGCGGATCCTCCGACCACCTTCAACCAGTCAAAGCT<br>GAACTCTTTCATCACGCAATACAGCACCGGACAGGTCAGCGTGGAAATTGAATGGGAGC<br>TGCAGAAGGAAAACAGCAAGCGCTGGAACCCCGAGATCCAGTACACCTCCAACTACTAC<br>AAATCTACAAGTGTGGACTTTGCTTGTTAATACAGAAGGCGTGTACTCTGAACCCCGCCCC<br>ATTGGCACCCGTTACCTCACCCGTAATCTGTAA |
| 91 | AAV8 Swap 7 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTATCCAGAACTCAGTCCAC<br>AGGAGGAACTCAAGGTACCCAGCAATTGTTATTTTCTCAAGCTGGGCCTGCAAACATGT<br>CGGCTCAGGCCAAGAACTGGCTGCCTGGACCTTGCTACCGGCAGCAGCGAGTCTCCAC<br>GACACTGTCGCAAAACAACAACAGCAACTTTGCTTGGACTGGTGCCACCAAATATCACCT<br>GAACGGCAGAAACTCGTTGGTTAATCCCGGCGTCGCCATGGCAACACACAAGGACGAC<br>GAGGACCGCTTTTTCCCATCCAGCGGAGTCCTGATTTTTGGAAAAACTGGAGCAACTAA<br>CAAAACTACATTGGAAAATGTGTTAATGACAAATGAAGAAGAAATTCGTCCTACTAATCC<br>TGTAGCCACGGAAGAATACGGGATAGTCAGCAGCAACTTACAAGCGGCTAATACTGCAG<br>CCCAGACACAAGTTGTCAACAACCAGGGAGCCTTACCTGGCATGGTCTGGCAGAACCGG<br>GACGTGTACCTGCAGGGTCCCATCTGGGCCAAGATTCCTCACACGGACGGCAACTTCCA<br>CCCGTCTCCGCTGATGGGCGGCTTTGGCCTGAAACATCCTCCGCCTCAGATCCTGATCA<br>AGAACACGCCTGTACCTGCGGATCCTCCGACCACCTTCAACCAGTCAAAGCTGAACTCTT |

TABLE 5-continued

| Capsid Sequences | | |
|---|---|---|
| SEQ ID NO | Name | Sequence |
| | | TCATCACGCAATACAGCACCGGACAGGTCAGCGTGGAAATTGAATGGGAGCTGCAGAA GGAAAACAGCAAGCGCTGGAACCCCGAGATCCAGTACACCTCCAACTACTACAAATCTA CAAGTGTGGACTTTGCTTGTTAATACAGAAGGCGTGTACTCTGAACCCCGCCCCATTGGC ACCCGTTACCTCACCCGTAATCTGTAA |
| 92 | AAV8 Swap 8 (nt) | ATGGCTGCCGATGGTTATCTTCCAGATTGGCTCGAGGACAACCTCTCTGAGGGCATTCG CGAGTGGTGGGCGCTGAAACCTGGAGCCCCGAAGCCCAAAGCCAACCAGCAAAAGCAG GACGACGGCCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTGCAGGCGGGTGACAATCCGTACCTGCGGTATAACCACGCCGAC GCCGAGTTTCAGGAGCGTCTGCAAGAAGATACGTCTTTTGGGGGCAACCTCGGGCGAG CAGTCTTCCAGGCCAAGAAGCGGGTTCTCGAACCTCTCGGTCTGGTTGAGGAAGGCGCT AAGACGGCTCCTGGAAAGAAGAGACCGGTAGAGCCATCACCCCAGCGTTCTCCAGACTC CTCTACGGGCATCGGCAAGAAAGGCCAACAGCCCGCCAGAAAAAGACTCAATTTTGGTC AGACTGGCGACTCAGAGTCAGTTCCAGACCCTCAACCTCTCGGAGAACCTCCAGCAGCG CCCTCTGGTGTGGGACCTAATACAATGGCTGCAGGCGGTGGCGCACCAATGGCAGACA ATAACGAAGGCGCCGACGGAGTGGGTAGTTCCTCGGGAAATTGGCATTGCGATTCCACA TGGCTGGGCGACAGAGTCATCACCACCAGCACCAGAACCTGGGCCCTGCCCACTTACAA CAACCATCTCTACAAGCAAATCTCCAGCCAATCAGGAGCTTCAAACGACAACCACTACTT CGGCTACAGCACCCCCTGGGGGTATTTTGACTTTAACAGATTCCACTGCCACTTTTCACC ACGTGACTGGCAGCGACTCATCAACAACAACTGGGGATTCCGGCCCAAGAGACTCAGCT TCAAGCTCTTCAACATCCAGGTCAAGGAGGTCACGCAGAATGAAGGCACCAAGACCATC GCCAATAACCTCACCAGCACCATCCAGGTGTTTACGGACTCGGAGTACCAGCTGCCGTA CGTTCTCGGCTCTGCCCACCAGGGCTGCCTGCCTCCGTTCCCGGCGGACGTGTTCATGA TTCCCCAGTACGGCTACCTAACACTCAACAACGGTAGTCAGGCCGTGGGACGCTCCTCC TTCTACTGCCTGGAATACTTTCCTTCGCAGATGCTGAGAACCGGCAACAACTTCCAGTTT ACTTACACCTTCGAGGACGTGCCTTTCCACAGCAGCTACGCCCACAGCCAGAGCTTGGA CCGGCTGATGAATCCTCTGATTGACCAGTACCTGTACTACTTATCCAGAACTCAGACCAC AGGAGGAACTGCAAATACCCAGACATTGGGATTTTCTCAAGGTGGGCCTAACACCATGG CGAATCAGGCCAAGAACTGGCTGCCTGGACCTTGCTACCGGCAGCAGCGAGTCTCCAC GACACTGTCGCAAAACAACAACAGCAACTTTGCTTGGACTGGTGCCACCAAATATCACCT GAACGGCAGAAACTCGTTGGTTAATCCCGGCGTCGCCATGGCAACACACAAGGACGAC GAGGACCGCTTTTTCCCATCCAGCGGAGTCCTGATTTTTGGAAAAACTGGAGCAACTAA CAAAACTACATTGGAAAATGTGTTAATGACAAATGAAGAAGAAATTCGTCCTACTAATCC TGTAGCCACGGAAGAATACGGGATAGTCAGCAGCAACTTACAAGCGGCTAATACTGCAG CCCAGACACAAGTTGTCAACAACCAGGGAGCCTTACCTGGCATGGTCTGGCAGAACCGG GACGTGTACCTGCAGGGTCCCATCTGGGCCAAGATTCCTCACACGGACGGCAACTTCCA CCCGTCTCCGCTGATGGGCGGCTTTGGCCTGAAACATCCTCCGCCTCAGATCCTGATCA AGAACACGCCTGTACCTGCGGATCCTCCGACCACCTTCAACCAGTCAAAGCTGAACTCTT TCATCACGCAATACAGCACCGGACAGGTCAGCGTGGAAATTGAATGGGAGCTGCAGAA GGAAAACAGCAAGCGCTGGAACCCCGAGATCCAGTACACCTCCAACTACTACAAATCTA CAAGTGTGGACTTTGCTGTTAATACAGAAGGCGTGTACTCTGAACCCCGCCCCATTGGC ACCCGTTACCTCACCCGTAATCTGTAA |
| 93 | AAV8 Swap 9 (nt) | ATGGCTGCCGATGGTTATCTTCCAGATTGGCTCGAGGACAACCTCTCTGAGGGCATTCG CGAGTGGTGGGCGCTGAAACCTGGAGCCCCGAAGCCCAAAGCCAACCAGCAAAAGCAG GACGACGGCCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTGCAGGCGGGTGACAATCCGTACCTGCGGTATAACCACGCCGAC GCCGAGTTTCAGGAGCGTCTGCAAGAAGATACGTCTTTTGGGGGCAACCTCGGGCGAG CAGTCTTCCAGGCCAAGAAGCGGGTTCTCGAACCTCTCGGTCTGGTTGAGGAAGGCGCT AAGACGGCTCCTGGAAAGAAGAGACCGGTAGAGCCATCACCCCAGCGTTCTCCAGACTC CTCTACGGGCATCGGCAAGAAAGGCCAACAGCCCGCCAGAAAAAGACTCAATTTTGGTC AGACTGGCGACTCAGAGTCAGTTCCAGACCCTCAACCTCTCGGAGAACCTCCAGCAGCG CCCTCTGGTGTGGGACCTAATACAATGGCTGCAGGCGGTGGCGCACCAATGGCAGACA ATAACGAAGGCGCCGACGGAGTGGGTAGTTCCTCGGGAAATTGGCATTGCGATTCCACA TGGCTGGGCGACAGAGTCATCACCACCAGCACCAGAACCTGGGCCCTGCCCACTTACAA CAACCATCTCTACAAGCAAATCTCCAGCCAATCAGGAGCTTCAAACGACAACCACTACTT CGGCTACAGCACCCCCTGGGGGTATTTTGACTTTAACAGATTCCACTGCCACTTTTCACC ACGTGACTGGCAGCGACTCATCAACAACAACTGGGGATTCCGGCCCAAGAGACTCAGCT TCAAGCTCTTCAACATCCAGGTCAAGGAGGTCACGCAGAATGAAGGCACCAAGACCATC GCCAATAACCTCACCAGCACCATCCAGGTGTTTACGGACTCGGAGTACCAGCTGCCGTA CGTTCTCGGCTCTGCCCACCAGGGCTGCCTGCCTCCGTTCCCGGCGGACGTGTTCATGA TTCCCCAGTACGGCTACCTAACACTCAACAACGGTAGTCAGGCCGTGGGACGCTCCTCC TTCTACTGCCTGGAATACTTTCCTTCGCAGATGCTGAGAACCGGCAACAACTTCCAGTTT ACTTACACCTTCGAGGACGTGCCTTTCCACAGCAGCTACGCCCACAGCCAGAGCTTGGA CCGGCTGATGAATCCTCTGATTGACCAGTACCTGTACTACTTATCCAGAACTCAGTCCAC AGGAGGAACTCAAGGTACCCAGCAATTGTTATTTTCTCAAGCTGGGCCTGCAAACATGT CGGCTCAGGCCAAGAACTGGCTGCCTGGACCTTGCTACCGGCAGCAGCGAGTCTCCAC GACAACGGGGCAAAACAACAACAGCAACTTTGCTTGGACTGCTGGCACCAAATATCACC TGAACGGCAGAAACTCGTTGGCTAATCCCGGCATCGCCATGGCAACACACAAGGACGAC GAGGACCGCTTTTTCCCATCCAGCGGAGTCCTGATTTTTGGAAAAACTGGAGCAACTAA CAAAACTACATTGGAAAATGTGTTAATGACAAATGAAGAAGAAATTCGTCCTACTAATCC TGTAGCCACGGAAGAATACGGGATAGTCAGCAGCAACTTACAAGCGGCTAATACTGCAG |

TABLE 5-continued

Capsid Sequences

| SEQ ID NO | Name | Sequence |
|---|---|---|
| | | CCCAGACACAAGTTGTCAACAACCAGGGAGCCTTACCTGGCATGGTCTGGCAGAACCGG GACGTGTACCTGCAGGGTCCCATCTGGGCCAAGATTCCTCACACGGACGGCAACTTCCA CCCGTCTCCGCTGATGGGCGGCTTTGGCCTGAAACATCCTCCGCCTCAGATCCTGATCA AGAACACGCCTGTACCTGCGGATCCTCCGACCACCTTCAACCAGTCAAAGCTGAACTCTT TCATCACGCAATACAGCACCGGACAGGTCAGCGTGGAAATTGAATGGGAGCTGCAGAA GGAAAACAGCAAGCGCTGGAACCCCGAGATCCAGTACACCTCCAACTACTACAAATCTA CAAGTGTGGACTTTGCTTGTTAATACAGAAGGCGTGTACTCTGAACCCCGCCCCATTGGC ACCCGTTACCTCACCCGTAATCTGTAA |
| 94 | AAV8 Swap 10 (nt) | ATGGCTGCCGATGGTTATCTTCCAGATTGGCTCGAGGACAACCTCTCTGAGGGCATTCG CGAGTGGTGGGCGCTGAAACCTGGAGCCCCGAAGCCCAAAGCCAACCAGCAAAAGCAG GACGACGGCCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTGCAGGCGGGTGACAATCCGTACCTGCGGTATAACCACGCCGAC GCCGAGTTTCAGGAGCGTCTGCAAGAAGATACGTCTTTTGGGGGCAACCTCGGGCGAG CAGTCTTCCAGGCCAAGAAGCGGGTTCTCGAACCTCTCGGTCTGGTTGAGGAAGGCGCT AAGACGGCTCCTGGAAAGAAGAGACCGGTAGAGCCATCACCCCAGCGTTCTCCAGACTC CTCTACGGGCATCGGCAAGAAAGGCCAACAGCCCGCCAGAAAAAGACTCAATTTTGGTC AGACTGGCGACTCAGAGTCAGTTCCAGACCCTCAACCTCTCGGAGAACCTCCAGCAGCG CCCTCTGGTGTGGGACCTAATACAATGGCTGCAGGCGGTGGCGCACCAATGGCAGACA ATAACGAAGGCGCCGACGGAGTGGGTAGTTCCTCGGGAAATTGGCATTGCGATTCCACA TGGCTGGGCGACAGAGTCATCACCACCAGCACCAGAACCTGGGCCCTGCCCACTTACAA CAACCATCTCTACAAGCAAATCTCCAGCCAATCAGGAGCTTCAAACGACAACCACTACTT CGGCTACAGCACCCCCTGGGGGTATTTTGACTTTAACAGATTCCACTGCCACTTTTCACC ACGTGACTGGCAGCGACTCATCAACAACAACTGGGGATTCCGGCCCAAGAGACTCAGCT TCAAGCTCTTCAACATCCAGGTCAAGGAGGTCACGCAGAATGAAGGCACCAAGACCATC GCCAATAACCTCACCAGCACCATCCAGGTGTTTACGGACTCGGAGTACCAGCTGCCGTA CGTTCTCGGCTCTGCCCACCAGGGCTGCCTGCCTCCGTTCCCGGCGGACGTGTTCATGA TTCCCCAGTACGGCTACCTAACACTCAACAACGGTAGTCAGGCCGTGGGACGCTCCTCC TTCTACTGCCTGGAATACTTTCCTTCGCAGATGCTGAGAACCGGCAACAACTTCCAGTTT ACTTACACCTTCGAGGACGTGCCTTTCCACAGCAGCTACGCCCACAGCCAGAGCTTGGA CCGGCTGATGAATCCTCTGATTGACCAGTACCTGTACTACTTATCCAGAACTCAGTCCAC AGGAGGAACTCAAGGTACCCAGCAATTGTTATTTTCTCAAGCTGGGCCTGCAAACATGT CGGCTCAGGCCAAGAACTGGCTGCCTGGACCTTGCTACCGGCAGCAGCGAGTCTCCAC GACACTGTCGCAAAACAACAACAGCAACTTTGCTTGGACTGGTGCCACCAAATATCACCT GAACGGCAGAAACTCGTTGGTTAATCCCGGCGTCGCCATGGCAACACACAAGGACGAC GAGGAGCGCTTTTTCCCATCCAACGGAATCCTGATTTTTGGAAAAACTGGAGCAACTAAC AAAACTACATTGGAAAATGTGTTAATGACAAATGAAGAAGAAATTCGTCCTACTAATCCT GTAGCCACGGAAGAATACGGGATAGTCAGCAGCAACTTACAAGCGGCTAATACTGCAGC CCAGACACAAGTTGTCAACAACCAGGGAGCCTTACCTGGCATGGTCTGGCAGAACCGG GACGTGTACCTGCAGGGTCCCATCTGGGCCAAGATTCCTCACACGGACGGCAACTTCCA CCCGTCTCCGCTGATGGGCGGCTTTGGCCTGAAACATCCTCCGCCTCAGATCCTGATCA AGAACACGCCTGTACCTGCGGATCCTCCGACCACCTTCAACCAGTCAAAGCTGAACTCTT TCATCACGCAATACAGCACCGGACAGGTCAGCGTGGAAATTGAATGGGAGCTGCAGAA GGAAAACAGCAAGCGCTGGAACCCCGAGATCCAGTACACCTCCAACTACTACAAATCTA CAAGTGTGGACTTTGCTTGTTAATACAGAAGGCGTGTACTCTGAACCCCGCCCCATTGGC ACCCGTTACCTCACCCGTAATCTGTAA |
| 95 | AAV8 Swap 11 (nt) | ATGGCTGCCGATGGTTATCTTCCAGATTGGCTCGAGGACAACCTCTCTGAGGGCATTCG CGAGTGGTGGGCGCTGAAACCTGGAGCCCCGAAGCCCAAAGCCAACCAGCAAAAGCAG GACGACGGCCGGGGTCTGGTGCTTCCTGGCTACAAGTACCTCGGACCCTTCAACGGACT CGACAAGGGGGAGCCCGTCAACGCGGCGGACGCAGCGGCCCTCGAGCACGACAAGGC CTACGACCAGCAGCTGCAGGCGGGTGACAATCCGTACCTGCGGTATAACCACGCCGAC GCCGAGTTTCAGGAGCGTCTGCAAGAAGATACGTCTTTTGGGGGCAACCTCGGGCGAG CAGTCTTCCAGGCCAAGAAGCGGGTTCTCGAACCTCTCGGTCTGGTTGAGGAAGGCGCT AAGACGGCTCCTGGAAAGAAGAGACCGGTAGAGCCATCACCCCAGCGTTCTCCAGACTC CTCTACGGGCATCGGCAAGAAAGGCCAACAGCCCGCCAGAAAAAGACTCAATTTTGGTC AGACTGGCGACTCAGAGTCAGTTCCAGACCCTCAACCTCTCGGAGAACCTCCAGCAGCG CCCTCTGGTGTGGGACCTAATACAATGGCTGCAGGCGGTGGCGCACCAATGGCAGACA ATAACGAAGGCGCCGACGGAGTGGGTAGTTCCTCGGGAAATTGGCATTGCGATTCCACA TGGCTGGGCGACAGAGTCATCACCACCAGCACCAGAACCTGGGCCCTGCCCACTTACAA CAACCATCTCTACAAGCAAATCTCCAGCCAATCAGGAGCTTCAAACGACAACCACTACTT CGGCTACAGCACCCCCTGGGGGTATTTTGACTTTAACAGATTCCACTGCCACTTTTCACC ACGTGACTGGCAGCGACTCATCAACAACAACTGGGGATTCCGGCCCAAGAGACTCAGCT TCAAGCTCTTCAACATCCAGGTCAAGGAGGTCACGCAGAATGAAGGCACCAAGACCATC GCCAATAACCTCACCAGCACCATCCAGGTGTTTACGGACTCGGAGTACCAGCTGCCGTA CGTTCTCGGCTCTGCCCACCAGGGCTGCCTGCCTCCGTTCCCGGCGGACGTGTTCATGA TTCCCCAGTACGGCTACCTAACACTCAACAACGGTAGTCAGGCCGTGGGACGCTCCTCC TTCTACTGCCTGGAATACTTTCCTTCGCAGATGCTGAGAACCGGCAACAACTTCCAGTTT ACTTACACCTTCGAGGACGTGCCTTTCCACAGCAGCTACGCCCACAGCCAGAGCTTGGA CCGGCTGATGAATCCTCTGATTGACCAGTACCTGTACTACTTATCCAGAACTCAGTCCAC AGGAGGAACTCAAGGTACCCAGCAATTGTTATTTTCTCAAGCTGGGCCTGCAAACATGT CGGCTCAGGCCAAGAACTGGCTGCCTGGACCTTGCTACCGGCAGCAGCGAGTCTCCAC GACACTGTCGCAAAACAACAACAGCAACTTTGCTTGGACTGGTGCCACCAAATATCACCT |

TABLE 5-continued

Capsid Sequences

| SEQ ID NO | Name | Sequence |
|---|---|---|
| | | GAACGGCAGAAACTCGTTGGTTAATCCCGGCGTCGCCATGGCAACACACAAGGACGAC<br>GAGGACCGCTTTTTCCCATCCAGCGGAGTCCTGATTTTTGGAAAACAGAATGCAGCAAG<br>GGACAACGCTGACTACTCAGATGTGATGTTGACAAGTGAAGAAGAAATTAAGACTACTA<br>ATCCTGTAGCCACGGAAGAATACGGGATAGTCAGCAGCAACTTACAAGCGGCTAATACT<br>GCAGCCCAGACACAAGTTGTCAACAACCAGGGAGCCTTACCTGGCATGGTCTGGCAGAA<br>CCGGGACGTGTACCTGCAGGGTCCCATCTGGGCCAAGATTCCTCACACGGACGGCAAC<br>TTCCACCCGTCTCCGCTGATGGGCGGCTTTGGCCTGAAACATCCTCCGCCTCAGATCCT<br>GATCAAGAACACGCCTGTACCTGCGGATCCTCCGACCACCTTCAACCAGTCAAAGCTGA<br>ACTCTTTCATCACGCAATACAGCACCGGACAGGTCAGCGTGGAAATTGAATGGGAGCTG<br>CAGAAGGAAAACAGCAAGCGCTGGAACCCCGAGATCCAGTACACCTCCAACTACTACAA<br>ATCTACAAGTGTGGACTTTGCTTGTTAATACAGAAGGCGTGTACTCTGAACCCCGCCCCAT<br>TGGCACCCGTTACCTCACCCGTAATCTGTAA |
| 96 | AAV8 Swap 12 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTATCCAGAACTCAGTCCAC<br>AGGAGGAACTCAAGGTACCCAGCAATTGTTATTTTCTCAAGCTGGGCCTGCAAACATGT<br>CGGCTCAGGCCAAGAACTGGCTGCCTGGACCTTGCTACCGGCAGCAGCGAGTCTCCAC<br>GACACTGTCGCAAAACAACAACAGCAACTTTGCTTGGACTGGTGCCACCAAATATCACCT<br>GAACGGCAGAAACTCGTTGGTTAATCCCGGCGTCGCCATGGCAACACACAAGGACGAC<br>GAGGACCGCTTTTTCCCATCCAGCGGAGTCCTGATTTTTGGAAAAACTGGAGCAACTAA<br>CAAAACTACATTGGAAAATGTGTTAATGACAAATGAAGAAGAAATTCGTCCTACTAATCC<br>TGTAGCCACGGAAGAATACGGGATAGTCGCCGACAACTTACAACAGCAGAATACTGCAC<br>CCCAGATAGGAACTGTCAACAGCCAGGGAGCCTTACCTGGCATGGTCTGGCAGAACCG<br>GGACGTGTACCTGCAGGGTCCCATCTGGGCCAAGATTCCTCACACGGACGGCAACTTCC<br>ACCCGTCTCCGCTGATGGGCGGCTTTGGCCTGAAACATCCTCCGCCTCAGATCCTGATC<br>AAGAACACGCCTGTACCTGCGGATCCTCCGACCACCTTCAACCAGTCAAAGCTGAACTC<br>TTTCATCACGCAATACAGCACCGGACAGGTCAGCGTGGAAATTGAATGGGAGCTGCAGA<br>AGGAAAACAGCAAGCGCTGGAACCCCGAGATCCAGTACACCTCCAACTACTACAAATCT<br>ACAAGTGTGGACTTTGCTTGTTAATACAGAAGGCGTGTACTCTGAACCCCGCCCCATTGG<br>CACCCGTTACCTCACCCGTAATCTGTAA |
| 97 | AAV8 Swap 13 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA |

TABLE 5-continued

Capsid Sequences

| SEQ ID NO | Name | Sequence |
|---|---|---|
| | | CCGGCTGATGAATCCTCTGATTGACCAGTACCTGTACTACTTATCCAGAACTCAGTCCAC<br>AGGAGGAACTCAAGGTACCCAGCAATTGTTATTTTCTCAAGCTGGGCCTGCAAACATGT<br>CGGCTCAGGCCAAGAACTGGCTGCCTGGACCTTGCTACCGGCAGCAGCGAGTCTCCAC<br>GACACTGTCGCAAAACAACAACAGCAACTTTGCTTGGACTGGTGCCACCAAATATCACCT<br>GAACGGCAGAAACTCGTTGGTTAATCCCGGCGTCGCCATGGCAACACACAAGGACGAC<br>GAGGACCGTTTTTTTCCCAGTAGCGGGGTCCTGATTTTTGGCAAACAAAATGCTGCCAG<br>AGACAATGCGGATTACAGCGATGTCATGCTCACCAGCGAGGAAGAAATCAAAACCACTA<br>ACCCTGTGGCTACAGAGGAATACGGTATCGTGGCAGATAACTTGCAGCAGCAAAACACG<br>GCTCCTCAAATTGGAACTGTCAACAGCCAGGGGGCCTTACCCGGTATGGTCTGGCAGAA<br>CCGGGACGTGTACCTGCAGGGTCCCATCTGGGCCAAGATTCCTCACACGGACGGCAAC<br>TTCCACCCGTCTCCGCTGATGGGCGGCTTTGGCCTGAAACATCCTCCGCCTCAGATCCT<br>GATCAAGAACACGCCTGTACCTGCGGATCCTCCGACCACCTTCAACCAGTCAAAGCTGA<br>ACTCTTTCATCACGCAATACAGCACCGGACAGGTCAGCGTGGAAATTGAATGGGAGCTG<br>CAGAAGGAAAACAGCAAGCGCTGGAACCCCGAGATCCAGTACACCTCCAACTACTACAA<br>ATCTACAAGTGTGGACTTTGCTGTTAATACAGAAGGCGTGTACTCTGAACCCCGCCCCAT<br>TGGCACCCGTTACCTCACCCGTAATCTGTAA |
| 98 | AAV8 Swap 14 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA<br>CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTATCCAGAACTCAGTCCAC<br>AGGAGGAACTCAAGGTACCCAGCAATTGTTATTTTCTCAAGCTGGGCCTGCAAACATGT<br>CGGCTCAGGCCAAGAACTGGCTGCCTGGACCTTGCTACCGGCAGCAGCGAGTCTCCAC<br>GACACTGTCGCAAAACAACAACAGCAACTTTGCTTGGACTGGTGCCACCAAATATCACCT<br>GAACGGCAGAAACTCGTTGGTTAATCCCGGCGTCGCCATGGCAACACACAAGGACGAC<br>GAGGAGCGTTTTTTTCCCAGTAACGGGATCCTGATTTTTGGCAAAACTGGTGCCACAAAC<br>AAAACGACTTTGGAGAATGTCTTGATGACCAACGAGGAAGAAATCAGACCCACTAACCC<br>TGTGGCTACAGAGGAATACGGTATCGTGGCAGATAACTTGCAGCAGCAAAACACGGCTC<br>CTCAAATTGGAACTGTCAACAGCCAGGGGGCCTTACCCGGTATGGTCTGGCAGAACCGG<br>GACGTGTACCTGCAGGGTCCCATCTGGGCCAAGATTCCTCACACGGACGGCAACTTCCA<br>CCCGTCTCCGCTGATGGGCGGCTTTGGCCTGAAACATCCTCCGCCTCAGATCCTGATCA<br>AGAACACGCCTGTACCTGCGGATCCTCCGACCACCTTCAACCAGTCAAAGCTGAACTCTT<br>TCATCACGCAATACAGCACCGGACAGGTCAGCGTGGAAATTGAATGGGAGCTGCAGAA<br>GGAAAACAGCAAGCGCTGGAACCCCGAGATCCAGTACACCTCCAACTACTACAAATCTA<br>CAAGTGTGGACTTTGCTTGTTAATACAGAAGGCGTGTACTCTGAACCCCGCCCCATTGGC<br>ACCCGTTACCTCACCCGTAATCTGTAA |
| 99 | AAV8 Swap 15 (nt) | ATGGCTGCCGATGGTTATCTTCCAGATTGGCTCGAGGACAACCTCTCTGAGGGCATTCG<br>CGAGTGGTGGGCGCTGAAACCTGGAGCCCCGAAGCCCAAAGCCAACCAGCAAAAGCAG<br>GACGACGGCCGGGGTCTGGTGCTTCCTGGCTACAAGTACCTCGGACCCTTCAACGGACT<br>CGACAAGGGGGAGCCCGTCAACGCGGCGGACGCAGCGGCCCTCGAGCACGACAAGGC<br>CTACGACCAGCAGCTGCAGGCGGGTGACAATCCGTACCTGCGGTATAACCACGCCGAC<br>GCCGAGTTTCAGGAGCGTCTGCAAGAAGATACGTCTTTTGGGGGCAACCTCGGGCGAG<br>CAGTCTTCCAGGCCAAGAAGCGGGTTCTCGAACCTCTCGGTCTGGTTGAGGAAGGCGCT<br>AAGACGGCTCCTGGAAAGAAGAGACCGGTAGAGCCATCACCCCAGCGTTCTCCAGACTC<br>CTCTACGGGCATCGGCAAGAAAGGCCAACAGCCCGCCAGAAAAAGACTCAATTTTGGTC<br>AGACTGGCGACTCAGAGTCAGTTCCAGACCCTCAACCTCTCGGAGAACCTCCAGCAGCG<br>CCCTCTGGTGTGGGACCTAATACAATGGCTGCAGGCGGTGGCGCACCAATGGCAGACA<br>ATAACGAAGGCGCCGACGGAGTGGGTAGTTCCTCGGGAAATTGGCATTGCGATTCCACA<br>TGGCTGGGCGACAGAGTCATCACCACCAGCACCAGAACCTGGGCCCTGCCCACTTACAA<br>CAACCATCTCTACAAGCAAATCTCCAGCCAATCAGGAGCTTCAAACGACAACCACTACTT<br>CGGCTACAGCACCCCCTGGGGGTATTTTGACTTTAACAGATTCCACTGCCACTTTTCACC<br>ACGTGACTGGCAGCGACTCATCAACAACAACTGGGGATTCCGGCCCAAGAGACTCAGCT<br>TCAAGCTCTTCAACATCCAGGTCAAGGAGGTCACGCAGAATGAAGGCACCAAGACCATC<br>GCCAATAACCTCACCAGCACCATCCAGGTGTTTACGGACTCGGAGTACCAGCTGCCGTA |

TABLE 5-continued

Capsid Sequences

| SEQ ID NO | Name | Sequence |
|---|---|---|
| | | CGTTCTCGGCTCTGCCCACCAGGGCTGCCTGCCTCCGTTCCCGGCGGACGTGTTCATGA<br>TTCCCCAGTACGGCTACCTAACACTCAACAACGGTAGTCAGGCCGTGGGACGCTCCTCC<br>TTCTACTGCCTGGAATACTTTCCTTCGCAGATGCTGAGAACCGGCAACAACTTCCAGTTT<br>ACTTACACCTTCGAGGACGTGCCTTTCCACAGCAGCTACGCCCACAGCCAGAGCTTGGA<br>CCGGCTGATGAATCCTCTGATTGACCAGTACCTGTACTACTTATCCAGAACTCAGTCCAC<br>AGGAGGAACTCAAGGTACCCAGCAATTGTTATTTTCTCAAGCTGGGCCTGCAAACATGT<br>CGGCTCAGGCCAAGAACTGGCTGCCTGGACCTTGCTACCGGCAGCAGCGAGTCTCCAC<br>GACACTGTCGCAAAACAACAACAGCAACTTTGCTTGGACTGGTGCCACCAAATATCACCT<br>GAACGGCAGAAACTCGTTGGTTAATCCCGGCGTCGCCATGGCAACACACAAGGACGAC<br>GAGGAGCGTTTTTTTCCCAGTAACGGGATCCTGATTTTTGGCAAACAAAATGCTGCCAGA<br>GACAATGCGGATTACAGCGATGTCATGCTCACCAGCGAGGAAGAAATCAAAACCACTAA<br>CCCTGTGGCTACAGAGGAATACGGTATCGTGTCATCTAACTTGCAGGCGGCAAACACGG<br>CTGCTCAAACTCAAGTTGTCAACAACCAGGGGGCCTTACCCGGTATGGTCTGGCAGAAC<br>CGGGACGTGTACCTGCAGGGTCCCATCTGGGCCAAGATTCCTCACACGGACGGCAACTT<br>CCACCCGTCTCCGCTGATGGGCGGCTTTGGCCTGAAACATCCTCCGCCTCAGATCCTGA<br>TCAAGAACACGCCTGTACCTGCGGATCCTCCGACCACCTTCAACCAGTCAAAGCTGAAC<br>TCTTTCATCACGCAATACAGCACCGGACAGGTCAGCGTGGAAATTGAATGGGAGCTGCA<br>GAAGGAAAACAGCAAGCGCTGGAACCCCGAGATCCAGTACACCTCCAACTACTACAAAT<br>CTACAAGTGTGGACTTTGCTGTTAATACAGAAGGCGTGTACTCTGAACCCCGCCCCATTG<br>GCACCCGTTACCTCACCCGTAATCTGTAA |

The invention claimed is:

1. A capsid polypeptide, comprising:

(i) the sequence of amino acids set forth in SEQ ID NO: 12, or a sequence having at least 99% sequence identity thereto;

(ii) the sequence of amino acids at positions 138-735 of SEQ ID NO: 12; or a sequence having at least 99% sequence identity thereto; and/or (iii) the sequence of amino acids at positions 204-735 of SEQ ID NO: 12; or a sequence having at least 99% sequence identity thereto.

2. A capsid polypeptide, comprising:

(i) the sequence of amino acids set forth in SEQ ID NO: 12 or a sequence having at least 95% sequence identity thereto;

(ii) the sequence of amino acids at positions 138-735 of SEQ ID NO: 12 or a sequence having at least 95% sequence identity thereto; and/or (iii) the sequence of amino acids at positions 204-735 of SEQ ID NO: 12 or a sequence having at least 95% sequence identity thereto;

wherein the capsid polypeptide comprises:

a) the sequence of amino acids ISSQSGASNDNH (SEQ ID NO:80) at positions 261-272, with numbering relative to SEQ ID NO: 12; and b) the sequence of amino acids KTGATNKTTLENVLMTNEEEIRP (SEQ ID NO:81) at positions 545-567, with numbering relative to SEQ ID NO: 12 and the sequence of amino acids SSNLQAANTAAQTQVVNN (SEQ ID NO:60) at positions 580-597, with numbering relative to SEQ ID NO: 12.

3. The capsid polypeptide of claim 2, comprising:

(i) amino acid residues D532, S538 and V540, with numbering relative to SEQ ID NO: 12;

(ii) amino acid residues S451, Q456, G457, Q460, L462, A466, A469, N470, S472 and A473, with numbering relative to SEQ ID NO: 12; or (iii) amino acid residues L493, S494, G505, A506, V518 and V522, with numbering relative to SEQ ID NO: 12.

4. The capsid polypeptide of claim 3, comprising:

(i) the sequence of amino acids DRFFPSSGV (SEQ ID NO:61) at positions 532-540, with numbering relative to SEQ ID NO: 12;

(ii) the sequence of amino acids AMATHKDDEDRFFPSSGV (SEQ ID NO:82) at positions 523-540, with numbering relative to SEQ ID NO: 12;

(iii) the sequence of amino acids STGGTQGTQQLLFSQAGPANMSA (SEQ ID NO: 62) at positions 451-473, with numbering relative to SEQ ID NO: 12;

(iv) the sequence of amino acids QSTGGTQGTQQLLFSQAGPANMSA (SEQ ID NO: 83) at positions 450-473, with numbering relative to SEQ ID NO: 12;

(v) the sequence of amino acids LSQNNNSNFAWTGATKYHLNGRNSLVNPGV (SEQ ID NO:63) at positions 493-522, with numbering relative to SEQ ID NO: 12; or (vi) the sequence of amino acids RVSTTLSQNNNSNFAWTGATKYHLNGRNSLVNPGV (SEQ ID NO:84) at positions 488-522, with numbering relative to SEQ ID NO: 12.

5. The capsid polypeptide of claim 2, comprising:

the sequence of amino acids ISSQSGASNDNH (SEQ ID NO: 80) at positions 261-272, with numbering relative to SEQ ID NO: 12; the sequence of amino acids QSTGGTQGTQQLLFSQAGPANMSA (SEQ ID NO:83) at positions 450-473; the sequence of amino acids RVSTTLSQNNNSNFAWTGATKYHLNGRNSLVNPGV (SEQ ID NO: 84) at positions 488-522; the sequence of amino acids AMATHKDDEDRFFPSSGV (SEQ ID NO:82) at positions 523-540; the sequence of amino acids KTGATNKTTLENVLMTNEEEIRP (SEQ ID NO:81) at positions 545-567, with numbering relative to SEQ ID NO:13; and the sequence of amino acids SSNLQAANTAAQTQVVNN (SEQ ID NO:60) at positions 580-597, with numbering relative to SEQ ID NO:13.

6. The capsid polypeptide of claim 1, comprising one or more of:

a) amino acid residues S263, Q264, S265, S268 and H272, with numbering relative to SEQ ID NO: 12;

b) amino acid residues T546, G547, T549, N550, K551, T552, T553, L554, E555, N556, L558, M559, N561, R566 and P567, with numbering relative to SEQ ID NO: 12;

c) amino acid residues S580, S581, A585, A586, A590, T592, Q593, V594, and N597, with numbering relative to SEQ ID NO: 12;

d) amino acid residues D532, S538 and V540, with numbering relative to SEQ ID NO: 12;

e) amino acid residues S451, Q456, G457, Q460, L462, A466, A469, N470, S472 and A473, with numbering relative to SEQ ID NO: 12;

f) amino acid residues L493, S494, G505, A506, V518 and V522, with numbering relative to SEQ ID NO: 12;

g) the sequence of amino acids SQSGASNDNH (SEQ ID NO:58) at positions 263-272, with numbering relative to SEQ ID NO: 12;

h) the sequence of amino acids TGATNKTTLENVLMTNEEEIRP (SEQ ID NO: 59) at positions 546-567, with numbering relative to SEQ ID NO: 12;

i) the sequence of amino acids SSNLQAANTAAQTQVVNN (SEQ ID NO:60) at positions 580-597, with numbering relative to SEQ ID NO: 12;

j) the sequence of amino acids DRFFPSSGV (SEQ ID NO:61) at positions 532-540, with numbering relative to SEQ ID NO: 12;

k) the sequence of amino acids STGGTQGTQQLLFSQAGPANMSA (SEQ ID NO: 62) at positions 451-473, with numbering relative to SEQ ID NO: 12; and l) the sequence of amino acids LSQNNNSNFAWTGATKYHLNGRNSLVNPGV (SEQ ID NO:63) at positions 493-522, with numbering relative to SEQ ID NO: 12.

7. An AAV vector, comprising the capsid polypeptide of claim 2.

8. The AAV vector of claim 7, wherein the vector exhibits increased in vivo transduction efficiency compared to an AAV vector comprising a capsid polypeptide comprising the sequence of amino acids set forth in SEQ ID NO:1 and/or increased resistance to neutralization by pooled human immunoglobulins compared to an AAV vector comprising a capsid polypeptide comprising the sequence of amino acids set forth in SEQ ID NO: 1.

9. An isolated nucleic acid molecule encoding the capsid polypeptide of claim 2.

10. An AAV vector, comprising the capsid polypeptide of claim 1.

11. An isolated nucleic acid molecule encoding the capsid polypeptide of claim 1.

* * * * *

SEQUENCE LISTING

```
<160> NUMBER OF SEQ ID NOS: 99

<210> SEQ ID NO 1
<211> LENGTH: 735
<212> TYPE: PRT
<213> ORGANISM: adeno-associated virus 2

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
```

```
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620
```

Asp Gly His Phe His Pro Ser Pro Leu Met Gly Gly Phe Gly Leu Lys
625 630 635 640

His Pro Pro Pro Gln Ile Leu Ile Lys Asn Thr Pro Val Pro Ala Asn
645 650 655

Pro Ser Thr Thr Phe Ser Ala Ala Lys Phe Ala Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Asn Lys Ser Val Asn Val Asp Phe Thr Val Asp Thr Asn Gly Val Tyr
705 710 715 720

Ser Glu Pro Arg Pro Ile Gly Thr Arg Tyr Leu Thr Arg Asn Leu
725 730 735

<210> SEQ ID NO 2
<211> LENGTH: 735
<212> TYPE: PRT
<213> ORGANISM: Artificial Sequence
<220> FEATURE:
<223> OTHER INFORMATION: AAVC11.01 capsid polypeptide (VP1)

<400> SEQUENCE: 2

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Ala Ala Lys Thr Ala Pro Gly Lys Lys Arg
130 135 140

Pro Val Glu Pro Ser Pro Gln Arg Ser Pro Asp Ser Ser Ser Gly Ile
145 150 155 160

Gly Lys Thr Gly Gln Gln Pro Ala Lys Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

```
Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Ser Gln Ala Lys Leu Ala Ser Phe Ile Thr Gln
            660                 665                 670
```

```
Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro Leu
                725                 730                 735


<210> SEQ ID NO 3
<211> LENGTH: 736
<212> TYPE: PRT
<213> ORGANISM: Artificial Sequence
<220> FEATURE:
<223> OTHER INFORMATION: AAVC11.02 capsid polypeptide (VP1)

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Ser Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300
```

```
Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Ser Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ala Arg
        435                 440                 445

Thr Gln Ser Asn Pro Gly Gly Thr Ala Gly Asn Arg Glu Leu Gln Phe
    450                 455                 460

Tyr Gln Gly Gly Pro Ser Thr Met Ala Glu Gln Ala Lys Asn Trp Leu
465                 470                 475                 480

Pro Gly Pro Cys Phe Arg Gln Gln Arg Val Ser Lys Thr Leu Asp Gln
                485                 490                 495

Asn Asn Asn Ser Asn Phe Ala Trp Thr Gly Ala Thr Lys Tyr His Leu
            500                 505                 510

Asn Gly Arg Asn Ser Leu Val Asn Pro Gly Val Ala Met Ala Thr His
        515                 520                 525

Lys Asp Asp Glu Asp Arg Phe Phe Pro Ser Ser Gly Val Leu Ile Phe
    530                 535                 540

Gly Lys Thr Gly Ala Thr Asn Lys Thr Thr Leu Glu Asn Val Leu Met
545                 550                 555                 560

Thr Asn Glu Glu Glu Ile Arg Pro Thr Asn Pro Val Ala Thr Glu Glu
                565                 570                 575

Tyr Gly Ile Val Ser Ser Asn Leu Gln Ala Ala Asn Thr Ala Ala Gln
            580                 585                 590

Thr Gln Val Val Asn Asn Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
```

725 730 735

<210> SEQ ID NO 4
<211> LENGTH: 737
<212> TYPE: PRT
<213> ORGANISM: Artificial Sequence
<220> FEATURE:
<223> OTHER INFORMATION: AAVC11.03 capsid polypeptide (VP1)

<400> SEQUENCE: 4

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Thr Pro Ala Ala Val Gly Pro Thr Thr Met Ala Ser Gly Gly
195 200 205

Gly Ala Pro Met Ala Asp Asn Asn Glu Gly Ala Asp Gly Val Gly Asn
210 215 220

Ala Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Ser Glu Thr Ala Gly Ser Thr Asn Asp Asn
260 265 270

Thr Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Asn Phe Lys Leu Phe Asn Ile
305 310 315 320

Gln Val Lys Glu Val Thr Thr Asn Asp Gly Val Thr Thr Ile Ala Asn
325 330 335

Asn Leu Thr Ser Thr Val Gln Val Phe Ser Asp Ser Glu Tyr Gln Leu
340 345 350

Pro Tyr Val Leu Gly Ser Ala His Gln Gly Cys Leu Pro Pro Phe Pro

```
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Asn Gln Ser Gly Ser Ala Gln Asn Lys Asp Leu Leu Phe
    450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
        515                 520                 525

Lys Asp Asp Glu Asp Lys Phe Phe Pro Met Ser Gly Val Met Ile Phe
    530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Phe Gln Ser Ser Ser Thr Asp Pro
            580                 585                 590

Ala Thr Gly Asp Val His Val Met Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Ser Gln Ala Lys Leu Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Val Gln Tyr Thr Ser
    690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu
```

<210> SEQ ID NO 5
<211> LENGTH: 734
<212> TYPE: PRT
<213> ORGANISM: Artificial Sequence
<220> FEATURE:

<223> OTHER INFORMATION: AAVC11.04 capsid polypeptide (VP1)

<400> SEQUENCE: 5

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Thr Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Ala Gly Pro Ser Gly Leu Gly Ser Gly Thr Val Ala Ala Gly Gly Gly
195 200 205

Ala Pro Met Ala Asp Asn Asn Glu Gly Ala Asp Gly Val Gly Asn Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Gln Ser Gly Ala Ser Asn Asp Asn His Tyr
260 265 270

Phe Gly Tyr Ser Thr Pro Trp Gly Tyr Phe Asp Phe Asn Arg Phe His
275 280 285

Cys His Phe Ser Pro Arg Asp Trp Gln Arg Leu Ile Asn Asn Asn Trp
290 295 300

Gly Phe Arg Pro Lys Arg Leu Ser Phe Lys Leu Phe Asn Ile Gln Val
305 310 315 320

Lys Glu Val Thr Thr Asn Asp Gly Val Thr Thr Ile Ala Asn Asn Leu
325 330 335

Thr Ser Thr Val Gln Val Phe Ser Asp Ser Glu Tyr Gln Leu Pro Tyr
340 345 350

Val Leu Gly Ser Ala His Gln Gly Cys Leu Pro Pro Phe Pro Ala Asp
355 360 365

Val Phe Met Ile Pro Gln Tyr Gly Tyr Leu Thr Leu Asn Asn Gly Ser
370 375 380

Gln Ala Val Gly Arg Ser Ser Phe Tyr Cys Leu Glu Tyr Phe Pro Ser
385 390 395 400

Gln Met Leu Arg Thr Gly Asn Asn Phe Glu Phe Ser Tyr Thr Phe Glu
405 410 415

Asp Val Pro Phe His Ser Ser Tyr Ala His Ser Gln Ser Leu Asp Arg
420 425 430

Leu Met Asn Pro Leu Ile Asp Gln Tyr Leu Tyr Tyr Leu Ser Arg Thr
435 440 445

Gln Ser Thr Gly Gly Thr Gln Gly Thr Gln Gln Leu Leu Phe Ser Gln
450 455 460

Ala Gly Pro Ala Asn Met Ser Ala Gln Ala Lys Asn Trp Leu Pro Gly
465 470 475 480

Pro Cys Tyr Arg Gln Gln Arg Val Ser Thr Thr Leu Ser Gln Asn Asn
485 490 495

Asn Ser Asn Phe Ala Trp Thr Gly Ala Thr Lys Tyr His Leu Asn Gly
500 505 510

Arg Asn Ser Leu Val Asn Pro Gly Val Ala Met Ala Thr His Lys Asp
515 520 525

Asp Glu Asp Arg Phe Phe Pro Ser Ser Gly Val Leu Ile Phe Gly Lys
530 535 540

Thr Gly Ala Thr Asn Lys Thr Thr Leu Glu Asn Val Leu Met Thr Asn
545 550 555 560

Glu Glu Glu Ile Arg Pro Thr Asn Pro Val Ala Thr Glu Glu Tyr Gly
565 570 575

Ile Val Ser Ser Asn Leu Gln Ala Ala Asn Thr Ala Ala Gln Thr Gln
580 585 590

Val Val Asn Asn Gln Gly Ala Leu Pro Gly Met Val Trp Gln Asn Arg
595 600 605

Asp Val Tyr Leu Gln Gly Pro Ile Trp Ala Lys Ile Pro His Thr Asp
610 615 620

Gly Asn Phe His Pro Ser Pro Leu Met Gly Gly Phe Gly Leu Lys His
625 630 635 640

Pro Pro Pro Gln Ile Leu Ile Lys Asn Thr Pro Val Pro Ala Asn Pro
645 650 655

Pro Glu Val Phe Thr Pro Ala Lys Phe Ala Ser Phe Ile Thr Gln Tyr
660 665 670

Ser Thr Gly Gln Val Ser Val Glu Ile Glu Trp Glu Leu Gln Lys Glu
675 680 685

Asn Ser Lys Arg Trp Asn Pro Glu Ile Gln Tyr Thr Ser Asn Tyr Asn
690 695 700

Lys Ser Val Ser Val Asp Phe Thr Val Asp Thr Asn Gly Val Tyr Ser
705 710 715 720

Glu Pro Arg Pro Ile Gly Thr Arg Tyr Leu Thr Arg Asn Leu
725 730

<210> SEQ ID NO 6
<211> LENGTH: 735
<212> TYPE: PRT
<213> ORGANISM: Artificial Sequence
<220> FEATURE:
<223> OTHER INFORMATION: AAVC11.05 capsid polypeptide (VP1)

<400> SEQUENCE: 6

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

```
Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Ser Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Glu Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
```

```
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Ser Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 7
<211> LENGTH: 735
<212> TYPE: PRT
<213> ORGANISM: Artificial Sequence
<220> FEATURE:
<223> OTHER INFORMATION: AAVC11.06 capsid polypeptide (VP1)

<400> SEQUENCE: 7

Met Ala Ala Asp Gly Tyr Leu Pro Asp Trp Leu Glu Asp Thr Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
```

```
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Ser Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510
```

```
Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Ser Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 8
<211> LENGTH: 734
<212> TYPE: PRT
<213> ORGANISM: Artificial Sequence
<220> FEATURE:
<223> OTHER INFORMATION: AAVC11.07 capsid polypeptide (VP1)

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140
```

-continued

```
Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Gly Pro Ser Gly Leu Gly Ser Gly Thr Val Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Ser Phe Lys Leu Phe Asn Ile Gln Val
305                 310                 315                 320

Lys Glu Val Thr Thr Asn Asp Gly Val Thr Thr Ile Ala Asn Asn Leu
                325                 330                 335

Thr Ser Thr Val Gln Val Phe Ser Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Glu Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Gln Ser Thr Gly Gly Thr Gln Gly Thr Gln Gln Leu Leu Phe Ser Gln
    450                 455                 460

Ala Gly Pro Ala Asn Met Ser Ala Gln Ala Lys Asn Trp Leu Pro Gly
465                 470                 475                 480

Pro Cys Tyr Arg Gln Gln Arg Val Ser Thr Thr Leu Ser Gln Asn Asn
                485                 490                 495

Asn Ser Asn Phe Ala Trp Thr Gly Ala Thr Lys Tyr His Leu Asn Gly
            500                 505                 510

Arg Asn Ser Leu Val Asn Pro Gly Val Ala Met Ala Thr His Lys Asp
        515                 520                 525

Asp Glu Asp Arg Phe Phe Pro Ser Ser Gly Val Leu Ile Phe Gly Lys
    530                 535                 540

Thr Gly Ala Thr Asn Lys Thr Thr Leu Glu Asn Val Leu Met Thr Asn
545                 550                 555                 560
```

Glu Glu Glu Ile Arg Pro Thr Asn Pro Val Ala Thr Glu Glu Tyr Gly
565 570 575

Ile Val Ser Ser Asn Leu Gln Ala Ala Asn Thr Ala Ala Gln Thr Gln
580 585 590

Val Val Asn Asn Gln Gly Ala Leu Pro Gly Met Val Trp Gln Asn Arg
595 600 605

Asp Val Tyr Leu Gln Gly Pro Ile Trp Ala Lys Ile Pro His Thr Asp
610 615 620

Gly Asn Phe His Pro Ser Pro Leu Met Gly Gly Phe Gly Leu Lys His
625 630 635 640

Pro Pro Pro Gln Ile Leu Ile Lys Asn Thr Pro Val Pro Ala Asn Pro
645 650 655

Pro Glu Val Phe Thr Pro Ala Lys Phe Ala Ser Phe Ile Thr Gln Tyr
660 665 670

Ser Thr Gly Gln Val Ser Val Glu Ile Glu Trp Glu Leu Gln Lys Glu
675 680 685

Asn Ser Lys Arg Trp Asn Pro Glu Ile Gln Tyr Thr Ser Asn Tyr Asn
690 695 700

Lys Ser Val Ser Val Asp Phe Thr Val Asp Thr Asn Gly Val Tyr Ser
705 710 715 720

Glu Pro Arg Pro Ile Gly Thr Arg Tyr Leu Thr Arg Asn Leu
725 730

<210> SEQ ID NO 9
<211> LENGTH: 735
<212> TYPE: PRT
<213> ORGANISM: Artificial Sequence
<220> FEATURE:
<223> OTHER INFORMATION: AAVC11.08 capsid polypeptide (VP1)

<400> SEQUENCE: 9

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Ala Ala Lys Thr Ala Pro Gly Lys Lys Arg
130 135 140

Pro Val Glu Pro Ser Pro Gln Arg Ser Pro Asp Ser Ser Ser Gly Ile
145 150 155 160

Gly Lys Thr Gly Gln Gln Pro Ala Lys Lys Arg Leu Asn Phe Gly Gln
165 170 175

Thr Gly Asp Ser Glu Ser Val Pro Asp Pro Gln Pro Leu Gly Glu Pro
180 185 190

```
Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Glu Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
```

```
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Ala Glu Phe Ser Ala Thr Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro Leu
                725                 730                 735


<210> SEQ ID NO 10
<211> LENGTH: 735
<212> TYPE: PRT
<213> ORGANISM: Artificial Sequence
<220> FEATURE:
<223> OTHER INFORMATION: AAVC11.09 capsid polypeptide (VP1)

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Ser Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
```

-continued

```
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Glu Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Ser Gln Ala Lys Leu Ala Ser Phe Ile Thr Gln
            660                 665                 670
```

```
Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro Leu
                725                 730                 735


<210> SEQ ID NO 11
<211> LENGTH: 734
<212> TYPE: PRT
<213> ORGANISM: Artificial Sequence
<220> FEATURE:
<223> OTHER INFORMATION: AAVC11.10 capsid polypeptide (VP1)

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Gly Pro Ser Gly Leu Gly Ser Gly Thr Val Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300
```

```
Gly Phe Arg Pro Lys Arg Leu Ser Phe Lys Leu Phe Asn Ile Gln Val
305                 310                 315                 320

Lys Glu Val Thr Thr Asn Asp Gly Val Thr Thr Ile Ala Asn Asn Leu
                325                 330                 335

Thr Ser Thr Val Gln Val Phe Ser Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Glu Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Gln Ser Thr Gly Gly Thr Gln Gly Thr Gln Gln Leu Leu Phe Ser Gln
    450                 455                 460

Ala Gly Pro Ala Asn Met Ser Ala Gln Ala Lys Asn Trp Leu Pro Gly
465                 470                 475                 480

Pro Cys Tyr Arg Gln Gln Arg Val Ser Thr Thr Leu Ser Gln Asn Asn
                485                 490                 495

Asn Ser Asn Phe Ala Trp Thr Gly Ala Thr Lys Tyr His Leu Asn Gly
            500                 505                 510

Arg Asn Ser Leu Val Asn Pro Gly Val Ala Met Ala Thr His Lys Asp
        515                 520                 525

Asp Glu Asp Arg Phe Phe Pro Ser Ser Gly Val Leu Ile Phe Gly Lys
    530                 535                 540

Thr Gly Ala Thr Asn Lys Thr Thr Leu Glu Asn Val Leu Met Thr Asn
545                 550                 555                 560

Glu Glu Glu Ile Arg Pro Thr Asn Pro Val Ala Thr Glu Glu Tyr Gly
                565                 570                 575

Ile Val Ser Ser Asn Leu Gln Ala Ala Asn Thr Ala Ala Gln Thr Gln
            580                 585                 590

Val Val Asn Asn Gln Gly Ala Leu Pro Gly Met Val Trp Gln Asn Arg
        595                 600                 605

Asp Val Tyr Leu Gln Gly Pro Ile Trp Ala Lys Ile Pro His Thr Asp
    610                 615                 620

Gly Asn Phe His Pro Ser Pro Leu Met Gly Gly Phe Gly Leu Lys His
625                 630                 635                 640

Pro Pro Pro Gln Ile Leu Ile Lys Asn Thr Pro Val Pro Ala Asp Pro
                645                 650                 655

Pro Thr Thr Phe Ser Gln Ala Lys Leu Ala Ser Phe Ile Thr Gln Tyr
            660                 665                 670

Ser Thr Gly Gln Val Ser Val Glu Ile Glu Trp Glu Leu Gln Lys Glu
        675                 680                 685

Asn Ser Lys Arg Trp Asn Pro Glu Val Gln Tyr Thr Ser Asn Tyr Ala
    690                 695                 700

Lys Ser Ala Asn Val Asp Phe Thr Val Asp Asn Asn Gly Leu Tyr Thr
705                 710                 715                 720
```

Glu Pro Arg Pro Ile Gly Thr Arg Tyr Leu Thr Arg Asn Leu
725 730

<210> SEQ ID NO 12
<211> LENGTH: 735
<212> TYPE: PRT
<213> ORGANISM: Artificial Sequence
<220> FEATURE:
<223> OTHER INFORMATION: AAVC11.11 capsid polypeptide (VP1)

<400> SEQUENCE: 12

Met Ala Ala Asp Gly Tyr Leu Pro Asp Trp Leu Glu Asp Thr Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Lys Gln Leu Glu Gln Gly Asp Asn Pro Tyr Leu Lys Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Ser Val Gly Ser Gly Thr Val Ala Ala Gly Gly
195 200 205

Gly Ala Pro Met Ala Asp Asn Asn Glu Gly Ala Asp Gly Val Gly Asn
210 215 220

Ala Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Ser Gln Ser Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Arg Leu Asn Phe Lys Leu Phe Asn Ile Gln
305 310 315 320

Val Lys Glu Val Thr Thr Asn Asp Gly Val Thr Thr Ile Ala Asn Asn
325 330 335

Leu Thr Ser Thr Val Gln Val Phe Ser Asp Ser Glu Tyr Gln Leu Pro
340 345 350

```
Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Ser Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

Asn Pro Pro Pro Gln Ile Leu Ile Lys Asn Thr Pro Val Pro Ala Asn
                645                 650                 655

Pro Pro Ala Glu Phe Ser Ala Thr Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro Leu
                725                 730                 735
```

<210> SEQ ID NO 13
<211> LENGTH: 735
<212> TYPE: PRT
<213> ORGANISM: Artificial Sequence
<220> FEATURE:
<223> OTHER INFORMATION: AAVC11.12 capsid polypeptide (VP1)

<400> SEQUENCE: 13

Met Ala Ala Asp Gly Tyr Leu Pro Asp Trp Leu Glu Asp Thr Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe

```
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Ser Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 14
<211> LENGTH: 735
<212> TYPE: PRT
<213> ORGANISM: Artificial Sequence
<220> FEATURE:
<223> OTHER INFORMATION: AAVC11.13 capsid polypeptide (VP1)

<400> SEQUENCE: 14

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
```

-continued

```
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460
```

Gln Ala Gly Pro Ala Asn Met Ser Ala Gln Ala Lys Asn Trp Leu Pro
465 470 475 480

Gly Pro Cys Phe Arg Gln Gln Arg Val Ser Lys Thr Leu Asp Gln Asn
485 490 495

Asn Asn Ser Asn Phe Ala Trp Thr Gly Ala Thr Lys Tyr His Leu Asn
500 505 510

Gly Arg Asn Ser Leu Val Asn Pro Gly Val Ala Met Ala Thr His Lys
515 520 525

Asp Asp Glu Asp Arg Phe Phe Pro Ser Ser Gly Val Leu Ile Phe Gly
530 535 540

Lys Thr Gly Ala Thr Asn Lys Thr Thr Leu Glu Asn Val Leu Met Thr
545 550 555 560

Asn Glu Glu Glu Ile Arg Pro Thr Asn Pro Val Ala Thr Glu Glu Tyr
565 570 575

Gly Ile Val Ser Ser Asn Leu Gln Ala Ala Asn Thr Ala Ala Gln Thr
580 585 590

Gln Val Val Asn Asn Gln Gly Ala Leu Pro Gly Met Val Trp Gln Asn
595 600 605

Arg Asp Val Tyr Leu Gln Gly Pro Ile Trp Ala Lys Ile Pro His Thr
610 615 620

Asp Gly Asn Phe His Pro Ser Pro Leu Met Gly Gly Phe Gly Leu Lys
625 630 635 640

His Pro Pro Pro Gln Ile Leu Ile Lys Asn Thr Pro Val Pro Ala Asn
645 650 655

Pro Pro Glu Val Phe Thr Pro Ala Lys Phe Ala Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Asn Lys Ser Val Ser Val Asp Phe Thr Val Asp Thr Asn Gly Val Tyr
705 710 715 720

Ser Glu Pro Arg Pro Ile Gly Thr Arg Tyr Leu Thr Arg Asn Leu
725 730 735

<210> SEQ ID NO 15
<211> LENGTH: 736
<212> TYPE: PRT
<213> ORGANISM: Artificial Sequence
<220> FEATURE:
<223> OTHER INFORMATION: AAVC11.14 capsid polypeptide (VP1)

<400> SEQUENCE: 15

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Gly Pro Ser Gly Leu Gly Ser Gly Thr Val Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Ser Thr Gly Gly Thr Gln Gly Thr Gln Gln Leu Leu Phe
    450                 455                 460

Ser Gln Ala Gly Pro Ala Asn Met Ser Ala Gln Ala Lys Asn Trp Leu
465                 470                 475                 480

Pro Gly Pro Cys Tyr Arg Gln Gln Arg Val Ser Thr Thr Leu Ser Gln
                485                 490                 495

Asn Asn Asn Ser Asn Phe Ala Trp Thr Gly Ala Thr Lys Tyr His Leu
            500                 505                 510
```

```
Asn Gly Arg Asn Ser Leu Val Asn Pro Gly Val Ala Met Ala Thr His
        515                 520                 525

Lys Asp Asp Glu Asp Arg Phe Phe Pro Ser Ser Gly Val Leu Ile Phe
    530                 535                 540

Gly Lys Thr Gly Ala Thr Asn Lys Thr Thr Leu Glu Asn Val Leu Met
545                 550                 555                 560

Thr Asn Glu Glu Glu Ile Arg Pro Thr Asn Pro Val Ala Thr Glu Glu
                565                 570                 575

Tyr Gly Ile Val Ser Ser Asn Leu Gln Ala Ala Asn Thr Ala Ala Gln
            580                 585                 590

Thr Gln Val Val Asn Asn Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 16
<211> LENGTH: 735
<212> TYPE: PRT
<213> ORGANISM: Artificial Sequence
<220> FEATURE:
<223> OTHER INFORMATION: AAVC11.15 capsid polypeptide (VP1)

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140
```

```
Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Gln Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
```

```
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

Asn Pro Pro Pro Gln Ile Leu Ile Lys Asn Thr Pro Val Pro Ala Asn
                645                 650                 655

Pro Pro Ala Glu Phe Ser Ala Thr Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Val Gln Tyr Thr Ser Asn Tyr
    690                 695                 700

Ala Lys Ser Ala Asn Val Asp Phe Thr Val Asp Asn Asn Gly Leu Tyr
705                 710                 715                 720

Thr Glu Pro Arg Pro Ile Gly Thr Arg Tyr Leu Thr Arg Pro Leu
                725                 730                 735


<210> SEQ ID NO 17
<211> LENGTH: 735
<212> TYPE: PRT
<213> ORGANISM: Artificial Sequence
<220> FEATURE:
<223> OTHER INFORMATION: AAVC11.16 capsid polypeptide (VP1)

<400> SEQUENCE: 17

Met Ala Ala Asp Gly Tyr Leu Pro Asp Trp Leu Glu Asp Thr Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
```

```
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620
```

Asp Gly Asn Phe His Pro Ser Pro Leu Met Gly Gly Phe Gly Leu Lys
625 630 635 640

His Pro Pro Pro Gln Ile Leu Ile Lys Asn Thr Pro Val Pro Ala Asp
645 650 655

Pro Pro Thr Thr Phe Ser Gln Ala Lys Leu Ala Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Val Gln Tyr Thr Ser Asn Tyr
690 695 700

Ala Lys Ser Ala Asn Val Asp Phe Thr Val Asp Asn Asn Gly Leu Tyr
705 710 715 720

Thr Glu Pro Arg Pro Ile Gly Thr Arg Tyr Leu Thr Arg Pro Leu
725 730 735

<210> SEQ ID NO 18
<211> LENGTH: 735
<212> TYPE: PRT
<213> ORGANISM: Artificial Sequence
<220> FEATURE:
<223> OTHER INFORMATION: AAVC11.17 capsid polypeptide (VP1)

<400> SEQUENCE: 18

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Ala Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Ser Gly Thr Val Ala Ala Gly Gly
195 200 205

Gly Ala Pro Met Ala Asp Asn Asn Glu Gly Ala Asp Gly Val Gly Asn
210 215 220

Ala Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

-continued

Leu Tyr Lys Gln Ile Ser Ser Gln Ser Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Lys Leu Arg Phe Lys Leu Phe Asn Ile Gln
305 310 315 320

Val Lys Glu Val Thr Thr Asn Asp Gly Val Thr Thr Ile Ala Asn Asn
325 330 335

Leu Thr Ser Thr Ile Gln Val Phe Ser Asp Ser Glu Tyr Gln Leu Pro
340 345 350

Tyr Val Leu Gly Ser Ala His Gln Gly Cys Leu Pro Pro Phe Pro Ala
355 360 365

Asp Val Phe Met Ile Pro Gln Tyr Gly Tyr Leu Thr Leu Asn Asn Gly
370 375 380

Ser Gln Ala Val Gly Arg Ser Ser Phe Tyr Cys Leu Glu Tyr Phe Pro
385 390 395 400

Ser Gln Met Leu Arg Thr Gly Asn Asn Phe Glu Phe Ser Tyr Ser Phe
405 410 415

Glu Asp Val Pro Phe His Ser Ser Tyr Ala His Ser Gln Ser Leu Asp
420 425 430

Arg Leu Met Asn Pro Leu Ile Asp Gln Tyr Leu Tyr Tyr Leu Ser Arg
435 440 445

Thr Gln Ser Thr Gly Gly Thr Gln Gly Thr Gln Gln Leu Leu Phe Ser
450 455 460

Gln Ala Gly Pro Ala Asn Met Ser Ala Gln Ala Lys Asn Trp Leu Pro
465 470 475 480

Gly Pro Cys Tyr Arg Gln Gln Arg Val Ser Thr Thr Leu Ser Gln Asn
485 490 495

Asn Asn Ser Asn Phe Ala Trp Thr Gly Ala Thr Lys Tyr His Leu Asn
500 505 510

Gly Arg Asn Ser Leu Val Asn Pro Gly Val Ala Met Ala Thr His Lys
515 520 525

Asp Asp Glu Asp Arg Phe Phe Pro Ser Ser Gly Val Leu Ile Phe Gly
530 535 540

Lys Thr Gly Ala Thr Asn Lys Thr Thr Leu Glu Asn Val Leu Met Thr
545 550 555 560

Asn Glu Glu Glu Ile Arg Pro Thr Asn Pro Val Ala Thr Glu Glu Tyr
565 570 575

Gly Ile Val Ser Ser Asn Leu Gln Ala Ala Asn Thr Ala Ala Gln Thr
580 585 590

Gln Val Val Asn Asn Gln Gly Ala Leu Pro Gly Met Val Trp Gln Asn
595 600 605

Arg Asp Val Tyr Leu Gln Gly Pro Ile Trp Ala Lys Ile Pro His Thr
610 615 620

Asp Gly Asn Phe His Pro Ser Pro Leu Met Gly Gly Phe Gly Leu Lys
625 630 635 640

His Pro Pro Pro Gln Ile Leu Ile Lys Asn Thr Pro Val Pro Ala Asn
645 650 655

Pro Pro Glu Val Phe Thr Pro Ala Lys Phe Ala Ser Phe Ile Thr Gln
660 665 670

```
Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Ser Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 19
<211> LENGTH: 735
<212> TYPE: PRT
<213> ORGANISM: Artificial Sequence
<220> FEATURE:
<223> OTHER INFORMATION: AAVC11.18 capsid polypeptide (VP1)

<400> SEQUENCE: 19

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Ser Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300
```

```
Trp Gly Phe Arg Pro Lys Arg Leu Ser Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Ser Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
```

```
                725                 730                 735


<210> SEQ ID NO 20
<211> LENGTH: 735
<212> TYPE: PRT
<213> ORGANISM: Artificial Sequence
<220> FEATURE:
<223> OTHER INFORMATION: AAVC11.19 capsid polypeptide (VP1)

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Ser Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
```

```
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Ser Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 21
<211> LENGTH: 2208
<212> TYPE: DNA
<213> ORGANISM: Artificial Sequence
<220> FEATURE:
<223> OTHER INFORMATION: AAVC11.01 capsid polynucleotide

<400> SEQUENCE: 21
atggctgctg acggttatct tccagattgg ctcgaggaca acctctctga gggcattcgc 60
gagtggtggg acctgaaacc tggagccccg aagcccaagg ccaaccagca gaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aagctgctaa gacggctcct 420
ggaaagaaga gaccggtaga accgtcacct cagcgttccc cagactcctc ctcgggcatc 480
ggcaagacag gccagcagcc cgctaaaaag agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacttaca acaaccatct ctacaagcaa 780
atctccagcc aatcaggagc ttcaaacgac aaccactact ttggctacag caccccttgg 840
gggtattttg acttcaacag attccactgc cacttctcac cacgtgactg gcagcgactc 900
atcaacaaca actggggatt ccggcctaag cgactcaact tcaagctctt caacattcag 960
gtcaaagagg ttacggacaa caatggagtc aagaccatcg ccaataacct taccagcacg 1020
gtccaggtct tcacggactc agactatcag ctcccgtacg tgctcgggtc ggctcaccag 1080
ggctgcctcc cgccgttccc agcggacgtc ttcatgattc ctcagtacgg ctacctaacg 1140
ctcaacaatg gcagccaggc agtgggacgg tcatcctttt actgcctgga atatttccca 1200
tcgcagatgc tgagaacggg caataacttt accttcagct acaccttcga ggacgtgcct 1260
ttccacagca gctacgctca cagccagagt ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgagac gtgtacctgc agggtcccat ctgggccaag 1860
attcctcaca cggacggcaa ctttcacccg tctcctctga tgggcggctt tggacttaaa 1920
cacccgcctc cacagatcct gatcaagaac acgccggtac ctgcggatcc tccaacaacg 1980
ttcagccagg cgaaattggc ttccttcatc acgcagtaca gcaccggaca ggtcagcgtg 2040
gagatcgagt gggagctgca gaaggaaaac agcaagcgct ggaatcccga agtgcagtac 2100
acatccaatt atgcaaaatc tgccaacgtt gattttactg tggacaacaa tggactttat 2160
actgagcctc gccccattgg cacccgttac cttacccgtc ccctgtaa 2208

<210> SEQ ID NO 22
<211> LENGTH: 2208

```
<212> TYPE: DNA
<213> ORGANISM: Artificial Sequence
<220> FEATURE:
<223> OTHER INFORMATION: AAVC11.02 capsid polynucleotide

<400> SEQUENCE: 22

atggctgctg acggttatct tccagattgg ctcgaggaca acctctctga gggcattcgc     60

gagtggtggg acctgaaacc tggagccccg aagcccaagg ccaaccagca gaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aagctgctaa gacggctcct    420

ggaaagaaga gaccggtaga accgtcacct cagcgttccc cagactcctc ctcgggcatc    480

ggcaagacag gccagcagcc cgctaaaaag agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcacccgaac ctgggccctg cccacttaca acaaccatct ctacaagcaa    780

atctccagcc aatcaggagc ttcaaacgac aaccactact ttggctacag caccccttgg    840

gggtattttg acttcaacag attccactgc cacttctcac cacgtgactg gcagcgactc    900

atcaacaaca actggggatt ccggcctaag cgactcaact tcaagctctt caacattcag    960

gtcaaagagg ttacggacaa caatggagtc aagaccatcg ccaataacct taccagcacg   1020

gtccaggtct tcacggactc agactatcag ctcccgtacg tgctcgggtc ggctcaccag   1080

ggctgcctcc cgccgttccc agcggacgtc ttcatgattc ctcagtacgg ctacctaacg   1140

ctcaacaatg gcagccaggc agtgggacgg tcatcctttt actgcctgga atatttccca   1200

tcgcagatgc tgagaacggg caataacttt accttcagct acaccttcga ggacgtgcct   1260

ttccacagca gctacgctca cagccagagt ttggaccgac tgatgaatcc tctcattgac   1320

cagtacctgt actacttatc cagaactcag tccacaggag gaactcaagg tacccagcaa   1380

ttgttatttt ctcaagctgg gcctgcaaac atgtcggctc aggccaagaa ctggctgcct   1440

ggaccttgct accggcagca gcgagtctcc acgacactgt cgcaaaacaa caacagcaac   1500

tttgcttgga ctggtgccac caaatatcac ctgaacggca gaaactcgtt ggttaatccc   1560

ggcgtcgcca tggcaactca caaggacgac gaggaccgct tttcccatc cagcggagtc    1620

ctgatttttg gaaaaactgg agcaactaac aaaactacat tggaaaatgt gttaatgaca   1680

aatgaagaag aaattcgtcc tactaatcct gtagccacgg aagaatacgg gatagtcagc   1740

agcaacttac aagcggctaa tactgcagcc cagacacaag ttgtcaacaa ccagggagcc   1800

ttacctggca tggtctggca gaaccgagac gtgtacctgc agggtcccat ctgggccaag   1860

attcctcaca cggacggcaa ctttcacccg tctcctctga tgggcggctt tggacttaaa   1920

cacccgcctc cacagatcct gatcaagaac acgccggtac ctgcggatcc tccaacaacg   1980

ttcagccagg cgaaattggc ttccttcatc acgcagtaca gcaccggaca ggtcagcgtg   2040

gagatcgagt gggagctgca gaaggaaaac agcaagcgct ggaatcccga agtgcagtac   2100

acatccaatt atgcaaaatc tgccaacgtt gattttactg tggacaacaa tggactttat   2160
```

actgagcctc gccccattgg cacccgttac cttacccgtc ccctgtaa 2208

<210> SEQ ID NO 23
<211> LENGTH: 2214
<212> TYPE: DNA
<213> ORGANISM: Artificial Sequence
<220> FEATURE:
<223> OTHER INFORMATION: AAVC11.03 capsid polynucleotide

<400> SEQUENCE: 23
atggctgctg acggttatct tccagattgg ctcgaggaca acctctctga aggcattcgc 60
gagtggtggg acctgaaacc tggagccccc aagcccaagg ccaaccagca gaagcaggac 120
gacggtcggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactaaatt tcggtcagac tggcgactca 540
gagtcagtcc cagaccctca acctctcgga gaacctccag caacccccgc tgctgtggga 600
cctactacaa tggcttcagg cggtggcgca ccaatggcag acaataacga aggcgccgac 660
ggagtgggta atgcctcagg aaattggcat tgcgattcca catggctggg cgacagagtc 720
atcaccacca gcacccgcac ctgggccttg cccacctaca acaaccacct ctacaagcaa 780
atctccagtg aaactgcagg tagtaccaac gacaacacct acttcggcta cagcaccccc 840
tgggggtatt ttgacttcaa cagattccac tgccactttt caccacgtga ctggcaaaga 900
ctcatcaaca acaactgggg attccggccc aagaggctca acttcaaact cttcaacatc 960
caagtcaagg aggtcacgac gaatgatggc gtcacaacca tcgctaataa ccttaccagc 1020
acggttcaag tcttctcgga ctcggagtac cagcttccgt acgtcctcgg ctctgcgcac 1080
cagggctgcc tccctccgtt cccggcggac gtgttcatga ttccgcaata cggctacctg 1140
acgctcaaca atggcagcca agccgtggga cgttcatcct tttactgcct ggaatatttc 1200
ccatcgcaga tgctgagaac gggcaacaac tttaccttca gctacacctt tgaggaagtg 1260
cctttccaca gcagctacgc gcacagccag agcctggacc ggctgatgaa tcctctcatc 1320
gaccaatacc tgtattacct gaacagaact caaaatcagt ccggaagtgc ccaaaacaag 1380
gacttgctgt ttagccgtgg gtctccagct ggcatgtctg ttcagcccaa aaactggcta 1440
cctggaccct gttatcggca gcagcgcgtt tctaaaacaa aaacagacaa caacaacagc 1500
aattttacct ggactggtgc ttcaaaatat aaccttaatg ggcgtgaatc tataatcaac 1560
cctggcactg ctatggcctc acacaaagac gacgaagaca agttctttcc catgagcggt 1620
gtcatgattt ttggaaaaga gagcgccgga gcttcaaaca ctgcattgga caatgtcatg 1680
attacagacg aagaggaaat taaagccact aaccctgtgg ccaccgaaag atttgggacc 1740
gtggcagtca atttccagag cagcagcaca gaccctgcga ccggagatgt gcatgttatg 1800
ggagccttac ctggaatggt gtggcaagac agagacgtat acctgcaggg tcctatttgg 1860
gccaaaattc ctcacacgga tggacacttt cacccgtctc ctctcatggg cggctttgga 1920
cttaagcacc cgcctcctca gatcctcatc aaaaacacgc cggtacctgc ggatcctcca 1980
acaacgttca gccaggcgaa attggcttcc ttcatcacgc agtacagcac cggacaggtc 2040
agcgtggaga tcgagtggga gctgcagaag gaaaacagca agcgctggaa tcccgaagtg 2100
cagtacacat ccaattatgc aaaatctgcc aacgttgatt ttactgtgga caacaatgga 2160
ctttatactg agcctcgccc cattggcacc cgttacctta cccgtcccct gtaa 2214

<210> SEQ ID NO 24
<211> LENGTH: 2205
<212> TYPE: DNA
<213> ORGANISM: Artificial Sequence
<220> FEATURE:
<223> OTHER INFORMATION: AAVC11.04 capsid polynucleotide

<400> SEQUENCE: 24
atggctgccg atggttatct tccagattgg ctcgaggaca acctttctga aggcattcgt 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaac gtccggtaga gcagtcgcca caagagccag actcctcctc gggcattggc 480
aagacaggcc agcagcccgc taaaaagaga ctcaattttg gtcagactgg cgactcagag 540
tcagtccccg acccacaacc tctcggagaa ccaccagcag gcccctctgg tctgggatct 600
ggtacagtgg ctgcaggcgg tggcgcacca atggcagaca ataacgaggg tgccgatgga 660
gtgggtaatt cctcaggaaa ttggcattgc gattcccaat ggctgggcga cagagtcatc 720
accaccagca ccagaacctg ggccctgccc acttacaaca accatctcta caagcaaatc 780
tccagccaat caggagcttc aaacgacaac cactacttcg gctacagcac cccctggggg 840
tattttgact ttaacagatt ccactgccac ttttcaccac gtgactggca gcgactcatc 900
aacaacaact ggggattccg gcccaagaga ctcagcttca agctcttcaa catccaagtc 960
aaggaggtca cgacgaatga tggcgtcacg accatcgcta ataaccttac cagcacggtt 1020
caagtcttct cggactcgga gtaccagctt ccgtacgtcc tcggctctgc gcaccagggc 1080
tgcctccctc cgttcccggc ggacgtgttc atgattccgc agtacggcta cctaacgctc 1140
aacaatggca gccaggcagt gggacggtca tccttttact gcctggaata ttttccatct 1200
caaatgctgc gaactggaaa caattttgaa ttcagctaca ccttcgagga cgtgcctttc 1260
cacagcagct acgcacacag ccagagcttg gaccgactga tgaatcctct cattgaccag 1320
tacctgtact acttatccag aactcagtcc acaggaggaa ctcaaggtac ccagcaattg 1380
ttattttctc aagctgggcc tgcaaacatg tcggctcagg ccaagaactg gctgcctgga 1440
ccttgctacc ggcagcagcg agtctccacg acactgtcgc aaaacaacaa cagcaacttt 1500
gcttggactg gtgccaccaa atatcacctg aacggcagaa actcgttggt taatcccggc 1560
gtcgccatgg caactcacaa ggacgacgag gaccgctttt tcccatccag cggagtcctg 1620
atttttggaa aaactggagc aactaacaaa actacattgg aaaatgtgtt aatgacaaat 1680
gaagaagaaa ttcgtcctac taatcctgta gccacggaag aatacgggat agtcagcagc 1740
aacttacaag cggctaatac tgcagcccag acacaagttg tcaacaacca gggagcctta 1800
cctggcatgg tctggcagaa ccgggacgtg tacctgcagg gtcccatctg ggccaagatt 1860
cctcacacgg atggcaactt tcacccgtct cctttgatgg gcggctttgg acttaaacat 1920
ccgcctcctc agatcctgat caagaacact cccgttcccg ctaatcctcc ggaggtgttt 1980
actcctgcca agtttgcttc gttcatcaca cagtacagca ccggacaagt cagcgtggaa 2040
atcgagtggg agctgcagaa ggaaaacagc aagcgctgga acccggagat tcagtacact 2100
tcaaactaca acaagtctgt tagtgtggac tttactgtag acactaatgg cgtgtattca 2160
gagcctcgcc ccattggcac cagatacctg actcgtaatc tgtaa 2205

<210> SEQ ID NO 25
<211> LENGTH: 2208
<212> TYPE: DNA
<213> ORGANISM: Artificial Sequence
<220> FEATURE:
<223> OTHER INFORMATION: AAVC11.05 capsid polynucleotide

<400> SEQUENCE: 25
atggctgctg acggttatct tccagattgg ctcgaggaca acctctctga gggcattcgc 60
gagtggtggg acctgaaacc tggagccccc aagcccaagg ccaaccagca gaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aagctgctaa gacggctcct 420
ggaaagaaga gaccggtaga accgtcacct cagcgttccc cagactcctc ctcgggcatc 480
ggcaagacag gccagcagcc cgctaaaaag agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacttaca acaaccatct ctacaagcaa 780
atctccagcc aatcaggagc ttcaaacgac aaccactact ttggctacag caccccttgg 840
gggtattttg acttcaacag attccactgc cacttctcac cacgtgactg gcagcgactc 900
atcaacaaca actggggatt ccggcctaag cgactcaact tcaagctctt caacattcag 960
gtcaaagagg ttacggacaa caatggagtc aagaccatcg ccaataacct taccagcacg 1020
gtccaggtct tcacggactc agactatcag ctcccgtacg tgctcgggtc ggctcacgag 1080
ggctgcctcc cgccgttccc agcggacgtc ttcatgattc ctcagtacgg ctacctaacg 1140
ctcaacaatg gcagccaggc agtgggacgg tcatcctttt actgcctgga atatttccca 1200
tcgcagatgc tgagaacggg caataacttt accttcagct acaccttcga ggacgtgcct 1260
ttccacagca gctacgctca cagccagagt ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggatggcaa ctttcacccg tctcctttga tgggcggctt tggacttaaa 1920
catccgcctc ctcagatcct gatcaagaac actcccgttc ccgctaatcc tccggaggtg 1980
tttactcctg ccaagtttgc ttcgttcatc acacagtaca gcaccggaca agtcagcgtg 2040
gaaatcgagt gggagctgca gaaggaaaac agcaagcgct ggaacccgga gattcagtac 2100
acttcaaact acaacaagtc tgttagtgtg gactttactg tagacactaa tggcgtgtat 2160
tcagagcctc gccccattgg caccagatac ctgactcgta atctgtaa 2208

<210> SEQ ID NO 26
<211> LENGTH: 2208
<212> TYPE: DNA
<213> ORGANISM: Artificial Sequence
<220> FEATURE:
<223> OTHER INFORMATION: AAVC11.06 capsid polynucleotide

<400> SEQUENCE: 26
atggctgccg atggttatct tccagattgg ctcgaggaca ctctctctga aggcattcgc 60
gagtggtggg cgctgaaacc tggagctcca caacccaagg ccaaccaaca gcatcaggac 120
aacggcaggg gtcttgtgct tcctggctac aagtacctcg gacccttcaa cggactcgac 180
aagggagagc cggtcaacga ggcagacgcc gcggccctcg agcacgacaa ggcctacgac 240
aagcagctcg agcaggggga caacccgtac ctcaagtaca accacgccga cgccgagttt 300
caggagcgtc ttcaagaaga tacgtctttt gggggcaacc ttggcagagc agtcttccag 360
gccaaaaaga ggatccttga gcctcttggt ctggttgagg aagctgctaa gacggctcct 420
ggaaagaaga gaccggtaga gccgtcacct cagcgttccc ccgactcctc cacgggcatc 480
ggcaagaaag gccagcagcc cgccagaaag agactcaatt tcggtcagac tggcgactca 540
gagtcagtcc ccgaccctca acctctcgga gaacctccag cagcgccctc tagtgtggga 600
tctggtacag tggctgcagg cggtggcgca ccaatggcag acaataacga aggtgccgac 660
ggagtgggta atgcctcagg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact ttggctacag caccccttgg 840
gggtattttg actttaacag attccactgc catttctcac cacgtgactg gcagcgactc 900
attaacaaca actggggatt ccggcccaag aaactcagct tcaagctctt caacatccaa 960
gttaaagagg tcacgcagaa cgatggcacg acgactattg ccaataacct taccagcacg 1020
gttcaagtgt ttacggactc ggaataccag ctgccgtacg tcctcggctc cgcgcaccag 1080
ggctgcctgc ctccgttccc ggcggatgtc ttcatgattc cccagtacgg ctacctgaca 1140
ctgaacaatg gaagtcaagc cgtaggccgt tcctccttct actgcctgga atattttcca 1200
tctcaaatgc tgcgaactgg aaacaatttt gaattcagct acaccttcga ggacgtgcct 1260
ttccacagca gctacgcaca cagccagagc ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560

```
ggcgtcgcca tggcaactca caaggacgac gaggaccgct ttttcccatc cagcggagtc   1620
ctgatttttg gaaaaactgg agcaactaac aaaactacat tggaaaatgt gttaatgaca   1680
aatgaggaag aaattcgtcc tactaatcct gtagccacgg aagaatacgg gatagtcagc   1740
agcaacttac aagcggctaa tactgcagcc cagacacaag ttgtcaacaa ccagggagcc   1800
ttacctggca tggtctggca gaaccgggac gtgtacctgc agggtcccat ctgggccaag   1860
attcctcaca cggatggcaa ctttcacccg tctcctttga tgggcggctt tggacttaaa   1920
catccgcctc ctcagatcct gatcaagaac actcccgttc ccgctaatcc tccggaggtg   1980
tttactcctg ccaagtttgc ttcgttcatc acacagtaca gcaccggaca agtcagcgtg   2040
gaaatcgagt gggagctgca gaaggaaaac agcaagcgct ggaacccgga gattcagtac   2100
acttcaaact acaacaagtc tgttagtgtg gactttactg tagacactaa tggcgtgtat   2160
tcagagcctc gccccattgg caccagatac ctgactcgta atctgtaa               2208
```

<210> SEQ ID NO 27
<211> LENGTH: 2205
<212> TYPE: DNA
<213> ORGANISM: Artificial Sequence
<220> FEATURE:
<223> OTHER INFORMATION: AAVC11.07 capsid polynucleotide

<400> SEQUENCE: 27

```
atggctgctg acggttatct tccagattgg ctcgaggaca acctctctga aggcattcgc     60
gagtggtggg acctgaaacc tggagccccc aagcccaagg ccaaccagca gaagcaggac    120
gacggtcggg gtctggtgct tcctggctac aagtacctcg gacccttcaa cggactcgac    180
aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag    540
tcagtccccg acccacaacc tctcggagaa ccaccagcag gcccctctgg tctgggatct    600
ggtacagtgg ctgcaggcgg tggcgcacca atggcagaca ataacgaggg tgccgatgga    660
gtgggtaatt cctcaggaaa ttggcattgc gattcccaat ggctgggcga cagagtcatc    720
accaccagca ccagaacctg ggccctgccc acttacaaca accatctcta caagcaaatc    780
tccagccaat caggagcttc aaacgacaac cactacttcg gctacagcac cccctggggg    840
tattttgact ttaacagatt ccactgccac ttttcaccac gtgactggca gcgactcatc    900
aacaacaact ggggattccg gcccaagaga ctcagcttca agctcttcaa catccaagtc    960
aaggaggtca cgacgaatga tggcgtcacg accatcgcta ataaccttac cagcacggtt   1020
caagtcttct cggactcgga gtaccagctt ccgtacgtcc tcggctctgc gcaccagggc   1080
tgcctccctc cgttcccggc ggatgtcttc atgattcccc agtacggcta cctgacactg   1140
aacaatggaa gtcaagccgt aggccgttcc tccttctact gcctggaata ttttccatct   1200
caaatgctgc gaactggaaa caattttgaa ttcagctaca ccttcgagga cgtgcctttc   1260
cacagcagct acgcacacag ccagagcttg gaccgactga tgaatcctct cattgaccag   1320
tacctgtact acttatccag aactcagtcc acaggaggaa ctcaaggtac ccagcaattg   1380
ttattttctc aagctgggcc tgcaaacatg tcggctcagg ccaagaactg gctgcctgga   1440
```

ccttgctacc ggcagcagcg agtctccacg acactgtcgc aaaacaacaa cagcaacttt 1500
gcttggactg gtgccaccaa atatcacctg aacggcagaa actcgttggt taatcccggc 1560
gtcgccatgg caactcacaa ggacgacgag gaccgctttt tcccatccag cggagtcctg 1620
atttttggaa aaactggagc aactaacaaa actacattgg aaaatgtgtt aatgacaaat 1680
gaggaagaaa ttcgtcctac taatcctgta gccacggaag aatacgggat agtcagcagc 1740
aacttacaag cggctaatac tgcagcccag acacaagttg tcaacaacca gggagcctta 1800
cctggcatgg tctggcagaa ccgggacgtg tacctgcagg gtcccatctg ggccaagatt 1860
cctcacacgg atggcaactt tcacccgtct cctttgatgg gcggctttgg acttaaacat 1920
ccgcctcctc agatcctgat caagaacact cctgttcctg cgaatcctcc ggaggtgttt 1980
actcctgcca agtttgcttc gttcatcaca cagtacagca ccggacaagt cagcgtggaa 2040
atcgagtggg agctgcagaa ggaaaacagc aagcgctgga acccggagat tcagtacact 2100
tcaaactaca acaagtctgt tagtgtggac tttactgtag acactaatgg cgtgtattca 2160
gagcctcgcc ccattggcac cagatacctg actcgtaatc tgtaa 2205

<210> SEQ ID NO 28
<211> LENGTH: 2208
<212> TYPE: DNA
<213> ORGANISM: Artificial Sequence
<220> FEATURE:
<223> OTHER INFORMATION: AAVC11.08 capsid polynucleotide

<400> SEQUENCE: 28
atggctgctg acggttatct tccagattgg ctcgaggaca acctctctga gggcattcgc 60
gagtggtggg acctgaaacc tggagccccg aagcccaagg ccaaccagca gaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aagctgctaa gacggctcct 420
ggaaagaaga gaccggtaga accgtcacct cagcgttccc cagactcctc ctcgggcatc 480
ggcaagacag gccagcagcc cgctaaaaag agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacttaca acaaccatct ctacaagcaa 780
atctccagcc aatcaggagc ttcaaacgac aaccactact ttggctacag caccccttgg 840
gggtattttg acttcaacag attccactgc cacttctcac cacgtgactg gcagcgactc 900
atcaacaaca actggggatt ccggcctaag cgactcaact tcaagctctt caacattcag 960
gtcaaagagg ttacggacaa caatggagtc aagaccatcg ccaataacct taccagcacg 1020
gtccaggtct tcacggactc agactatcag ctcccgtacg tgctcgggtc ggctcacgag 1080
ggctgcctcc cgccgttccc agcggatgtc ttcatgattc ctcagtacgg ctacctaacg 1140
ctcaacaatg gcagccaggc agtgggacgg tcatcctttt actgcctgga atatttccca 1200
tcgcagatgc tgagaacggg caataacttt accttcagct acaccttcga ggacgtgcct 1260
ttccacagca gctacgctca cagccagagt ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgagac gtgtacctgc agggtcccat ctgggccaag 1860
attcctcaca cggacggcaa ctttcacccg tctcctctga tgggcggctt tggacttaaa 1920
cacccgcctc cacagatcct catcaaaaac acgcctgttc ctgcgaatcc tccggcggag 1980
ttttcagcta caaagtttgc ttcattcatc acccaatact ccacaggaca agtgagtgtg 2040
gaaattgaat gggagctgca gaaagaaaac agcaagcgct ggaatcccga agtgcagtac 2100
acatccaatt atgcaaaatc tgccaacgtt gattttactg tggacaacaa tggactttat 2160
actgagcctc gccccattgg cacccgttac ctcacccgtc ccctgtaa 2208

<210> SEQ ID NO 29
<211> LENGTH: 2208
<212> TYPE: DNA
<213> ORGANISM: Artificial Sequence
<220> FEATURE:
<223> OTHER INFORMATION: AAVC11.09 capsid polynucleotide

<400> SEQUENCE: 29
atggctgctg acggttatct tccagattgg ctcgaggaca acctctctga gggcattcgc 60
gagtggtggg acctgaaacc tggagccccg aagcccaagg ccaaccagca gaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aagctgctaa gacggctcct 420
ggaaagaaga gaccggtaga accgtcacct cagcgttccc cagactcctc ctcgggcatc 480
ggcaagacag gccagcagcc cgctaaaaag agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacttaca acaaccatct ctacaagcaa 780
atctccagcc aatcaggagc ttcaaacgac aaccactact ttggctacag caccccttgg 840
gggtattttg acttcaacag attccactgc cacttctcac cacgtgactg gcagcgactc 900
atcaacaaca actggggatt ccggcctaag cgactcaact tcaagctctt caacattcag 960
gtcaaagagg ttacggacaa caatggagtc aagaccatcg ccaataacct taccagcacg 1020
gtccaggtct tcacggactc agactatcag ctcccgtacg tgctcgggtc ggctcacgag 1080
ggctgcctcc cgccgttccc agcggacgtc ttcatgattc ctcagtacgg ctacctaacg 1140
ctcaacaatg gcagccaggc agtgggacgg tcatcctttt actgcctgga atatttccca 1200
tcgcagatgc tgagaacggg caataacttt accttcagct acaccttcga ggacgtgcct 1260
ttccacagca gctacgctca cagccagagt ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgagac gtgtacctgc agggtcccat ctgggccaag 1860
attcctcaca cggacggcaa ctttcacccg tctcctctga tgggcggctt tggacttaaa 1920
cacccgcctc cacagatcct gatcaagaac acgccggtac ctgcggatcc tccaacaacg 1980
ttcagccagg cgaaattggc ttccttcatc acgcagtaca gcaccggaca ggtcagcgtg 2040
gagatcgagt gggagctgca gaaggaaaac agcaagcgct ggaatcccga agtgcagtac 2100
acatccaatt atgcaaaatc tgccaacgtt gattttactg tggacaacaa tggactttat 2160
actgagcctc gccccattgg cacccgttac cttacccgtc ccctgtaa 2208

<210> SEQ ID NO 30
<211> LENGTH: 2205
<212> TYPE: DNA
<213> ORGANISM: Artificial Sequence
<220> FEATURE:
<223> OTHER INFORMATION: AAVC11.10 capsid polynucleotide

<400> SEQUENCE: 30
atggctgccg atggttatct tccagattgg ctcgaggaca acctctctga gggcattcgc 60
gagtggtggg acttgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaac gtccggtaga gcagtcgcca caagagccag actcctcctc gggcattggc 480
aagacaggcc agcagcccgc taaaaagaga ctcaattttg gtcagactgg cgactcagag 540
tcagtccccg acccacaacc tctcggagaa ccaccagcag gcccctctgg tctgggatct 600
ggtacagtgg ctgcaggcgg tggcgcacca atggcagaca ataacgaggg tgccgatgga 660
gtgggtaatt cctcaggaaa ttggcattgc gattcccaat ggctgggcga cagagtcatc 720
accaccagca ccagaacctg ggccctgccc acttacaaca accatctcta caagcaaatc 780
tccagccaat caggagcttc aaacgacaac cactacttcg gctacagcac cccctggggg 840
tattttgact ttaacagatt ccactgccac ttttcaccac gtgactggca gcgactcatc 900
aacaacaact ggggattccg gcccaagaga ctcagcttca agctcttcaa catccaagtc 960
aaggaggtca cgacgaatga tggcgtcacg accatcgcta ataaccttac cagcacggtt 1020
caagtcttct cggactcgga gtaccagctt ccgtacgtcc tcggctctgc gcaccagggc 1080
tgcctccctc cgttcccggc ggacgtgttc atgattccgc agtacggcta cctaacgctc 1140
aacaatggca gccaggcagt gggacggtca tccttttact gcctggaata ttttccatct 1200
caaatgctgc gaactggaaa caattttgaa ttcagctaca ccttcgagga cgtgcctttc 1260
cacagcagct acgcacacag ccagagcttg gaccgactga tgaatcctct cattgaccag 1320
tacctgtact acttatccag aactcagtcc acaggaggaa ctcaaggtac ccagcaattg 1380
ttattttctc aagctgggcc tgcaaacatg tcggctcagg ccaagaactg gctgcctgga 1440
ccttgctacc ggcagcagcg agtctccacg acactgtcgc aaaacaacaa cagcaacttt 1500
gcttggactg gtgccaccaa atatcacctg aacggcagaa actcgttggt taatcccggc 1560
gtcgccatgg caactcacaa ggacgacgag gaccgctttt tcccatccag cggagtcctg 1620
atttttggaa aaactggagc aactaacaaa actacattgg aaaatgtgtt aatgacaaat 1680
gaagaagaaa ttcgtcctac taatcctgta gccacggaag aatacgggat agtcagcagc 1740
aacttacaag cggctaatac tgcagcccag acacaagttg tcaacaacca gggagcctta 1800
cctggcatgg tctggcagaa ccgagacgtg tacctgcagg gtcccatctg ggccaagatt 1860
cctcacacgg acggcaactt tcacccgtct cctctgatgg gcggctttgg acttaaacac 1920
ccgcctccac agatcctgat caagaacacg ccggtacctg cggatcctcc aacaacgttc 1980
agccaggcga aattggcttc cttcatcacg cagtacagca ccggacaggt cagcgtggag 2040
atcgagtggg agctgcagaa ggaaaacagc aagcgctgga atcccgaagt gcagtacaca 2100
tccaattatg caaaatctgc caacgttgat tttactgtgg acaacaatgg actttatact 2160
gagcctcgcc ccattggcac cagatacctg actcgtaatc tgtaa 2205

<210> SEQ ID NO 31
<211> LENGTH: 2208
<212> TYPE: DNA
<213> ORGANISM: Artificial Sequence
<220> FEATURE:
<223> OTHER INFORMATION: AAVC11.11 capsid polynucleotide

<400> SEQUENCE: 31
atggctgccg atggttatct tccagattgg ctcgaggaca ctctctctga aggcattcgc 60
gagtggtggg cgctgaaacc tggagctcca caacccaagg ccaaccaaca gcatcaggac 120
aacggcaggg gtcttgtgct tcctgggtac aagtacctcg gacccttcaa cggactcgac 180
aagggagagc cggtcaacga ggcagacgcc gcggccctcg agcacgacaa ggcctacgac 240
aagcagctcg agcaggggga caacccgtac ctcaagtaca accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccgtcacct cagcgttccc ccgactcctc cacgggcatc 480
ggcaagaaag gccagcagcc cgccagaaag agactcaatt tcggtcagac tggcgactca 540
gagtcagtcc ccgaccctca acctctcgga gaacctccag cagcgccctc tagtgtggga 600
tctggtacag tggctgcagg cggtggcgca ccaatggcag acaataacga aggtgccgac 660
ggagtgggta atgcctcagg aaattggcat tgcgattcca catggctggg cgacagagtc 720
attaccacca gcacccgaac ctgggccctg cccacctaca acaaccacct ctacaagcaa 780
atctccagcc aatcaggagc ttcaaacgac aaccactact ttggctacag caccccttgg 840

```
gggtattttg actttaacag attccactgc cacttctcac cacgtgactg gcagcgactc    900
attaacaaca actggggatt ccggcccaag agactcaact tcaagctctt caacatccaa    960
gtcaaggagg tcacgacgaa tgatggcgtc acgaccatcg ctaataacct taccagcacg   1020
gttcaagtct tctcggactc ggagtaccag ttgccgtacg tcctcggctc tgcgcaccag   1080
ggctgcctcc ctccgttccc ggcggacgtg ttcatgattc cccagtacgg ctacctaaca   1140
ctcaacaacg gtagtcaggc cgtgggacgc tcctcctttt actgcctgga atatttccca   1200
tcgcagatgc tgagaacggg caataacttt gagttcagct acagcttcga ggacgtgcct   1260
ttccacagca gctacgcaca cagccagagc ttggaccgac tgatgaatcc tctcattgac   1320
cagtacctgt actacttatc cagaactcag tccacaggag gaactcaagg tacccagcaa   1380
ttgttatttt ctcaagctgg gcctgcaaac atgtcggctc aggccaagaa ctggctgcct   1440
ggaccttgct accggcagca gcgagtctcc acgacactgt cgcaaaacaa caacagcaac   1500
tttgcttgga ctggtgccac caaatatcac ctgaacggca gaaactcgtt ggttaatccc   1560
ggcgtcgcca tggcaactca caaggacgac gaggaccgct tttcccatc cagcggagtc    1620
ctgatttttg gaaaaactgg agcaactaac aaaactacat tggaaaatgt gttaatgaca   1680
aatgaagaag aaattcgtcc tactaatcct gtagccacgg aagaatacgg gatagtcagc   1740
agcaacttac aagcggctaa tactgcagcc cagacacaag ttgtcaacaa ccagggagcc   1800
ttacctggca tggtctggca gaaccgggac gtgtacctgc agggtcccat ttgggccaaa   1860
attcctcaca cagatggaca ctttcacccg tctcctctta tgggcggctt tggactcaag   1920
aacccgcctc ctcagatcct catcaaaaac acgcctgttc ctgcgaatcc tccggcggag   1980
ttttcagcta caaagtttgc ttcattcatc acccagtatt ccacaggaca agtgagcgtg   2040
gagattgaat gggagctgca gaaagaaaac agcaaacgct ggaatcccga agtgcagtat   2100
acatctaact atgcaaaatc tgccaacgtt gatttcactg tggacaacaa tggactttat   2160
actgagcctc gccccattgg cacccgttac cttacccgtc ccctgtaa                2208
```

<210> SEQ ID NO 32
<211> LENGTH: 2208
<212> TYPE: DNA
<213> ORGANISM: Artificial Sequence
<220> FEATURE:
<223> OTHER INFORMATION: AAVC11.12 capsid polynucleotide

<400> SEQUENCE: 32

```
atggctgccg atggttatct tccagattgg ctcgaggaca ctctctctga aggcattcgc     60
gagtggtggg cgctgaaacc tggagctcca caacccaagg ccaaccaaca gcatcaggac    120
aacggcaggg gtcttgtgct tcctgggtac aagtacctcg gacccttcaa cggactcgac    180
aagggagagc cggtcaacga ggcagacgcc gcggccctcg agcacgacaa ggcctacgac    240
aagcagctcg agcaggggga caacccgtac ctcaagtaca accacgccga cgccgagttt    300
caggagcgtc ttcaagaaga tacgtctttt gggggcaacc ttggcagagc agtcttccag    360
gccaaaaaga ggatccttga gcctcttggt ctggttgagg aagctgctaa gacggctcct    420
ggaaagaaga gaccggtaga accgtcacct cagcgttccc ccgactcctc cacgggcatc    480
ggcaagaaag gccagcagcc cgccagaaag agactcaatt tcggtcagac tggcgactca    540
gagtcagtcc ccgaccctca acctctcgga gaacctccag cagcgccctc tagtgtggga    600
tctggtacag tggctgcagg cggtggcgca ccaatggcag acaataacga aggtgccgac    660
```

ggagtgggta atgcctcagg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact tcggctacag cacccccctgg 840 gggtattttg actttaacag attccactgc cacttttcac cacgtgactg gcagcgactc 900
atcaacaaca actggggatt ccggcccaag agactcagct tcaagctctt caacatccaa 960
gtcaaggagg tcacgacgaa tgatggcgtc acgaccatcg ctaataacct taccagcacg 1020
gttcaagtct tctcggactc ggagtaccag cttccgtacg tcctcggctc tgcgcaccag 1080
ggctgcctcc ctccgttccc ggcggacgtg ttcatgattc cgcagtacgg ctacctaacg 1140
ctcaacaatg gcagccaggc agtgggacgg tcatcctttt actgcctgga atattttcca 1200
tctcaaatgc tgcgaactgg aaacaatttt gaattcagct acaccttcga ggacgtgcct 1260
ttccacagca gctacgcaca cagccagagc ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggatggcaa ctttcacccg tctcctttga tgggcggctt tggacttaaa 1920
catccgcctc ctcagatcct gatcaagaac actcccgttc ccgctaatcc tccggaggtg 1980
tttactcctg ccaagtttgc ttcgttcatc acacagtaca gcaccggaca agtcagcgtg 2040
gaaatcgagt gggagctgca gaaggaaaac agcaagcgct ggaacccgga gattcagtac 2100
acttcaaact acaacaagtc tgttagtgtg gactttactg tagacactaa tggcgtgtat 2160
tcagagcctc gccccattgg caccagatac ctgactcgta atctgtaa 2208

<210> SEQ ID NO 33
<211> LENGTH: 2208
<212> TYPE: DNA
<213> ORGANISM: Artificial Sequence
<220> FEATURE:
<223> OTHER INFORMATION: AAVC11.13 capsid polynucleotide

<400> SEQUENCE: 33
atggctgctg acggttatct tccagattgg ctcgaggaca acctctctga gggcattcgc 60
gagtggtggg acctgaaacc tggagccccg aagcccaagg ccaaccagca gaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc ttggcagagc agtcttccag 360
gccaaaaaga ggatccttga gcctcttggt ctggttgagg aagctgctaa gacggctcct 420
ggaaagaaga gaccggtaga accgtcacct cagcgttccc ccgactcctc cacgggcatc 480
ggcaagaaag gccagcagcc cgccagaaag agactcaatt tcggtcagac tggcgactca 540

```
gagtcagtcc ccgaccctca acctctcgga gaacctccag cagcgccctc tagtgtggga    600
tctggtacag tggctgcagg cggtggcgca ccaatggcag acaataacga aggtgccgac    660
ggagtgggta atgcctcagg aaattggcat tgcgattcca catggctggg cgacagagtc    720
attaccacca gcacccgaac ctgggccctg cccacctaca acaaccacct ctacaagcaa    780
atctccagcc aatcaggagc ttcaaacgac aaccactact ttggctacag caccccttgg    840
gggtattttg actttaacag attccactgc cacttctcac cacgtgactg gcagcgactc    900
attaacaaca actggggatt ccggcccaag agactcaact tcaagctctt caacatccaa    960
gtcaaggagg tcacgacgaa tgatggcgtc acgaccatcg ctaataacct taccagcacg   1020
gttcaagtct tctcggactc ggagtaccag cttccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atatttccca   1200
tcgcagatgc tgagaacggg caataacttt gagttcagct acaccttcga ggacgtgcct   1260
ttccacagca gctacgcaca cagccagagc ttggaccgac tgatgaatcc tctcattgac   1320
cagtacctgt actacttatc cagaactcag tccacaggag gaactcaagg tacccagcaa   1380
ttgttatttt ctcaagctgg gcctgcaaac atgtcggctc aggccaagaa ctggctgcct   1440
ggaccttgct tccggcaaca aagagtctcc aaaacgctgg atcaaaacaa caacagcaac   1500
tttgcttgga ctggtgccac caaatatcac ctgaacggca gaaactcgtt ggttaatccc   1560
ggcgtcgcca tggcaactca caaggacgac gaggaccgct tttcccatc cagcggagtc    1620
ctgatttttg gaaaaactgg agcaactaac aaaactacat tggaaaatgt gttaatgaca   1680
aatgaagaag aaattcgtcc tactaatcct gtagccacgg aagaatacgg gatagtcagc   1740
agcaacttac aagcggctaa tactgcagcc cagacacaag ttgtcaacaa ccagggagcc   1800
ttacctggca tggtctggca gaaccgggac gtgtacctgc agggtcccat ctgggccaag   1860
attcctcaca cggatggcaa ctttcacccg tctcctttga tgggcggctt tggacttaaa   1920
catccgcctc ctcagatcct gatcaagaac actcccgttc ccgctaatcc tccggaggtg   1980
tttactcctg ccaagtttgc ttcgttcatc acacagtaca gcaccggaca agtcagcgtg   2040
gaaatcgagt gggagctgca gaaggaaaac agcaagcgct ggaacccgga gattcagtac   2100
acttcaaact acaacaagtc tgttagtgtg gactttactg tagacactaa tggcgtgtat   2160
tcagagcctc gccccattgg caccagatac ctgactcgta atctgtaa                2208
```

<210> SEQ ID NO 34
<211> LENGTH: 2211
<212> TYPE: DNA
<213> ORGANISM: Artificial Sequence
<220> FEATURE:
<223> OTHER INFORMATION: AAVC11.14 capsid polynucleotide

<400> SEQUENCE: 34

```
atggctgctg acggttatct tccagattgg ctcgaggaca acctctctga aggcattcgc     60
gagtggtggg acctgaaacc tggagccccc aagcccaagg ccaaccagca gaagcaggac    120
gacggtcggg gtctggtgct tcctggctac aagtacctcg gacccttcaa cggactcgac    180
aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
```

```
gccaagaagc gggttctcga acctctcggt ctggttgagg aaggcgctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag    540
tcagtccccg acccacaacc tctcggagaa ccaccagcag gcccctctgg tctgggatct    600
ggtacagtgg cttcaggcgg tggcgcacca atggcagaca ataacgaggg tgccgatgga    660
gtgggtaatt cctcaggaaa ttggcattgc gattcccaat ggctgggcga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccatttct caccacgtga ctggcagcga    900
ctcatcaaca acaattgggg attccggccc aagagactca acttcaagct cttcaacatc    960
caagtcaagg aggtcacgac gaatgatggc gtcacgacca tcgctaataa ccttaccagc   1020
acggttcaag tcttctcgga ctcggagtac cagttgccgt acgtcctcgg ctctgcgcac   1080
cagggctgcc tccctccgtt cccggcggac gtgttcatga ttccccagta cggctaccta   1140
acactcaaca acggtagtca ggccgtggga cgctcctcct tttactgcct ggaatatttc   1200
ccatctcaaa tgctgcgaac tggaaacaat tttgaattca gctacacctt cgaggacgtg   1260
cctttccaca gcagctacgc acacagccag agcttggacc gactgatgaa tcctctcatt   1320
gaccagtacc tgtactactt atccagaact cagtccacag gaggaactca aggtacccag   1380
caattgttat tttctcaagc tgggcctgca aacatgtcgg ctcaggccaa gaactggctg   1440
cctggacctt gctaccggca gcagcgagtc tccacgacac tgtcgcaaaa caacaacagc   1500
aactttgctt ggactggtgc caccaaatat cacctgaacg gcagaaactc gttggttaat   1560
cccggcgtcg ccatggcaac tcacaaggac gacgaggacc gcttttttccc atccagcgga  1620
gtcctgattt ttggaaaaac tggagcaact aacaaaaacta cattggaaaa tgtgttaatg  1680
acaaatgagg aagaaattcg tcctactaat cctgtagcca cggaagaata cgggatagtc   1740
agcagcaact tacaagcggc taatactgca gcccagacac aagttgtcaa caaccaggga   1800
gccttacctg gcatggtctg gcagaaccgg gacgtgtacc tgcagggtcc catctgggcc   1860
aagattcctc acacggatgg caactttcac ccgtctcctt tgatgggcgg ctttggactt   1920
aaacatccgc ctcctcagat cctgatcaag aacactcctg ttcctgcgaa tcctccggca   1980
gagttttcgg ctacaaagtt tgcttcattc atcacccaat actccacagg acaagtgagt   2040
gtggaaattg aatgggagct gcagaaagaa aacagcaagc gctggaatcc cgaagtgcag   2100
tatacatcta actatgcaaa atctgccaac gttgatttta ctgtggacaa caatggactt   2160
tatactgagc ctcgccccat tggcacccgt taccttaccc gtcccctgta a            2211
```

<210> SEQ ID NO 35
<211> LENGTH: 2208
<212> TYPE: DNA
<213> ORGANISM: Artificial Sequence
<220> FEATURE:
<223> OTHER INFORMATION: AAVC11.15 capsid polynucleotide

<400> SEQUENCE: 35

```
atggctgccg atggttatct tccagattgg ctcgaggaca acctctctga gggcattcgc     60
gagtggtggg acttgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
```

```
cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aagctgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagtcc ccgacccaca acctctcgga gaaccaccag caggcccctc tggtctggga    600

tctggtacag tggctgcagg cggtggcgca ccaatggcag acaataacga gggtgccgat    660

ggagtgggta attcctcagg aaattggcat tgcgattccc aatggctggg cgacagagtc    720

atcaccacca gcaccagaac ctgggccctg cccacttaca acaaccatct ctacaagcaa    780

atctccagcc aatcaggagc ttcaaacgac aaccactact tcggctacag cacccccctgg   840

gggtattttg actttaacag attccactgc cacttttcac cacgtgactg gcagcgactc    900

atcaacaaca actggggatt ccggcccaag agactcagct tcaagctctt caacatccaa    960

gtcaaggagg tcacgacgaa tgatggcgtc acgaccatcg ctaataacct taccagcacg   1020

gttcaagtct tctcggactc ggagtaccag cttccgtacg tcctcggctc tgcgcaccag   1080

ggctgcctcc ctccgttccc ggcggacgtg ttcatgattc cgcagtacgg ctacctaacg   1140

ctcaacaatg gcagccaggc agtgggacgg tcatcctttt actgcctgga atattttcca   1200

tctcaaatgc tgcgaactgg aaacaatttt gaattcagct acaccttcga ggacgtgcct   1260

ttccacagca gctacgcaca cagccagagc ttggaccgac tgatgaatcc tctcattgac   1320

cagtacctgt actacttatc cagaactcag tccacaggag gaactcaagg tacccagcaa   1380

ttgttatttt ctcaagctgg gcctgcaaac atgtcggctc aggccaagaa ctggctgcct   1440

ggaccttgct accggcagca gcgagtctcc acgacactgt cgcaaaacaa caacagcaac   1500

tttgcttgga ctggtgccac caaatatcac ctgaacggca gaaactcgtt ggttaatccc   1560

ggcgtcgcca tggcaactca caaggacgac gaggaccgct tttcccatc cagcggagtc    1620

ctgatttttg gaaaaactgg agcaactaac aaaactacat tggaaaatgt gttaatgaca   1680

aatgaagaag aaattcgtcc tactaatcct gtagccacgg aagaatacgg gatagtcagc   1740

agcaacttac aagcggctaa tactgcagcc cagacacaag ttgtcaacaa ccagggagcc   1800

ttacctggca tggtctggca gaaccgggac gtgtacctgc agggtcccat ttgggccaaa   1860

attcctcaca cagatggaca ctttcacccg tctcctctta tgggcggctt tggactcaag   1920

aacccgcctc ctcagatcct catcaaaaac acgcctgttc ctgcgaatcc tccggcggag   1980

ttttcagcta caaagtttgc ttcattcatc acccagtatt ccacaggaca agtgagcgtg   2040

gagattgaat gggagctgca gaaagaaaac agcaaacgct ggaatcccga agtgcagtat   2100

acatctaact atgcaaaatc tgccaacgtt gatttcactg tggacaacaa tggactttat   2160

actgagcctc gccccattgg cacccgttac cttacccgtc ccctgtaa                2208
```

```
<210> SEQ ID NO 36
<211> LENGTH: 2208
<212> TYPE: DNA
<213> ORGANISM: Artificial Sequence
<220> FEATURE:
<223> OTHER INFORMATION: AAVC11.16 capsid polynucleotide

<400> SEQUENCE: 36

atggctgccg atggttatct tccagattgg ctcgaggaca ctctctctga aggcattcgc     60
```

gagtggtggg cgctgaaacc tggagctcca caacccaagg ccaaccaaca gcatcaggac 120
aacggcaggg gtcttgtgct tcctgggtac aagtacctcg gacccttcaa cggactcgac 180
aagggagagc cggtcaacga ggcagacgcc gcggccctcg agcacgacaa ggcctacgac 240
aagcagctcg agcaggggga caacccgtac ctcaagtaca accacgccga cgccgagttt 300
caggagcgtc ttcaagaaga tacgtctttt gggggcaacc ttggcagagc agtcttccag 360
gccaaaaaga ggatccttga gcctcttggt ctggttgagg aagctgctaa gacggctcct 420
ggaaagaaga gaccggtaga accgtcacct cagcgttccc ccgactcctc cacgggcatc 480
ggcaagaaag gccagcagcc cgccagaaag agactcaatt tcggtcagac tggcgactca 540
gagtcagtcc ccgaccctca acctctcgga gaacctccag cagcgccctc tagtgtggga 600
tctggtacag tggctgcagg cggtggcgca ccaatggcag acaataacga aggtgccgac 660
ggagtgggta atgcctcagg aaattggcat tgcgattcca catggctggg cgacagagtc 720
attaccacca gcacccgaac ctgggccctg cccacctaca acaaccacct ctacaagcaa 780
atctccagcc aatcaggagc ttcaaacgac aaccactact ttggctacag cacccccttgg 840
gggtattttg actttaacag attccactgc cacttctcac cacgtgactg gcagcgactc 900
attaacaaca actggggatt ccggcccaag agactcaact tcaagctctt caacatccaa 960
gtcaaggagg tcacgacgaa tgatggcgtc acgaccatcg ctaataacct taccagcacg 1020
gttcaagtct tctcggactc ggagtaccag cttccgtacg tcctcggctc tgcgcaccag 1080
ggctgcctcc ctccgttccc ggcggacgtg ttcatgattc cgcagtacgg ctacctaacg 1140
ctcaacaatg gcagccaggc agtgggacgg tcatcctttt actgcctgga atatttccca 1200
tcgcagatgc tgagaacggg caataacttt gagttcagct acaccttcga ggacgtgcct 1260
ttccacagca gctacgcaca cagccagagc ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttcccatc cagcggagtc 1620
ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgagac gtgtacctgc agggtcccat ctgggccaag 1860
attcctcaca cggacggcaa ctttcacccg tctcctctga tgggcggctt tggacttaaa 1920
cacccgcctc cacagatcct gatcaagaac acgccggtac ctgcggatcc tccaacaacg 1980
ttcagccagg cgaaattggc ttccttcatc acgcagtaca gcaccggaca ggtcagcgtg 2040
gagatcgagt gggagctgca gaaggaaaac agcaagcgct ggaatcccga agtgcagtac 2100
acatccaatt atgcaaaatc tgccaacgtt gattttactg tggacaacaa tggactttat 2160
actgagcctc gccccattgg cacccgttac cttacccgtc ccctgtaa 2208

<210> SEQ ID NO 37
<211> LENGTH: 2208
<212> TYPE: DNA
<213> ORGANISM: Artificial Sequence
<220> FEATURE:
<223> OTHER INFORMATION: AAVC11.17 capsid polynucleotide

<400> SEQUENCE: 37

```
atggctgctg acggttatct tccagattgg ctcgaggaca acctctctga aggcattcgc     60
gagtggtggg acctgaaacc tggagccccc aagcccaagg ccaaccagca gaagcaggac    120
gacggtcggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aagctgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
tctggtacag tggctgcagg cggtggcgca ccaatggcag acaataacga aggtgccgac    660
ggagtgggta atgcctcagg aaattggcat tgcgattcca catggctggg cgacagagtc    720
attaccacca gcacccgaac ctgggccctg cccacttaca acaaccatct ctacaagcaa    780
atctccagcc aatcaggagc ttcaaacgac aaccactact ttggctacag caccccttgg    840
gggtattttg actttaacag attccactgc cacttctcac cacgtgactg gcagcgactc    900
atcaacaaca actggggatt ccggcccaag aagctgcggt tcaagctctt caacatccag    960
gtcaaggagg tcacgacgaa tgacggcgtt acgaccatcg ctaataacct taccagcacg   1020
attcaggtat tctcggactc ggaataccag ctgccgtacg tcctcggctc tgcgcaccag   1080
ggctgcctcc ctccgttccc ggcggacgtg ttcatgattc cgcagtacgg ctacctaaca   1140
ctcaacaacg gtagtcaggc cgtgggacgc tcatcctttt actgcctgga gtacttcccc   1200
tctcagatgc tgagaacggg caacaacttt gagttcagct acagcttcga ggacgtgcct   1260
ttccacagca gctacgcaca cagccagagc ttggaccgac tgatgaatcc tctcattgac   1320
cagtacctgt actacttatc cagaactcag tccacaggag gaactcaagg tacccagcaa   1380
ttgttatttt ctcaagctgg gcctgcaaac atgtcggctc aggccaagaa ctggctgcct   1440
ggaccttgct accggcagca gcgagtctcc acgacactgt cgcaaaacaa caacagcaac   1500
tttgcttgga ctggtgccac caaatatcac ctgaacggca gaaactcgtt ggttaatccc   1560
ggcgtcgcca tggcaactca caaggacgac gaggaccgct tttcccatc cagcggagtc    1620
ctgatttttg gaaaaactgg agcaactaac aaaactacat tggaaaatgt gttaatgaca   1680
aatgaagaag aaattcgtcc tactaatcct gtagccacgg aagaatacgg gatagtcagc   1740
agcaacttac aagcggctaa tactgcagcc cagacacaag ttgtcaacaa ccagggagcc   1800
ttacctggca tggtctggca gaaccgggac gtgtacctgc agggtcccat ctgggccaag   1860
attcctcaca cggatggcaa ctttcacccg tctcctttga tgggcggctt tggacttaaa   1920
catccgcctc ctcagatcct gatcaagaac actcccgttc ccgctaatcc tccggaggtg   1980
tttactcctg ccaagtttgc ttcgttcatc acacagtaca gcaccggaca agtcagcgtg   2040
gaaatcgagt gggagctgca gaaggaaaac agcaagcgct ggaacccgga gattcagtac   2100
acttcaaact acaacaagtc tgttagtgtg gactttactg tagacactaa tggcgtgtat   2160
tcagagcctc gccccattgg caccagatac ctgactcgta atctgtaa                2208
```

<210> SEQ ID NO 38

<211> LENGTH: 2208
<212> TYPE: DNA
<213> ORGANISM: Artificial Sequence
<220> FEATURE:
<223> OTHER INFORMATION: AAVC11.18 capsid polynucleotide

<400> SEQUENCE: 38

```
atggctgccg atggttatct tccagattgg ctcgaggaca acctctctga gggcattcgc     60
gagtggtggg acctgaaacc tggagccccg aagcccaagg ccaaccagca gaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc ctcgggcatt    480
ggcaagacag gccagcagcc cgctaaaaag agactcaatt tcggtcagac tggcgactca    540
gagtcagtcc ccgaccctca acctctcgga gaacctccag cagcgccctc tagtgtggga    600
tctggtacag tggctgcagg cggtggcgca ccaatggcag acaataacga aggtgccgac    660
ggagtgggta atgcctcagg aaattggcat tgcgattcca catggctggg cgacagagtc    720
atcaccacca gcaccagaac ctgggccctg cccacttaca acaaccatct ctacaagcaa    780
atctccagcc aatcaggagc ttcaaacgac aaccactact tcggctacag cacccccctgg   840
gggtattttg actttaacag attccactgc cacttttcac cacgtgactg gcagcgactc    900
atcaacaaca actggggatt ccggcccaag agactcagct tcaagctctt caacatccaa    960
gtcaaggagg tcacgacgaa tgatggcgtc acgaccatcg ctaataacct taccagcacg   1020
gttcaagtct tctcggactc ggagtaccag cttccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atattttcca   1200
tctcaaatgc tgcgaactgg aaacaatttt gaattcagct acaccttcga ggacgtgcct   1260
ttccacagca gctacgcaca cagccagagc ttggaccgac tgatgaatcc tctcattgac   1320
cagtacctgt actacttatc cagaactcag tccacaggag gaactcaagg tacccagcaa   1380
ttgttatttt ctcaagctgg gcctgcaaac atgtcggctc aggccaagaa ctggctgcct   1440
ggaccttgct accggcagca gcgagtctcc acgacactgt cgcaaaacaa caacagcaac   1500
tttgcttgga ctggtgccac caaatatcac ctgaacggca gaaactcgtt ggttaatccc   1560
ggcgtcgcca tggcaactca caaggacgac gaggaccgct tttcccatc cagcggagtc    1620
ctgatttttg gaaaaactgg agcaactaac aaaactacat tggaaaatgt gttaatgaca   1680
aatgaagaag aaattcgtcc tactaatcct gtagccacgg aagaatacgg gatagtcagc   1740
agcaacttac aagcggctaa tactgcagcc cagacacaag ttgtcaacaa ccagggagcc   1800
ttacctggca tggtctggca gaaccgggac gtgtacctgc agggtcccat ctgggccaag   1860
attcctcaca cggatggcaa ctttcacccg tctcctttga tgggcggctt tggacttaaa   1920
catccgcctc ctcagatcct gatcaagaac actcccgttc ccgctaatcc tccggaggtg   1980
tttactcctg ccaagtttgc ttcgttcatc acacagtaca gcaccggaca agtcagcgtg   2040
gaaatcgagt gggagctgca gaaggaaaac agcaagcgct ggaacccgga gattcagtac   2100
acttcaaact acaacaagtc tgttagtgtg gactttactg tagacactaa tggcgtgtat   2160
```

tcagagcctc gccccattgg caccagatac ctgactcgta atctgtaa 2208

<210> SEQ ID NO 39
<211> LENGTH: 2208
<212> TYPE: DNA
<213> ORGANISM: Artificial Sequence
<220> FEATURE:
<223> OTHER INFORMATION: AAVC11.19 capsid polynucleotide

<400> SEQUENCE: 39
atggctgccg atggttatct tccagattgg ctcgaggaca acctctctga gggcattcgc 60
gagtggtggg cgctgaaacc tggagccccg aagcccaaag ccaaccagca gaagcaggac 120
gacggccggg gtctggtgct tcctggctac aagtacctcg gacccttcaa cggactcgac 180
aagggagagc cggtcaacga ggcagacgcc gcggccctcg agcacgacaa agcctacgac 240
cagcagctca aagcgggtga caatccgtac ctgcggtata accacgccga cgccgagttt 300
caggagcgtc tgcaagaaga tacgtcattt gggggcaacc tcgggcgagc agtcttccag 360
gccaagaagc gggttctcga acctctcggt ctggttgagg aaggcgctaa gacggctcct 420
ggaaagaaga gaccggtaga gccgtcacct cagcgttccc ccgactcctc cacgggcatc 480
ggcaagaaag gccagcagcc cgccagaaag agactcaatt tcggtcagac tggcgactca 540
gagtcagtcc ccgaccctca acctctcgga gaacctccag cagcgccctc tagtgtggga 600
tctggtacag tggctgcagg cggtggcgca ccaatggcag acaataacga aggtgccgac 660
ggagtgggta atgcctcagg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact ttggctacag caccccttgg 840
gggtattttg actttaacag attccactgc catttctcac cacgtgactg gcagcgactc 900
attaacaaca actggggatt ccggcccaag aaactcagct tcaagctctt caacatccaa 960
gttaaagagg tcacgcagaa cgatggcacg acgactattg ccaataacct taccagcacg 1020
gttcaagtgt ttacggactc ggaataccag ctgccgtacg tcctcggctc cgcgcaccag 1080
ggctgcctgc ctccgttccc ggcggatgtc ttcatgattc cccagtacgg ctacctgaca 1140
ctgaacaatg gaagtcaagc cgtaggccgt tcctccttct actgcctgga atattttcca 1200
tctcaaatgc tgcgaactgg aaacaatttt gaattcagct acaccttcga ggacgtgcct 1260
ttccacagca gctacgcaca cagccagagc ttggaccgac tgatgaatcc tctcattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaactca caaggacgac gaggaccgct tttttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggatggcaa ctttcacccg tctcctttga tgggcggctt tggacttaaa 1920
catccgcctc ctcagatcct gatcaagaac actcccgttc ccgctaatcc tccggaggtg 1980
tttactcctg ccaagtttgc ttcgttcatc acacagtaca gcaccggaca agtcagcgtg 2040
gaaatcgagt gggagctgca gaaggaaaac agcaagcgct ggaacccgga gattcagtac 2100
acttcaaact acaacaagtc tgttagtgtg gactttactg tagacactaa tggcgtgtat 2160
tcagagcctc gccccattgg caccagatac ctgactcgta atctgtaa 2208

<210> SEQ ID NO 40
<211> LENGTH: 20
<212> TYPE: DNA
<213> ORGANISM: Artificial Sequence
<220> FEATURE:
<223> OTHER INFORMATION: Shuffling_Rescue-F primer

<400> SEQUENCE: 40
gtcggaaagc atatgccgcg 20

<210> SEQ ID NO 41
<211> LENGTH: 21
<212> TYPE: DNA
<213> ORGANISM: Artificial Sequence
<220> FEATURE:
<223> OTHER INFORMATION: Shuffling_Rescue-R primer

<400> SEQUENCE: 41
gacgtcgcat gcaactagta t 21

<210> SEQ ID NO 42
<211> LENGTH: 23
<212> TYPE: DNA
<213> ORGANISM: Artificial Sequence
<220> FEATURE:
<223> OTHER INFORMATION: BB_GAR-F primer

<400> SEQUENCE: 42
acttgttcac tttgatggcg agg 23

<210> SEQ ID NO 43
<211> LENGTH: 22
<212> TYPE: DNA
<213> ORGANISM: Artificial Sequence
<220> FEATURE:
<223> OTHER INFORMATION: BB_GAR-R primer

<400> SEQUENCE: 43
ctgcacacga catgacatca cg 22

<210> SEQ ID NO 44
<211> LENGTH: 45
<212> TYPE: DNA
<213> ORGANISM: Artificial Sequence
<220> FEATURE:
<223> OTHER INFORMATION: CapRescue-F primer

<400> SEQUENCE: 44
ccctgcagac aatgcgagag aatgaatcag aattcaaata tctgc 45

<210> SEQ ID NO 45
<211> LENGTH: 33
<212> TYPE: DNA
<213> ORGANISM: Artificial Sequence
<220> FEATURE:
<223> OTHER INFORMATION: CapRescue-R primer

<400> SEQUENCE: 45
atgcatatgg aaactagata agaaagaaat acg 33

<210> SEQ ID NO 46
<211> LENGTH: 26
<212> TYPE: DNA
<213> ORGANISM: Artificial Sequence
<220> FEATURE:
<223> OTHER INFORMATION: pHelperF primer

<400> SEQUENCE: 46
cgcattgtct gcagggaaac agcatc 26

<210> SEQ ID NO 47
<211> LENGTH: 50
<212> TYPE: DNA
<213> ORGANISM: Artificial Sequence
<220> FEATURE:
<223> OTHER INFORMATION: pHelperR primer

<400> SEQUENCE: 47
tttctttctt atctagtttc catatgcatg tagataagta gcatggcggg 50

<210> SEQ ID NO 48
<211> LENGTH: 20
<212> TYPE: DNA
<213> ORGANISM: Artificial Sequence
<220> FEATURE:
<223> OTHER INFORMATION: GFP-F1 primer

<400> SEQUENCE: 48
tcaagatccg ccacaacatc 20

<210> SEQ ID NO 49
<211> LENGTH: 20
<212> TYPE: DNA
<213> ORGANISM: Artificial Sequence
<220> FEATURE:
<223> OTHER INFORMATION: GFP-R1 primer

<400> SEQUENCE: 49
ttctcgttgg ggtctttgct 20

<210> SEQ ID NO 50
<211> LENGTH: 20
<212> TYPE: DNA
<213> ORGANISM: Artificial Sequence
<220> FEATURE:
<223> OTHER INFORMATION: rep-F1 primer

<400> SEQUENCE: 50
ctcaacccgt ttctgtcgtc 20

<210> SEQ ID NO 51
<211> LENGTH: 20
<212> TYPE: DNA
<213> ORGANISM: Artificial Sequence
<220> FEATURE:
<223> OTHER INFORMATION: rep-R2 primer

<400> SEQUENCE: 51
cacattgacc agatcgcagg 20

<210> SEQ ID NO 52
<211> LENGTH: 20
<212> TYPE: DNA
<213> ORGANISM: Artificial Sequence
<220> FEATURE:

<223> OTHER INFORMATION: BC_F primer

<400> SEQUENCE: 52
gctggagttc gtgaccgccg 20

<210> SEQ ID NO 53
<211> LENGTH: 52
<212> TYPE: DNA
<213> ORGANISM: Artificial Sequence
<220> FEATURE:
<223> OTHER INFORMATION: BC_R primer

<400> SEQUENCE: 53
caacatagtt aagaatacca gtcaatcttt cacaaatttt gtaatccaga gg 52

<210> SEQ ID NO 54
<211> LENGTH: 19
<212> TYPE: DNA
<213> ORGANISM: Artificial Sequence
<220> FEATURE:
<223> OTHER INFORMATION: External_5_Seq primer

<400> SEQUENCE: 54
tgtggatttg gatgactgc 19

<210> SEQ ID NO 55
<211> LENGTH: 21
<212> TYPE: DNA
<213> ORGANISM: Artificial Sequence
<220> FEATURE:
<223> OTHER INFORMATION: External_3_Seq primer

<400> SEQUENCE: 55
gaccaaagtt caactgaaac g 21

<210> SEQ ID NO 56
<211> LENGTH: 22
<212> TYPE: DNA
<213> ORGANISM: Artificial Sequence
<220> FEATURE:
<223> OTHER INFORMATION: human_AAAVC._F primer

<400> SEQUENCE: 56
tgctgtcatc tcttgtgggc tg 22

<210> SEQ ID NO 57
<211> LENGTH: 22
<212> TYPE: DNA
<213> ORGANISM: Artificial Sequence
<220> FEATURE:
<223> OTHER INFORMATION: human_AAAVC._R primer

<400> SEQUENCE: 57
aactcatggg agctgctggt tc 22

<210> SEQ ID NO 58
<211> LENGTH: 10
<212> TYPE: PRT
<213> ORGANISM: Artificial Sequence
<220> FEATURE:
<223> OTHER INFORMATION: residues 263-272 of SEQ ID NO:13

<400> SEQUENCE: 58

Ser Gln Ser Gly Ala Ser Asn Asp Asn His
1 5 10

<210> SEQ ID NO 59
<211> LENGTH: 22
<212> TYPE: PRT
<213> ORGANISM: Artificial Sequence
<220> FEATURE:
<223> OTHER INFORMATION: residues 546-567 of SEQ ID NO:13)

<400> SEQUENCE: 59

Thr Gly Ala Thr Asn Lys Thr Thr Leu Glu Asn Val Leu Met Thr Asn
1               5                   10                  15

Glu Glu Glu Ile Arg Pro
            20

<210> SEQ ID NO 60
<211> LENGTH: 18
<212> TYPE: PRT
<213> ORGANISM: Artificial Sequence
<220> FEATURE:
<223> OTHER INFORMATION: residues 582-597 of SEQ ID NO:13

<400> SEQUENCE: 60

Ser Ser Asn Leu Gln Ala Ala Asn Thr Ala Ala Gln Thr Gln Val Val
1               5                   10                  15

Asn Asn

<210> SEQ ID NO 61
<211> LENGTH: 9
<212> TYPE: PRT
<213> ORGANISM: Artificial Sequence
<220> FEATURE:
<223> OTHER INFORMATION: residues 532-540 of SEQ ID NO:13

<400> SEQUENCE: 61

Asp Arg Phe Phe Pro Ser Ser Gly Val
1               5

<210> SEQ ID NO 62
<211> LENGTH: 23
<212> TYPE: PRT
<213> ORGANISM: Artificial Sequence
<220> FEATURE:
<223> OTHER INFORMATION: residues 451-473 of SEQ ID NO:13

<400> SEQUENCE: 62

Ser Thr Gly Gly Thr Gln Gly Thr Gln Gln Leu Leu Phe Ser Gln Ala
1               5                   10                  15

Gly Pro Ala Asn Met Ser Ala
            20

<210> SEQ ID NO 63
<211> LENGTH: 30
<212> TYPE: PRT
<213> ORGANISM: Artificial Sequence
<220> FEATURE:
<223> OTHER INFORMATION: residues 493-522 of SEQ ID NO:13

<400> SEQUENCE: 63

Leu Ser Gln Asn Asn Asn Ser Asn Phe Ala Trp Thr Gly Ala Thr Lys
1               5                   10                  15

Tyr His Leu Asn Gly Arg Asn Ser Leu Val Asn Pro Gly Val
            20                  25                  30

<210> SEQ ID NO 64
<211> LENGTH: 738

<212> TYPE: PRT
<213> ORGANISM: Adeno-associated virus 8

<400> SEQUENCE: 64

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Asn Gly Thr Ser Gly Gly Ala Thr Asn Asp
260 265 270

Asn Thr Tyr Phe Gly Tyr Ser Thr Pro Trp Gly Tyr Phe Asp Phe Asn
275 280 285

Arg Phe His Cys His Phe Ser Pro Arg Asp Trp Gln Arg Leu Ile Asn
290 295 300

Asn Asn Trp Gly Phe Arg Pro Lys Arg Leu Ser Phe Lys Leu Phe Asn
305 310 315 320

Ile Gln Val Lys Glu Val Thr Gln Asn Glu Gly Thr Lys Thr Ile Ala
325 330 335

Asn Asn Leu Thr Ser Thr Ile Gln Val Phe Thr Asp Ser Glu Tyr Gln
340 345 350

Leu Pro Tyr Val Leu Gly Ser Ala His Gln Gly Cys Leu Pro Pro Phe
355 360 365

Pro Ala Asp Val Phe Met Ile Pro Gln Tyr Gly Tyr Leu Thr Leu Asn
370 375 380

Asn Gly Ser Gln Ala Val Gly Arg Ser Ser Phe Tyr Cys Leu Glu Tyr
385 390 395 400

```
Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 65
<211> LENGTH: 736
<212> TYPE: PRT
<213> ORGANISM: Artificial Sequence
<220> FEATURE:
<223> OTHER INFORMATION: AAV8 Swap 1 capsid polypeptide

<400> SEQUENCE: 65

```
Met Ala Ala Asp Gly Tyr Leu Pro Asp Trp Leu Glu Asp Asn Leu Ser
1               5                   10                  15
```

```
Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
```

```
        435                 440                 445

Thr Gln Thr Thr Gly Gly Thr Ala Asn Thr Gln Thr Leu Gly Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Ala Asn Pro Gly Ile Ala Met Ala Thr His Lys
        515                 520                 525

Asp Asp Glu Glu Arg Phe Phe Pro Ser Asn Gly Ile Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 66
<211> LENGTH: 738
<212> TYPE: PRT
<213> ORGANISM: Artificial Sequence
<220> FEATURE:
<223> OTHER INFORMATION: AAV8 Swap 2 capsid polypeptide

<400> SEQUENCE: 66

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
```

```
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495
```

```
Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 67
<211> LENGTH: 737
<212> TYPE: PRT
<213> ORGANISM: Artificial Sequence
<220> FEATURE:
<223> OTHER INFORMATION: AAV8 Swap 3 capsid polypeptide

<400> SEQUENCE: 67

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Asp Arg Phe Phe Pro Ser Ser Gly Val Leu Ile
```

```
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu


<210> SEQ ID NO 68
<211> LENGTH: 736
<212> TYPE: PRT
<213> ORGANISM: Artificial Sequence
<220> FEATURE:
<223> OTHER INFORMATION: AAV8 Swap 4 capsid polypeptide

<400> SEQUENCE: 68

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

```
Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Glu Arg Phe Phe Pro Ser Asn Gly Ile Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575
```

```
Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 69
<211> LENGTH: 735
<212> TYPE: PRT
<213> ORGANISM: Artificial Sequence
<220> FEATURE:
<223> OTHER INFORMATION: AAV8 Swap 5 capsid polypeptide

<400> SEQUENCE: 69

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205
```

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Gly Gly Thr Ala Asn Thr Gln Thr Leu Gly Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Ala Asn Pro Gly Ile Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
```

625 630 635 640

His Pro Pro Pro Gln Ile Leu Ile Lys Asn Thr Pro Val Pro Ala Asp
645 650 655

Pro Pro Thr Thr Phe Asn Gln Ser Lys Leu Asn Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Tyr Lys Ser Thr Ser Val Asp Phe Ala Val Asn Thr Glu Gly Val Tyr
705 710 715 720

Ser Glu Pro Arg Pro Ile Gly Thr Arg Tyr Leu Thr Arg Asn Leu
725 730 735

<210> SEQ ID NO 70
<211> LENGTH: 737
<212> TYPE: PRT
<213> ORGANISM: Artificial Sequence
<220> FEATURE:
<223> OTHER INFORMATION: AAV8 Swap 6 capsid polypeptide

<400> SEQUENCE: 70

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Asn Gly Thr Ser Gly Gly Ala Thr Asn Asp

```
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685
```

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 71
<211> LENGTH: 735
<212> TYPE: PRT
<213> ORGANISM: Artificial Sequence
<220> FEATURE:
<223> OTHER INFORMATION: AAV8 Swap 7 capsid polypeptide

<400> SEQUENCE: 71

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

-continued

```
Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
```

725 730 735

<210> SEQ ID NO 72
<211> LENGTH: 735
<212> TYPE: PRT
<213> ORGANISM: Artificial Sequence
<220> FEATURE:
<223> OTHER INFORMATION: AAV8 Swap 8 capsid polypeptide

<400> SEQUENCE: 72

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Ser Gln Ser Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Arg Leu Ser Phe Lys Leu Phe Asn Ile Gln
305 310 315 320

Val Lys Glu Val Thr Gln Asn Glu Gly Thr Lys Thr Ile Ala Asn Asn
325 330 335

Leu Thr Ser Thr Ile Gln Val Phe Thr Asp Ser Glu Tyr Gln Leu Pro
340 345 350

Tyr Val Leu Gly Ser Ala His Gln Gly Cys Leu Pro Pro Phe Pro Ala

```
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Gly Gly Thr Ala Asn Thr Gln Thr Leu Gly Phe Ser
    450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 73
<211> LENGTH: 735
<212> TYPE: PRT
<213> ORGANISM: Artificial Sequence
<220> FEATURE:
<223> OTHER INFORMATION: AAV8 Swap 9 capsid polypeptide

<400> SEQUENCE: 73

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Ser Gln Ser Gly Ala Ser Asn Asp Asn His
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Arg Leu Ser Phe Lys Leu Phe Asn Ile Gln
305 310 315 320

Val Lys Glu Val Thr Gln Asn Glu Gly Thr Lys Thr Ile Ala Asn Asn
325 330 335

Leu Thr Ser Thr Ile Gln Val Phe Thr Asp Ser Glu Tyr Gln Leu Pro
340 345 350

Tyr Val Leu Gly Ser Ala His Gln Gly Cys Leu Pro Pro Phe Pro Ala
355 360 365

Asp Val Phe Met Ile Pro Gln Tyr Gly Tyr Leu Thr Leu Asn Asn Gly
370 375 380

Ser Gln Ala Val Gly Arg Ser Ser Phe Tyr Cys Leu Glu Tyr Phe Pro
385 390 395 400

Ser Gln Met Leu Arg Thr Gly Asn Asn Phe Gln Phe Thr Tyr Thr Phe
405 410 415

```
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Ala Asn Pro Gly Ile Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ser Ser Asn Leu Gln Ala Ala Asn Thr Ala Ala Gln Thr
            580                 585                 590

Gln Val Val Asn Asn Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735


<210> SEQ ID NO 74
<211> LENGTH: 735
<212> TYPE: PRT
<213> ORGANISM: Artificial Sequence
<220> FEATURE:
<223> OTHER INFORMATION: AAV8 Swap 10 capsid polypeptide

<400> SEQUENCE: 74

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

```
Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460
```

Gln Ala Gly Pro Ala Asn Met Ser Ala Gln Ala Lys Asn Trp Leu Pro
465 470 475 480

Gly Pro Cys Tyr Arg Gln Gln Arg Val Ser Thr Thr Leu Ser Gln Asn
485 490 495

Asn Asn Ser Asn Phe Ala Trp Thr Gly Ala Thr Lys Tyr His Leu Asn
500 505 510

Gly Arg Asn Ser Leu Val Asn Pro Gly Val Ala Met Ala Thr His Lys
515 520 525

Asp Asp Glu Glu Arg Phe Phe Pro Ser Asn Gly Ile Leu Ile Phe Gly
530 535 540

Lys Thr Gly Ala Thr Asn Lys Thr Thr Leu Glu Asn Val Leu Met Thr
545 550 555 560

Asn Glu Glu Glu Ile Arg Pro Thr Asn Pro Val Ala Thr Glu Glu Tyr
565 570 575

Gly Ile Val Ser Ser Asn Leu Gln Ala Ala Asn Thr Ala Ala Gln Thr
580 585 590

Gln Val Val Asn Asn Gln Gly Ala Leu Pro Gly Met Val Trp Gln Asn
595 600 605

Arg Asp Val Tyr Leu Gln Gly Pro Ile Trp Ala Lys Ile Pro His Thr
610 615 620

Asp Gly Asn Phe His Pro Ser Pro Leu Met Gly Gly Phe Gly Leu Lys
625 630 635 640

His Pro Pro Pro Gln Ile Leu Ile Lys Asn Thr Pro Val Pro Ala Asp
645 650 655

Pro Pro Thr Thr Phe Asn Gln Ser Lys Leu Asn Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Tyr Lys Ser Thr Ser Val Asp Phe Ala Val Asn Thr Glu Gly Val Tyr
705 710 715 720

Ser Glu Pro Arg Pro Ile Gly Thr Arg Tyr Leu Thr Arg Asn Leu
725 730 735

<210> SEQ ID NO 75
<211> LENGTH: 736
<212> TYPE: PRT
<213> ORGANISM: Artificial Sequence
<220> FEATURE:
<223> OTHER INFORMATION: AAV8 Swap 11 capsid polypeptide

<400> SEQUENCE: 75

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
```

```
        515                 520                 525

Asp Asp Glu Asp Arg Phe Phe Pro Ser Ser Gly Val Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ser Ser Asn Leu Gln Ala Ala Asn Thr Ala Ala Gln
            580                 585                 590

Thr Gln Val Val Asn Asn Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 76
<211> LENGTH: 735
<212> TYPE: PRT
<213> ORGANISM: Artificial Sequence
<220> FEATURE:
<223> OTHER INFORMATION: AAV8 Swap 12 capsid polypeptide

<400> SEQUENCE: 76

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
```

```
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575
```

```
Gly Ile Val Ala Asp Asn Leu Gln Gln Gln Asn Thr Ala Pro Gln Ile
            580                 585                 590

Gly Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735


<210> SEQ ID NO 77
<211> LENGTH: 736
<212> TYPE: PRT
<213> ORGANISM: Artificial Sequence
<220> FEATURE:
<223> OTHER INFORMATION: AAV8 Swap 13 capsid polypeptide

<400> SEQUENCE: 77

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205
```

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Asp Arg Phe Phe Pro Ser Ser Gly Val Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620
```

Thr Asp Gly Asn Phe His Pro Ser Pro Leu Met Gly Gly Phe Gly Leu
625 630 635 640

Lys His Pro Pro Pro Gln Ile Leu Ile Lys Asn Thr Pro Val Pro Ala
645 650 655

Asp Pro Pro Thr Thr Phe Asn Gln Ser Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Thr Ser Val Asp Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 78
<211> LENGTH: 735
<212> TYPE: PRT
<213> ORGANISM: Artificial Sequence
<220> FEATURE:
<223> OTHER INFORMATION: AAV8 Swap 14 capsid polypeptide

<400> SEQUENCE: 78

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Arg Lys Arg Leu Asn Phe Gly Gln
165 170 175

Thr Gly Asp Ser Glu Ser Val Pro Asp Pro Gln Pro Leu Gly Glu Pro
180 185 190

Pro Ala Ala Pro Ser Gly Val Gly Pro Asn Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

```
Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Glu Arg Phe Phe Pro Ser Asn Gly Ile Leu Ile Phe Gly
    530                 535                 540

Lys Thr Gly Ala Thr Asn Lys Thr Thr Leu Glu Asn Val Leu Met Thr
545                 550                 555                 560

Asn Glu Glu Glu Ile Arg Pro Thr Asn Pro Val Ala Thr Glu Glu Tyr
                565                 570                 575

Gly Ile Val Ala Asp Asn Leu Gln Gln Gln Asn Thr Ala Pro Gln Ile
            580                 585                 590

Gly Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asp
                645                 650                 655

Pro Pro Thr Thr Phe Asn Gln Ser Lys Leu Asn Ser Phe Ile Thr Gln
            660                 665                 670

Tyr Ser Thr Gly Gln Val Ser Val Glu Ile Glu Trp Glu Leu Gln Lys
```

```
        675                 680                 685

Glu Asn Ser Lys Arg Trp Asn Pro Glu Ile Gln Tyr Thr Ser Asn Tyr
    690                 695                 700

Tyr Lys Ser Thr Ser Val Asp Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735


<210> SEQ ID NO 79
<211> LENGTH: 736
<212> TYPE: PRT
<213> ORGANISM: Artificial Sequence
<220> FEATURE:
<223> OTHER INFORMATION: AAV8 Swap 15 capsid polypeptide

<400> SEQUENCE: 79

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
```

```
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Ser Thr Gly Gly Thr Gln Gly Thr Gln Gln Leu Leu Phe Ser
    450                 455                 460

Gln Ala Gly Pro Ala Asn Met Ser Ala Gln Ala Lys Asn Trp Leu Pro
465                 470                 475                 480

Gly Pro Cys Tyr Arg Gln Gln Arg Val Ser Thr Thr Leu Ser Gln Asn
                485                 490                 495

Asn Asn Ser Asn Phe Ala Trp Thr Gly Ala Thr Lys Tyr His Leu Asn
            500                 505                 510

Gly Arg Asn Ser Leu Val Asn Pro Gly Val Ala Met Ala Thr His Lys
        515                 520                 525

Asp Asp Glu Glu Arg Phe Phe Pro Ser Asn Gly Ile Leu Ile Phe Gly
    530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ser Ser Asn Leu Gln Ala Ala Asn Thr Ala Ala Gln
            580                 585                 590

Thr Gln Val Val Asn Asn Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 80
<211> LENGTH: 12
<212> TYPE: PRT
<213> ORGANISM: Artificial Sequence
<220> FEATURE:
<223> OTHER INFORMATION: residues 261-272 of SEQ ID NO:13

<400> SEQUENCE: 80

Ile Ser Ser Gln Ser Gly Ala Ser Asn Asp Asn His
1 5 10

<210> SEQ ID NO 81
<211> LENGTH: 23
<212> TYPE: PRT
<213> ORGANISM: Artificial Sequence
<220> FEATURE:
<223> OTHER INFORMATION: residues 545-567 of SEQ ID NO:13

<400> SEQUENCE: 81

Lys Thr Gly Ala Thr Asn Lys Thr Thr Leu Glu Asn Val Leu Met Thr
1 5 10 15

Asn Glu Glu Glu Ile Arg Pro
20

<210> SEQ ID NO 82
<211> LENGTH: 18
<212> TYPE: PRT
<213> ORGANISM: Artificial Sequence
<220> FEATURE:
<223> OTHER INFORMATION: residues 523-540 of SEQ ID NO:13

<400> SEQUENCE: 82

Ala Met Ala Thr His Lys Asp Asp Glu Asp Arg Phe Phe Pro Ser Ser
1 5 10 15

Gly Val

<210> SEQ ID NO 83
<211> LENGTH: 24
<212> TYPE: PRT
<213> ORGANISM: Artificial Sequence
<220> FEATURE:
<223> OTHER INFORMATION: residues 450-473 of SEQ ID NO:13

<400> SEQUENCE: 83

Gln Ser Thr Gly Gly Thr Gln Gly Thr Gln Gln Leu Leu Phe Ser Gln
1 5 10 15

Ala Gly Pro Ala Asn Met Ser Ala
20

<210> SEQ ID NO 84
<211> LENGTH: 35
<212> TYPE: PRT
<213> ORGANISM: Artificial Sequence
<220> FEATURE:
<223> OTHER INFORMATION: residues 488-522 of SEQ ID NO:13

<400> SEQUENCE: 84

Arg Val Ser Thr Thr Leu Ser Gln Asn Asn Asn Ser Asn Phe Ala Trp
1 5 10 15

Thr Gly Ala Thr Lys Tyr His Leu Asn Gly Arg Asn Ser Leu Val Asn
20 25 30

Pro Gly Val
35

<210> SEQ ID NO 85
<211> LENGTH: 2211
<212> TYPE: DNA
<213> ORGANISM: Artificial Sequence
<220> FEATURE:
<223> OTHER INFORMATION: AAV8 Swap 1 capsid polynucleotide

<400> SEQUENCE: 85
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact tcggctacag caccccctgg 840
gggtattttg actttaacag attccactgc cacttttcac cacgtgactg gcagcgactc 900
atcaacaaca actggggatt ccggcccaag agactcagct tcaagctctt caacatccag 960
gtcaaggagg tcacgcagaa tgaaggcacc aagaccatcg ccaataacct caccagcacc 1020
atccaggtgt ttacggactc ggagtaccag ctgccgtacg ttctcggctc tgcccaccag 1080
ggctgcctgc ctccgttccc ggcggacgtg ttcatgattc cccagtacgg ctacctaaca 1140
ctcaacaacg gtagtcaggc cgtgggacgc tcctccttct actgcctgga atactttcct 1200
tcgcagatgc tgagaaccgg caacaacttc cagtttactt acaccttcga ggacgtgcct 1260
ttccacagca gctacgccca cagccagagc ttggaccggc tgatgaatcc tctgattgac 1320
cagtacctgt actacttgtc tcggactcaa acaacaggag gcacggcaaa tacgcagact 1380
ctgggcttca gccaaggtgg gcctaataca atggccaatc aggcaaagaa ctggctgcca 1440
ggaccctgtt accgccaaca acgcgtctca acgacaaccg ggcaaaacaa caatagcaac 1500
tttgcctgga ctgctgggac caaataccat ctgaatggaa gaaattcatt ggctaatcct 1560
ggcatcgcta tggcaacaca caaggacgac gaggagcgtt tttttcccag taacgggatc 1620
ctgatttttg gcaaacaaaa tgctgccaga gacaatgcgg attacagcga tgtcatgctc 1680
accagcgagg aagaaatcaa aaccactaac cctgtggcta cagaggaata cggtatcgtg 1740
gcagataact tgcagcagca aaacacggct cctcaaattg gaactgtcaa cagccagggg 1800
gccttacccg gtatggtctg gcagaaccgg gacgtgtacc tgcagggtcc catctgggcc 1860
aagattcctc acacggacgg caacttccac ccgtctccgc tgatgggcgg ctttggcctg 1920
aaacatcctc cgcctcagat cctgatcaag aacacgcctg tacctgcgga tcctccgacc 1980
accttcaacc agtcaaagct gaactctttc atcacgcaat acagcaccgg acaggtcagc 2040
gtggaaattg aatgggagct gcagaaggaa aacagcaagc gctggaaccc cgagatccag 2100
tacacctcca actactacaa atctacaagt gtggactttg ctgttaatac agaaggcgtg 2160
tactctgaac cccgccccat tggcacccgt tacctcaccc gtaatctgta a 2211

<210> SEQ ID NO 86
<211> LENGTH: 2217
<212> TYPE: DNA
<213> ORGANISM: Artificial Sequence
<220> FEATURE:
<223> OTHER INFORMATION: AAV8 Swap 2 capsid polynucleotide

<400> SEQUENCE: 86
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttatccaga actcagtcca caggaggaac tcaaggtacc 1380
cagcaattgt tattttctca agctgggcct gcaaacatgt cggctcaggc caagaactgg 1440
ctgcctggac cttgctaccg gcagcagcga gtctccacga cactgtcgca aaacaacaac 1500
agcaactttg cttggactgg tgccaccaaa tatcacctga acggcagaaa ctcgttggtt 1560
aatcccggcg tcgccatggc aacacacaag gacgacgagg agcgtttttt tcccagtaac 1620
gggatcctga tttttggcaa acaaaatgct gccagagaca atgcggatta cagcgatgtc 1680
atgctcacca gcgaggaaga aatcaaaacc actaaccctg tggctacaga ggaatacggt 1740
atcgtggcag ataacttgca gcagcaaaac acggctcctc aaattggaac tgtcaacagc 1800 caggggggcct tacccggtat ggtctggcag aaccgggacg tgtacctgca gggtcccatc 1860
tgggccaaga ttcctcacac ggacggcaac ttccacccgt ctccgctgat gggcggcttt 1920
ggcctgaaac atcctccgcc tcagatcctg atcaagaaca cgcctgtacc tgcggatcct 1980
ccgaccacct tcaaccagtc aaagctgaac tctttcatca cgcaatacag caccggacag 2040
gtcagcgtgg aaattgaatg ggagctgcag aaggaaaaca gcaagcgctg gaaccccgag 2100
atccagtaca cctccaacta ctacaaatct acaagtgtgg actttgctgt taatacagaa 2160
ggcgtgtact ctgaaccccg ccccattggc acccgttacc tcacccgtaa tctgtaa 2217

<210> SEQ ID NO 87
<211> LENGTH: 2214
<212> TYPE: DNA
<213> ORGANISM: Artificial Sequence
<220> FEATURE:
<223> OTHER INFORMATION: AAV8 Swap 3 capsid polynucleotide

<400> SEQUENCE: 87
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttgtctcgg actcaaacaa caggaggcac ggcaaatacg 1380
cagactctgg gcttcagcca aggtgggcct aatacaatgg ccaatcaggc aaagaactgg 1440
ctgccaggac cctgttaccg ccaacaacgc gtctcaacga caaccgggca aaacaacaat 1500
agcaactttg cctggactgc tgggaccaaa taccatctga atggaagaaa ttcattggct 1560
aatcctggca tcgctatggc aacacacaag gacgacgagg accgcttttt cccatccagc 1620
ggagtcctga tttttggaaa aactggagca actaacaaaa ctacattgga aaatgtgtta 1680
atgacaaatg aagaagaaat tcgtcctact aatcctgtag ccacggaaga atacgggata 1740
gtcagcagca acttacaagc ggctaatact gcagcccaga cacaagttgt caacaaccag 1800
ggagccttac ctggcatggt ctggcagaac cgggacgtgt acctgcaggg tcccatctgg 1860
gccaagattc ctcacacgga cggcaacttc cacccgtctc cgctgatggg cggctttggc 1920
ctgaaacatc ctccgcctca gatcctgatc aagaacacgc ctgtacctgc ggatcctccg 1980
accaccttca accagtcaaa gctgaactct ttcatcacgc aatacagcac cggacaggtc 2040
agcgtggaaa ttgaatggga gctgcagaag gaaaacagca agcgctggaa ccccgagatc 2100
cagtacacct ccaactacta caaatctaca agtgtggact ttgctgttaa tacagaaggc 2160
gtgtactctg aaccccgccc cattggcacc cgttacctca cccgtaatct gtaa 2214

<210> SEQ ID NO 88
<211> LENGTH: 2211
<212> TYPE: DNA
<213> ORGANISM: Artificial Sequence
<220> FEATURE:
<223> OTHER INFORMATION: AAV8 Swap 4 capsid polynucleotide

<400> SEQUENCE: 88
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact tcggctacag caccccctgg 840
gggtattttg actttaacag attccactgc cacttttcac cacgtgactg gcagcgactc 900
atcaacaaca actggggatt ccggcccaag agactcagct tcaagctctt caacatccag 960
gtcaaggagg tcacgcagaa tgaaggcacc aagaccatcg ccaataacct caccagcacc 1020
atccaggtgt ttacggactc ggagtaccag ctgccgtacg ttctcggctc tgcccaccag 1080
ggctgcctgc ctccgttccc ggcggacgtg ttcatgattc cccagtacgg ctacctaaca 1140
ctcaacaacg gtagtcaggc cgtgggacgc tcctccttct actgcctgga atactttcct 1200
tcgcagatgc tgagaaccgg caacaacttc cagtttactt acaccttcga ggacgtgcct 1260
ttccacagca gctacgccca cagccagagc ttggaccggc tgatgaatcc tctgattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaacaca caaggacgac gaggagcgtt tttttcccag taacgggatc 1620

```
ctgatttttg gcaaacaaaa tgctgccaga gacaatgcgg attacagcga tgtcatgctc   1680

accagcgagg aagaaatcaa aaccactaac cctgtggcta cagaggaata cggtatcgtg   1740

gcagataact tgcagcagca aaacacggct cctcaaattg gaactgtcaa cagccagggg   1800

gccttacccg gtatggtctg gcagaaccgg gacgtgtacc tgcagggtcc catctgggcc   1860

aagattcctc acacggacgg caacttccac ccgtctccgc tgatgggcgg ctttggcctg   1920

aaacatcctc cgcctcagat cctgatcaag aacacgcctg tacctgcgga tcctccgacc   1980

accttcaacc agtcaaagct gaactctttc atcacgcaat acagcaccgg acaggtcagc   2040

gtggaaattg aatgggagct gcagaaggaa aacagcaagc gctggaaccc cgagatccag   2100

tacacctcca actactacaa atctacaagt gtggactttg ctgttaatac agaaggcgtg   2160

tactctgaac cccgccccat tggcacccgt tacctcaccc gtaatctgta a            2211
```

<210> SEQ ID NO 89
<211> LENGTH: 2208
<212> TYPE: DNA
<213> ORGANISM: Artificial Sequence
<220> FEATURE:
<223> OTHER INFORMATION: AAV8 Swap 5 capsid polynucleotide

<400> SEQUENCE: 89

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcaccagaac ctgggccctg cccacttaca acaaccatct ctacaagcaa    780

atctccagcc aatcaggagc ttcaaacgac aaccactact tcggctacag caccccctgg    840

gggtattttg actttaacag attccactgc cacttttcac cacgtgactg gcagcgactc    900

atcaacaaca actggggatt ccggcccaag agactcagct tcaagctctt caacatccag    960

gtcaaggagg tcacgcagaa tgaaggcacc aagaccatcg ccaataacct caccagcacc   1020

atccaggtgt ttacggactc ggagtaccag ctgccgtacg ttctcggctc tgcccaccag   1080

ggctgcctgc ctccgttccc ggcggacgtg ttcatgattc cccagtacgg ctacctaaca   1140

ctcaacaacg gtagtcaggc cgtgggacgc tcctccttct actgcctgga atactttcct   1200

tcgcagatgc tgagaaccgg caacaacttc cagtttactt acaccttcga ggacgtgcct   1260

ttccacagca gctacgccca cagccagagc ttggaccggc tgatgaatcc tctgattgac   1320

cagtacctgt actacttgtc tcggactcaa acaacaggag gcacggcaaa tacgcagact   1380

ctgggcttca gccaaggtgg gcctaataca atggccaatc aggcaaagaa ctggctgcca   1440
```

ggaccctgtt accgccaaca acgcgtctca acgacaaccg ggcaaaacaa caatagcaac 1500
tttgcctgga ctgctgggac caaataccat ctgaatggaa gaaattcatt ggctaatcct 1560
ggcatcgcta tggcaacaca caaggacgac gaggaccgct tttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggacggcaa cttccacccg tctccgctga tgggcggctt tggcctgaaa 1920
catcctccgc ctcagatcct gatcaagaac acgcctgtac ctgcggatcc tccgaccacc 1980
ttcaaccagt caaagctgaa ctctttcatc acgcaataca gcaccggaca ggtcagcgtg 2040
gaaattgaat gggagctgca gaaggaaaac agcaagcgct ggaaccccga gatccagtac 2100
acctccaact actacaaatc tacaagtgtg gactttgctg ttaatacaga aggcgtgtac 2160
tctgaacccc gccccattgg cacccgttac ctcacccgta atctgtaa 2208

<210> SEQ ID NO 90
<211> LENGTH: 2214
<212> TYPE: DNA
<213> ORGANISM: Artificial Sequence
<220> FEATURE:
<223> OTHER INFORMATION: AAV8 Swap 6 capsid polynucleotide

<400> SEQUENCE: 90
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacatcggg aggagccacc aacgacaaca cctacttcgg ctacagcacc 840
ccctgggggt attttgactt taacagattc cactgccact tttcaccacg tgactggcag 900
cgactcatca acaacaactg gggattccgg cccaagagac tcagcttcaa gctcttcaac 960
atccaggtca aggaggtcac gcagaatgaa ggcaccaaga ccatcgccaa taacctcacc 1020
agcaccatcc aggtgtttac ggactcggag taccagctgc cgtacgttct cggctctgcc 1080
caccagggct gcctgcctcc gttcccggcg gacgtgttca tgattcccca gtacggctac 1140
ctaacactca acaacggtag tcaggccgtg ggacgctcct ccttctactg cctggaatac 1200
tttccttcgc agatgctgag aaccggcaac aacttccagt ttacttacac cttcgaggac 1260
gtgcctttcc acagcagcta cgcccacagc cagagcttgg accggctgat gaatcctctg 1320
attgaccagt acctgtacta cttatccaga actcagtcca caggaggaac tcaaggtacc 1380
cagcaattgt tattttctca agctgggcct gcaaacatgt cggctcaggc caagaactgg 1440
ctgcctggac cttgctaccg gcagcagcga gtctccacga cactgtcgca aaacaacaac 1500
agcaactttg cttggactgg tgccaccaaa tatcacctga acggcagaaa ctcgttggtt 1560
aatcccggcg tcgccatggc aacacacaag gacgacgagg accgcttttt cccatccagc 1620
ggagtcctga tttttggaaa aactggagca actaacaaaa ctacattgga aaatgtgtta 1680
atgacaaatg aagaagaaat tcgtcctact aatcctgtag ccacggaaga atacgggata 1740
gtcagcagca acttacaagc ggctaatact gcagcccaga cacaagttgt caacaaccag 1800
ggagccttac ctggcatggt ctggcagaac cgggacgtgt acctgcaggg tcccatctgg 1860
gccaagattc ctcacacgga cggcaacttc cacccgtctc cgctgatggg cggctttggc 1920
ctgaaacatc ctccgcctca gatcctgatc aagaacacgc ctgtacctgc ggatcctccg 1980
accaccttca accagtcaaa gctgaactct ttcatcacgc aatacagcac cggacaggtc 2040
agcgtggaaa ttgaatggga gctgcagaag gaaaacagca agcgctggaa ccccgagatc 2100
cagtacacct ccaactacta caaatctaca agtgtggact ttgctgttaa tacagaaggc 2160
gtgtactctg aaccccgccc cattggcacc cgttacctca cccgtaatct gtaa 2214

<210> SEQ ID NO 91
<211> LENGTH: 2208
<212> TYPE: DNA
<213> ORGANISM: Artificial Sequence
<220> FEATURE:
<223> OTHER INFORMATION: AAV8 Swap 7 capsid polynucleotide

<400> SEQUENCE: 91
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact tcggctacag cacccccctgg 840 gggtattttg actttaacag attccactgc cacttttcac cacgtgactg gcagcgactc 900
atcaacaaca actggggatt ccggcccaag agactcagct tcaagctctt caacatccag 960
gtcaaggagg tcacgcagaa tgaaggcacc aagaccatcg ccaataacct caccagcacc 1020
atccaggtgt ttacggactc ggagtaccag ctgccgtacg ttctcggctc tgcccaccag 1080
ggctgcctgc ctccgttccc ggcggacgtg ttcatgattc cccagtacgg ctacctaaca 1140

```
ctcaacaacg gtagtcaggc cgtgggacgc tcctccttct actgcctgga atactttcct   1200

tcgcagatgc tgagaaccgg caacaacttc cagtttactt acaccttcga ggacgtgcct   1260

ttccacagca gctacgccca cagccagagc ttggaccggc tgatgaatcc tctgattgac   1320

cagtacctgt actacttatc cagaactcag tccacaggag gaactcaagg tacccagcaa   1380

ttgttatttt ctcaagctgg gcctgcaaac atgtcggctc aggccaagaa ctggctgcct   1440

ggaccttgct accggcagca gcgagtctcc acgacactgt cgcaaaacaa caacagcaac   1500

tttgcttgga ctggtgccac caaatatcac ctgaacggca gaaactcgtt ggttaatccc   1560

ggcgtcgcca tggcaacaca caaggacgac gaggaccgct tttcccatc cagcggagtc    1620

ctgatttttg gaaaaactgg agcaactaac aaaactacat tggaaaatgt gttaatgaca   1680

aatgaagaag aaattcgtcc tactaatcct gtagccacgg aagaatacgg gatagtcagc   1740

agcaacttac aagcggctaa tactgcagcc cagacacaag ttgtcaacaa ccagggagcc   1800

ttacctggca tggtctggca gaaccgggac gtgtacctgc agggtcccat ctgggccaag   1860

attcctcaca cggacggcaa cttccacccg tctccgctga tgggcggctt tggcctgaaa   1920

catcctccgc ctcagatcct gatcaagaac acgcctgtac ctgcggatcc tccgaccacc   1980

ttcaaccagt caaagctgaa ctctttcatc acgcaataca gcaccggaca ggtcagcgtg   2040

gaaattgaat gggagctgca gaaggaaaac agcaagcgct ggaaccccga gatccagtac   2100

acctccaact actacaaatc tacaagtgtg gactttgctg ttaatacaga aggcgtgtac   2160

tctgaacccc gccccattgg cacccgttac ctcacccgta atctgtaa                 2208
```

<210> SEQ ID NO 92
<211> LENGTH: 2208
<212> TYPE: DNA
<213> ORGANISM: Artificial Sequence
<220> FEATURE:
<223> OTHER INFORMATION: AAV8 Swap 8 capsid polynucleotide

<400> SEQUENCE: 92

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcaccagaac ctgggccctg cccacttaca acaaccatct ctacaagcaa    780

atctccagcc aatcaggagc ttcaaacgac aaccactact tcggctacag caccccctgg    840

gggtattttg actttaacag attccactgc cacttttcac cacgtgactg gcagcgactc    900

atcaacaaca actggggatt ccggcccaag agactcagct tcaagctctt caacatccag    960

gtcaaggagg tcacgcagaa tgaaggcacc aagaccatcg ccaataacct caccagcacc   1020
```

atccaggtgt ttacggactc ggagtaccag ctgccgtacg ttctcggctc tgcccaccag 1080
ggctgcctgc ctccgttccc ggcggacgtg ttcatgattc cccagtacgg ctacctaaca 1140
ctcaacaacg gtagtcaggc cgtgggacgc tcctccttct actgcctgga atactttcct 1200
tcgcagatgc tgagaaccgg caacaacttc cagtttactt acaccttcga ggacgtgcct 1260
ttccacagca gctacgccca cagccagagc ttggaccggc tgatgaatcc tctgattgac 1320
cagtacctgt actacttatc cagaactcag accacaggag gaactgcaaa tacccagaca 1380
ttgggatttt ctcaaggtgg gcctaacacc atggcgaatc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaacaca caaggacgac gaggaccgct tttcccatc cagcggagtc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggacggcaa cttccacccg tctccgctga tgggcggctt tggcctgaaa 1920
catcctccgc ctcagatcct gatcaagaac acgcctgtac ctgcggatcc tccgaccacc 1980
ttcaaccagt caaagctgaa ctctttcatc acgcaataca gcaccggaca ggtcagcgtg 2040
gaaattgaat gggagctgca gaaggaaaac agcaagcgct ggaaccccga gatccagtac 2100
acctccaact actacaaatc tacaagtgtg gactttgctg ttaatacaga aggcgtgtac 2160
tctgaacccc gccccattgg cacccgttac ctcacccgta atctgtaa 2208

<210> SEQ ID NO 93
<211> LENGTH: 2208
<212> TYPE: DNA
<213> ORGANISM: Artificial Sequence
<220> FEATURE:
<223> OTHER INFORMATION: AAV8 Swap 9 capsid polynucleotide

<400> SEQUENCE: 93
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact tcggctacag cacccctgg 840 gggtattttg actttaacag attccactgc cacttttcac cacgtgactg gcagcgactc 900
atcaacaaca actggggatt ccggcccaag agactcagct tcaagctctt caacatccag 960
gtcaaggagg tcacgcagaa tgaaggcacc aagaccatcg ccaataacct caccagcacc 1020
atccaggtgt ttacggactc ggagtaccag ctgccgtacg ttctcggctc tgcccaccag 1080
ggctgcctgc ctccgttccc ggcggacgtg ttcatgattc cccagtacgg ctacctaaca 1140
ctcaacaacg gtagtcaggc cgtgggacgc tcctccttct actgcctgga atactttcct 1200
tcgcagatgc tgagaaccgg caacaacttc cagtttactt acaccttcga ggacgtgcct 1260
ttccacagca gctacgccca cagccagagc ttggaccggc tgatgaatcc tctgattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacaacgg ggcaaaacaa caacagcaac 1500
tttgcttgga ctgctggcac caaatatcac ctgaacggca gaaactcgtt ggctaatccc 1560
ggcatcgcca tggcaacaca caaggacgac gaggaccgct tttcccatc cagcggagtc 1620
ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggacggcaa cttccacccg tctccgctga tgggcggctt tggcctgaaa 1920
catcctccgc ctcagatcct gatcaagaac acgcctgtac ctgcggatcc tccgaccacc 1980
ttcaaccagt caaagctgaa ctctttcatc acgcaataca gcaccggaca ggtcagcgtg 2040
gaaattgaat gggagctgca gaaggaaaac agcaagcgct ggaaccccga gatccagtac 2100
acctccaact actacaaatc tacaagtgtg gactttgctg ttaatacaga aggcgtgtac 2160
tctgaacccc gccccattgg cacccgttac ctcacccgta atctgtaa 2208

<210> SEQ ID NO 94
<211> LENGTH: 2208
<212> TYPE: DNA
<213> ORGANISM: Artificial Sequence
<220> FEATURE:
<223> OTHER INFORMATION: AAV8 Swap 10 capsid polynucleotide

<400> SEQUENCE: 94
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540
gagtcagttc cagaccctca acctctcgga gaacctccag cagcgccctc tggtgtggga 600
cctaatacaa tggctgcagg cggtggcgca ccaatggcag acaataacga aggcgccgac 660
ggagtgggta gttcctcggg aaattggcat tgcgattcca catggctggg cgacagagtc 720
atcaccacca gcaccagaac ctgggccctg cccacttaca acaaccatct ctacaagcaa 780
atctccagcc aatcaggagc ttcaaacgac aaccactact tcggctacag cacccctgg 840 gggtattttg actttaacag attccactgc cacttttcac cacgtgactg gcagcgactc 900
atcaacaaca actggggatt ccggcccaag agactcagct tcaagctctt caacatccag 960
gtcaaggagg tcacgcagaa tgaaggcacc aagaccatcg ccaataacct caccagcacc 1020
atccaggtgt ttacggactc ggagtaccag ctgccgtacg ttctcggctc tgcccaccag 1080
ggctgcctgc ctccgttccc ggcggacgtg ttcatgattc cccagtacgg ctacctaaca 1140
ctcaacaacg gtagtcaggc cgtgggacgc tcctccttct actgcctgga atactttcct 1200
tcgcagatgc tgagaaccgg caacaacttc cagtttactt acaccttcga ggacgtgcct 1260
ttccacagca gctacgccca cagccagagc ttggaccggc tgatgaatcc tctgattgac 1320
cagtacctgt actacttatc cagaactcag tccacaggag gaactcaagg tacccagcaa 1380
ttgttatttt ctcaagctgg gcctgcaaac atgtcggctc aggccaagaa ctggctgcct 1440
ggaccttgct accggcagca gcgagtctcc acgacactgt cgcaaaacaa caacagcaac 1500
tttgcttgga ctggtgccac caaatatcac ctgaacggca gaaactcgtt ggttaatccc 1560
ggcgtcgcca tggcaacaca caaggacgac gaggagcgct tttcccatc caacggaatc 1620 ctgatttttg gaaaaactgg agcaactaac aaaactacat tggaaaatgt gttaatgaca 1680
aatgaagaag aaattcgtcc tactaatcct gtagccacgg aagaatacgg gatagtcagc 1740
agcaacttac aagcggctaa tactgcagcc cagacacaag ttgtcaacaa ccagggagcc 1800
ttacctggca tggtctggca gaaccgggac gtgtacctgc agggtcccat ctgggccaag 1860
attcctcaca cggacggcaa cttccacccg tctccgctga tgggcggctt tggcctgaaa 1920
catcctccgc ctcagatcct gatcaagaac acgcctgtac ctgcggatcc tccgaccacc 1980
ttcaaccagt caaagctgaa ctctttcatc acgcaataca gcaccggaca ggtcagcgtg 2040
gaaattgaat gggagctgca gaaggaaaac agcaagcgct ggaaccccga gatccagtac 2100
acctccaact actacaaatc tacaagtgtg gactttgctg ttaatacaga aggcgtgtac 2160
tctgaacccc gccccattgg cacccgttac ctcacccgta atctgtaa 2208

<210> SEQ ID NO 95
<211> LENGTH: 2211
<212> TYPE: DNA
<213> ORGANISM: Artificial Sequence
<220> FEATURE:
<223> OTHER INFORMATION: AAV8 Swap 11 capsid polynucleotide

<400> SEQUENCE: 95
atggctgccg atggttatct tccagattgg ctcgaggaca acctctctga gggcattcgc 60
gagtggtggg cgctgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctgc aggcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gccatcaccc cagcgttctc cagactcctc tacgggcatc 480
ggcaagaaag gccaacagcc cgccagaaaa agactcaatt ttggtcagac tggcgactca 540

```
gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcaccagaac ctgggccctg cccacttaca acaaccatct ctacaagcaa    780

atctccagcc aatcaggagc ttcaaacgac aaccactact tcggctacag caccccctgg    840

gggtattttg actttaacag attccactgc cacttttcac cacgtgactg gcagcgactc    900

atcaacaaca actggggatt ccggcccaag agactcagct tcaagctctt caacatccag    960

gtcaaggagg tcacgcagaa tgaaggcacc aagaccatcg ccaataacct caccagcacc   1020

atccaggtgt ttacggactc ggagtaccag ctgccgtacg ttctcggctc tgcccaccag   1080

ggctgcctgc ctccgttccc ggcggacgtg ttcatgattc cccagtacgg ctacctaaca   1140

ctcaacaacg gtagtcaggc cgtgggacgc tcctccttct actgcctgga atactttcct   1200

tcgcagatgc tgagaaccgg caacaacttc cagtttactt acaccttcga ggacgtgcct   1260

ttccacagca gctacgccca cagccagagc ttggaccggc tgatgaatcc tctgattgac   1320

cagtacctgt actacttatc cagaactcag tccacaggag gaactcaagg tacccagcaa   1380

ttgttatttt ctcaagctgg gcctgcaaac atgtcggctc aggccaagaa ctggctgcct   1440

ggaccttgct accggcagca gcgagtctcc acgacactgt cgcaaaacaa caacagcaac   1500

tttgcttgga ctggtgccac caaatatcac ctgaacggca gaaactcgtt ggttaatccc   1560

ggcgtcgcca tggcaacaca caaggacgac gaggaccgct tttcccatc cagcggagtc    1620

ctgatttttg gaaaacagaa tgcagcaagg gacaacgctg actactcaga tgtgatgttg   1680

acaagtgaag aagaaattaa gactactaat cctgtagcca cggaagaata cgggatagtc   1740

agcagcaact tacaagcggc taatactgca gcccagacac aagttgtcaa caaccaggga   1800

gccttacctg gcatggtctg gcagaaccgg gacgtgtacc tgcagggtcc catctgggcc   1860

aagattcctc acacggacgg caacttccac ccgtctccgc tgatgggcgg ctttggcctg   1920

aaacatcctc cgcctcagat cctgatcaag aacacgcctg tacctgcgga tcctccgacc   1980

accttcaacc agtcaaagct gaactctttc atcacgcaat acagcaccgg acaggtcagc   2040

gtggaaattg aatgggagct gcagaaggaa aacagcaagc gctggaaccc cgagatccag   2100

tacacctcca actactacaa atctacaagt gtggactttg ctgttaatac agaaggcgtg   2160

tactctgaac ccgccccat tggcacccgt tacctcaccc gtaatctgta a             2211
```

<210> SEQ ID NO 96
<211> LENGTH: 2208
<212> TYPE: DNA
<213> ORGANISM: Artificial Sequence
<220> FEATURE:
<223> OTHER INFORMATION: AAV8 Swap 12 capsid polynucleotide

<400> SEQUENCE: 96

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctgc aggcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420
```

```
ggaaagaaga gaccggtaga gccatcaccc cagcgttctc cagactcctc tacgggcatc    480

ggcaagaaag gccaacagcc cgccagaaaa agactcaatt ttggtcagac tggcgactca    540

gagtcagttc cagaccctca acctctcgga gaacctccag cagcgccctc tggtgtggga    600

cctaatacaa tggctgcagg cggtggcgca ccaatggcag acaataacga aggcgccgac    660

ggagtgggta gttcctcggg aaattggcat tgcgattcca catggctggg cgacagagtc    720

atcaccacca gcaccagaac ctgggccctg cccacttaca acaaccatct ctacaagcaa    780

atctccagcc aatcaggagc ttcaaacgac aaccactact tcggctacag cacccccctgg    840

gggtattttg actttaacag attccactgc cacttttcac cacgtgactg gcagcgactc    900

atcaacaaca actggggatt ccggcccaag agactcagct tcaagctctt caacatccag    960

gtcaaggagg tcacgcagaa tgaaggcacc aagaccatcg ccaataacct caccagcacc   1020

atccaggtgt ttacggactc ggagtaccag ctgccgtacg ttctcggctc tgcccaccag   1080

ggctgcctgc ctccgttccc ggcggacgtg ttcatgattc cccagtacgg ctacctaaca   1140

ctcaacaacg gtagtcaggc cgtgggacgc tcctccttct actgcctgga atactttcct   1200

tcgcagatgc tgagaaccgg caacaacttc cagtttactt acaccttcga ggacgtgcct   1260

ttccacagca gctacgccca cagccagagc ttggaccggc tgatgaatcc tctgattgac   1320

cagtacctgt actacttatc cagaactcag tccacaggag gaactcaagg tacccagcaa   1380

ttgttatttt ctcaagctgg gcctgcaaac atgtcggctc aggccaagaa ctggctgcct   1440

ggaccttgct accggcagca gcgagtctcc acgacactgt cgcaaaacaa caacagcaac   1500

tttgcttgga ctggtgccac caaatatcac ctgaacggca gaaactcgtt ggttaatccc   1560

ggcgtcgcca tggcaacaca caaggacgac gaggaccgct tttcccatc cagcggagtc    1620

ctgatttttg gaaaaactgg agcaactaac aaaactacat tggaaaatgt gttaatgaca   1680

aatgaagaag aaattcgtcc tactaatcct gtagccacgg aagaatacgg gatagtcgcc   1740

gacaacttac aacagcagaa tactgcaccc cagataggaa ctgtcaacag ccagggagcc   1800

ttacctggca tggtctggca gaaccgggac gtgtacctgc agggtcccat ctgggccaag   1860

attcctcaca cggacggcaa cttccacccg tctccgctga tgggcggctt tggcctgaaa   1920

catcctccgc ctcagatcct gatcaagaac acgcctgtac ctgcggatcc tccgaccacc   1980

ttcaaccagt caaagctgaa ctctttcatc acgcaataca gcaccggaca ggtcagcgtg   2040

gaaattgaat gggagctgca gaaggaaaac agcaagcgct ggaaccccga gatccagtac   2100

acctccaact actacaaatc tacaagtgtg gactttgctg ttaatacaga aggcgtgtac   2160

tctgaacccc gccccattgg cacccgttac ctcacccgta atctgtaa                2208
```

<210> SEQ ID NO 97
<211> LENGTH: 2211
<212> TYPE: DNA
<213> ORGANISM: Artificial Sequence
<220> FEATURE:
<223> OTHER INFORMATION: AAV8 Swap 13 capsid polynucleotide

<400> SEQUENCE: 97

```
atggctgccg atggttatct tccagattgg ctcgaggaca acctctctga gggcattcgc     60

gagtggtggg cgctgaaacc tggagccccg aagcccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240
```

```
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcaccagaac ctgggccctg cccacttaca acaaccatct ctacaagcaa    780
atctccagcc aatcaggagc ttcaaacgac aaccactact tcggctacag caccccctgg    840
gggtattttg actttaacag attccactgc cacttttcac cacgtgactg gcagcgactc    900
atcaacaaca actggggatt ccggcccaag agactcagct tcaagctctt caacatccag    960
gtcaaggagg tcacgcagaa tgaaggcacc aagaccatcg ccaataacct caccagcacc   1020
atccaggtgt ttacggactc ggagtaccag ctgccgtacg ttctcggctc tgcccaccag   1080
ggctgcctgc ctccgttccc ggcggacgtg ttcatgattc cccagtacgg ctacctaaca   1140
ctcaacaacg gtagtcaggc cgtgggacgc tcctccttct actgcctgga atactttcct   1200
tcgcagatgc tgagaaccgg caacaacttc cagtttactt acaccttcga ggacgtgcct   1260
ttccacagca gctacgccca cagccagagc ttggaccggc tgatgaatcc tctgattgac   1320
cagtacctgt actacttatc cagaactcag tccacaggag gaactcaagg tacccagcaa   1380
ttgttatttt ctcaagctgg gcctgcaaac atgtcggctc aggccaagaa ctggctgcct   1440
ggaccttgct accggcagca gcgagtctcc acgacactgt cgcaaaacaa caacagcaac   1500
tttgcttgga ctggtgccac caaatatcac ctgaacggca gaaactcgtt ggttaatccc   1560
ggcgtcgcca tggcaacaca caaggacgac gaggaccgtt tttttcccag tagcggggtc   1620
ctgatttttg gcaaacaaaa tgctgccaga gacaatgcgg attacagcga tgtcatgctc   1680
accagcgagg aagaaatcaa aaccactaac cctgtggcta cagaggaata cggtatcgtg   1740
gcagataact tgcagcagca aaacacggct cctcaaattg gaactgtcaa cagccagggg   1800
gccttacccg gtatggtctg gcagaaccgg gacgtgtacc tgcagggtcc catctgggcc   1860
aagattcctc acacggacgg caacttccac ccgtctccgc tgatgggcgg ctttggcctg   1920
aaacatcctc cgcctcagat cctgatcaag aacacgcctg tacctgcgga tcctccgacc   1980
accttcaacc agtcaaagct gaactctttc atcacgcaat acagcaccgg acaggtcagc   2040
gtggaaattg aatgggagct gcagaaggaa aacagcaagc gctggaaccc cgagatccag   2100
tacacctcca actactacaa atctacaagt gtggactttg ctgttaatac agaaggcgtg   2160
tactctgaac cccgccccat tggcacccgt tacctcaccc gtaatctgta a             2211
```

```
<210> SEQ ID NO 98
<211> LENGTH: 2208
<212> TYPE: DNA
<213> ORGANISM: Artificial Sequence
<220> FEATURE:
<223> OTHER INFORMATION: AAV8 Swap 14 capsid polynucleotide

<400> SEQUENCE: 98

atggctgccg atggttatct tccagattgg ctcgaggaca acctctctga gggcattcgc      60
gagtggtggg cgctgaaacc tggagccccg aagcccaaag ccaaccagca aaagcaggac    120
```

```
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc cagcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcaccagaac ctgggccctg cccacttaca acaaccatct ctacaagcaa    780
atctccagcc aatcaggagc ttcaaacgac aaccactact tcggctacag cacccccctgg    840
gggtattttg actttaacag attccactgc cacttttcac cacgtgactg gcagcgactc    900
atcaacaaca actggggatt ccggcccaag agactcagct tcaagctctt caacatccag    960
gtcaaggagg tcacgcagaa tgaaggcacc aagaccatcg ccaataacct caccagcacc   1020
atccaggtgt ttacggactc ggagtaccag ctgccgtacg ttctcggctc tgcccaccag   1080
ggctgcctgc ctccgttccc ggcggacgtg ttcatgattc cccagtacgg ctacctaaca   1140
ctcaacaacg gtagtcaggc cgtgggacgc tcctccttct actgcctgga atactttcct   1200
tcgcagatgc tgagaaccgg caacaacttc cagtttactt acaccttcga ggacgtgcct   1260
ttccacagca gctacgccca cagccagagc ttggaccggc tgatgaatcc tctgattgac   1320
cagtacctgt actacttatc cagaactcag tccacaggag gaactcaagg tacccagcaa   1380
ttgttatttt ctcaagctgg gcctgcaaac atgtcggctc aggccaagaa ctggctgcct   1440
ggaccttgct accggcagca gcgagtctcc acgacactgt cgcaaaacaa caacagcaac   1500
tttgcttgga ctggtgccac caaatatcac ctgaacggca gaaactcgtt ggttaatccc   1560
ggcgtcgcca tggcaacaca caaggacgac gaggagcgtt tttttcccag taacgggatc   1620
ctgatttttg gcaaaactgg tgccacaaac aaaacgactt tggagaatgt cttgatgacc   1680
aacgaggaag aaatcagacc cactaaccct gtggctacag aggaatacgg tatcgtggca   1740
gataacttgc agcagcaaaa cacggctcct caaattggaa ctgtcaacag ccagggggcc   1800
ttacccggta tggtctggca gaaccgggac gtgtacctgc agggtcccat ctgggccaag   1860
attcctcaca cggacggcaa cttccacccg tctccgctga tgggcggctt tggcctgaaa   1920
catcctccgc ctcagatcct gatcaagaac acgcctgtac ctgcggatcc tccgaccacc   1980
ttcaaccagt caaagctgaa ctctttcatc acgcaataca gcaccggaca ggtcagcgtg   2040
gaaattgaat gggagctgca gaaggaaaac agcaagcgct ggaaccccga gatccagtac   2100
acctccaact actacaaatc tacaagtgtg gactttgctg ttaatacaga aggcgtgtac   2160
tctgaacccc gccccattgg cacccgttac ctcacccgta atctgtaa                2208
```

<210> SEQ ID NO 99
<211> LENGTH: 2211
<212> TYPE: DNA
<213> ORGANISM: Artificial Sequence
<220> FEATURE:
<223> OTHER INFORMATION: AAV8 Swap 15 capsid polynucleotide

<400> SEQUENCE: 99

```
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg gacccttcaa cggactcgac     180
aagggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag gccaacagcc cgccagaaaa agactcaatt ttggtcagac tggcgactca     540
gagtcagttc cagaccctca acctctcgga gaacctccag cagcgccctc tggtgtggga     600
cctaatacaa tggctgcagg cggtggcgca ccaatggcag acaataacga aggcgccgac     660
ggagtgggta gttcctcggg aaattggcat tgcgattcca catggctggg cgacagagtc     720
atcaccacca gcaccagaac ctgggccctg cccacttaca acaaccatct ctacaagcaa     780
atctccagcc aatcaggagc ttcaaacgac aaccactact tcggctacag caccccctgg     840
gggtattttg actttaacag attccactgc cacttttcac cacgtgactg gcagcgactc     900
atcaacaaca actggggatt ccggcccaag agactcagct tcaagctctt caacatccag     960
gtcaaggagg tcacgcagaa tgaaggcacc aagaccatcg ccaataacct caccagcacc    1020
atccaggtgt ttacggactc ggagtaccag ctgccgtacg ttctcggctc tgcccaccag    1080
ggctgcctgc ctccgttccc ggcggacgtg ttcatgattc cccagtacgg ctacctaaca    1140
ctcaacaacg gtagtcaggc cgtgggacgc tcctccttct actgcctgga atactttcct    1200
tcgcagatgc tgagaaccgg caacaacttc cagtttactt acaccttcga ggacgtgcct    1260
ttccacagca gctacgccca cagccagagc ttggaccggc tgatgaatcc tctgattgac    1320
cagtacctgt actacttatc cagaactcag tccacaggag gaactcaagg tacccagcaa    1380
ttgttatttt ctcaagctgg gcctgcaaac atgtcggctc aggccaagaa ctggctgcct    1440
ggaccttgct accggcagca gcgagtctcc acgacactgt cgcaaaacaa caacagcaac    1500
tttgcttgga ctggtgccac caaatatcac ctgaacggca gaaactcgtt ggttaatccc    1560
ggcgtcgcca tggcaacaca caaggacgac gaggagcgtt tttttcccag taacgggatc    1620
ctgatttttg gcaaacaaaa tgctgccaga gacaatgcgg attacagcga tgtcatgctc    1680
accagcgagg aagaaatcaa aaccactaac cctgtggcta cagaggaata cggtatcgtg    1740
tcatctaact tgcaggcggc aaacacggct gctcaaactc aagttgtcaa caaccagggg    1800
gccttacccg gtatggtctg gcagaaccgg gacgtgtacc tgcagggtcc catctgggcc    1860
aagattcctc acacggacgg caacttccac ccgtctccgc tgatgggcgg ctttggcctg    1920
aaacatcctc cgcctcagat cctgatcaag aacacgcctg tacctgcgga tcctccgacc    1980
accttcaacc agtcaaagct gaactctttc atcacgcaat acagcaccgg acaggtcagc    2040
gtggaaattg aatgggagct gcagaaggaa aacagcaagc gctggaaccc cgagatccag    2100
tacacctcca actactacaa atctacaagt gtggactttg ctgttaatac agaaggcgtg    2160
tactctgaac cccgccccat tggcacccgt tacctcaccc gtaatctgta a             2211
```